US009555064B2

(12) United States Patent
Pomerantsev et al.

(10) Patent No.: US 9,555,064 B2
(45) Date of Patent: Jan. 31, 2017

(54) **PROTEASE-DEFICIENT *BACILLUS ANTHRACIS***

(75) Inventors: Andrei P. Pomerantsev, Bethesda, MD (US); Stephen H. Leppla, Bethesda, MD (US)

(73) Assignee: The United States of America, as represented by the Secretary Dept. of Health and Human Services, Washington, DC (US)

( * ) Notice: Subject to any disclaimer, the term of this patent is extended or adjusted under 35 U.S.C. 154(b) by 143 days.

(21) Appl. No.: 14/236,430

(22) PCT Filed: Aug. 2, 2012

(86) PCT No.: PCT/US2012/049321
§ 371 (c)(1),
(2), (4) Date: May 12, 2014

(87) PCT Pub. No.: WO2013/019946
PCT Pub. Date: Feb. 7, 2013

(65) Prior Publication Data
US 2014/0314716 A1    Oct. 23, 2014

Related U.S. Application Data

(60) Provisional application No. 61/514,384, filed on Aug. 2, 2011, provisional application No. 61/521,617, filed on Aug. 9, 2011.

(51) Int. Cl.
| | |
|---|---|
| *C12N 15/20* | (2006.01) |
| *A61K 35/74* | (2015.01) |
| *C12P 21/02* | (2006.01) |
| *C12N 9/54* | (2006.01) |
| *C12N 15/75* | (2006.01) |
| *A61K 35/00* | (2006.01) |

(52) U.S. Cl.
CPC .................. *A61K 35/74* (2013.01); *C12N 9/54* (2013.01); *C12N 15/75* (2013.01); *C12P 21/02* (2013.01); *A61K 2035/11* (2013.01); *Y02P 20/52* (2015.11)

(58) Field of Classification Search
None
See application file for complete search history.

(56) References Cited

FOREIGN PATENT DOCUMENTS

WO    WO 03/006649 A2    1/2003

OTHER PUBLICATIONS

Pomerantsev et al, Genome Engineering in Bacillus anthracis Using Cre Recombinase. Infection and Immunity, Jan. 2006, p. 682-693.*
Kastrup et al, Spatial localization of bacteria controls coagulation of human blood by 'quorum acting'. Nat Chem Biol. Dec. 2008; 4(12): 742-750.*
Wu et al, Engineering a Bacillus subtilis expression-secretion system with a strain deficient in six extracellular proteases. J Bacteriol. Aug. 1991;173(16):4952-8.*
Pomerantsev, Andrei P. et al., "A Bacillus anthracis strain deleted for six proteases serves as an effective host for production of recombinant proteins", Protein Expression and Purification, vol. 80, No. 1, Aug. 7, 2011, pp. 80-90.
Murashima, Koichiro, et al., "Heterologous production of Clostridium cellulovorans engB, using protease-deficient Bacillus subtilis, and preparation of active recombinant ellulosomes", Journal of Bacteriology, American Society for Microbiology, Washington, DC; US, vol. 184, No. 1, Jan. 1, 2002, pp. 76-81.
Fedhila, S. et al., "The Bacillus thuringiensis PlcR-regulated gene inhA2 is necessary, but not sufficient, for virulence", Journal of Bacteriology, vol. 185, No. 9, May 2003, pp. 2820-2825.
Gohar, M. et al., "A comparative study of Bacillus cereus, Bacillus thuringiensis and Bacillus anthracis extracellular proteomes", Proteomics, vol. 5, No. 14, Sep. 2005, pp. 3696-3711.
Guillemet, E. et al., "The InhA metalloproteases of Bacillus cereus contribute concomitantly to virulence", Journal of Bacteriology 2010 American Society for Microbiology USA, vol. 192, No. 1, Jan. 2010, pp. 286-294.
Pflughoeft, K.J., et al., "Bacillus anthracis sin locus and regulation of secreted proteases", Journal of Bacteriology 2011 American Society for Microbiology USA, vol. 193, No. 3, Feb. 2011, pp. 631-639.
Kumar, P. et al., "Anthrax Edema Factor: Purification From *Escherichia coli* and Identification of Residues Required for Binding to Anthrax Protective Antigen", Molecular Biology of the Cell, American Society for Cell Biology, US, vol. 12, No. Suppl, Nov. 1, 2001, p. 393A.
Kumar, Thakasi D.K., et al., "Monoclonal Antibodies Against Recombinant Hemolysin BL Complex of Bacillus cereus", Hybridoma, vol. 29, No. 1, Feb. 2010, pp. 67-71.
Park, E., et al., "Optimized Production and Purification of Bacillus anthracis Lethal Factor", Protein Expression and Purification, Academic Press, San Diego, CA, vol. 18, No. 3, Apr. 1, 2000, pp. 293-302.

(Continued)

*Primary Examiner* — Sheridan Swope
(74) *Attorney, Agent, or Firm* — Sheridan Ross, P.C.

(57) ABSTRACT

The invention relates to a *Bacillus anthracis* (*B. anthracis*) in which more than one secreted protease is inactivated by genetic modification. Such a protease-deficient *B. anthracis* has an improved ability to produce recombinant secreted proteins compared to other bacteria, particularly other *Bacillus*. Improvements include production of intact (i.e., mature full-length) proteins, often at high yield. The disclosure provides a *B. anthracis* that comprises a genetic modification that inactivates a protease of the M4 family of metalloproteases and a genetic modification that inactivates a protease of the M6 family of metalloproteases. Also provided is a modified *B. anthracis* comprising such genetic modification transformed with a recombinant molecule encoding a product, as well as methods to prepare and use such *B. anthracis*.

8 Claims, 14 Drawing Sheets

(56) References Cited

OTHER PUBLICATIONS

International Search Report prepared by the European Patent Office on Apr. 19, 2013, for International Application No. PCT/US2012/049321.
Written Opinion prepared by the European Patent Office on Apr. 19, 2013, for International Application No. PCT/US2012/049321.
Kumar P et al., "Purification of Anthrax edema factor from *Escherichia coli* and identification of residues required for binding to anthrax protective antigen", Infection and Immunity, vol. 69, No. 10, pp. 6532-6536.
English Translation of Official Action for China Patent Application No. 201280048638.1, dated Jul. 22, 2015 8 pages.
English Translation of Official Action for China Patent Application No. 201280048638.1, dated Feb. 22, 2016 4 pages.
Official Action for European Patent Application No. 12753853.6, dated Jun. 1, 2015 5 pages.
Official Action for European Patent Application No. 12753853.6, dated Oct. 27, 2015 4 pages.
Official Action for European Patent Application No. 12753853.6, dated Jun. 14, 2016 4 pages.

\* cited by examiner

Figure 1A

NprB

| T | T | Y | G | S | P | V | L | V | N | L | F | E | G | P | N | N | F | V | * |
|---|---|---|---|---|---|---|---|---|---|---|---|---|---|---|---|---|---|---|---|
| aca | aca | tat | gga | tct | cca | gta | cta | gtg | aac | ctc | ttc | gag | gga | cct | aat | aac | ttc | gta | tag |

| H | T | L | Y | E | V | I | L | R | V | |
|---|---|---|---|---|---|---|---|---|---|---|
| cat | aca | tta | tac | gaa | gtt | ata | tta | agg | gtt | (SEQ ID NO:3) |

MKKKSLALVLATGMAVTTFGGTGSAFADSKNVLSTKKYNETVQSPEFISGDLTEATGKKAESVVFDYLNAAKGDYKLGEKSAQ
DSFKVKQAKKDAVTDSTVLRLQQVYEGVPVWGSTQVAHVSKDGSLKVLSGTVAPDLDKKEKLKNKNKIEGAKAIEIAQKDLGV
TPKYEVEPKADLYVYQNGEETTYAYVVNLNFLEPSPGNYYYFIEADSGKVLNKYNKLDHVANEDKSPVKQEAPKQEAKPAVKP
VTGTNAVGTGKGVLGDTKSLNTTLSASSYYLQDNTRGATIFTYDAKNRSTLPGTLWVDADNVFNAAYDAAAVDAHYYAGRTYD
YYKATFNRNSINDAGAPLKSTVHYGSRYNNAFWNGSQMVYGDGDGVTFTSLSGGIDVIGHELTHAVTEYSSDLIYQNESGALN
EAISDVFGTLVEYYDNRNPDWEIGEDIYTPGKAGDALRSMSDPTKYGDPDHYSKRYTGTGDNGGVHTNSGIINKAAYLLANGG
THYGVTVNGIGKDKVGAIYYRANTQYFTQSTTFSQARAGLVQAAADLYGASSAEVAAVKQSYSAVGVN (SEQ ID NO:1)

InhA1

| G | G | K | I | R | I | R | F | P | Q | I | S | D | H | I | N | N | P | * |
|---|---|---|---|---|---|---|---|---|---|---|---|---|---|---|---|---|---|---|
| ggt | gga | aag | att | cga | att | cgc | ttc | ccc | cag | atc | tcc | gat | cat | atc | aat | aac | cct | taa |

| Y | N | F | V | * | C | M | L | Y | E | V | I | |
|---|---|---|---|---|---|---|---|---|---|---|---|---|
| tat | aac | ttc | gta | taa | tgt | atg | cta | tac | gaa | ctt | att | (SEQ ID NO:19) |

MNKKPFKVLSSIALTAVLGLSFGAGGQSVYAETPVNKTATSPVDDHLIPEERLADALKKRGVIDSKASEK
ETKKAVEKYVENKKGENPGKEVTNGDPLTKEASDFVKKVKDAKADTKEKLDKPATGTPAATGPVRGGLNG
KVPTSPAKQKAYNGDVRKDKVLVLLVEYADFKHNNIDKEPGYMYSEDFNKEHYEKMLFGDEPFTLDDGSK
IETFKQYYEEQSGGSYTVDGTVTKWLTVPGKAADYGADAATGHDNKGPKGPRDLVKDALKAAVDSGLDLS
EFDQFDQYDVNGDGNKNQPDGLIDHLMIIHAGVGQEAGGGKLGDDAIWSHRWTVGPKPFPIEGTQAKVPY
WGGKMAAFDYTIEPEDGAVGVFAHEYGHDLGLPDEYDTQYSGHGEPVQAWSIMSGGSWAGKIAGTTPTSF
SPQNKEFFQKTIGGNWANIVEVDYEKLNKGIGLATYLDQSVTKTNRPGMIRVNLPDKDIKTIDPAFGKQY
YYSTKGDDLHTKLETPLFDLTNATTAKFDFKSLYEIEAEYDFLEVHAVTEDGQQTLIERLGEKANNGNAD
STNGKWIDKSYDLSQFKGKKVKLTFDYITDGGLALNGFLLDNASLTVDGKVVFSDDAEGTPQFKLDGFAV
SNGTEKKSHNYYVEWRNYAGSDNALKFARGPEYNTGMVVWYADSAYTDNWVGVHPGHGFLGVVDSHPEAI
VGTLNGKPTVESSTRFQIADAAFSFDKTPAWKVVSPTRGTYTYNGLAGVPKFDDSKTYINQQIPDAGRIL
PNLGLKFEVVGQADDNSAGAVRLYR (SEQ ID NO:17)

Figure 1B

InhA2

| H | R | S | R | Y | R | I | R | F | P | Q | I | S | D | H | I | N | N | P | * |
|---|---|---|---|---|---|---|---|---|---|---|---|---|---|---|---|---|---|---|---|
| cat | cgt | tca | aga | tat | cga | att | cga | ttc | ccc | cag | atc | tcc | gat | cat | atc | aat | aac | cct | taa |

| Y | N | F | V | * | C | M | L | Y | E | V | I | R | S | L | E | E | V | H | * |
|---|---|---|---|---|---|---|---|---|---|---|---|---|---|---|---|---|---|---|---|
| tat | aac | ttc | gta | taa | tgt | atg | cta | tac | gaa | gtt | att | agg | tcc | ctc | gaa | gag | gtt | cac | tag |

(SEQ ID NO:7)

MRRKAPLKVLSSLAIAAIIGCTSVMSAPLAYAETPAKEKENVSTTPIDYNLIQEDRLAEALKERGTINPASSKEETKKAVEKYIEKKQGDQANK
EILPADTAKEASDFVKKVKEKKMEEKEKVKKPEKNVSPEQKPEPNKKQLNGQVPTSKAKQAPYKGSVRTDKVLVLLVEFSDYKHNNIDQTPGYM
YSNDFSREHYQKMLFGNEPYTLFDGSKVKTFKQYYEEQSGGSYTTDGYVTEWLTVPGKASDYGADGSSGHDNKGPKGARDLVKEALHAAAEKGL
DLSQFDQFDRYDTNSDGNQNEPDGVIDHLMVIHAGVGQEAGGGKLGDDAIWSHRSKLAIDPVAIEGTKSKVDYFGGKVAAHDYTIEPEDGAVGV
FAHEFGHDLGLPDEYDTKYTGTGSPVEAWSLMSGGSWTGKIAGTEPTSFSPQNKDFLQKNMGGNWAKILEVDYDKIKRGVGVPTYIDQSVTKSN
RPGVVRVNLPGKSVETIKPEFGKHAYYSTRGDDMHTTLETPFFDLTKGTNAKFDYKANYELEAECDFVEVHAVTEDGTKTLIDRLGEKVVQGDK
DTTDGKWIDKSYDLSQFKGKKVKLQFDYITDPAVTYKGFAMDHVNVTVDGQVVFSDDAEGQSKMNLNGFVVSDGTEKKAHYYYLEWRNYAGSDN
GLKAGKGPVYNTGLVVWYADDSFKDNWVGVHPGEGFLGVVDSHPEAFVGNLNGKPTYGNTGMQIADAAFSFDQTPAWSVNSLTRGQFNYSGLQG
VTTFDDSKVYSNNQIADAGRKVPKLGLKFQVVGQADDKSAGAVWIKR (SEQ ID NO:5)

TasA

| K | P | G | P | G | S | N | H | * | F | * | S | G | R | H | R | G | G | A | H |
|---|---|---|---|---|---|---|---|---|---|---|---|---|---|---|---|---|---|---|---|
| aaa | cct | ggc | ccg | ggc | agt | aat | cac | tag | ttc | tag | agc | ggc | cgc | cac | cgc | ggt | gga | gct | cat |

| N | F | V | * | C | M | L | Y | E | V | I | S | C | S | R | S | T | V | S | I |
|---|---|---|---|---|---|---|---|---|---|---|---|---|---|---|---|---|---|---|---|
| aac | ttc | gta | taa | tgt | atg | cta | tac | gaa | gtt | atc | agc | tgc | tcg | agg | tcg | acg | gta | tcg | ata |

(SEQ ID NO:11)

MTLKKKLGMGIASAVLGAALVGGGTFAFFSDKEVSNNTFATGTLDLALNPSTVVNVSNLKPGDTVEKEFKLENKGTLDIKKVLLKTDYNVEDVK
KDNKDDFGKHIKVTFLKNVDKHETIVKETALDKLKGDTLTAVNNDLAAWFWDEKGISAGKSDKFKVKFEFVDNKKDQNEFQGDKLQLTWTFDAQ
QGDGETK (SEQ ID NO:9)

Camelysin

| L | D | L | R | S | Y | Q | * | P | L | I | * | L | R | I | M | Y | A | I | R |
|---|---|---|---|---|---|---|---|---|---|---|---|---|---|---|---|---|---|---|---|
| tta | gat | ctc | cga | tca | tat | caa | taa | ccc | tta | ata | taa | ctt | cgt | ata | atg | tat | gct | ata | cga |

| S | Y | * | V | P | R | R | G | S | L | V | L | E | I | F | * |
|---|---|---|---|---|---|---|---|---|---|---|---|---|---|---|---|
| agt | tat | tag | gtc | cct | cga | aga | ggt | tca | cta | gta | ctg | gag | atc | ttt | tag |

(SEQ ID NO:15)

MSLKKKLGMVASAALGLSLIGGGTFAYFSDKEVSNNTFAAGTLDLTLDPKTLVDIKDLKPGDSVKKEFLLKNSGSLTIKDVKLATKYTVKDVK
GDNAGEDFGKHVKVKFLWNWDKQSEPVYETTLADLQKTDPDLLAQDIFAPEWGEKGGLEAGTEDYLWVQFEFVDDGKDQNIFQGDSLNLEWTFN
ANQEAGEEK (SEQ ID NO:13)

MmpZ

| V | F | S | L | V | L | E | R | P | P | P | R | W | S | S | * | L | R | I | M | Y |
|---|---|---|---|---|---|---|---|---|---|---|---|---|---|---|---|---|---|---|---|---|
| gtt | ttt | tca | cta | gtt | cta | gag | cgg | ccg | cca | Ccg | Cgg | Tgg | agc | tca | taa | ctt | cgt | ata | atg | tat |

| A | I | R | S | Y | Q | L | L | E | G | W |
|---|---|---|---|---|---|---|---|---|---|---|
| gct | ata | cga | agt | tat | cag | ctg | ctc | gag | ggt | tgg |

(SEQ ID NO:23)

MNFKKGITAFLLGTVFVFSSVGVSEAYVKEGWKLPSKSATYKWGDRLDDGSSIIKSGWQAADSAWYTASRINFTVSASSVNTLNSWFESSSTYY
GRMKTSYNTSTKKVTKFAGDINAGNTNITKSNVAKSTGVHEFGHAIGIGHNSGTSIMNSRRNRTTMHVPQTDDKNGVNAIY (SEQ ID NO:21)

TasA-InhA1

| K | P | G | P | G | S | N | H | * | F | * | S | G | R | H | R | G | G | A | H |
|---|---|---|---|---|---|---|---|---|---|---|---|---|---|---|---|---|---|---|---|
| aaa | cct | ggc | ccg | ggc | agt | aat | cac | tag | ttc | tag | agc | ggc | cgc | cac | cgc | ggt | gga | gct | cat |

| N | F | V | * | C | M | L | Y | E | V | I | R | S | L | E | G | S | L | V | L |
|---|---|---|---|---|---|---|---|---|---|---|---|---|---|---|---|---|---|---|---|
| aac | ttc | gta | taa | tgt | atg | cta | tac | gaa | gtt | att | agg | tcc | ctc | gaa | ggt | tca | cta | gta | ctg |

(SEQ ID NO:26)

MTLKKKLGMGIASAVLGAALVGGGTFAFFSDKEVSNNTFATGTLDLALNPSTVVNVSNLKPGPGSNH*F*SGRHRGGAHNFV*CMLYEVIRSLE
..............
AWSIMSGGSWAGKIAGTTPTSFS.............. (residues 1-59 of SEQ ID NO:9, residues 1-32 of SEQ ID NO:26 and residues 399-421 of SEQ ID NO:17)

Figure 1C

CysP1

```
  C   S   T   T   S   S   R   A   A   A   T   A   V   E   L
tgt tca act act agt tct aga gcg gcc gcc acc gcg gtg gag ctc E   V   P   I   P   K   F   L   F   S   R   K   Y   R   N
gaa gtt cct att ccg aag ttc cta ttc tct aga aag tat agg aac F   Q   L   L   E   N   E   I   N   W   P   K   G   A   K
ttc cag ctg ctc gag aat gaa ata aac tgg cca aaa ggt gca aag R   V   S   Y   Q   V   A   P   Y   S   A   M   A   D   Y
cgt gta tct tat caa gta gca cca tat agt gct atg gca gat tat S   L   A   T   I   T   F   T   Y   *   S
tca tta gcg aca att aca ttt acg tat taa tcg     (SEQ ID NO:73)
```

MGKTSKYVTAAALCSTIVMGGLHASSVSYAATNPTVATLQSDAKLLNDFKKELKKQIDN
REENITITYKTKDRNARNIMDELYGEFNKIVDADEYVKYNIASTRYSIKGLPGNYTFTL
QVKYRESKEQTQYVKSQAKAIIGSIVKPGMDEHEKVKAIHDYVVKHVSYDTSYQAYTAY
EALANRSAVCQGYTLLTYELLKEAGIQNRIVTGTGNGQAHSWNLVNIENKWYHLDTTFD
DPVPDKAGRVTYSYFNMSDEQLSKDHDWDRSKYPAATTSYFNELTNKIKAGSSKTATYE
QMLKETNLKYLSAQYGADNYSEFKEKLQQQFASKPEKVEVRYKQSMDGTMQDIKKVLNE
INWPKGAKRVSYQVAPYSAMADYSLATITFTY     (SEQ ID NO:71)

VpR

```
  M   A   L   D   *   F   *   S   G   R   H   R   G   G   A
atg gca ctc gac tag ttc tag agc ggc cgc cac cgc ggt ggt gga R   S   S   Y   S   E   V   P   I   L   *   K   V   *   E
gct cga agt tat tcc gaa gtt cct att ctc tag aaa gta tag gaa L   P   A   A   R
ctt cca gct gct cga     (SEQ ID NO:77)
```

MKKTTSILLSMALVFSSFGALSAHAESLQKEKQFSPQLKTTIEQWGESKIAQHVETKTT
KEISVIVELQHAPLAAQSNIQHAPDLQNSHAQSYHTELKKAQEETTKKIKEKAPGAKIK
EVYNTLFSGFSISVPGDQITALASLPEVKTVYPNLTYKLHETTKSATSEEAPNIGGPTI
GAPEAWNLKDPSGKSLDGKGMKVAIIDSGVDYTHPDLKANYIGGYDTVDEDADPMDGNV
HGTHVAGIIAGNGKIKGVAPNASILAYRVMNDGGTGTTDDIIQGIERAIQDGADVLNLS
LGQDLNVPDQPVTLTLERAAKLGITAVVSNGNDGPKPWSVDAPGNASSVISVGASTVSI

Figure 1C - Continuted

PFPTFQVAGSSKTYQGLSLSKSDFPIGNDSPLVYVGYGNPSDYAKQDVKGKFALVLQGT
SSTLVKAEQAKQAGAIGVLFISTEKEMNSMPEYFTRENLALPVMQLSNVNGEELKNLIT
KRKKNIKIGQPVPTELIGNFSSRGPSQGSWLIKPDIVAPGVQITSTVPRGGYESHNGTS
MAAPQVAGAVALLRQMHPDWTTQQLKASLANTAKTLKDVNENTYPIMTQGSGLINIPKA
AQTDVLVKPNNVSFGLIKPNSGKVKLTQNITLQNLSSKKKSFSTRVELLDTNTKTKVKT
SVPSSISIQPNSSTEKPFTITVDSSLPQGVYTGNVYVKEQGAKEETRIPFTFSIDPKDY
KRIDGLEIINSTFSPNGDQILDDNLINYYLVAPVDDVTLHANLVTKERVTYQGIIHQAK
NETAGYKPFKWDGTKADGTPLADGLYQIEAVASNSGGETKQTAAVFLDRTAPKLTYEID
QENLVITGKVDDILLDWMTESGWVAPGIPVRLQYEINGNGVWESAFLNPWEKNYGIYLD
RTQLQEGKNTIHIVATDAAGNTSNLNVDLDVK  (SEQ ID NO:75)

SEQUENCE LISTING

```
<160> NUMBER OF SEQ ID NOS: 95

<210> SEQ ID NO 1
<211> LENGTH: 566
<212> TYPE: PRT
<213> ORGANISM: Bacillus anthracis

<400> SEQUENCE: 1

Met Lys Lys Lys Ser Leu Ala Leu Val Leu Ala Thr Gly Met Ala Val
1               5                   10                  15

Thr Thr Phe Gly Gly Thr Gly Ser Ala Phe Ala Asp Ser Lys Asn Val
            20                  25                  30

Leu Ser Thr Lys Lys Tyr Asn Glu Thr Val Gln Ser Pro Glu Phe Ile
        35                  40                  45
```

```
Ser Gly Asp Leu Thr Glu Ala Thr Gly Lys Lys Ala Glu Ser Val Val
     50                  55                  60

Phe Asp Tyr Leu Asn Ala Ala Lys Gly Asp Tyr Lys Leu Gly Glu Lys
 65                  70                  75                  80

Ser Ala Gln Asp Ser Phe Lys Val Lys Gln Ala Lys Lys Asp Ala Val
                 85                  90                  95

Thr Asp Ser Thr Val Leu Arg Leu Gln Gln Val Tyr Glu Gly Val Pro
            100                 105                 110

Val Trp Gly Ser Thr Gln Val Ala His Val Ser Lys Asp Gly Ser Leu
        115                 120                 125

Lys Val Leu Ser Gly Thr Val Ala Pro Asp Leu Asp Lys Lys Glu Lys
130                 135                 140

Leu Lys Asn Lys Asn Lys Ile Glu Gly Ala Lys Ala Ile Glu Ile Ala
145                 150                 155                 160

Gln Lys Asp Leu Gly Val Thr Pro Lys Tyr Glu Val Glu Pro Lys Ala
                165                 170                 175

Asp Leu Tyr Val Tyr Gln Asn Gly Glu Glu Thr Thr Tyr Ala Tyr Val
            180                 185                 190

Val Asn Leu Asn Phe Leu Glu Pro Ser Pro Gly Asn Tyr Tyr Tyr Phe
        195                 200                 205

Ile Glu Ala Asp Ser Gly Lys Val Leu Asn Lys Tyr Asn Lys Leu Asp
210                 215                 220

His Val Ala Asn Glu Asp Lys Ser Pro Val Lys Gln Glu Ala Pro Lys
225                 230                 235                 240

Gln Glu Ala Lys Pro Ala Val Lys Pro Val Thr Gly Thr Asn Ala Val
                245                 250                 255

Gly Thr Gly Lys Gly Val Leu Gly Asp Thr Lys Ser Leu Asn Thr Thr
            260                 265                 270

Leu Ser Ala Ser Ser Tyr Tyr Leu Gln Asp Asn Thr Arg Gly Ala Thr
        275                 280                 285

Ile Phe Thr Tyr Asp Ala Lys Asn Arg Ser Thr Leu Pro Gly Thr Leu
290                 295                 300

Trp Val Asp Ala Asp Asn Val Phe Asn Ala Ala Tyr Asp Ala Ala Ala
305                 310                 315                 320

Val Asp Ala His Tyr Tyr Ala Gly Arg Thr Tyr Asp Tyr Tyr Lys Ala
                325                 330                 335

Thr Phe Asn Arg Asn Ser Ile Asn Asp Ala Gly Ala Pro Leu Lys Ser
            340                 345                 350

Thr Val His Tyr Gly Ser Arg Tyr Asn Asn Ala Phe Trp Asn Gly Ser
        355                 360                 365

Gln Met Val Tyr Gly Asp Gly Asp Gly Val Thr Phe Thr Ser Leu Ser
370                 375                 380

Gly Gly Ile Asp Val Ile Gly His Glu Leu Thr His Ala Val Thr Glu
385                 390                 395                 400

Tyr Ser Ser Asp Leu Ile Tyr Gln Asn Glu Ser Gly Ala Leu Asn Glu
                405                 410                 415

Ala Ile Ser Asp Val Phe Gly Thr Leu Val Glu Tyr Tyr Asp Asn Arg
            420                 425                 430

Asn Pro Asp Trp Glu Ile Gly Glu Asp Ile Tyr Thr Pro Gly Lys Ala
        435                 440                 445

Gly Asp Ala Leu Arg Ser Met Ser Asp Pro Thr Lys Tyr Gly Asp Pro
450                 455                 460
```

```
Asp His Tyr Ser Lys Arg Tyr Thr Gly Thr Gly Asp Asn Gly Gly Val
465                 470                 475                 480

His Thr Asn Ser Gly Ile Ile Asn Lys Ala Ala Tyr Leu Leu Ala Asn
            485                 490                 495

Gly Gly Thr His Tyr Gly Val Thr Val Asn Gly Ile Gly Lys Asp Lys
                500                 505                 510

Val Gly Ala Ile Tyr Tyr Arg Ala Asn Thr Gln Tyr Phe Thr Gln Ser
            515                 520                 525

Thr Thr Phe Ser Gln Ala Arg Ala Gly Leu Val Gln Ala Ala Ala Asp
        530                 535                 540

Leu Tyr Gly Ala Ser Ser Ala Glu Val Ala Ala Val Lys Gln Ser Tyr
545                 550                 555                 560

Ser Ala Val Gly Val Asn
                565

<210> SEQ ID NO 2
<211> LENGTH: 205
<212> TYPE: PRT
<213> ORGANISM: Artificial Sequence
<220> FEATURE:
<223> OTHER INFORMATION: Synthetic

<400> SEQUENCE: 2

Met Lys Lys Lys Ser Leu Ala Leu Val Leu Ala Thr Gly Met Ala Val
1               5                   10                  15

Thr Thr Phe Gly Gly Thr Gly Ser Ala Phe Ala Asp Ser Lys Asn Val
            20                  25                  30

Leu Ser Thr Lys Lys Tyr Asn Glu Thr Val Gln Ser Pro Glu Phe Ile
        35                  40                  45

Ser Gly Asp Leu Thr Glu Ala Thr Gly Lys Lys Ala Glu Ser Val Val
    50                  55                  60

Phe Asp Tyr Leu Asn Ala Ala Lys Gly Asp Tyr Lys Leu Gly Glu Lys
65                  70                  75                  80

Ser Ala Gln Asp Ser Phe Lys Val Lys Gln Ala Lys Lys Asp Ala Val
                85                  90                  95

Thr Asp Ser Thr Val Leu Arg Leu Gln Gln Val Tyr Glu Gly Val Pro
            100                 105                 110

Val Trp Gly Ser Thr Gln Val Ala His Val Ser Lys Asp Gly Ser Leu
        115                 120                 125

Lys Val Leu Ser Gly Thr Val Ala Pro Asp Leu Asp Lys Lys Glu Lys
    130                 135                 140

Leu Lys Asn Lys Asn Lys Ile Glu Gly Ala Lys Ala Ile Glu Ile Ala
145                 150                 155                 160

Gln Lys Asp Leu Gly Val Thr Pro Lys Tyr Glu Val Glu Pro Lys Ala
                165                 170                 175

Asp Leu Tyr Val Tyr Gln Asn Gly Glu Glu Thr Thr Tyr Gly Ser Pro
            180                 185                 190

Val Leu Val Asn Leu Phe Glu Gly Pro Asn Asn Phe Val
        195                 200                 205

<210> SEQ ID NO 3
<211> LENGTH: 90
<212> TYPE: DNA
<213> ORGANISM: Artificial Sequence
<220> FEATURE:
<223> OTHER INFORMATION: Synthetic
<220> FEATURE:
<221> NAME/KEY: exon
```

```
<222> LOCATION: (1)..(90)

<400> SEQUENCE: 3 aca aca tat gga tct cca gta cta gtg aac ctc ttc gag gga cct aat      48
Thr Thr Tyr Gly Ser Pro Val Leu Val Asn Leu Phe Glu Gly Pro Asn
1               5                   10                  15 aac ttc gta tag cat aca tta tac gaa gtt ata tta agg gtt              90
Asn Phe Val     His Thr Leu Tyr Glu Val Ile Leu Arg Val
                20                  25

<210> SEQ ID NO 4
<211> LENGTH: 19
<212> TYPE: PRT
<213> ORGANISM: Artificial Sequence
<220> FEATURE:
<223> OTHER INFORMATION: Synthetic

<400> SEQUENCE: 4

Thr Thr Tyr Gly Ser Pro Val Leu Val Asn Leu Phe Glu Gly Pro Asn
1               5                   10                  15

Asn Phe Val

<210> SEQ ID NO 5
<211> LENGTH: 799
<212> TYPE: PRT
<213> ORGANISM: Bacillus anthracis

<400> SEQUENCE: 5

Met Arg Arg Lys Ala Pro Leu Lys Val Leu Ser Ser Leu Ala Ile Ala
1               5                   10                  15

Ala Ile Ile Gly Cys Thr Ser Val Met Ser Ala Pro Leu Ala Tyr Ala
                20                  25                  30

Glu Thr Pro Ala Lys Glu Lys Glu Asn Val Ser Thr Thr Pro Ile Asp
            35                  40                  45

Tyr Asn Leu Ile Gln Glu Asp Arg Leu Ala Glu Ala Leu Lys Glu Arg
        50                  55                  60

Gly Thr Ile Asn Pro Ala Ser Ser Lys Glu Glu Thr Lys Lys Ala Val
65                  70                  75                  80

Glu Lys Tyr Ile Glu Lys Lys Gln Gly Asp Gln Ala Asn Lys Glu Ile
                85                  90                  95

Leu Pro Ala Asp Thr Ala Lys Glu Ala Ser Asp Phe Val Lys Lys Val
            100                 105                 110

Lys Glu Lys Lys Met Glu Glu Lys Glu Lys Val Lys Lys Pro Glu Lys
        115                 120                 125

Asn Val Ser Pro Glu Gln Lys Pro Glu Pro Asn Lys Lys Gln Leu Asn
130                 135                 140

Gly Gln Val Pro Thr Ser Lys Ala Lys Gln Ala Pro Tyr Lys Gly Ser
145                 150                 155                 160

Val Arg Thr Asp Lys Val Leu Val Leu Leu Val Glu Phe Ser Asp Tyr
                165                 170                 175

Lys His Asn Asn Ile Asp Gln Thr Pro Gly Tyr Met Tyr Ser Asn Asp
            180                 185                 190

Phe Ser Arg Glu His Tyr Gln Lys Met Leu Phe Gly Asn Glu Pro Tyr
        195                 200                 205

Thr Leu Phe Asp Gly Ser Lys Val Lys Thr Phe Lys Gln Tyr Tyr Glu
    210                 215                 220

Glu Gln Ser Gly Gly Ser Tyr Thr Thr Asp Gly Tyr Val Thr Glu Trp
225                 230                 235                 240
```

```
Leu Thr Val Pro Gly Lys Ala Ser Asp Tyr Gly Ala Asp Gly Ser Ser
            245                 250                 255

Gly His Asp Asn Lys Gly Pro Lys Gly Ala Arg Asp Leu Val Lys Glu
            260                 265                 270

Ala Leu His Ala Ala Ala Glu Lys Gly Leu Asp Leu Ser Gln Phe Asp
            275                 280                 285

Gln Phe Asp Arg Tyr Asp Thr Asn Ser Asp Gly Asn Gln Asn Glu Pro
    290                 295                 300

Asp Gly Val Ile Asp His Leu Met Val Ile His Ala Val Gly Gln
305                 310                 315                 320

Glu Ala Gly Gly Lys Leu Gly Asp Asp Ala Ile Trp Ser His Arg
                325                 330                 335

Ser Lys Leu Ala Ile Asp Pro Val Ala Ile Glu Gly Thr Lys Ser Lys
            340                 345                 350

Val Asp Tyr Phe Gly Gly Lys Val Ala Ala His Asp Tyr Thr Ile Glu
            355                 360                 365

Pro Glu Asp Gly Ala Val Gly Val Phe Ala His Glu Phe Gly His Asp
    370                 375                 380

Leu Gly Leu Pro Asp Glu Tyr Asp Thr Lys Tyr Thr Gly Thr Gly Ser
385                 390                 395                 400

Pro Val Glu Ala Trp Ser Leu Met Ser Gly Ser Trp Thr Gly Lys
                405                 410                 415

Ile Ala Gly Thr Glu Pro Thr Ser Phe Ser Pro Gln Asn Lys Asp Phe
            420                 425                 430

Leu Gln Lys Asn Met Gly Gly Asn Trp Ala Lys Ile Leu Glu Val Asp
            435                 440                 445

Tyr Asp Lys Ile Lys Arg Gly Val Gly Val Pro Thr Tyr Ile Asp Gln
    450                 455                 460

Ser Val Thr Lys Ser Asn Arg Pro Gly Val Val Arg Val Asn Leu Pro
465                 470                 475                 480

Gly Lys Ser Val Glu Thr Ile Lys Pro Glu Phe Gly Lys His Ala Tyr
                485                 490                 495

Tyr Ser Thr Arg Gly Asp Asp Met His Thr Thr Leu Glu Thr Pro Phe
            500                 505                 510

Phe Asp Leu Thr Lys Gly Thr Asn Ala Lys Phe Asp Tyr Lys Ala Asn
            515                 520                 525

Tyr Glu Leu Glu Ala Glu Cys Asp Phe Val Glu Val His Ala Val Thr
    530                 535                 540

Glu Asp Gly Thr Lys Thr Leu Ile Asp Arg Leu Gly Glu Lys Val Val
545                 550                 555                 560

Gln Gly Asp Lys Asp Thr Thr Asp Gly Lys Trp Ile Asp Lys Ser Tyr
                565                 570                 575

Asp Leu Ser Gln Phe Lys Gly Lys Val Lys Leu Gln Phe Asp Tyr
            580                 585                 590

Ile Thr Asp Pro Ala Val Thr Tyr Lys Gly Phe Ala Met Asp His Val
    595                 600                 605

Asn Val Thr Val Asp Gly Gln Val Val Phe Ser Asp Ala Glu Gly
610                 615                 620

Gln Ser Lys Met Asn Leu Asn Gly Phe Val Val Ser Asp Gly Thr Glu
625                 630                 635                 640

Lys Lys Ala His Tyr Tyr Tyr Leu Glu Trp Arg Asn Tyr Ala Gly Ser
                645                 650                 655
```

Asp Asn Gly Leu Lys Ala Gly Lys Gly Pro Val Tyr Asn Thr Gly Leu
            660                 665                 670

Val Val Trp Tyr Ala Asp Asp Ser Phe Lys Asp Asn Trp Val Gly Val
        675                 680                 685

His Pro Gly Glu Gly Phe Leu Gly Val Val Asp Ser His Pro Glu Ala
    690                 695                 700

Phe Val Gly Asn Leu Asn Gly Lys Pro Thr Tyr Gly Asn Thr Gly Met
705                 710                 715                 720

Gln Ile Ala Asp Ala Phe Ser Phe Asp Gln Thr Pro Ala Trp Ser
                725                 730                 735

Val Asn Ser Leu Thr Arg Gly Gln Phe Asn Tyr Ser Gly Leu Gln Gly
            740                 745                 750

Val Thr Thr Phe Asp Asp Ser Lys Val Tyr Ser Asn Asn Gln Ile Ala
        755                 760                 765

Asp Ala Gly Arg Lys Val Pro Lys Leu Gly Leu Lys Phe Gln Val Val
    770                 775                 780

Gly Gln Ala Asp Asp Lys Ser Ala Gly Ala Val Trp Ile Lys Arg
785                 790                 795

<210> SEQ ID NO 6
<211> LENGTH: 353
<212> TYPE: PRT
<213> ORGANISM: Artificial Sequence
<220> FEATURE:
<223> OTHER INFORMATION: Synthetic

<400> SEQUENCE: 6

Met Arg Arg Lys Ala Pro Leu Lys Val Leu Ser Ser Leu Ala Ile Ala
1               5                   10                  15

Ala Ile Ile Gly Cys Thr Ser Val Met Ser Ala Pro Leu Ala Tyr Ala
            20                  25                  30

Glu Thr Pro Ala Lys Glu Lys Glu Asn Val Ser Thr Thr Pro Ile Asp
        35                  40                  45

Tyr Asn Leu Ile Gln Glu Asp Arg Leu Ala Glu Ala Leu Lys Glu Arg
    50                  55                  60

Gly Thr Ile Asn Pro Ala Ser Ser Lys Glu Thr Lys Lys Ala Val
65                  70                  75                  80

Glu Lys Tyr Ile Glu Lys Lys Gln Gly Asp Gln Ala Asn Lys Glu Ile
                85                  90                  95

Leu Pro Ala Asp Thr Ala Lys Glu Ala Ser Asp Phe Val Lys Lys Val
            100                 105                 110

Lys Glu Lys Lys Met Glu Glu Lys Glu Lys Val Lys Lys Pro Glu Lys
        115                 120                 125

Asn Val Ser Pro Glu Gln Lys Pro Glu Pro Asn Lys Lys Gln Leu Asn
    130                 135                 140

Gly Gln Val Pro Thr Ser Lys Ala Lys Gln Ala Pro Tyr Lys Gly Ser
145                 150                 155                 160

Val Arg Thr Asp Lys Val Leu Val Leu Leu Val Glu Phe Ser Asp Tyr
                165                 170                 175

Lys His Asn Asn Ile Asp Gln Thr Pro Gly Tyr Met Tyr Ser Asn Asp
            180                 185                 190

Phe Ser Arg Glu His Tyr Gln Lys Met Leu Phe Gly Asn Glu Pro Tyr
        195                 200                 205

Thr Leu Phe Asp Gly Ser Lys Val Lys Thr Phe Lys Gln Tyr Tyr Glu
    210                 215                 220

-continued

```
Glu Gln Ser Gly Gly Ser Tyr Thr Thr Asp Gly Tyr Val Thr Glu Trp
225                 230                 235                 240

Leu Thr Val Pro Gly Lys Ala Ser Asp Tyr Gly Ala Asp Gly Ser Ser
            245                 250                 255

Gly His Asp Asn Lys Gly Pro Lys Gly Ala Arg Asp Leu Val Lys Glu
        260                 265                 270

Ala Leu His Ala Ala Ala Glu Lys Gly Leu Asp Leu Ser Gln Phe Asp
    275                 280                 285

Gln Phe Asp Arg Tyr Asp Thr Asn Ser Asp Gly Asn Gln Asn Glu Pro
290                 295                 300

Asp Gly Val Ile Asp His Leu Met Val Ile His Ala Gly Val Gly Gln
305                 310                 315                 320

Glu Ala Gly Gly Gly Lys Leu Gly Asp Asp Ala Ile Trp Ser His Arg
                325                 330                 335

Ser Arg Tyr Arg Ile Arg Phe Pro Gln Ile Ser Asp His Ile Asn Asn
            340                 345                 350

Pro

<210> SEQ ID NO 7
<211> LENGTH: 120
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (1)..(120)

<400> SEQUENCE: 7 cat cgt tca aga tat cga att cga ttc ccc cag atc tcc gat cat atc      48
His Arg Ser Arg Tyr Arg Ile Arg Phe Pro Gln Ile Ser Asp His Ile
1               5                   10                  15 aat aac cct taa tat aac ttc gta taa tgt atg cta tac gaa gtt att      96
Asn Asn Pro     Tyr Asn Phe Val     Cys Met Leu Tyr Glu Val Ile
                20                      25                  30 agg tcc ctc gaa gag gtt cac tag                                     120
Arg Ser Leu Glu Glu Val His
            35

<210> SEQ ID NO 8
<211> LENGTH: 19
<212> TYPE: PRT
<213> ORGANISM: Artificial Sequence
<220> FEATURE:
<223> OTHER INFORMATION: Synthetic

<400> SEQUENCE: 8

His Arg Ser Arg Tyr Arg Ile Arg Phe Pro Gln Ile Ser Asp His Ile
1               5                   10                  15

Asn Asn Pro

<210> SEQ ID NO 9
<211> LENGTH: 195
<212> TYPE: PRT
<213> ORGANISM: Bacillus anthracis

<400> SEQUENCE: 9

Met Thr Leu Lys Lys Lys Leu Gly Met Gly Ile Ala Ser Ala Val Leu
1               5                   10                  15

Gly Ala Ala Leu Val Gly Gly Thr Phe Ala Phe Phe Ser Asp Lys
            20                  25                  30
```

```
Glu Val Ser Asn Asn Thr Phe Ala Thr Gly Thr Leu Asp Leu Ala Leu
            35                  40                  45

Asn Pro Ser Thr Val Val Asn Val Ser Asn Leu Lys Pro Gly Asp Thr
        50                  55                  60

Val Glu Lys Glu Phe Lys Leu Glu Asn Lys Gly Thr Leu Asp Ile Lys
 65                  70                  75                  80

Lys Val Leu Leu Lys Thr Asp Tyr Asn Val Glu Asp Val Lys Lys Asp
                85                  90                  95

Asn Lys Asp Asp Phe Gly Lys His Ile Lys Val Thr Phe Leu Lys Asn
            100                 105                 110

Val Asp Lys His Glu Thr Ile Val Lys Glu Thr Ala Leu Asp Lys Leu
        115                 120                 125

Lys Gly Asp Thr Leu Thr Ala Val Asn Asn Asp Leu Ala Ala Trp Phe
    130                 135                 140

Trp Asp Glu Lys Gly Ile Ser Ala Gly Lys Ser Asp Lys Phe Lys Val
145                 150                 155                 160

Lys Phe Glu Phe Val Asp Asn Lys Lys Asp Gln Asn Glu Phe Gln Gly
                165                 170                 175

Asp Lys Leu Gln Leu Thr Trp Thr Phe Asp Ala Gln Gly Asp Gly
            180                 185                 190

Glu Thr Lys
        195

<210> SEQ ID NO 10
<211> LENGTH: 67
<212> TYPE: PRT
<213> ORGANISM: Artificial Sequence
<220> FEATURE:
<223> OTHER INFORMATION: Synthetic

<400> SEQUENCE: 10

Met Thr Leu Lys Lys Lys Leu Gly Met Gly Ile Ala Ser Ala Val Leu
 1               5                  10                  15

Gly Ala Ala Leu Val Gly Gly Gly Thr Phe Ala Phe Phe Ser Asp Lys
            20                  25                  30

Glu Val Ser Asn Asn Thr Phe Ala Thr Gly Thr Leu Asp Leu Ala Leu
            35                  40                  45

Asn Pro Ser Thr Val Val Asn Val Ser Asn Leu Lys Pro Gly Pro Gly
        50                  55                  60

Ser Asn His
 65

<210> SEQ ID NO 11
<211> LENGTH: 120
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (1)..(120)

<400> SEQUENCE: 11 aaa cct ggc ccg ggc agt aat cac tag ttc tag agc ggc cgc cac cgc      48
Lys Pro Gly Pro Gly Ser Asn His     Phe     Ser Gly Arg His Arg
 1               5                                  10 ggt gga gct cat aac ttc gta taa tgt atg cta tac gaa gtt atc agc      96
Gly Gly Ala His Asn Phe Val     Cys Met Leu Tyr Glu Val Ile Ser
            15                      20                  25
```

```
tgc tcg agg tcg acg gta tcg ata                                         120
Cys Ser Arg Ser Thr Val Ser Ile
 30                  35
```

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

```
Lys Pro Gly Pro Gly Ser Asn His
 1               5
```

<210> SEQ ID NO 13
<211> LENGTH: 197
<212> TYPE: PRT
<213> ORGANISM: Bacillus anthracis

<400> SEQUENCE: 13

```
Met Ser Leu Lys Lys Lys Leu Gly Met Gly Val Ala Ser Ala Ala Leu
 1               5                  10                  15

Gly Leu Ser Leu Ile Gly Gly Gly Thr Phe Ala Tyr Phe Ser Asp Lys
                20                  25                  30

Glu Val Ser Asn Asn Thr Phe Ala Ala Gly Thr Leu Asp Leu Thr Leu
            35                  40                  45

Asp Pro Lys Thr Leu Val Asp Ile Lys Asp Leu Lys Pro Gly Asp Ser
        50                  55                  60

Val Lys Lys Glu Phe Leu Leu Lys Asn Ser Gly Ser Leu Thr Ile Lys
 65                  70                  75                  80

Asp Val Lys Leu Ala Thr Lys Tyr Thr Val Asp Val Lys Gly Asp
                85                  90                  95

Asn Ala Gly Glu Asp Phe Gly Lys His Val Lys Val Lys Phe Leu Trp
            100                 105                 110

Asn Trp Asp Lys Gln Ser Glu Pro Val Tyr Glu Thr Thr Leu Ala Asp
        115                 120                 125

Leu Gln Lys Thr Asp Pro Asp Leu Leu Ala Gln Asp Ile Phe Ala Pro
    130                 135                 140

Glu Trp Gly Glu Lys Gly Gly Leu Glu Ala Gly Thr Glu Asp Tyr Leu
145                 150                 155                 160

Trp Val Gln Phe Glu Phe Val Asp Asp Gly Lys Asp Gln Asn Ile Phe
                165                 170                 175

Gln Gly Asp Ser Leu Asn Leu Glu Trp Thr Phe Asn Ala Asn Gln Glu
            180                 185                 190

Ala Gly Glu Glu Lys
        195
```

<210> SEQ ID NO 14
<211> LENGTH: 50
<212> TYPE: PRT
<213> ORGANISM: Artificial Sequence
<220> FEATURE:
<223> OTHER INFORMATION: Synthetic

<400> SEQUENCE: 14

```
Met Ser Leu Lys Lys Lys Leu Gly Met Gly Val Ala Ser Ala Ala Leu
 1               5                  10                  15

Gly Leu Ser Leu Ile Gly Gly Gly Thr Phe Ala Tyr Phe Ser Asp Lys
```

```
                    20                   25                   30

Glu Val Ser Asn Asn Thr Phe Ala Ala Gly Thr Leu Asp Leu Arg Ser
            35                   40                   45

Tyr Gln
    50

<210> SEQ ID NO 15
<211> LENGTH: 108
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (1)..(108)

<400> SEQUENCE: 15 tta gat ctc cga tca tat caa taa ccc tta ata taa ctt cgt ata atg     48
Leu Asp Leu Arg Ser Tyr Gln     Pro Leu Ile     Leu Arg Ile Met
 1               5                      10 tat gct ata cga agt tat tag gtc cct cga aga ggt tca cta gta ctg     96
Tyr Ala Ile Arg Ser Tyr     Val Pro Arg Arg Gly Ser Leu Val Leu
 15              20                      25 gag atc ttt tag                                                    108
Glu Ile Phe
 30

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Leu Asp Leu Arg Ser Tyr Gln
 1               5

<210> SEQ ID NO 17
<211> LENGTH: 795
<212> TYPE: PRT
<213> ORGANISM: Bacillus anthracis

<400> SEQUENCE: 17

Met Asn Lys Lys Pro Phe Lys Val Leu Ser Ile Ala Leu Thr Ala
 1               5                  10                  15

Val Leu Gly Leu Ser Phe Gly Ala Gly Gly Gln Ser Val Tyr Ala Glu
                20                  25                  30

Thr Pro Val Asn Lys Thr Ala Thr Ser Pro Val Asp Asp His Leu Ile
            35                  40                  45

Pro Glu Glu Arg Leu Ala Asp Ala Leu Lys Lys Arg Gly Val Ile Asp
        50                  55                  60

Ser Lys Ala Ser Glu Lys Glu Thr Lys Lys Ala Val Glu Lys Tyr Val
 65                  70                  75                  80

Glu Asn Lys Lys Gly Glu Asn Pro Gly Lys Glu Val Thr Asn Gly Asp
                85                  90                  95

Pro Leu Thr Lys Glu Ala Ser Asp Phe Val Lys Val Lys Asp Ala
            100                 105                 110

Lys Ala Asp Thr Lys Glu Lys Leu Asp Lys Pro Ala Thr Gly Thr Pro
        115                 120                 125

Ala Ala Thr Gly Pro Val Arg Gly Gly Leu Asn Gly Lys Val Pro Thr
```

```
             130                 135                 140
Ser Pro Ala Lys Gln Lys Ala Tyr Asn Gly Asp Val Arg Lys Asp Lys
145                 150                 155                 160

Val Leu Val Leu Leu Val Glu Tyr Ala Asp Phe Lys His Asn Asn Ile
                165                 170                 175

Asp Lys Glu Pro Gly Tyr Met Tyr Ser Glu Asp Phe Asn Lys Glu His
                180                 185                 190

Tyr Glu Lys Met Leu Phe Gly Asp Glu Pro Phe Thr Leu Asp Asp Gly
                195                 200                 205

Ser Lys Ile Glu Thr Phe Lys Gln Tyr Glu Glu Gln Ser Gly Gly
    210                 215                 220

Ser Tyr Thr Val Asp Gly Thr Val Thr Lys Trp Leu Thr Val Pro Gly
225                 230                 235                 240

Lys Ala Ala Asp Tyr Gly Ala Asp Ala Thr Gly His Asp Asn Lys
                245                 250                 255

Gly Pro Lys Gly Pro Arg Asp Leu Val Lys Asp Ala Leu Lys Ala Ala
                260                 265                 270

Val Asp Ser Gly Leu Asp Leu Ser Glu Phe Asp Gln Phe Asp Gln Tyr
                275                 280                 285

Asp Val Asn Gly Asp Gly Asn Lys Asn Gln Pro Asp Gly Leu Ile Asp
                290                 295                 300

His Leu Met Ile Ile His Ala Gly Val Gly Gln Glu Ala Gly Gly Gly
305                 310                 315                 320

Lys Leu Gly Asp Asp Ala Ile Trp Ser His Arg Trp Thr Val Gly Pro
                325                 330                 335

Lys Pro Phe Pro Ile Glu Gly Thr Gln Ala Lys Val Pro Tyr Trp Gly
                340                 345                 350

Gly Lys Met Ala Ala Phe Asp Tyr Thr Ile Glu Pro Glu Asp Gly Ala
                355                 360                 365

Val Gly Val Phe Ala His Glu Tyr Gly His Asp Leu Gly Leu Pro Asp
                370                 375                 380

Glu Tyr Asp Thr Gln Tyr Ser Gly His Gly Glu Pro Val Gln Ala Trp
385                 390                 395                 400

Ser Ile Met Ser Gly Gly Ser Trp Ala Gly Lys Ile Ala Gly Thr Thr
                405                 410                 415

Pro Thr Ser Phe Ser Pro Gln Asn Lys Glu Phe Phe Gln Lys Thr Ile
                420                 425                 430

Gly Gly Asn Trp Ala Asn Ile Val Glu Val Asp Tyr Glu Lys Leu Asn
                435                 440                 445

Lys Gly Ile Gly Leu Ala Thr Tyr Leu Asp Gln Ser Val Thr Lys Thr
    450                 455                 460

Asn Arg Pro Gly Met Ile Arg Val Asn Leu Pro Asp Lys Asp Ile Lys
465                 470                 475                 480

Thr Ile Asp Pro Ala Phe Gly Lys Gln Tyr Tyr Ser Thr Lys Gly
                485                 490                 495

Asp Asp Leu His Thr Lys Leu Glu Thr Pro Leu Phe Asp Leu Thr Asn
                500                 505                 510

Ala Thr Thr Ala Lys Phe Asp Phe Lys Ser Leu Tyr Glu Ile Glu Ala
                515                 520                 525

Glu Tyr Asp Phe Leu Glu Val His Ala Val Thr Glu Asp Gly Gln Gln
                530                 535                 540

Thr Leu Ile Glu Arg Leu Gly Glu Lys Ala Asn Asn Gly Asn Ala Asp
545                 550                 555                 560
```

```
Ser Thr Asn Gly Lys Trp Ile Asp Lys Ser Tyr Asp Leu Ser Gln Phe
                565                 570                 575
Lys Gly Lys Lys Val Lys Leu Thr Phe Asp Tyr Ile Thr Asp Gly Gly
            580                 585                 590
Leu Ala Leu Asn Gly Phe Leu Leu Asp Asn Ala Ser Leu Thr Val Asp
        595                 600                 605
Gly Lys Val Val Phe Ser Asp Asp Ala Glu Gly Thr Pro Gln Phe Lys
    610                 615                 620
Leu Asp Gly Phe Ala Val Ser Asn Gly Thr Glu Lys Lys Ser His Asn
625                 630                 635                 640
Tyr Tyr Val Glu Trp Arg Asn Tyr Ala Gly Ser Asp Asn Ala Leu Lys
                645                 650                 655
Phe Ala Arg Gly Pro Glu Tyr Asn Thr Gly Met Val Val Trp Tyr Ala
            660                 665                 670
Asp Ser Ala Tyr Thr Asp Asn Trp Val Gly Val His Pro Gly His Gly
        675                 680                 685
Phe Leu Gly Val Val Asp Ser His Pro Glu Ala Ile Val Gly Thr Leu
    690                 695                 700
Asn Gly Lys Pro Thr Val Glu Ser Ser Thr Arg Phe Gln Ile Ala Asp
705                 710                 715                 720
Ala Ala Phe Ser Phe Asp Lys Thr Pro Ala Trp Lys Val Val Ser Pro
                725                 730                 735
Thr Arg Gly Thr Tyr Thr Tyr Asn Gly Leu Ala Gly Val Pro Lys Phe
            740                 745                 750
Asp Asp Ser Lys Thr Tyr Ile Asn Gln Gln Ile Pro Asp Ala Gly Arg
        755                 760                 765
Ile Leu Pro Asn Leu Gly Leu Lys Phe Glu Val Val Gly Gln Ala Asp
    770                 775                 780
Asp Asn Ser Ala Gly Ala Val Arg Leu Tyr Arg
785                 790                 795

<210> SEQ ID NO 18
<211> LENGTH: 370
<212> TYPE: PRT
<213> ORGANISM: Artificial Sequence
<220> FEATURE:
<223> OTHER INFORMATION: Synthetic

<400> SEQUENCE: 18

Met Asn Lys Lys Pro Phe Lys Val Leu Ser Ser Ile Ala Leu Thr Ala
1               5                   10                  15
Val Leu Gly Leu Ser Phe Gly Ala Gly Gly Gln Ser Val Tyr Ala Glu
            20                  25                  30
Thr Pro Val Asn Lys Thr Ala Thr Ser Pro Val Asp Asp His Leu Ile
        35                  40                  45
Pro Glu Glu Arg Leu Ala Asp Ala Leu Lys Lys Arg Gly Val Ile Asp
    50                  55                  60
Ser Lys Ala Ser Glu Lys Thr Lys Ala Val Glu Lys Tyr Val
65                  70                  75                  80
Glu Asn Lys Lys Gly Glu Asn Pro Gly Lys Glu Val Thr Asn Gly Asp
                85                  90                  95
Pro Leu Thr Lys Glu Ala Ser Asp Phe Val Lys Val Lys Asp Ala
            100                 105                 110
Lys Ala Asp Thr Lys Glu Lys Leu Asp Lys Pro Ala Thr Gly Thr Pro
        115                 120                 125
```

Ala Ala Thr Gly Pro Val Arg Gly Gly Leu Asn Gly Lys Val Pro Thr
         130                 135                 140

Ser Pro Ala Lys Gln Lys Ala Tyr Asn Gly Asp Val Arg Lys Asp Lys
145                 150                 155                 160

Val Leu Val Leu Leu Val Glu Tyr Ala Asp Phe Lys His Asn Asn Ile
                165                 170                 175

Asp Lys Glu Pro Gly Tyr Met Tyr Ser Glu Asp Phe Asn Lys Glu His
            180                 185                 190

Tyr Glu Lys Met Leu Phe Gly Asp Glu Pro Phe Thr Leu Asp Asp Gly
        195                 200                 205

Ser Lys Ile Glu Thr Phe Lys Gln Tyr Glu Glu Gln Ser Gly Gly
    210                 215                 220

Ser Tyr Thr Val Asp Gly Thr Val Thr Lys Trp Leu Thr Val Pro Gly
225                 230                 235                 240

Lys Ala Ala Asp Tyr Gly Ala Asp Ala Ala Thr Gly His Asp Asn Lys
                245                 250                 255

Gly Pro Lys Gly Pro Arg Asp Leu Val Lys Asp Ala Leu Lys Ala Ala
            260                 265                 270

Val Asp Ser Gly Leu Asp Leu Ser Glu Phe Asp Gln Phe Asp Gln Tyr
        275                 280                 285

Asp Val Asn Gly Asp Gly Asn Lys Asn Gln Pro Asp Gly Leu Ile Asp
    290                 295                 300

His Leu Met Ile Ile His Ala Gly Val Gly Gln Ala Gly Gly Gly
305                 310                 315                 320

Lys Leu Gly Asp Asp Ala Ile Trp Ser His Arg Trp Thr Val Gly Pro
                325                 330                 335

Lys Pro Phe Pro Ile Glu Gly Thr Gln Ala Lys Val Pro Tyr Trp Gly
            340                 345                 350

Gly Lys Met Ile Arg Ile Arg Phe Pro Gln Ile Ser Asp His Ile Asn
        355                 360                 365

Asn Pro
    370

<210> SEQ ID NO 19
<211> LENGTH: 93
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (1)..(93)

<400> SEQUENCE: 19 ggt gga aag att cga att cgc ttc ccc cag atc tcc gat cat atc aat      48
Gly Gly Lys Ile Arg Ile Arg Phe Pro Gln Ile Ser Asp His Ile Asn
1               5                   10                  15 aac cct taa tat aac ttc gta taa tgt atg cta tac gaa ctt att         93
Asn Pro     Tyr Asn Phe Val     Cys Met Leu Tyr Glu Leu Ile
                    20                  25

<210> SEQ ID NO 20
<211> LENGTH: 18
<212> TYPE: PRT
<213> ORGANISM: Artificial Sequence
<220> FEATURE:
<223> OTHER INFORMATION: Synthetic

<400> SEQUENCE: 20

```
Gly Gly Lys Ile Arg Ile Arg Phe Pro Gln Ile Ser Asp His Ile Asn
1               5                   10                  15

Asn Pro

<210> SEQ ID NO 21
<211> LENGTH: 175
<212> TYPE: PRT
<213> ORGANISM: Bacillus anthracis

<400> SEQUENCE: 21

Met Asn Phe Lys Lys Gly Ile Thr Ala Phe Leu Leu Gly Thr Val Phe
1               5                   10                  15

Val Phe Ser Ser Val Gly Val Ser Glu Ala Tyr Val Lys Glu Gly Trp
            20                  25                  30

Lys Leu Pro Ser Lys Ser Ala Thr Tyr Lys Trp Gly Asp Arg Leu Asp
        35                  40                  45

Asp Gly Ser Ser Ile Ile Lys Ser Gly Trp Gln Ala Ala Asp Ser Ala
    50                  55                  60

Trp Tyr Thr Ala Ser Arg Ile Asn Phe Thr Val Ser Ala Ser Ser Val
65                  70                  75                  80

Asn Thr Leu Asn Ser Trp Phe Glu Ser Ser Thr Tyr Tyr Gly Arg
                85                  90                  95

Met Lys Ser Tyr Asn Thr Ser Thr Lys Lys Val Thr Lys Phe Ala
            100                 105                 110

Gly Asp Ile Asn Ala Gly Asn Thr Asn Ile Thr Lys Ser Asn Val Ala
        115                 120                 125

Lys Ser Thr Gly Val His Glu Phe Gly His Ala Ile Gly Ile Gly His
    130                 135                 140

Asn Ser Gly Thr Ser Ile Met Asn Ser Asn Arg Asn Arg Thr Thr Met
145                 150                 155                 160

His Val Pro Gln Thr Asp Asp Lys Asn Gly Val Asn Ala Ile Tyr
                165                 170                 175

<210> SEQ ID NO 22
<211> LENGTH: 31
<212> TYPE: PRT
<213> ORGANISM: Artificial Sequence
<220> FEATURE:
<223> OTHER INFORMATION: Synthetic

<400> SEQUENCE: 22

Met Asn Phe Lys Lys Gly Ile Thr Ala Phe Leu Leu Gly Thr Val Phe
1               5                   10                  15

Val Phe Ser Leu Val Leu Glu Arg Pro Pro Pro Arg Trp Ser Ser
            20                  25                  30

<210> SEQ ID NO 23
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (1)..(96)

<400> SEQUENCE: 23 gtt ttt tca cta gtt cta gag cgg ccg cca ccg cgg tgg agc tca taa     48
Val Phe Ser Leu Val Leu Glu Arg Pro Pro Pro Arg Trp Ser Ser
1               5                   10                  15
```

```
ctt cgt ata atg tat gct ata cga agt tat cag ctg ctc gag ggt tgg      96
Leu Arg Ile Met Tyr Ala Ile Arg Ser Tyr Gln Leu Leu Glu Gly Trp
         20                  25                  30

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Val Phe Ser Leu Val Leu Glu Arg Pro Pro Arg Trp Ser Ser
1               5                  10                  15

<210> SEQ ID NO 25
<211> LENGTH: 67
<212> TYPE: PRT
<213> ORGANISM: Artificial Sequence
<220> FEATURE:
<223> OTHER INFORMATION: Synthetic

<400> SEQUENCE: 25

Met Thr Leu Lys Lys Leu Gly Met Gly Ile Ala Ser Ala Val Leu
1               5                  10                  15

Gly Ala Ala Leu Val Gly Gly Gly Thr Phe Ala Phe Phe Ser Asp Lys
                20                  25                  30

Glu Val Ser Asn Asn Thr Phe Ala Thr Gly Thr Leu Asp Leu Ala Leu
            35                  40                  45

Asn Pro Ser Thr Val Val Asn Val Ser Asn Leu Lys Pro Gly Pro Gly
        50                  55                  60

Ser Asn His
65

<210> SEQ ID NO 26
<211> LENGTH: 120
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (1)..(120)

<400> SEQUENCE: 26 aaa cct ggc ccg ggc agt aat cac tag ttc tag agc ggc cgc cac cgc      48
Lys Pro Gly Pro Gly Ser Asn His     Phe     Ser Gly Arg His Arg
1               5                              10 ggt gga gct cat aac ttc gta taa tgt atg cta tac gaa gtt att agg      96
Gly Gly Ala His Asn Phe Val     Cys Met Leu Tyr Glu Val Ile Arg
15                  20                      25 tcc ctc gaa ggt tca cta gta ctg                                     120
Ser Leu Glu Gly Ser Leu Val Leu
30                  35

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Lys Pro Gly Pro Gly Ser Asn His
```

<210> SEQ ID NO 28
<211> LENGTH: 386
<212> TYPE: PRT
<213> ORGANISM: Bacillus anthracis

<400> SEQUENCE: 28

```
Met Gly Lys Thr Ser Lys Tyr Val Thr Ala Ala Leu Cys Ser Thr
 1               5                  10                  15

Ile Val Met Gly Gly Leu His Ala Ser Ser Val Ser Tyr Ala Ala Thr
                20                  25                  30

Asn Pro Thr Val Ala Thr Leu Gln Ser Asp Ala Lys Leu Leu Asn Asp
                35                  40                  45

Phe Lys Lys Glu Leu Lys Lys Gln Ile Asp Asn Arg Glu Glu Asn Ile
 50                  55                  60

Thr Ile Thr Tyr Lys Thr Lys Asp Arg Asn Ala Arg Asn Ile Met Asp
 65                  70                  75                  80

Glu Leu Tyr Gly Glu Phe Asn Lys Ile Val Asp Ala Asp Glu Tyr Val
                85                  90                  95

Lys Tyr Asn Ile Ala Ser Thr Arg Tyr Ser Ile Lys Gly Leu Pro Gly
                100                 105                 110

Asn Tyr Thr Phe Thr Leu Gln Val Lys Tyr Arg Glu Ser Lys Glu Gln
                115                 120                 125

Thr Gln Tyr Val Lys Ser Gln Ala Lys Ala Ile Ile Gly Ser Ile Val
 130                 135                 140

Lys Pro Gly Met Asp Glu His Glu Lys Val Lys Ala Ile His Asp Tyr
 145                 150                 155                 160

Val Val Lys His Val Ser Tyr Asp Thr Ser Tyr Gln Ala Tyr Thr Ala
                165                 170                 175

Tyr Glu Ala Leu Ala Asn Arg Ser Ala Val Cys Gln Gly Tyr Thr Leu
                180                 185                 190

Leu Thr Tyr Glu Leu Leu Lys Glu Ala Gly Ile Gln Asn Arg Ile Val
                195                 200                 205

Thr Gly Thr Gly Asn Gly Gln Ala His Ser Trp Asn Leu Val Asn Ile
 210                 215                 220

Glu Asn Lys Trp Tyr His Leu Asp Thr Thr Phe Asp Asp Pro Val Pro
 225                 230                 235                 240

Asp Lys Ala Gly Arg Val Thr Tyr Ser Tyr Phe Asn Met Ser Asp Glu
                245                 250                 255

Gln Leu Ser Lys Asp His Asp Trp Asp Arg Ser Lys Tyr Pro Ala Ala
                260                 265                 270

Thr Thr Ser Tyr Phe Asn Glu Leu Thr Asn Lys Ile Lys Ala Gly Ser
                275                 280                 285

Ser Lys Thr Ala Thr Tyr Glu Gln Met Leu Lys Glu Thr Asn Leu Lys
 290                 295                 300

Tyr Leu Ser Ala Gln Tyr Gly Ala Asp Asn Tyr Ser Glu Phe Lys Glu
 305                 310                 315                 320

Lys Leu Gln Gln Gln Phe Ala Ser Lys Pro Glu Lys Val Glu Val Arg
                325                 330                 335

Tyr Lys Gln Ser Met Asp Gly Thr Met Gln Asp Ile Lys Lys Val Leu
                340                 345                 350

Asn Glu Ile Asn Trp Pro Lys Gly Ala Lys Arg Val Ser Tyr Gln Val
                355                 360                 365
```

```
Ala Pro Tyr Ser Ala Met Ala Asp Tyr Ser Leu Ala Thr Ile Thr Phe
    370                 375                 380

Thr Tyr
385

<210> SEQ ID NO 29
<211> LENGTH: 917
<212> TYPE: PRT
<213> ORGANISM: Bacillus anthracis

<400> SEQUENCE: 29

Met Lys Lys Thr Thr Ser Ile Leu Leu Ser Met Ala Leu Val Phe Ser
1               5                   10                  15

Ser Phe Gly Ala Leu Ser Ala His Ala Glu Ser Leu Gln Lys Glu Lys
            20                  25                  30

Gln Phe Ser Pro Gln Leu Lys Thr Thr Ile Glu Gln Trp Gly Glu Ser
        35                  40                  45

Lys Ile Ala Gln His Val Glu Thr Lys Thr Thr Lys Glu Ile Ser Val
50                  55                  60

Ile Val Glu Leu Gln His Ala Pro Leu Ala Ala Gln Ser Asn Ile Gln
65                  70                  75                  80

His Ala Pro Asp Leu Gln Asn Ser His Ala Gln Ser Tyr His Thr Glu
                85                  90                  95

Leu Lys Lys Ala Gln Glu Glu Thr Thr Lys Lys Ile Lys Glu Lys Ala
            100                 105                 110

Pro Gly Ala Lys Ile Lys Glu Val Tyr Asn Thr Leu Phe Ser Gly Phe
        115                 120                 125

Ser Ile Ser Val Pro Gly Asp Gln Ile Thr Ala Leu Ala Ser Leu Pro
130                 135                 140

Glu Val Lys Thr Val Tyr Pro Asn Leu Thr Tyr Lys Leu His Glu Thr
145                 150                 155                 160

Thr Lys Ser Ala Thr Ser Glu Glu Ala Pro Asn Ile Gly Gly Pro Thr
                165                 170                 175

Ile Gly Ala Pro Glu Ala Trp Asn Leu Lys Asp Pro Ser Gly Lys Ser
            180                 185                 190

Leu Asp Gly Lys Gly Met Lys Val Ala Ile Ile Asp Ser Gly Val Asp
        195                 200                 205

Tyr Thr His Pro Asp Leu Lys Ala Asn Tyr Ile Gly Gly Tyr Asp Thr
210                 215                 220

Val Asp Glu Asp Ala Asp Pro Met Asp Gly Asn Val His Gly Thr His
225                 230                 235                 240

Val Ala Gly Ile Ile Ala Gly Asn Gly Lys Ile Lys Gly Val Ala Pro
                245                 250                 255

Asn Ala Ser Ile Leu Ala Tyr Arg Val Met Asn Asp Gly Gly Thr Gly
            260                 265                 270

Thr Thr Asp Asp Ile Ile Gln Gly Ile Glu Arg Ala Ile Gln Asp Gly
        275                 280                 285

Ala Asp Val Leu Asn Leu Ser Leu Gly Gln Asp Leu Asn Val Pro Asp
290                 295                 300

Gln Pro Val Thr Leu Thr Leu Glu Arg Ala Ala Lys Leu Gly Ile Thr
305                 310                 315                 320

Ala Val Val Ser Asn Gly Asn Asp Gly Pro Lys Pro Trp Ser Val Asp
                325                 330                 335

Ala Pro Gly Asn Ala Ser Ser Val Ile Ser Val Gly Ala Ser Thr Val
            340                 345                 350
```

```
Ser Ile Pro Phe Pro Thr Phe Gln Val Ala Gly Ser Ser Lys Thr Tyr
        355                 360                 365

Gln Gly Leu Ser Leu Ser Lys Ser Asp Phe Pro Ile Gly Asn Asp Ser
    370                 375                 380

Pro Leu Val Tyr Val Gly Tyr Gly Asn Pro Ser Asp Tyr Ala Lys Gln
385                 390                 395                 400

Asp Val Lys Gly Lys Phe Ala Leu Val Leu Gln Gly Thr Ser Ser Thr
                405                 410                 415

Leu Val Lys Ala Glu Gln Ala Lys Gln Ala Gly Ala Ile Gly Val Leu
            420                 425                 430

Phe Ile Ser Thr Glu Lys Glu Met Asn Ser Met Pro Glu Tyr Phe Thr
        435                 440                 445

Arg Glu Asn Leu Ala Leu Pro Val Met Gln Leu Ser Asn Val Asn Gly
    450                 455                 460

Glu Glu Leu Lys Asn Leu Ile Thr Lys Arg Lys Asn Ile Lys Ile
465                 470                 475                 480

Gly Gln Pro Val Pro Thr Glu Leu Ile Gly Asn Phe Ser Ser Arg Gly
                485                 490                 495

Pro Ser Gln Gly Ser Trp Leu Ile Lys Pro Asp Ile Val Ala Pro Gly
            500                 505                 510

Val Gln Ile Thr Ser Thr Val Pro Arg Gly Gly Tyr Glu Ser His Asn
        515                 520                 525

Gly Thr Ser Met Ala Ala Pro Gln Val Ala Gly Ala Val Ala Leu Leu
    530                 535                 540

Arg Gln Met His Pro Asp Trp Thr Thr Gln Leu Lys Ala Ser Leu
545                 550                 555                 560

Ala Asn Thr Ala Lys Thr Leu Lys Asp Val Asn Glu Asn Thr Tyr Pro
                565                 570                 575

Ile Met Thr Gln Gly Ser Gly Leu Ile Asn Ile Pro Lys Ala Ala Gln
            580                 585                 590

Thr Asp Val Leu Val Lys Pro Asn Asn Val Ser Phe Gly Leu Ile Lys
        595                 600                 605

Pro Asn Ser Gly Lys Val Lys Leu Thr Gln Asn Ile Thr Leu Gln Asn
    610                 615                 620

Leu Ser Ser Lys Lys Lys Ser Phe Ser Thr Arg Val Glu Leu Leu Asp
625                 630                 635                 640

Thr Asn Thr Lys Thr Lys Val Lys Thr Ser Val Pro Ser Ser Ile Ser
                645                 650                 655

Ile Gln Pro Asn Ser Ser Thr Glu Lys Pro Phe Thr Ile Thr Val Asp
            660                 665                 670

Ser Ser Leu Pro Gln Gly Val Tyr Thr Gly Asn Val Tyr Val Lys Glu
        675                 680                 685

Gln Gly Ala Lys Glu Glu Thr Arg Ile Pro Phe Thr Phe Ser Ile Asp
    690                 695                 700

Pro Lys Asp Tyr Lys Arg Ile Asp Gly Leu Glu Ile Ile Asn Ser Thr
705                 710                 715                 720

Phe Ser Pro Asn Gly Asp Gln Ile Leu Asp Asp Asn Leu Ile Asn Tyr
                725                 730                 735

Tyr Leu Val Ala Pro Val Asp Asp Val Thr Leu His Ala Asn Leu Val
            740                 745                 750

Thr Lys Glu Arg Val Thr Tyr Gln Gly Ile Ile His Gln Ala Lys Asn
        755                 760                 765
```

-continued

```
Glu Thr Ala Gly Tyr Lys Pro Phe Lys Trp Asp Gly Thr Lys Ala Asp
770                 775                 780
Gly Thr Pro Leu Ala Asp Gly Leu Tyr Gln Ile Glu Ala Val Ala Ser
785                 790                 795                 800
Asn Ser Gly Gly Glu Thr Lys Gln Thr Ala Ala Val Phe Leu Asp Arg
                805                 810                 815
Thr Ala Pro Lys Leu Thr Tyr Glu Ile Asp Gln Glu Asn Leu Val Ile
            820                 825                 830
Thr Gly Lys Val Asp Asp Ile Leu Leu Asp Trp Met Thr Glu Ser Gly
        835                 840                 845
Trp Val Ala Pro Gly Ile Pro Val Arg Leu Gln Tyr Glu Ile Asn Gly
850                 855                 860
Asn Gly Val Trp Glu Ser Ala Phe Leu Asn Pro Trp Glu Lys Asn Tyr
865                 870                 875                 880
Gly Ile Tyr Leu Asp Arg Thr Gln Leu Gln Glu Gly Lys Asn Thr Ile
                885                 890                 895
His Ile Val Ala Thr Ala Ala Gly Asn Thr Ser Asn Leu Asn Val
            900                 905                 910
Asp Leu Asp Val Lys
            915

<210> SEQ ID NO 30
<211> LENGTH: 469
<212> TYPE: PRT
<213> ORGANISM: Bacillus anthracis

<400> SEQUENCE: 30

Met Val Val Ala Phe Leu Ile Gly Ala Gly Met Phe Ala Gly Met
1               5                   10                  15
Ser Leu Phe Gly Val Asn Pro Ala Glu Val Thr Gln Thr Ile Ser Ser
            20                  25                  30
Gly Asn Ala Ser Thr Ala Gln Gly Asn Leu Ala Lys Ile Asn Glu Ala
        35                  40                  45
Tyr Ala Leu Ile Asp Ser Arg Tyr Val Glu Asp Val Lys Asp Glu Lys
    50                  55                  60
Leu Val Glu Gly Ala Ile Gln Gly Met Leu Ser Thr Leu Lys Asp Pro
65                  70                  75                  80
Tyr Ser Thr Tyr Met Asp Lys Glu Thr Ala Lys Gln Phe Ser Glu Ser
                85                  90                  95
Leu Asp Pro Glu Leu Glu Gly Ile Gly Ala Glu Val Asn Lys Thr Asp
            100                 105                 110
Gly Lys Leu Ile Ile Val Ser Pro Ile Lys Gly Ser Pro Ala Glu Lys
        115                 120                 125
Ile Gly Ile Lys Pro Asn Asp Gln Ile Leu Ser Val Asp Gly Asn Ser
    130                 135                 140
Val Lys Asp Leu Ser Arg Glu Glu Ala Val Leu Lys Ile Arg Gly Lys
145                 150                 155                 160
Lys Gly Thr Thr Val Ala Ile Glu Ile Lys Arg Ala Gly Val Ala Asp
                165                 170                 175
Pro Ile Val Phe Lys Ile Lys Arg Glu Lys Ile Pro Ile Phe Thr Val
            180                 185                 190
Phe Ser Ser Val Lys Gln Glu Ser Gly Lys Asp Ile Gly Tyr Met Gln
        195                 200                 205
Ile Thr Ser Phe Ala Glu Asn Thr Ala Lys Glu Phe Lys Asp Gln Leu
    210                 215                 220
```

```
Lys Glu Leu Glu Lys Lys Asn Ile Lys Gly Leu Val Ile Asp Val Arg
225                 230                 235                 240

Gly Asn Pro Gly Gly Tyr Leu Asn Ser Val Glu Glu Ile Leu Gly Glu
            245                 250                 255

Ile Met Thr Asp Lys Lys Pro Met Leu Gln Val Glu Gln Arg Asn Gly
                260                 265                 270

Glu Lys Lys Lys Phe Ser Thr Glu Leu Lys Glu Arg Lys Pro Tyr Pro
            275                 280                 285

Ile Ser Val Leu Ile Asp Asn Gly Ser Ala Ser Ala Ser Glu Ile Leu
            290                 295                 300

Ala Gly Ala Leu Lys Glu Gly Glu Gly Tyr Asp Leu Ile Gly Glu Lys
305                 310                 315                 320

Thr Phe Gly Lys Gly Thr Val Gln Gln Ala Val Pro Phe Lys Asp Gly
                325                 330                 335

Ser Asn Ile Lys Leu Thr Met Phe Lys Trp Leu Thr Pro Asp Gly Asn
                340                 345                 350

Trp Ile His Lys Lys Gly Ile Lys Pro Thr Val Glu Val Lys Gln Pro
            355                 360                 365

Asp Tyr Tyr His Ala Thr Pro Ile Gln Ile Glu Lys Thr Leu Ser Tyr
370                 375                 380

Asn Ala Asn Asp Val Gln Val Lys His Ala Gln Glu Met Leu Lys Ser
385                 390                 395                 400

Leu Gly Tyr Val Pro Gly Arg Glu Asp Gly Tyr Phe Ser Lys Glu Thr
                405                 410                 415

Glu Ser Ala Leu Lys Ala Phe Gln Asn Ala Asn Lys Met Glu Ala Thr
            420                 425                 430

Gly Gln Leu Asp Lys Lys Thr Ala Glu Ala Ile Gln Thr Lys Ile Ile
            435                 440                 445

Glu Lys Ile Arg Ser Gly Glu Asn Asp Leu Gln Leu Gln Ser Ala Leu
            450                 455                 460

Lys Leu Met Ala Lys
465

<210> SEQ ID NO 31
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid

<400> SEQUENCE: 31

His Glu Xaa Xaa His
1               5

<210> SEQ ID NO 32
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
```

```
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa at position 8 = Gly or Asn
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa at position 8 = His or Asp

<400> SEQUENCE: 32

His Glu Xaa Xaa His Xaa Xaa Xaa Xaa Xaa Xaa
1               5                   10

<210> SEQ ID NO 33
<211> LENGTH: 20
<212> TYPE: PRT
<213> ORGANISM: Bacillus anthracis

<400> SEQUENCE: 33

Ile Met Ser Gly Gly Ser Trp Ala Gly Lys Ile Ala Gly Thr Thr Pro
1               5                   10                  15

Thr Ser Phe Ser
            20

<210> SEQ ID NO 34
<211> LENGTH: 29
<212> TYPE: DNA
<213> ORGANISM: Artificial Sequence
<220> FEATURE:
<223> OTHER INFORMATION: Synthetic

<400> SEQUENCE: 34
gctcgagcgg atgtacatct gtaatgagt                                   29

<210> SEQ ID NO 35
<211> LENGTH: 27
<212> TYPE: DNA
<213> ORGANISM: Artificial Sequence
<220> FEATURE:
<223> OTHER INFORMATION: Synthetic

<400> SEQUENCE: 35
ggatatcttg aacgatgtga ccaaatg                                     27

<210> SEQ ID NO 36
<211> LENGTH: 27
<212> TYPE: DNA
<213> ORGANISM: Artificial Sequence
<220> FEATURE:
<223> OTHER INFORMATION: Synthetic

<400> SEQUENCE: 36
gcccgggcct gtcgaagctt ggtcatt                                     27

<210> SEQ ID NO 37
<211> LENGTH: 27
<212> TYPE: DNA
<213> ORGANISM: Artificial Sequence
<220> FEATURE:
<223> OTHER INFORMATION: Synthetic

<400> SEQUENCE: 37
```

-continued gccgcggttt gcatacctgt gttaccg                                               27

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
ggtcaagaag ctggtggagg ta                                                    22

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
tctgttcctg caattttccc                                                       20

<210> SEQ ID NO 40
<211> LENGTH: 27
<212> TYPE: DNA
<213> ORGANISM: Artificial Sequence
<220> FEATURE:
<223> OTHER INFORMATION: Synthetic

<400> SEQUENCE: 40
gctcgagtaa tttggaaggt gattagc                                               27

<210> SEQ ID NO 41
<211> LENGTH: 29
<212> TYPE: DNA
<213> ORGANISM: Artificial Sequence
<220> FEATURE:
<223> OTHER INFORMATION: Synthetic

<400> SEQUENCE: 41
gcccgggttc acatcttcta cattgtaat                                             29

<210> SEQ ID NO 42
<211> LENGTH: 29
<212> TYPE: DNA
<213> ORGANISM: Artificial Sequence
<220> FEATURE:
<223> OTHER INFORMATION: Synthetic

<400> SEQUENCE: 42
gactagtaac aatcgtaaaa gaaacagcg                                             29

<210> SEQ ID NO 43
<211> LENGTH: 27
<212> TYPE: DNA
<213> ORGANISM: Artificial Sequence
<220> FEATURE:
<223> OTHER INFORMATION: Synthetic

<400> SEQUENCE: 43
ggagctctat cgatcgcctg taaattc                                               27

<210> SEQ ID NO 44
<211> LENGTH: 20
<212> TYPE: DNA

```
<213> ORGANISM: Artificial Sequence
<220> FEATURE:
<223> OTHER INFORMATION: Synthetic

<400> SEQUENCE: 44
ggggatatgg acatgacttt                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
cagtaagtgt gtcacccttc                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
gagaagatag ctgctgagag                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
tagagggagt ttaatgggga                                              20

<210> SEQ ID NO 48
<211> LENGTH: 18
<212> TYPE: DNA
<213> ORGANISM: Artificial Sequence
<220> FEATURE:
<223> OTHER INFORMATION: Synthetic

<400> SEQUENCE: 48
gaaattgcgc aaaaagat                                                18

<210> SEQ ID NO 49
<211> LENGTH: 18
<212> TYPE: DNA
<213> ORGANISM: Artificial Sequence
<220> FEATURE:
<223> OTHER INFORMATION: Synthetic

<400> SEQUENCE: 49
agagccattc cagaacgc                                                18

<210> SEQ ID NO 50
<211> LENGTH: 30
<212> TYPE: DNA
<213> ORGANISM: Artificial Sequence
<220> FEATURE:
<223> OTHER INFORMATION: Synthetic

<400> SEQUENCE: 50
gctcgagggg taataacttt caattaatac                                   30
```

```
<210> SEQ ID NO 51
<211> LENGTH: 27
<212> TYPE: DNA
<213> ORGANISM: Artificial Sequence
<220> FEATURE:
<223> OTHER INFORMATION: Synthetic

<400> SEQUENCE: 51
ggatatcgaa aaacaaaca cagtacc                                              27

<210> SEQ ID NO 52
<211> LENGTH: 27
<212> TYPE: DNA
<213> ORGANISM: Artificial Sequence
<220> FEATURE:
<223> OTHER INFORMATION: Synthetic

<400> SEQUENCE: 52
gcccgggggt tggcaagctg ccgattc                                             27

<210> SEQ ID NO 53
<211> LENGTH: 27
<212> TYPE: DNA
<213> ORGANISM: Artificial Sequence
<220> FEATURE:
<223> OTHER INFORMATION: Synthetic

<400> SEQUENCE: 53
gccgcggcga atggttcaat tgctccg                                             27

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
ggtactgtgt ttgtttttc                                                      20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
gaatcggcag cttgccaacc                                                     20

<210> SEQ ID NO 56
<211> LENGTH: 29
<212> TYPE: DNA
<213> ORGANISM: Artificial Sequence
<220> FEATURE:
<223> OTHER INFORMATION: Synthetic

<400> SEQUENCE: 56
cctcgagttt cattttgaa gtcttcttc                                            29

<210> SEQ ID NO 57
<211> LENGTH: 29
<212> TYPE: DNA
<213> ORGANISM: Artificial Sequence
<220> FEATURE:
```

<223> OTHER INFORMATION: Synthetic

<400> SEQUENCE: 57
cactagtcag cgaaacgatg attgatttt                                29

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
tccgattagg aagttgacaa                                          20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
cagttaccac caattgtttt                                          20

<210> SEQ ID NO 60
<211> LENGTH: 35
<212> TYPE: DNA
<213> ORGANISM: Artificial Sequence
<220> FEATURE:
<223> OTHER INFORMATION: Synthetic

<400> SEQUENCE: 60
cctcgagttt tcttattgca tttctaatgt gttcg                         35

<210> SEQ ID NO 61
<211> LENGTH: 27
<212> TYPE: DNA
<213> ORGANISM: Artificial Sequence
<220> FEATURE:
<223> OTHER INFORMATION: Synthetic

<400> SEQUENCE: 61
cccgcggtta gcgatataag cgaacag                                  27

<210> SEQ ID NO 62
<211> LENGTH: 8997
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (3659)..(6049)

<400> SEQUENCE: 62
caggagaaca aaaacgattt tttgaggaaa gttataaatt attttccgaa cgatatggca      60
agcaaaatat tgcttatgca acagttcata atgatgagca aaccccctcac atgcatttag    120 gtgttgtgcc tatgcgtgat ggaaaactgc aaggaaaaaa tgtgtttaat cgtcaagaac    180
tgttatggct acaagataaa ttccccgagc atatgaaaaa acagggtttt gagttgaagc    240
gtggtgaacg tggctctgac cgtaaacata ttgagacagc taaatttaaa aaacaaactt    300
tggaaaaaga gattgatttt ctagaaaaaa atttagcagt taaaaaagat gaatggactg    360

```
cttatagcga taaagttaaa tcagatttag aagtaccagc gaaacgacac atgaaaagtg    420
ttgaagtgcc aacgggtgaa aagtccatgt ttggtttggg aaaagaaata atgaaaacag    480 aaagaaacc  aaccaaaaat gttgttatat cggagcgtga ttataaaaac ttagtgactg    540
ctgcgagaga taacgatagg ttaaaacagc atgttagaaa tctcatgagt actgatatgg    600
cgagagaata taaaaaatta agtaaagaac atgggcaagt taaagaaaaa tatagtggtc    660
ttgtagagcg atttaatgaa aatgtaaatg attataatga gttgcttgaa gaaacaagt     720 cttttaaagtc taaaataagc gatttaaagc gtgatgtgag tttaatctat gaaagcacta   780
aggaattcct taaggaacgt acagacggct taaaagcctt taaaaacgtt tttaaggggt    840
ttgtagacaa ggtaaaggat aaaacagcac aattccaaga aaaacacgat ttagaaccta    900
aaaagaacga atttgaacta actcataacc gagaggtaaa aaagaacga agtcgagatc     960 agggaatgag tttataaaat aaaaaagca cctgaaaagg tgtctttttt tgatggtttt    1020
gaacttgttc tttcttatct tgatacatat agaaataacg tcattttttat tttagttgct  1080 gaaaggtgcg ttgaagtgtt ggtatgtatg tgttttaaag tattgaaaac ccttaaaatt   1140
ggttgcacag aaaaccccca tctgttaaag ttataagtga ctaaacaaat aactaaatag   1200
atgggggttt ctttttaatat tatgtgtcct aatagtagca tttattcaga tgaaaaatca  1260
agggttttag tggacaagac aaaaagtgga aaagtgagac catggagaga aagaaaatc    1320 gctaatgttg attactttga acttctgcat attcttgaat ttaaaaggc tgaaagagta    1380 aaagattgtg ctgaaatatt agagtataaa caaaatcgtg aaacaggcga agaaagttg    1440 tatcgagtgt ggttttgtaa atccaggctt tgtccaatgt gcaactggag gagagcaatg   1500
aaacatggca ttcagtcaca aaaggttgtt gctgaagtta ttaaacaaaa gccaacagtt   1560
cgttggttgt ttctcacatt aacagttaaa aatgtttatg atggcgaaga attaaataag   1620
agtttgtcag atatggctca aggatttcgc cgaatgatgc aatataaaaa aattaataaa   1680
aatcttgttg gttttatgcg tgcaacggaa gtgacaataa ataataaaga taattcttat   1740
aatcagcaca tgcatgtatt ggtatgtgtg gaaccaactt attttaagaa tacagaaaac   1800
tacgtgaatc aaaaacaatg gattcaattt tggaaaaagg caatgaaatt agactatgat   1860
ccaaatgtaa aagttcaaat gattcgaccg aaaaataaat ataaatcgga tatacaatcg   1920
gcaattgacg aaactgcaaa atatcctgta aaggatacgg attttatgac cgatgatgaa   1980 gaaagaatt  tgaaacgttt gtctgatttg gaggaaggtt tacaccgtaa aaggttaatc   2040
tcctatggtg gtttgttaaa agaaatacat aaaaaattaa accttgatga cacagaagaa   2100
ggcgatttga ttcatacaga tgatgacgaa aaagccgatg aagatggatt ttctattatt   2160
gcaatgtgga attgggaacg gaaaaattat tttattaaag agtagttcaa caaacgggcc   2220
agtttgttga agattagatg ctataattgt tattaaaagg attgaaggat gcttaggaag   2280
acgagttatt aatagctgaa taagaacggt gctctccaaa tattcttatt tagaaaagca   2340
aatctaaaat tatctgaaaa gggaatgaga atagtgaatg gaccaataat aatgactaga   2400
gaagaaagaa tgaagattgt tcatgaaatt aaggaacgaa tattggataa atatggggat   2460
gatgttaagg ctattggtgt ttatggctct cttggtcgtc agactgatgg gccctattcg   2520
gatattgaga tgatgtgtgt catgtcaaca gaggaagcag agttcagcca tgaatggaca   2580
accggtgagt ggaaggtgga agtgaatttt gatagcgaag agattctact agattatgca   2640
tctcaggtgg aatcagattg gccgcttaca catggtcaat ttttctctat tttgccgatt   2700
tatgattcag gtggatactt agagaaagtg tatcaaactg ctaaatcggt agaagcccaa   2760
```

-continued

```
acgttccacg atgcgatttg tgcccttatc gtagaagagc tgtttgaata tgcaggcaaa    2820
tggcgtaata ttcgtgtgca aggaccgaca acatttctac catccttgac tgtacaggta    2880
gcaatggcag gtgccatgtt gattggtctg catcatcgca tctgttatac gacgagcgct    2940
tcggtcttaa ctgaagcagt taagcaatca gatcttcctt caggttatga ccatctgtgc    3000
cagttcgtaa tgtctggtca actttccgac tctgagaaac ttctggaatc gctagagaat    3060
ttctggaatg ggattcagga gtggacagaa cgacacggat atatagtgga tgtgtcaaaa    3120
cgcataccat tttgaacgat gacctctaat aattgttaat catgttggtt acgtatttat    3180
taacttctcc tagtattagt aattatcatg gctgtcatgg cgcattaacg gaataaaggg    3240
tgtgcttaaa tcgggccatt ttgcgtaata agaaaaagga ttaattatga gcgaattgaa    3300
ttaataataa ggtaatagat ttacattaga aaatgaaagg ggattttatg cgtgagaatg    3360
ttacagtcta tcccggcatt gccagtcggg gatattaaaa agagtatagg ttttattgc    3420 gataaactag gtttcacttt ggttcaccat gaagatggat tcgcagttct aatgtgtaat    3480
gaggttcgga ttcatctatt aaacatataa attcttttt atgttatata tttataaaag    3540
ttctgtttaa aaagccaaaa ataaataatt atctctttt atttatatta tattgaaact    3600
aaagtttatt aatttcaata taatataaat ttaattttat acaaaaagga gaacgtat     3658
```

| | | | | | | | | | | | | | | | | |
|---|---|---|---|---|---|---|---|---|---|---|---|---|---|---|---|---|
| atg | aaa | aaa | cga | aaa | gtg | tta | ata | cca | tta | atg | gca | ttg | tct | acg | ata | 3706 |
| Met | Lys | Lys | Arg | Lys | Val | Leu | Ile | Pro | Leu | Met | Ala | Leu | Ser | Thr | Ile | |
| 1 | | | | 5 | | | | | 10 | | | | | 15 | | |

| tta | gtt | tca | agc | aca | ggt | aat | tta | gag | gtg | att | cag | gca | atg | aat | gaa | 3754 |
|---|---|---|---|---|---|---|---|---|---|---|---|---|---|---|---|---|
| Leu | Val | Ser | Ser | Thr | Gly | Asn | Leu | Glu | Val | Ile | Gln | Ala | Met | Asn | Glu | |
| | | | 20 | | | | | 25 | | | | | 30 | | | |

| cat | tac | act | gag | agt | gat | att | aaa | aga | aac | cat | aaa | act | gaa | aaa | aat | 3802 |
|---|---|---|---|---|---|---|---|---|---|---|---|---|---|---|---|---|
| His | Tyr | Thr | Glu | Ser | Asp | Ile | Lys | Arg | Asn | His | Lys | Thr | Glu | Lys | Asn | |
| | | 35 | | | | | 40 | | | | | 45 | | | | |

| aaa | act | gaa | aaa | gaa | aaa | ttt | aaa | gac | agt | att | aat | aac | tta | gtt | aaa | 3850 |
|---|---|---|---|---|---|---|---|---|---|---|---|---|---|---|---|---|
| Lys | Thr | Glu | Lys | Glu | Lys | Phe | Lys | Asp | Ser | Ile | Asn | Asn | Leu | Val | Lys | |
| 50 | | | | | 55 | | | | | 60 | | | | | | |

| aca | gaa | ttt | acc | aat | gaa | act | tta | gat | aaa | ata | cag | cag | aca | caa | gac | 3898 |
|---|---|---|---|---|---|---|---|---|---|---|---|---|---|---|---|---|
| Thr | Glu | Phe | Thr | Asn | Glu | Thr | Leu | Asp | Lys | Ile | Gln | Gln | Thr | Gln | Asp | |
| 65 | | | | | 70 | | | | | 75 | | | | | 80 | |

| tta | tta | aaa | aag | ata | cct | aag | gat | gta | ctt | gaa | att | tat | agt | gaa | tta | 3946 |
|---|---|---|---|---|---|---|---|---|---|---|---|---|---|---|---|---|
| Leu | Leu | Lys | Lys | Ile | Pro | Lys | Asp | Val | Leu | Glu | Ile | Tyr | Ser | Glu | Leu | |
| | | | | 85 | | | | | 90 | | | | | 95 | | |

| gga | gga | gaa | atc | tat | ttt | aca | gat | ata | gat | tta | gta | gaa | cat | aag | gag | 3994 |
|---|---|---|---|---|---|---|---|---|---|---|---|---|---|---|---|---|
| Gly | Gly | Glu | Ile | Tyr | Phe | Thr | Asp | Ile | Asp | Leu | Val | Glu | His | Lys | Glu | |
| | | | 100 | | | | | 105 | | | | | 110 | | | |

| tta | caa | gat | tta | agt | gaa | gaa | gag | aaa | aat | agt | atg | aat | agt | aga | ggt | 4042 |
|---|---|---|---|---|---|---|---|---|---|---|---|---|---|---|---|---|
| Leu | Gln | Asp | Leu | Ser | Glu | Glu | Glu | Lys | Asn | Ser | Met | Asn | Ser | Arg | Gly | |
| | | 115 | | | | | 120 | | | | | 125 | | | | |

| gaa | aaa | gtt | ccg | ttt | gca | tcc | cgt | ttt | gta | ttt | gaa | aag | aaa | agg | gaa | 4090 |
|---|---|---|---|---|---|---|---|---|---|---|---|---|---|---|---|---|
| Glu | Lys | Val | Pro | Phe | Ala | Ser | Arg | Phe | Val | Phe | Glu | Lys | Lys | Arg | Glu | |
| | 130 | | | | | 135 | | | | | 140 | | | | | |

| aca | cct | aaa | tta | att | ata | aat | atc | aaa | gat | tat | gca | att | aat | agt | gaa | 4138 |
|---|---|---|---|---|---|---|---|---|---|---|---|---|---|---|---|---|
| Thr | Pro | Lys | Leu | Ile | Ile | Asn | Ile | Lys | Asp | Tyr | Ala | Ile | Asn | Ser | Glu | |
| 145 | | | | | 150 | | | | | 155 | | | | | 160 | |

| caa | agt | aaa | gaa | gta | tat | tat | gaa | att | gga | aag | ggg | att | tct | ctt | gat | 4186 |
|---|---|---|---|---|---|---|---|---|---|---|---|---|---|---|---|---|
| Gln | Ser | Lys | Glu | Val | Tyr | Tyr | Glu | Ile | Gly | Lys | Gly | Ile | Ser | Leu | Asp | |
| | | | | 165 | | | | | 170 | | | | | 175 | | |

| att | ata | agt | aag | gat | aaa | tct | cta | gat | cca | gag | ttt | tta | aat | tta | att | 4234 |
|---|---|---|---|---|---|---|---|---|---|---|---|---|---|---|---|---|
| Ile | Ile | Ser | Lys | Asp | Lys | Ser | Leu | Asp | Pro | Glu | Phe | Leu | Asn | Leu | Ile | |
| | | | | 180 | | | | | 185 | | | | | 190 | | |

```
                                       -continued
aag agt tta agc gat gat agt gat agt agc gac ctt tta ttt agt caa    4282
Lys Ser Leu Ser Asp Asp Ser Asp Ser Ser Asp Leu Leu Phe Ser Gln
    195                 200                 205 aaa ttt aaa gag aag cta gaa ttg aat aat aaa agt ata gat ata aat    4330
Lys Phe Lys Glu Lys Leu Glu Leu Asn Asn Lys Ser Ile Asp Ile Asn
210                 215                 220 ttt ata aaa gaa aat tta act gaa ttt cag cat gcg ttt tct tta gcg    4378
Phe Ile Lys Glu Asn Leu Thr Glu Phe Gln His Ala Phe Ser Leu Ala
225                 230                 235                 240 ttt tct tat tat ttt gca cct gac cat aga acg gta tta gag tta tat    4426
Phe Ser Tyr Tyr Phe Ala Pro Asp His Arg Thr Val Leu Glu Leu Tyr
                245                 250                 255 gcc ccc gac atg ttt gag tat atg aat aag tta gaa aaa ggg gga ttt    4474
Ala Pro Asp Met Phe Glu Tyr Met Asn Lys Leu Glu Lys Gly Gly Phe
            260                 265                 270 gag aaa ata agt gaa agt ttg aag aaa gaa ggt gtg gaa aaa gat agg    4522
Glu Lys Ile Ser Glu Ser Leu Lys Lys Glu Gly Val Glu Lys Asp Arg
        275                 280                 285 att gat gtg ctg aaa gga gaa aaa gca ctt aaa gct tca ggt tta gta    4570
Ile Asp Val Leu Lys Gly Glu Lys Ala Leu Lys Ala Ser Gly Leu Val
    290                 295                 300 cca gaa cat gca gat gct ttt aaa aaa att gct aga gaa tta aat aca    4618
Pro Glu His Ala Asp Ala Phe Lys Lys Ile Ala Arg Glu Leu Asn Thr
305                 310                 315                 320 tat att ctt ttt agg cct gtt aat aag tta gct aca aac ctt att aaa    4666
Tyr Ile Leu Phe Arg Pro Val Asn Lys Leu Ala Thr Asn Leu Ile Lys
                325                 330                 335 agt ggt gtg gct aca aag gga ttg aat gtt cat gga aag agt tcg gat    4714
Ser Gly Val Ala Thr Lys Gly Leu Asn Val His Gly Lys Ser Ser Asp
            340                 345                 350 tgg ggc cct gta gct gga tac ata cca ttt gat caa gat tta tct aag    4762
Trp Gly Pro Val Ala Gly Tyr Ile Pro Phe Asp Gln Asp Leu Ser Lys
        355                 360                 365 aag cat ggt caa caa tta gct gtc gag aaa gga aat tta gaa aat aaa    4810
Lys His Gly Gln Gln Leu Ala Val Glu Lys Gly Asn Leu Glu Asn Lys
    370                 375                 380 aaa tca att aca gag cat gaa ggt gaa ata ggt aaa ata cca tta aag    4858
Lys Ser Ile Thr Glu His Glu Gly Glu Ile Gly Lys Ile Pro Leu Lys
385                 390                 395                 400 tta gac cat tta aga ata gaa gag tta aag gaa aat ggg ata att ttg    4906
Leu Asp His Leu Arg Ile Glu Glu Leu Lys Glu Asn Gly Ile Ile Leu
                405                 410                 415 aag ggt aaa aaa gaa att gat aat ggt aaa aaa tat tat ttg tta gaa    4954
Lys Gly Lys Lys Glu Ile Asp Asn Gly Lys Lys Tyr Tyr Leu Leu Glu
            420                 425                 430 tcg aat aat cag gta tat gaa ttt aga att agc gat gaa aac aac gaa    5002
Ser Asn Asn Gln Val Tyr Glu Phe Arg Ile Ser Asp Glu Asn Asn Glu
        435                 440                 445 gta caa tac aag aca aaa gaa ggt aaa att act gtt tta ggg gaa aaa    5050
Val Gln Tyr Lys Thr Lys Glu Gly Lys Ile Thr Val Leu Gly Glu Lys
    450                 455                 460 ttc aat tgg aga aat ata gaa gtg atg gct aaa aat gta gaa ggg gtc    5098
Phe Asn Trp Arg Asn Ile Glu Val Met Ala Lys Asn Val Glu Gly Val
465                 470                 475                 480 ttg aag ccg tta aca gct gac tat gat tta ttt gca ctt gcc cca agt    5146
Leu Lys Pro Leu Thr Ala Asp Tyr Asp Leu Phe Ala Leu Ala Pro Ser
                485                 490                 495 tta aca gaa ata aaa aaa caa ata cca caa aaa gaa tgg gat aaa gta    5194
Leu Thr Glu Ile Lys Lys Gln Ile Pro Gln Lys Glu Trp Asp Lys Val
            500                 505                 510
```

```
gtt aac acc cca aat tca tta gaa aag caa aaa ggt gtt act aat tta      5242
Val Asn Thr Pro Asn Ser Leu Glu Lys Gln Lys Gly Val Thr Asn Leu
            515                 520                 525 ttg att aaa tat gga att gag agg aaa ccg gat tca act aag gga act      5290
Leu Ile Lys Tyr Gly Ile Glu Arg Lys Pro Asp Ser Thr Lys Gly Thr
    530                 535                 540 tta tca aat tgg caa aaa caa atg ctt gat cgt ttg aat gaa gca gtc      5338
Leu Ser Asn Trp Gln Lys Gln Met Leu Asp Arg Leu Asn Glu Ala Val
545                 550                 555                 560 aaa tat aca gga tat aca ggg ggg gat gtg gtt aac cat ggc aca gag      5386
Lys Tyr Thr Gly Tyr Thr Gly Gly Asp Val Val Asn His Gly Thr Glu
                565                 570                 575 caa gat aat gaa gag ttt cct gaa aaa gat aac gaa att ttt ata att      5434
Gln Asp Asn Glu Glu Phe Pro Glu Lys Asp Asn Glu Ile Phe Ile Ile
            580                 585                 590 aat cca gaa ggt gaa ttt ata tta act aaa aat tgg gag atg aca ggt      5482
Asn Pro Glu Gly Glu Phe Ile Leu Thr Lys Asn Trp Glu Met Thr Gly
    595                 600                 605 aga ttt ata gaa aaa aac att acg gga aaa gat tat tta tat tat ttt     5530
Arg Phe Ile Glu Lys Asn Ile Thr Gly Lys Asp Tyr Leu Tyr Tyr Phe
610                 615                 620 aac cgt tct tat aat aaa ata gct cct ggt aat aaa gct tat att gag      5578
Asn Arg Ser Tyr Asn Lys Ile Ala Pro Gly Asn Lys Ala Tyr Ile Glu
625                 630                 635                 640 tgg act gat ccg att aca aaa gcc aaa ata aat acc atc cct acg tca      5626
Trp Thr Asp Pro Ile Thr Lys Ala Lys Ile Asn Thr Ile Pro Thr Ser
                645                 650                 655 gca gag ttt ata aaa aac tta tcc agt atc aga aga tct tca aat gta      5674
Ala Glu Phe Ile Lys Asn Leu Ser Ser Ile Arg Arg Ser Ser Asn Val
            660                 665                 670 gga gtt tat aaa gat agt ggc gac aaa gac gaa ttt gca aaa aaa gaa      5722
Gly Val Tyr Lys Asp Ser Gly Asp Lys Asp Glu Phe Ala Lys Lys Glu
    675                 680                 685 agc gtg aaa aaa att gca gga tat ttg tca gac tat tac aat tca gca      5770
Ser Val Lys Lys Ile Ala Gly Tyr Leu Ser Asp Tyr Tyr Asn Ser Ala
690                 695                 700 aat cat att ttt tct cag gaa aaa aag cgt aaa ata tca ata ttt cgt      5818
Asn His Ile Phe Ser Gln Glu Lys Lys Arg Lys Ile Ser Ile Phe Arg
705                 710                 715                 720 gga atc caa gcc tat aat gaa att gaa aat gtt cta aaa tct aaa caa      5866
Gly Ile Gln Ala Tyr Asn Glu Ile Glu Asn Val Leu Lys Ser Lys Gln
                725                 730                 735 ata gca cca gaa tac aaa aat tat ttt caa tat tta aag gaa agg att      5914
Ile Ala Pro Glu Tyr Lys Asn Tyr Phe Gln Tyr Leu Lys Glu Arg Ile
            740                 745                 750 acc aat caa gtt caa ttg ctt cta aca cat caa aaa tct aat att gaa      5962
Thr Asn Gln Val Gln Leu Leu Leu Thr His Gln Lys Ser Asn Ile Glu
    755                 760                 765 ttt aaa tta ttg tat aaa caa tta aac ttt aca gaa aat gaa acg gat      6010
Phe Lys Leu Leu Tyr Lys Gln Leu Asn Phe Thr Glu Asn Glu Thr Asp
770                 775                 780 aat ttt gag gtc ttc caa aaa att att gat gaa aaa taa ggatcccggg      6059
Asn Phe Glu Val Phe Gln Lys Ile Ile Asp Glu Lys
785                 790                 795 taagaattcg gctgctaaca aagcccgaaa ggaagctgag ttggctgctg ccaccgctga    6119
gcaataacta gcataacccc ttggggcctc taaacgggtc ttgaggggtt ttttgctgaa    6179
aggaggaact atatccggat cggagatcaa ttctggcgta atagcgaaga ggcccgcacc    6239
```

-continued

```
gatcgccctt cccaacagtt gcgtagcctg aatggcgaat gggacgcgcc ctgtagcggc    6299
gcattaagcg cggcgggtgt ggtggttacg cgcagcgtga ccgctacact tgccagcgcc    6359
ctagcgcccg ctcctttcgc tttcttccct tcctttctcg ccacgttcgc cggctttccc    6419
cgtcaagctc taaatcgggg gctcccttta ggttccgat ttagtgcttt acggcacctc     6479
gaccccaaaa aacttgatta gggtgatggt tcacgtagtg ggccatcgcc ctgatagacg    6539
gtttttcgcc ctttgacgtt ggagtccacg ttctttaata gtggactctt gttccaaact    6599
ggaacaacac tcaaccctat ctcggtctat tcttttgatt tataagggat tttgccgatt    6659
tcggcctatt ggttaaaaaa tgagctgatt taacaaaaat ttaacgcgaa ttttaacaaa    6719
atattaacgt ttacaatttc aggtggcact tttcgggaa atgtgcgcgg aacccctatt     6779
tgtttatttt tctaaataca ttcaaatatg tatccgctca tgagacaata accctgataa    6839
atgcttcaat aatattgaaa aaggaagagt atgagtattc aacatttccg tgtcgccctt    6899
attccctttt ttgcggcatt ttgccttcct gttttgctc acccagaaac gctggtgaaa      6959
gtaaaagatg ctgaagatca gttgggtgca cgagtgggtt acatcgaact ggatctcaac    7019
agcggtaaga tccttgagag ttttcgcccc gaagaacgtt ttccaatgat gagcactttt    7079
aaagttctgc tatgtggcgc ggtattatcc cgtattgacg ccgggcaaga gcaactcggt    7139
cgccgcatac actattctca gaatgacttg gttgagtact caccagtcac agaaaagcat    7199 cttacgatg gcatgacagt aagagaatta tgcagtgctg ccataagcat gagtgataac     7259
actgcggcca acttacttct gacaacgatc ggaggaccga aggagctaac cgcttttttt    7319
cacaacatgg gggatcatgt aactcgcctt gatcgttggg aaccggagct gaatgaagcc    7379
ataccaaacg acgagcgtga caccacgatg cctgtagcaa tggcaacaac gttgcgcaaa    7439
ctattaactg gcgaactact tactctagct tcccggcaac aattaataga ctggatggag    7499
gcggataaag ttgcaggacc acttctgcgc tcggcccttc cggctggctg gtttattgct    7559
gataaatctg gagccggtga gcgtgggtct cgcggtatca ttgcagcact ggggccagat    7619
ggtaagccct cccgtatcgt agttatctac acgacgggca gtcaggcaac tatggatgaa    7679
cgaaatagac agatcgctga ataggtgcc tcactgatta agcattggta actgtcagac      7739
caagtttact catatatact ttagattgat ttaaaacttc attttaattt taaaaggatc    7799
taggtgaaga tcctttttga taatctcatg accaaaatcc cttaacgtga gttttcgttc    7859
cactgagcgt cagaccccgt agaaaagatc aaaggatctt cttgagatcc ttttttctg     7919 cgcgtaatct gctgcttgca acaaaaaaa ccaccgctac cagcggtggt ttgtttgccg     7979
gatcaagagc taccaactct ttttccgaag gtaactggct tcagcagagc gcagatacca    8039
aatactgtcc ttctagtgta gccgtagtta ggccaccact tcaagaactc tgtagcaccg    8099
cctacatacc tcgctctgct aatcctgtta ccagtggctg ctgccagtgg cgataagtcg    8159
tgtcttaccg ggttggactc aagacgatag ttaccggata aggcgcagcg gtcgggctga    8219
acggggggtt cgtgcacaca gcccagcttg gagcgaacga cctacaccga actgagatac    8279
ctacagcgtg agcattgaga aagcgccacg cttcccgaag ggagaaaggc ggacaggtat    8339
ccggtaagcg gcagggtcgg aacaggagag cgcacgaggg agcttccagg ggggaacgcc    8399
tggtatcttt atagtcctgt cgggtttcgc cacctctgac ttgagcgtcg attttgtga    8459 tgctcgtcag gggggccgag cctatggaaa aacgccagca acgcggcctt tttacggttc    8519 ctggccttt gctggccttt tgctcacatg ttctttcctg cgttatcccc tgattctgtg     8579
gataaccgta ttaccgcctt tgagtgagct gataccgctc gccgcagccg aacgaccgag    8639
```

-continued

```
cgcagcgagt cagtgagcga ggaagcggaa gagcgcctga tgcggtattt tctccttacg    8699
catctgtgcg gtatttcaca ccgcatatat ggtgcactct cagtacaatc tgctctgatg    8759
ccgcatagtt aagccagtat acactccgct atcgctacgt gactgcaagg agatggcgcc    8819
caacagtccc ccggccacgg ggcctgccac catacccacg ccgaaacaag cgctcatgag    8879
cccgaagtgg cgagcccgat cttccccatc ggtgatgtcg gcgatatagg cgccagcaac    8939
cgcacctgtg cgccggtga tgccggccac gatgcgtccg cgtagagga tcgagatc       8997
```

<210> SEQ ID NO 63
<211> LENGTH: 796
<212> TYPE: PRT
<213> ORGANISM: Artificial Sequence
<220> FEATURE:
<223> OTHER INFORMATION: Synthetic

<400> SEQUENCE: 63

```
Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Met Asn Glu
            20                  25                  30

His Tyr Thr Glu Ser Asp Ile Lys Arg Asn His Lys Thr Glu Lys Asn
        35                  40                  45

Lys Thr Glu Lys Glu Lys Phe Lys Asp Ser Ile Asn Asn Leu Val Lys
    50                  55                  60

Thr Glu Phe Thr Asn Glu Thr Leu Asp Lys Ile Gln Gln Thr Gln Asp
65                  70                  75                  80

Leu Leu Lys Lys Ile Pro Lys Asp Val Leu Glu Ile Tyr Ser Glu Leu
                85                  90                  95

Gly Gly Glu Ile Tyr Phe Thr Asp Ile Asp Leu Val Glu His Lys Glu
            100                 105                 110

Leu Gln Asp Leu Ser Glu Glu Lys Asn Ser Met Asn Ser Arg Gly
        115                 120                 125

Glu Lys Val Pro Phe Ala Ser Arg Phe Val Phe Glu Lys Lys Arg Glu
    130                 135                 140

Thr Pro Lys Leu Ile Ile Asn Ile Lys Asp Tyr Ala Ile Asn Ser Glu
145                 150                 155                 160

Gln Ser Lys Glu Val Tyr Tyr Glu Ile Gly Lys Gly Ile Ser Leu Asp
                165                 170                 175

Ile Ile Ser Lys Asp Lys Ser Leu Asp Pro Glu Phe Leu Asn Leu Ile
            180                 185                 190

Lys Ser Leu Ser Asp Asp Ser Asp Ser Ser Asp Leu Leu Phe Ser Gln
        195                 200                 205

Lys Phe Lys Glu Lys Leu Glu Leu Asn Asn Lys Ser Ile Asp Ile Asn
    210                 215                 220

Phe Ile Lys Glu Asn Leu Thr Glu Phe Gln His Ala Phe Ser Leu Ala
225                 230                 235                 240

Phe Ser Tyr Tyr Phe Ala Pro Asp His Arg Thr Val Leu Glu Leu Tyr
                245                 250                 255

Ala Pro Asp Met Phe Glu Tyr Met Asn Lys Leu Glu Lys Gly Gly Phe
            260                 265                 270

Glu Lys Ile Ser Glu Ser Leu Lys Lys Glu Gly Val Glu Lys Asp Arg
        275                 280                 285

Ile Asp Val Leu Lys Gly Glu Lys Ala Leu Lys Ala Ser Gly Leu Val
    290                 295                 300
```

-continued

Pro Glu His Ala Asp Ala Phe Lys Lys Ile Ala Arg Glu Leu Asn Thr
305                 310                 315                 320

Tyr Ile Leu Phe Arg Pro Val Asn Lys Leu Ala Thr Asn Leu Ile Lys
            325                 330                 335

Ser Gly Val Ala Thr Lys Gly Leu Asn Val His Gly Lys Ser Ser Asp
        340                 345                 350

Trp Gly Pro Val Ala Gly Tyr Ile Pro Phe Asp Gln Asp Leu Ser Lys
    355                 360                 365

Lys His Gly Gln Gln Leu Ala Val Glu Lys Gly Asn Leu Glu Asn Lys
370                 375                 380

Lys Ser Ile Thr Glu His Glu Gly Glu Ile Gly Lys Ile Pro Leu Lys
385                 390                 395                 400

Leu Asp His Leu Arg Ile Glu Glu Leu Lys Glu Asn Gly Ile Ile Leu
                405                 410                 415

Lys Gly Lys Lys Glu Ile Asp Asn Gly Lys Lys Tyr Tyr Leu Leu Glu
            420                 425                 430

Ser Asn Asn Gln Val Tyr Glu Phe Arg Ile Ser Asp Glu Asn Asn Glu
        435                 440                 445

Val Gln Tyr Lys Thr Lys Glu Gly Lys Ile Thr Val Leu Gly Glu Lys
    450                 455                 460

Phe Asn Trp Arg Asn Ile Glu Val Met Ala Lys Asn Val Glu Gly Val
465                 470                 475                 480

Leu Lys Pro Leu Thr Ala Asp Tyr Asp Leu Phe Ala Leu Ala Pro Ser
                485                 490                 495

Leu Thr Glu Ile Lys Lys Gln Ile Pro Gln Lys Glu Trp Asp Lys Val
            500                 505                 510

Val Asn Thr Pro Asn Ser Leu Glu Lys Gln Lys Gly Val Thr Asn Leu
        515                 520                 525

Leu Ile Lys Tyr Gly Ile Glu Arg Lys Pro Asp Ser Thr Lys Gly Thr
    530                 535                 540

Leu Ser Asn Trp Gln Lys Gln Met Leu Asp Arg Leu Asn Glu Ala Val
545                 550                 555                 560

Lys Tyr Thr Gly Tyr Thr Gly Gly Asp Val Val Asn His Gly Thr Glu
                565                 570                 575

Gln Asp Asn Glu Glu Phe Pro Glu Lys Asp Asn Glu Ile Phe Ile Ile
            580                 585                 590

Asn Pro Glu Gly Glu Phe Ile Leu Thr Lys Asn Trp Glu Met Thr Gly
        595                 600                 605

Arg Phe Ile Glu Lys Asn Ile Thr Gly Lys Asp Tyr Leu Tyr Tyr Phe
    610                 615                 620

Asn Arg Ser Tyr Asn Lys Ile Ala Pro Gly Asn Lys Ala Tyr Ile Glu
625                 630                 635                 640

Trp Thr Asp Pro Ile Thr Lys Ala Lys Ile Asn Thr Ile Pro Thr Ser
                645                 650                 655

Ala Glu Phe Ile Lys Asn Leu Ser Ser Ile Arg Arg Ser Ser Asn Val
            660                 665                 670

Gly Val Tyr Lys Asp Ser Gly Asp Lys Asp Glu Phe Ala Lys Lys Glu
        675                 680                 685

Ser Val Lys Lys Ile Ala Gly Tyr Leu Ser Asp Tyr Tyr Asn Ser Ala
    690                 695                 700

Asn His Ile Phe Ser Gln Glu Lys Lys Arg Lys Ile Ser Ile Phe Arg
705                 710                 715                 720

```
Gly Ile Gln Ala Tyr Asn Glu Ile Glu Asn Val Leu Lys Ser Lys Gln
                725                 730                 735

Ile Ala Pro Glu Tyr Lys Asn Tyr Phe Gln Tyr Leu Lys Glu Arg Ile
            740                 745                 750

Thr Asn Gln Val Gln Leu Leu Leu Thr His Gln Lys Ser Asn Ile Glu
        755                 760                 765

Phe Lys Leu Leu Tyr Lys Gln Leu Asn Phe Thr Glu Asn Glu Thr Asp
    770                 775                 780

Asn Phe Glu Val Phe Gln Lys Ile Ile Asp Glu Lys
785                 790                 795

<210> SEQ ID NO 64
<211> LENGTH: 767
<212> TYPE: PRT
<213> ORGANISM: Artificial Sequence
<220> FEATURE:
<223> OTHER INFORMATION: Synthetic

<400> SEQUENCE: 64

Met Asn Glu His Tyr Thr Glu Ser Asp Ile Lys Arg Asn His Lys Thr
1               5                   10                  15

Glu Lys Asn Lys Thr Lys Glu Lys Phe Lys Asp Ser Ile Asn Asn
            20                  25                  30

Leu Val Lys Thr Glu Phe Thr Asn Glu Thr Leu Asp Lys Ile Gln Gln
        35                  40                  45

Thr Gln Asp Leu Leu Lys Lys Ile Pro Lys Asp Val Leu Glu Ile Tyr
    50                  55                  60

Ser Glu Leu Gly Gly Glu Ile Tyr Phe Thr Asp Ile Asp Leu Val Glu
65                  70                  75                  80

His Lys Glu Leu Gln Asp Leu Ser Glu Glu Lys Asn Ser Met Asn
                85                  90                  95

Ser Arg Gly Glu Lys Val Pro Phe Ala Ser Arg Phe Val Phe Glu Lys
            100                 105                 110

Lys Arg Glu Thr Pro Lys Leu Ile Ile Asn Ile Lys Asp Tyr Ala Ile
        115                 120                 125

Asn Ser Glu Gln Ser Lys Glu Val Tyr Tyr Glu Ile Gly Lys Gly Ile
    130                 135                 140

Ser Leu Asp Ile Ile Ser Lys Asp Lys Ser Leu Asp Pro Glu Phe Leu
145                 150                 155                 160

Asn Leu Ile Lys Ser Leu Ser Asp Asp Ser Asp Ser Ser Asp Leu Leu
                165                 170                 175

Phe Ser Gln Lys Phe Lys Glu Lys Leu Glu Leu Asn Asn Lys Ser Ile
            180                 185                 190

Asp Ile Asn Phe Ile Lys Glu Asn Leu Thr Glu Phe Gln His Ala Phe
        195                 200                 205

Ser Leu Ala Phe Ser Tyr Tyr Phe Ala Pro Asp His Arg Thr Val Leu
    210                 215                 220

Glu Leu Tyr Ala Pro Asp Met Phe Glu Tyr Met Asn Lys Leu Glu Lys
225                 230                 235                 240

Gly Gly Phe Glu Lys Ile Ser Glu Ser Leu Lys Lys Glu Gly Val Glu
                245                 250                 255

Lys Asp Arg Ile Asp Val Leu Lys Gly Glu Lys Ala Leu Lys Ala Ser
            260                 265                 270

Gly Leu Val Pro Glu His Ala Asp Ala Phe Lys Lys Ile Ala Arg Glu
        275                 280                 285
```

```
Leu Asn Thr Tyr Ile Leu Phe Arg Pro Val Asn Lys Leu Ala Thr Asn
290                 295                 300

Leu Ile Lys Ser Gly Val Ala Thr Lys Gly Leu Asn Val His Gly Lys
305                 310                 315                 320

Ser Ser Asp Trp Gly Pro Val Ala Gly Tyr Ile Pro Phe Asp Gln Asp
                325                 330                 335

Leu Ser Lys Lys His Gly Gln Gln Leu Ala Val Glu Lys Gly Asn Leu
            340                 345                 350

Glu Asn Lys Lys Ser Ile Thr Glu His Glu Gly Glu Ile Gly Lys Ile
        355                 360                 365

Pro Leu Lys Leu Asp His Leu Arg Ile Glu Glu Leu Lys Glu Asn Gly
370                 375                 380

Ile Ile Leu Lys Gly Lys Lys Glu Ile Asp Asn Gly Lys Lys Tyr Tyr
385                 390                 395                 400

Leu Leu Glu Ser Asn Asn Gln Val Tyr Glu Phe Arg Ile Ser Asp Glu
                405                 410                 415

Asn Asn Glu Val Gln Tyr Lys Thr Lys Glu Gly Lys Ile Thr Val Leu
            420                 425                 430

Gly Glu Lys Phe Asn Trp Arg Asn Ile Glu Val Met Ala Lys Asn Val
        435                 440                 445

Glu Gly Val Leu Lys Pro Leu Thr Ala Asp Tyr Asp Leu Phe Ala Leu
450                 455                 460

Ala Pro Ser Leu Thr Glu Ile Lys Lys Gln Ile Pro Gln Lys Glu Trp
465                 470                 475                 480

Asp Lys Val Val Asn Thr Pro Asn Ser Leu Glu Lys Gln Lys Gly Val
                485                 490                 495

Thr Asn Leu Leu Ile Lys Tyr Gly Ile Glu Arg Lys Pro Asp Ser Thr
            500                 505                 510

Lys Gly Thr Leu Ser Asn Trp Gln Lys Gln Met Leu Asp Arg Leu Asn
        515                 520                 525

Glu Ala Val Lys Tyr Thr Gly Tyr Thr Gly Gly Asp Val Val Asn His
530                 535                 540

Gly Thr Glu Gln Asp Asn Glu Glu Phe Pro Glu Lys Asp Asn Glu Ile
545                 550                 555                 560

Phe Ile Ile Asn Pro Glu Gly Glu Phe Ile Leu Thr Lys Asn Trp Glu
                565                 570                 575

Met Thr Gly Arg Phe Ile Glu Lys Asn Ile Thr Gly Lys Asp Tyr Leu
            580                 585                 590

Tyr Tyr Phe Asn Arg Ser Tyr Asn Lys Ile Ala Pro Gly Asn Lys Ala
        595                 600                 605

Tyr Ile Glu Trp Thr Asp Pro Ile Thr Lys Ala Lys Ile Asn Thr Ile
610                 615                 620

Pro Thr Ser Ala Glu Phe Ile Lys Asn Leu Ser Ser Ile Arg Arg Ser
625                 630                 635                 640

Ser Asn Val Gly Val Tyr Lys Asp Ser Gly Asp Lys Asp Glu Phe Ala
                645                 650                 655

Lys Lys Glu Ser Val Lys Lys Ile Ala Gly Tyr Leu Ser Asp Tyr Tyr
            660                 665                 670

Asn Ser Ala Asn His Ile Phe Ser Gln Glu Lys Lys Arg Lys Ile Ser
        675                 680                 685

Ile Phe Arg Gly Ile Gln Ala Tyr Asn Glu Ile Glu Asn Val Leu Lys
690                 695                 700

Ser Lys Gln Ile Ala Pro Glu Tyr Lys Asn Tyr Phe Gln Tyr Leu Lys
```

```
                    705                 710                 715                 720
Glu Arg Ile Thr Asn Gln Val Gln Leu Leu Leu Thr His Gln Lys Ser
                        725                 730                 735

Asn Ile Glu Phe Lys Leu Leu Tyr Lys Gln Leu Asn Phe Thr Glu Asn
                740                 745                 750

Glu Thr Asp Asn Phe Glu Val Phe Gln Lys Ile Ile Asp Glu Lys
                755                 760                 765

<210> SEQ ID NO 65
<211> LENGTH: 7853
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (6611)..(7853)

<400> SEQUENCE: 65
gatcccgggg ggtaagaatt cggctgctaa caaagcccga aggaagctg agttggctgc      60 tgccaccgct gagcaataac tagcataacc ccttggggcc tctaaacggg tcttgagggg    120 tttttgctg aaaggaggaa ctatatccgg atcggagatc aattctggcg taatagcgaa    180
gaggcccgca ccgatcgccc ttcccaacag ttgcgtagcc tgaatggcga atgggacgcg    240
ccctgtagcg gcgcattaag cgcggcgggt gtggtggtta cgcgcagcgt gaccgctaca    300
cttgccagcg ccctagcgcc cgctcctttc gctttcttcc cttcctttct cgccacgttc    360
gccggctttc cccgtcaagc tctaaatcgg ggctccctt tagggttccg atttagtgct    420
ttacggcacc tcgaccccaa aaaacttgat tagggtgatg gttcacgtag tgggccatcg    480
ccctgataga cggtttttcg ccctttgacg ttggagtcca cgttctttaa tagtggactc    540
ttgttccaaa ctggaacaac actcaaccct atctcggtct attctttga tttataaggg    600 attttgccga tttcggccta ttggttaaaa aatgagctga tttaacaaaa atttaacgcg    660
aattttaaca aaatattaac gtttacaatt tcaggtggca cttttcgggg aaatgtgcgc    720 ggaacccta tttgtttatt tttctaaata cattcaaata tgtatccgct catgagacaa    780
taaccctgat aaatgcttca ataatattga aaaaggaaga gtatgagtat tcaacatttc    840
cgtgtcgccc ttattccctt ttttgcggca ttttgccttc ctgttttgc tcacccagaa    900 acgctggtga agtaaaaga tgctgaagat cagttgggtg cacgagtggg ttacatcgaa    960
ctggatctca acagcggtaa gatccttgag agttttcgcc ccgaagaacg ttttccaatg   1020
atgagcactt ttaaagttct gctatgtggc gcggtattat cccgtattga cgccgggcaa   1080
gagcaactcg gtcgccgcat acactattct cagaatgact tggttgagta ctcaccagtc   1140
acagaaaagc atcttacgga tggcatgaca gtaagagaat tatgcagtgc tgccataagc   1200
atgagtgata acactgcggc caacttactt ctgacaacga tcggaggacc gaaggagcta   1260
accgcttttt ttcacaacat gggggatcat gtaactcgcc ttgatcgttg ggaaccggag   1320
ctgaatgaag ccataccaaa cgacgagcgt gacaccacga tgcctgtagc aatggcaaca   1380
acgttgcgca aactattaac tggcgaacta cttactctag cttcccggca acaattaata   1440
gactggatgg aggcggataa agttgcagga ccacttctgc gctcggccct tccggctggc   1500
tggtttattg ctgataaatc tggagccggt gagcgtgggt ctcgcggtat cattgcagca   1560
ctggggccag atggtaagcc ctcccgtatc gtagttatct acacgacggg cagtcaggca   1620
actatggatg aacgaaatag acagatcgct gagataggtg cctcactgat taagcattgg   1680
```

-continued

```
taactgtcag accaagttta ctcatatata ctttagattg atttaaaact tcattttaa    1740
tttaaaagga tctaggtgaa gatccttttt gataatctca tgaccaaaat cccttaacgt    1800
gagttttcgt tccactgagc gtcagacccc gtagaaaaga tcaaaggatc ttcttgagat    1860
cctttttttc tgcgcgtaat ctgctgcttg caaacaaaaa aaccaccgct accagcggtg    1920
gtttgtttgc cggatcaaga gctaccaact cttttccga aggtaactgg cttcagcaga    1980
gcgcagatac caaatactgt ccttctagtg tagccgtagt taggccacca cttcaagaac    2040
tctgtagcac cgcctacata cctcgctctg ctaatcctgt taccagtggc tgctgccagt    2100
ggcgataagt cgtgtcttac cgggttggac tcaagacgat agttaccgga taaggcgcag    2160
cggtcgggct gaacggggg ttcgtgcaca gcccagct tggagcgaac gacctacacc    2220
gaactgagat acctacagcg tgagcattga gaaagcgcca cgcttcccga agggagaaag    2280
gcggacaggt atccggtaag cggcagggtc ggaacaggag agcgcacgag ggagcttcca    2340
gggggaacg cctggtatct ttatagtcct gtcgggtttc gccacctctg acttgagcgt    2400
cgatttttgt gatgctcgtc aggggggcg agcctatgga aaaacgccag caacgcggcc    2460
tttttacggt tcctggcctt ttgctggcct tttgctcaca tgttctttcc tgcgttatcc    2520
cctgattctg tggataaccg tattaccgcc tttgagtgag ctgataccgc tcgccgcagc    2580
cgaacgaccg agcgcagcga gtcagtgagc gaggaagcgg aagagcgcct gatgcggtat    2640
tttctcctta cgcatctgtg cggtatttca caccgcatat atggtgcact ctcagtacaa    2700
tctgctctga tgccgcatag ttaagccagt atacactccg ctatcgctac gtgactgcaa    2760
ggagatggcg cccaacagtc ccccggccac ggggcctgcc accatacca cgccgaaaca    2820
agcgctcatg agcccgaagt ggcgagcccg atcttcccca tcggtgatgt cggcgatata    2880
ggcgccagca accgcacctg tggcgccggt gatgccggcc acgatgcgtc cggcgtagag    2940
gatcgagatc caggagaaca aaaacgattt tttgaggaaa gttataaatt attttccgaa    3000
cgatatggca agcaaaatat tgcttatgca acagttcata atgatgagca aaccctcac    3060
atgcatttag gtgttgtgcc tatgcgtgat ggaaaactgc aaggaaaaaa tgtgtttaat    3120
cgtcaagaac tgttatggct acaagataaa ttccccgagc acatgaaaaa acagggtttt    3180
gagttgaagc gtggtgaacg tggctctgac cgtaaacata ttgagacagc taaatttaaa    3240
aaacaaactt tggaaaaaga gattgatttt ctagaaaaaa atttagcagt taaaaaagat    3300
gaatggactg cttatagcga taaagttaaa tcagatttag aagtaccagc gaaacgacac    3360
atgaaaagtg ttgaagtgcc aacgggtgaa aagtccatgt ttggtttggg aaaagaaata    3420
atgaaaacag aaaagaaacc aaccaaaaat gttgttatat cggagcgtga ttataaaaac    3480
ttagtgactg ctgcgagaga taacgatagg ttaaaacagc atgttagaaa tctcatgagt    3540
actgatatgg cgagagaata taaaaaatta agtaaagaac atgggcaagt taagaaaaa    3600
tatagtggtc ttgtagagcg atttaatgaa aatgtaaatg attataatga gttgcttgaa    3660
gaaaacaagt ctttaaagtc taaaataagc gatttaaagc gtgatgtgag tttaatctat    3720
gaaagcacta aggaattcct taaggaacgt acagacggct aaaagccctt taaaacgtt    3780
tttaaggggt ttgtagacaa ggtaaaggat aaaacagcac aattccaaga aaacacgat    3840
ttagaaccta aaaagaacga atttgaacta actcataacc gagaggtaaa aaaagaacga    3900
agtcgagatc agggaatgag tttataaaat aaaaaagca cctgaaaagg tgtctttttt    3960
tgatggtttt gaacttgttc tttcttatct tgatacatat agaaataacg tcattttat    4020
```

```
tttagttgct gaaaggtgcg ttgaagtgtt ggtatgtatg tgttttaaag tattgaaaac    4080
ccttaaaatt ggttgcacag aaaaacccca tctgttaaag ttataagtga ctaaacaaat    4140
aactaaatag atgggggttt cttttaatat tatgtgtcct aatagtagca tttattcaga    4200
tgaaaaatca agggttttag tggacaagac aaaaagtgga aaagtgagac catggagaga    4260
aaagaaaatc gctaatgttg attactttga acttctgcat attcttgaat ttaaaaaggc    4320
tgaaagagta aaagattgtg ctgaaatatt agagtataaa caaatcgtg aaacaggcga     4380 aagaaagttg tatcgagtgt ggttttgtaa atccaggctt tgtccaatgt gcaactggag    4440
gagagcaatg aaacatggca ttcagtcaca aaaggttgtt gctgaagtta ttaaacaaaa    4500
gccaacagtt cgttggttgt ttctcacatt aacagttaaa aatgtttatg atggcgaaga    4560
attaaataag agtttgtcag atatggctca aggatttcgc cgaatgatgc aatataaaaa    4620
aattaataaa aatcttgttg gttttatgcg tgcaacggaa gtgacaataa ataataaaga    4680
taattcttat aatcagcaca tgcatgtatt ggtatgtgtg gaaccaactt attttaagaa    4740
tacagaaaac tacgtgaatc aaaaacaatg gattcaattt tggaaaaagg caatgaaatt    4800
agactatgat ccaaatgtaa aagttcaaat gattcgaccg aaaaataaat ataaatcgga    4860
tatacaatcg gcaattgacg aaactgcaaa atatcctgta aaggatacgg attttatgac    4920
cgatgatgaa gaaagaatt tgaaacgttt gtctgatttg gaggaaggtt tacaccgtaa     4980
aaggttaatc tcctatggtg gtttgttaaa agaaatacat aaaaaattaa accttgatga    5040
cacagaagaa ggcgatttga ttcatacaga tgatgacgaa aaagccgatg aagatggatt    5100
ttctattatt gcaatgtgga attgggaacg gaaaaattat tttattaaag agtagttcaa    5160
caaacgggcc agtttgttga agattagatg ctataattgt tattaaaagg attgaaggat    5220
gcttaggaag acgagttatt aatagctgaa taagaacggt gctctccaaa tattcttatt    5280
tagaaaagca aatctaaaat tatctgaaaa gggaatgaga atagtgaatg gaccaataat    5340
aatgactaga gaagaaagaa tgaagattgt tcatgaaatt aaggaacgaa tattggataa    5400
atatggggat gatgttaagg ctattggtgt ttatggctct cttggtcgtc agactgatgg    5460
gccctattcg gatattgaga tgatgtgtgt catgtcaaca gaggaagcag agttcagcca    5520
tgaatggaca accggtgagt ggaaggtgga agtgaatttt gatagcgaag agattctact    5580
agattatgca tctcaggtgg aatcagattg gccgcttaca catggtcaat ttttctctat    5640
tttgccgatt tatgattcag gtggatactt agagaaagtg tatcaaactg ctaaatcggt    5700
agaagcccaa acgttccacg atgcgatttg tgcccttatc gtagaagagc tgtttgaata    5760
tgcaggcaaa tggcgtaata ttcgtgtgca aggaccgaca acatttctac catccttgac    5820
tgtacaggta gcaatggcag gtgccatgtt gattggtctg catcatcgca tctgttatac    5880
gacgagcgct tcggtcttaa ctgaagcagt taagcaatca gatcttcctt caggttatga    5940
ccatctgtgc cagttcgtaa tgtctggtca actttccgac tctgagaaac ttctggaatc    6000
gctagagaat ttctggaatg ggattcagga gtggacagaa cgacacggat atatagtgga    6060
tgtgtcaaaa cgcataccat tttgaacgat gacctctaat aattgttaat catgttggtt    6120
acgtatttat taacttctcc tagtattagt aattatcatg gctgtcatgg cgcattaacg    6180
gaataaaggg tgtgcttaaa tcgggccatt ttgcgtaata agaaaaagga ttaattatga    6240
gcgaattgaa ttaataataa ggtaatagat ttacattaga aaatgaaagg ggatttttatg    6300 cgtgagaatg ttacagtcta tcccggcatt gccagtcggg gatattaaaa agagtatagg    6360
tttttattgc gataaactag gtttcacttt ggttcaccat gaagatggat tcgcagttct    6420
```

```
aatgtgtaat gaggttcgga ttcatcctat taaacatata aattcttttt tatgttatat       6480
atttataaaa gttctgttta aaagccaaa aataaataat tatctctttt tatttatatt         6540
atattgaaac taaagtttat taatttcaat ataatataaa tttaatttta tacaaaaagg        6600
agaacgcata atg aaa aaa ttt cca ttc aaa gta cta act tta gct aca           6649
           Met Lys Lys Phe Pro Phe Lys Val Leu Thr Leu Ala Thr
            1               5                  10 tta gca act gtt ata act gct act acc ggt aac act att cat gca ttt          6697
Leu Ala Thr Val Ile Thr Ala Thr Thr Gly Asn Thr Ile His Ala Phe
     15                  20                  25 gca caa gaa acg acc gct caa gaa caa aaa gta ggc aat tat gca tta          6745
Ala Gln Glu Thr Thr Ala Gln Glu Gln Lys Val Gly Asn Tyr Ala Leu
 30              35                  40                  45 ggc ccc gaa gga ctg aag aaa gca ttg gct gaa aca ggg tct cat att          6793
Gly Pro Glu Gly Leu Lys Lys Ala Leu Ala Glu Thr Gly Ser His Ile
                 50                  55                  60 cta gta atg gat tta tat gca aaa aca atg att aag caa cca aat gta          6841
Leu Val Met Asp Leu Tyr Ala Lys Thr Met Ile Lys Gln Pro Asn Val
             65                  70                  75 aat tta tct aat atc gat tta ggg tca gag ggg gga gag ttg ctc aaa          6889
Asn Leu Ser Asn Ile Asp Leu Gly Ser Glu Gly Gly Glu Leu Leu Lys
         80                  85                  90 aat att cac ctt aat caa gag ctg tca cga atc aat gcg aat tac tgg          6937
Asn Ile His Leu Asn Gln Glu Leu Ser Arg Ile Asn Ala Asn Tyr Trp
     95                  100                 105 tta gat aca gcg aag cca cag att caa aaa act gct cgt aat att gta          6985
Leu Asp Thr Ala Lys Pro Gln Ile Gln Lys Thr Ala Arg Asn Ile Val
110              115                 120                 125 aat tac gat gaa caa ttt caa aat tat tac gac aca tta gta gaa act          7033
Asn Tyr Asp Glu Gln Phe Gln Asn Tyr Tyr Asp Thr Leu Val Glu Thr
                 130                 135                 140 gta caa aag aaa gat aag gca ggt cta aaa gag ggt ata aat gat tta          7081
Val Gln Lys Lys Asp Lys Ala Gly Leu Lys Glu Gly Ile Asn Asp Leu
             145                 150                 155 att act aca atc aat aca aat tca aaa gaa gtt aca gat gtg att aag          7129
Ile Thr Thr Ile Asn Thr Asn Ser Lys Glu Val Thr Asp Val Ile Lys
         160                 165                 170 atg cta caa gac ttc aaa ggg aaa cta tat caa aat tct aca gat ttt          7177
Met Leu Gln Asp Phe Lys Gly Lys Leu Tyr Gln Asn Ser Thr Asp Phe
     175                 180                 185 aaa aat aat gtt ggt ggt cca gat ggg aaa ggt gga tta act gca ata          7225
Lys Asn Asn Val Gly Gly Pro Asp Gly Lys Gly Gly Leu Thr Ala Ile
190              195                 200                 205 tta gca ggt caa cag gca acg att cca caa ctt caa gct gaa att gag          7273
Leu Ala Gly Gln Gln Ala Thr Ile Pro Gln Leu Gln Ala Glu Ile Glu
                 210                 215                 220 caa ctt cgt tct act cag aaa aaa cat ttt gat gat gta tta gca tgg          7321
Gln Leu Arg Ser Thr Gln Lys Lys His Phe Asp Asp Val Leu Ala Trp
             225                 230                 235 tca att ggt ggt gga ttg gga gca gct att tta gtt att gca gct att          7369
Ser Ile Gly Gly Gly Leu Gly Ala Ala Ile Leu Val Ile Ala Ala Ile
         240                 245                 250 gga gga gcg gta gtt att gtt gta act ggc ggt aca gca aca ccg gct          7417
Gly Gly Ala Val Val Ile Val Val Thr Gly Gly Thr Ala Thr Pro Ala
     255                 260                 265 gtt gtt ggt gga ctc tcg gct ctt ggt gca gct ggt atc ggt cta gga          7465
Val Val Gly Gly Leu Ser Ala Leu Gly Ala Ala Gly Ile Gly Leu Gly
270              275                 280                 285
```

```
aca gcg gct ggt gtc aca gca tct aag cat atg gac tcc tat aat gaa      7513
Thr Ala Ala Gly Val Thr Ala Ser Lys His Met Asp Ser Tyr Asn Glu
            290                 295                 300 att tct aac aaa atc gga gaa tta agt atg aaa gca gat cgt gct aat      7561
Ile Ser Asn Lys Ile Gly Glu Leu Ser Met Lys Ala Asp Arg Ala Asn
            305                 310                 315 caa gca gtt ctt tcg ctt act aac gcg aaa gaa aca ttg gca tat tta      7609
Gln Ala Val Leu Ser Leu Thr Asn Ala Lys Glu Thr Leu Ala Tyr Leu
            320                 325                 330 tat cag act gta gat caa gcg ata ttg tct cta aca aat att caa aag      7657
Tyr Gln Thr Val Asp Gln Ala Ile Leu Ser Leu Thr Asn Ile Gln Lys
        335                 340                 345 caa tgg aat aca atg ggt gca aat tat aca gat tta ttg gat aat atc      7705
Gln Trp Asn Thr Met Gly Ala Asn Tyr Thr Asp Leu Leu Asp Asn Ile
350                 355                 360                 365 gat tct atg caa gac cac aaa ttc tct tta ata cca gat gat tta aaa      7753
Asp Ser Met Gln Asp His Lys Phe Ser Leu Ile Pro Asp Asp Leu Lys
                370                 375                 380 gcc gct aaa gaa agt tgg aat gat att cat aaa gat gca gaa ttc att      7801
Ala Ala Lys Glu Ser Trp Asn Asp Ile His Lys Asp Ala Glu Phe Ile
            385                 390                 395 tca aaa gat att gct ttt aaa cag gag cat cat cat cac cat cac taa      7849
Ser Lys Asp Ile Ala Phe Lys Gln Glu His His His His His His
            400                 405                 410 taa g                                                                 7853

<210> SEQ ID NO 66
<211> LENGTH: 412
<212> TYPE: PRT
<213> ORGANISM: Artificial Sequence
<220> FEATURE:
<223> OTHER INFORMATION: Synthetic

<400> SEQUENCE: 66

Met Lys Lys Phe Pro Phe Lys Val Leu Thr Leu Ala Thr Leu Ala Thr
1               5                   10                  15

Val Ile Thr Ala Thr Thr Gly Asn Thr Ile His Ala Phe Ala Gln Glu
            20                  25                  30

Thr Thr Ala Gln Glu Gln Lys Val Gly Asn Tyr Ala Leu Gly Pro Glu
        35                  40                  45

Gly Leu Lys Lys Ala Leu Ala Glu Thr Gly Ser His Ile Leu Val Met
    50                  55                  60

Asp Leu Tyr Ala Lys Thr Met Ile Lys Gln Pro Asn Val Asn Leu Ser
65                  70                  75                  80

Asn Ile Asp Leu Gly Ser Glu Gly Gly Glu Leu Leu Lys Asn Ile His
                85                  90                  95

Leu Asn Gln Glu Leu Ser Arg Ile Asn Ala Asn Tyr Trp Leu Asp Thr
            100                 105                 110

Ala Lys Pro Gln Ile Gln Lys Thr Ala Arg Asn Ile Val Asn Tyr Asp
        115                 120                 125

Glu Gln Phe Gln Asn Tyr Tyr Asp Thr Leu Val Glu Thr Val Gln Lys
    130                 135                 140

Lys Asp Lys Ala Gly Leu Lys Glu Gly Ile Asn Asp Leu Ile Thr Thr
145                 150                 155                 160

Ile Asn Thr Asn Ser Lys Glu Val Thr Asp Val Ile Lys Met Leu Gln
                165                 170                 175

Asp Phe Lys Gly Lys Leu Tyr Gln Asn Ser Thr Asp Phe Lys Asn Asn
            180                 185                 190
```

Val Gly Gly Pro Asp Gly Lys Gly Gly Leu Thr Ala Ile Leu Ala Gly
            195                 200                 205

Gln Gln Ala Thr Ile Pro Gln Leu Gln Ala Glu Ile Glu Gln Leu Arg
        210                 215                 220

Ser Thr Gln Lys Lys His Phe Asp Asp Val Leu Ala Trp Ser Ile Gly
225                 230                 235                 240

Gly Gly Leu Gly Ala Ala Ile Leu Val Ile Ala Ala Ile Gly Gly Ala
                245                 250                 255

Val Val Ile Val Val Thr Gly Gly Thr Ala Thr Pro Ala Val Val Gly
                260                 265                 270

Gly Leu Ser Ala Leu Gly Ala Ala Gly Ile Gly Leu Gly Thr Ala Ala
            275                 280                 285

Gly Val Thr Ala Ser Lys His Met Asp Ser Tyr Asn Glu Ile Ser Asn
        290                 295                 300

Lys Ile Gly Glu Leu Ser Met Lys Ala Asp Arg Ala Asn Gln Ala Val
305                 310                 315                 320

Leu Ser Leu Thr Asn Ala Lys Glu Thr Leu Ala Tyr Leu Tyr Gln Thr
                325                 330                 335

Val Asp Gln Ala Ile Leu Ser Leu Thr Asn Ile Gln Lys Gln Trp Asn
                340                 345                 350

Thr Met Gly Ala Asn Tyr Thr Asp Leu Leu Asp Asn Ile Asp Ser Met
            355                 360                 365

Gln Asp His Lys Phe Ser Leu Ile Pro Asp Leu Lys Ala Ala Lys
        370                 375                 380

Glu Ser Trp Asn Asp Ile His Lys Asp Ala Glu Phe Ile Ser Lys Asp
385                 390                 395                 400

Ile Ala Phe Lys Gln Glu His His His His His
                405                 410

<210> SEQ ID NO 67
<211> LENGTH: 7951
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (3660)..(4997)

<400> SEQUENCE: 67
caggagaaca aaacgatttt tttgaggaaa gttataaatt attttccgaa cgatatggca      60
agcaaaatat tgcttatgca acagttcata atgatgagca aaccoctcac atgcatttag    120 gtgttgtgcc tatgcgtgat ggaaaactgc aaggaaaaaa tgtgtttaat cgtcaagaac    180
tgttatggct acaagataaa ttccccgagc acatgaaaaa cagggttttt gagttgaagc    240
gtggtgaacg tggctctgac cgtaaacata ttgagacagc taaatttaaa aaacaaactt    300
tggaaaaaga gattgatttt ctagaaaaaa atttagcagt taaaaagat gaatggactg    360 cttatagcga taaagttaaa tcagatttag aagtaccagc gaaacgacac atgaaaagtg    420
ttgaagtgcc aacgggtgaa aagtccatgt tggtttggg aaagaaata atgaaaacag    480 aaaagaaacc aaccaaaaat gttgttatat cggagcgtga ttataaaaac ttagtgactg    540
ctgcgagaga taacgatagg ttaaaacagc atgttagaaa tctcatgagt actgatatgg    600
cgagagaata taaaaatta agtaaagaac atgggcaagt taagaaaaaa tatagtggtc    660
ttgtagagcg atttaatgaa aatgtaaatg attataatga gttgcttgaa gaaaacaagt    720

```
ctttaaagtc taaaataagc gatttaaagc gtgatgtgag tttaatctat gaaagcacta    780
aggaattcct taaggaacgt acagacggct taaaagcctt taaaaacgtt tttaaggggt    840
ttgtagacaa ggtaaaggat aaaacagcac aattccaaga aaaacacgat ttagaaccta    900
aaaagaacga atttgaacta actcataacc gagaggtaaa aaaagaacga agtcgagatc    960
agggaatgag tttataaaat aaaaaaagca cctgaaaagg tgtcttttt  tgatggtttt   1020
gaacttgttc tttcttatct tgatacatat agaaataacg tcatttttat tttagttgct   1080
gaaaggtgcg ttgaagtgtt ggtatgtatg tgttttaaag tattgaaaac ccttaaaatt   1140
ggttgcacag aaaaacccca tctgttaaag ttataagtga ctaaacaaat aactaaatag   1200
atggggttt  cttttaatat tatgtgtcct aatagtagca tttattcaga tgaaaaatca   1260
agggttttag tggacaagac aaaaagtgga aaagtgagac catggagaga aaagaaaatc   1320
gctaatgttg attactttga acttctgcat attcttgaat ttaaaaggc  tgaaagagta   1380
aaagattgtg ctgaaatatt agagtataaa caaaatcgtg aaacaggcga agaaagttg    1440
tatcgagtgt ggttttgtaa atccaggctt tgtccaatgt gcaactggag gagagcaatg   1500
aaacatggca ttcagtcaca aaaggttgtt gctgaagtta ttaaacaaaa gccaacagtt   1560
cgttggttgt ttctcacatt aacagttaaa aatgtttatg atggcgaaga attaaataag   1620
agtttgtcag atatggctca aggatttcgc cgaatgatgc aatataaaaa aattaataaa   1680
aatcttgttg gttttatgcg tgcaacggaa gtgacaataa ataataaaga taattcttat   1740
aatcagcaca tgcatgtatt ggtatgtgtg gaaccaactt attttaagaa tacagaaaac   1800
tacgtgaatc aaaaacaatg gattcaattt tggaaaaagg caatgaaatt agactatgat   1860
ccaaatgtaa aagttcaaat gattcgaccg aaaaataaat ataaatcgga tatacaatcg   1920
gcaattgacg aaactgcaaa atatcctgta aaggatacgg attttatgac cgatgatgaa   1980
gaaaagaatt tgaaacgttt gtctgatttg gaggaaggtt tacaccgtaa aaggttaatc   2040
tcctatggtg gtttgttaaa agaaatacat aaaaaattaa accttgatga cacagaagaa   2100
ggcgatttga ttcatacaga tgatgacgaa aaagccgatg aagatggatt ttctattatt   2160
gcaatgtgga attgggaacg gaaaaattat tttattaaag agtagttcaa caaacgggcc   2220
agtttgttga agattagatg ctataattgt tattaaaagg attgaaggat gcttaggaag   2280
acgagttatt aatagctgaa taagaacggt gctctccaaa tattcttatt tagaaaagca   2340
aatctaaaat tatctgaaaa gggaatgaga atagtgaatg gaccaataat aatgactaga   2400
gaagaaagaa tgaagattgt tcatgaaatt aaggaacgaa tattggataa atatggggat   2460
gatgttaagg ctattggtgt ttatggctct cttggtcgtc agactgatgg gccctattcg   2520
gatattgaga tgatgtgtgt catgtcaaca gaggaagcag agttcagcca tgaatggaca   2580
accggtgagt ggaaggtgga agtgaatttt gatagcgaag agattctact agattatgca   2640
tctcaggtgg aatcagattg gccgcttaca catggtcaat tttctctat  tttgccgatt   2700
tatgattcag gtggatactt agagaaagtg tatcaaactg ctaaatcggt agaagcccaa   2760
acgttccacg atgcgatttg tgcccttatc gtagaagagc tgtttgaata tgcaggcaaa   2820
tggcgtaata ttcgtgtgca aggaccgaca acatttctac catccttgac tgtacaggta   2880
gcaatggcag gtgccatgtt gattggtctg catcatcgca tctgttatac gacgagcgct   2940
tcggtcttaa ctgaagcagt taagcaatca gatcttcctt caggttatga ccatctgtgc   3000
cagttcgtaa tgtctggtca actttccgac tctgagaaac ttctggaatc gctagagaat   3060
```

```
ttctggaatg ggattcagga gtggacagaa cgacacggat atatagtgga tgtgtcaaaa    3120
cgcataccat tttgaacgat gacctctaat aattgttaat catgttggtt acgtatttat    3180
taacttctcc tagtattagt aattatcatg gctgtcatgg cgcattaacg gaataaaggg    3240
tgtgcttaaa tcgggccatt ttgcgtaata agaaaaagga ttaattatga gcgaattgaa    3300
ttaataataa ggtaatagat ttacattaga aaatgaaagg ggattttatg cgtgagaatg    3360
ttacagtcta tcccggcatt gccagtcggg gatattaaaa agagtatagg tttttattgc    3420
gataaactag gtttcacttt ggttcaccat gaagatggat tcgcagttct aatgtgtaat    3480
gaggttcgga ttcatcctat taaacatata aattctttt tatgttatat atttataaaa    3540
gttctgttta aaaagccaaa aataaataat tatctctttt tatttatatt atattgaaac    3600
taaagtttat taatttcaat ataatataaa tttaatttta tacaaaaagg agaacgcat     3659
```

| | | | | | | | | | | | | | | | | |
|---|---|---|---|---|---|---|---|---|---|---|---|---|---|---|---|---|
| atg | aaa | act | aaa | ata | atg | aca | gga | ttt | tta | ata | aca | tcc | att | gta | act | 3707 |
| Met | Lys | Thr | Lys | Ile | Met | Thr | Gly | Phe | Leu | Ile | Thr | Ser | Ile | Val | Thr | |
| 1 | | | | 5 | | | | | 10 | | | | | 15 | | |

gga gca act att cct atc aat act ctt gca aca cca atc gtt caa gca    3755
Gly Ala Thr Ile Pro Ile Asn Thr Leu Ala Thr Pro Ile Val Gln Ala
            20                  25                  30 gaa act caa caa gaa aac atg gat att tct tca tca tta cga aaa tta    3803
Glu Thr Gln Gln Glu Asn Met Asp Ile Ser Ser Ser Leu Arg Lys Leu
        35                  40                  45 ggt gca cat tct aaa tta gtc caa acg tat att gat caa tct tta atg    3851
Gly Ala His Ser Lys Leu Val Gln Thr Tyr Ile Asp Gln Ser Leu Met
    50                  55                  60 agt cct aat gta cag cta gag gaa gtg cca gct tta aat acc aat caa    3899
Ser Pro Asn Val Gln Leu Glu Glu Val Pro Ala Leu Asn Thr Asn Gln
65                  70                  75                  80 ttc cta atc aaa caa gat atg aag gaa tgg tca tcg gaa ctc tat cca    3947
Phe Leu Ile Lys Gln Asp Met Lys Glu Trp Ser Ser Glu Leu Tyr Pro
                85                  90                  95 cag tta att cta tta aat tca aaa agt aaa gga ttt gta aca aaa ttt    3995
Gln Leu Ile Leu Leu Asn Ser Lys Ser Lys Gly Phe Val Thr Lys Phe
            100                 105                 110 aat agt tat tac ccg aca tta aaa ttg ttt gta gac aat aaa gaa gat    4043
Asn Ser Tyr Tyr Pro Thr Leu Lys Leu Phe Val Asp Asn Lys Glu Asp
        115                 120                 125 aga gaa ggg ttt tcg gat aga ctt gaa gta ctt caa gaa atg gct atg    4091
Arg Glu Gly Phe Ser Asp Arg Leu Glu Val Leu Gln Glu Met Ala Met
    130                 135                 140 acg aat caa gaa aat gcg caa cga caa atc aat gaa tta aca gat ctt    4139
Thr Asn Gln Glu Asn Ala Gln Arg Gln Ile Asn Glu Leu Thr Asp Leu
145                 150                 155                 160 aaa tta cag ctt gat aaa aaa tta aaa gat ttt gat act gat gtg gca    4187
Lys Leu Gln Leu Asp Lys Lys Leu Lys Asp Phe Asp Thr Asp Val Ala
                165                 170                 175 act gcg caa ggc ata cta agt aca gat gga aca gga aaa ata gat cag    4235
Thr Ala Gln Gly Ile Leu Ser Thr Asp Gly Thr Gly Lys Ile Asp Gln
            180                 185                 190 tta aaa aat gaa ata tta aat acc aaa aaa gca att caa aat gat tta    4283
Leu Lys Asn Glu Ile Leu Asn Thr Lys Lys Ala Ile Gln Asn Asp Leu
        195                 200                 205 caa caa att gca tta ata cca gga gct tta aat gag cag gga ttt gct    4331
Gln Gln Ile Ala Leu Ile Pro Gly Ala Leu Asn Glu Gln Gly Phe Ala
    210                 215                 220 ata ttc aaa gaa gtt tat agt ctt tca aaa gaa att att gaa ccg gct    4379
Ile Phe Lys Glu Val Tyr Ser Leu Ser Lys Glu Ile Ile Glu Pro Ala
225                 230                 235                 240

```
gct caa gca ggg gtg gca gcg tat aac aaa gga aaa gaa att aac aac       4427
Ala Gln Ala Gly Val Ala Ala Tyr Asn Lys Gly Lys Glu Ile Asn Asn
                245                 250                 255 tct att cta gaa gcg gag aaa aaa gcg gcg caa gaa gcg aca gaa caa       4475
Ser Ile Leu Glu Ala Glu Lys Lys Ala Ala Gln Glu Ala Thr Glu Gln
            260                 265                 270 ggt aaa act gct cta gag att gaa tca gca aaa aaa gca gct cgt gaa       4523
Gly Lys Thr Ala Leu Glu Ile Glu Ser Ala Lys Lys Ala Ala Arg Glu
        275                 280                 285 gca att gag aaa agc aaa caa ggt gaa ata gca gcc gca gcc gca gca       4571
Ala Ile Glu Lys Ser Lys Gln Gly Glu Ile Ala Ala Ala Ala Ala Ala
    290                 295                 300 aaa aca caa gag tat gac ctg atg aaa gcc att gat acc gaa aag att       4619
Lys Thr Gln Glu Tyr Asp Leu Met Lys Ala Ile Asp Thr Glu Lys Ile
305                 310                 315                 320 aag aaa aca ttt ggc gtt ttt gct gaa gta aat aaa tta aca gca gaa       4667
Lys Lys Thr Phe Gly Val Phe Ala Glu Val Asn Lys Leu Thr Ala Glu
                325                 330                 335 cag cga gca tat tta gat gat tta gag aaa caa aat caa aaa ata tat       4715
Gln Arg Ala Tyr Leu Asp Asp Leu Glu Lys Gln Asn Gln Lys Ile Tyr
            340                 345                 350 gat tta aca acg aaa tta tca ata gct gat tta caa aaa tca atg ctt       4763
Asp Leu Thr Thr Lys Leu Ser Ile Ala Asp Leu Gln Lys Ser Met Leu
        355                 360                 365 ctt ctt aca caa aat gat ttg cat acg ttt gca aat caa gta gat gta       4811
Leu Leu Thr Gln Asn Asp Leu His Thr Phe Ala Asn Gln Val Asp Val
    370                 375                 380 gaa ctt gat cta cta aag cgc tat aaa gaa gat tta aat cta ata aaa       4859
Glu Leu Asp Leu Leu Lys Arg Tyr Lys Glu Asp Leu Asn Leu Ile Lys
385                 390                 395                 400 aat agc att aca aaa tta tct act aat gtt gat aca act aac gag cag       4907
Asn Ser Ile Thr Lys Leu Ser Thr Asn Val Asp Thr Thr Asn Glu Gln
                405                 410                 415 tct caa aaa gat aca tta aga caa tta aaa aat gta ata agt tac ctt       4955
Ser Gln Lys Asp Thr Leu Arg Gln Leu Lys Asn Val Ile Ser Tyr Leu
            420                 425                 430 gaa gaa caa gta tat aaa ttt cat cat cat cac cat cac taa              4997
Glu Glu Gln Val Tyr Lys Phe His His His His His His
        435                 440                 445 taaggatccc gggggggtaag aattcggctg ctaacaaagc ccgaaaggaa gctgagttgg    5057
ctgctgccac cgctgagcaa taactagcat aaccccttgg ggcctctaaa cgggtcttga    5117 ggggttttt gctgaaagga ggaactatat ccggatcgga gatcaattct ggcgtaatag    5177
cgaagaggcc cgcaccgatc gcccttccca acagttgcgt agcctgaatg gcgaatggga    5237
cgcgccctgt agcggcgcat taagcgcggc gggtgtggtg gttacgcgca gcgtgaccgc    5297
tacacttgcc agcgccctag cgcccgctcc tttcgctttc ttcccttcct ttctcgccac    5357
gttcgccggc tttccccgtc aagctctaaa tcggggggctc cctttagggt tccgatttag   5417
tgctttacgg cacctcgacc ccaaaaaact tgattagggt gatggttcac gtagtgggcc    5477
atcgccctga tagacggttt ttcgcccttt gacgttggag tccacgttct ttaatagtgg    5537
actcttgttc caaactggaa caacactcaa ccctatctcg gtctattctt ttgatttata    5597
agggattttg ccgatttcgg cctattggtt aaaaaatgag ctgatttaac aaaaatttaa    5657
cgcgaatttt aacaaaatat taacgtttac aatttcaggt ggcactttct ggggaaatgt    5717
gcgcggaacc cctatttgtt tatttttcta aatacattca aatatgtatc cgctcatgag    5777
```

```
acaataaccc tgataaatgc ttcaataata ttgaaaaagg aagagtatga gtattcaaca    5837
tttccgtgtc gcccttattc cctttttttgc ggcattttgc cttcctgttt ttgctcaccc   5897
agaaacgctg gtgaaagtaa aagatgctga agatcagttg ggtgcacgag tgggttacat    5957
cgaactggat ctcaacagcg gtaagatcct tgagagtttt cgccccgaag aacgttttcc    6017
aatgatgagc acttttaaag ttctgctatg tggcgcggta ttatcccgta ttgacgccgg    6077
gcaagagcaa ctcggtcgcc gcatacacta ttctcagaat gacttggttg agtactcacc    6137
agtcacagaa aagcatctta cggatggcat gacagtaaga gaattatgca gtgctgccat    6197
aagcatgagt gataacactg cggccaactt acttctgaca acgatcggag gaccgaagga    6257
gctaaccgct ttttttcaca acatggggga tcatgtaact cgccttgatc gttgggaacc    6317
ggagctgaat gaagccatac caaacgacga gcgtgacacc acgatgcctg tagcaatggc    6377
aacaacgttg cgcaaactat taactggcga actacttact ctagcttccc ggcaacaatt    6437
aatagactgg atggaggcgg ataaagttgc aggaccactt ctgcgctcgg cccttccggc    6497
tggctggttt attgctgata atctggagcc ggtgagcgt gggtctcgcg gtatcattgc     6557
agcactgggg ccagatggta agccctcccg tatcgtagtt atctacacga cgggcagtca    6617
ggcaactatg atgaacgaa atagacagat cgctgagata ggtgcctcac tgattaagca     6677
ttggtaactg tcagaccaag tttactcata tatactttag attgatttaa aacttcattt    6737
ttaatttaaa aggatctagg tgaagatcct ttttgataat ctcatgacca aaatccctta    6797
acgtgagttt tcgttccact gagcgtcaga ccccgtagaa aagatcaaag gatcttcttg    6857
agatcctttt tttctgcgcg taatctgctg cttgcaaaca aaaaaaccac cgctaccagc    6917
ggtggtttgt ttgccggatc aagagctacc aactcttttt ccgaaggtaa ctggcttcag    6977
cagagcgcag ataccaaata ctgtccttct agtgtagccg tagttaggcc accacttcaa    7037
gaactctgta gcaccgccta catacctcgc tctgctaatc ctgttaccag tggctgctgc    7097
cagtggcgat aagtcgtgtc ttaccgggtt ggactcaaga cgatagttac cggataaggc    7157
gcagcggtcg ggctgaacgg ggggttcgtg cacacagccc agcttggagc gaacgaccta    7217
caccgaactg agatacctac agcgtgagca ttgagaaagc gccacgcttc ccgaagggag    7277
aaaggcggac aggtatccgg taagcggcag ggtcggaaca ggagagcgca cgagggagct    7337
tccagggggg aacgcctggt atctttatag tcctgtcggg tttcgccacc tctgacttga    7397
gcgtcgattt ttgtgatgct cgtcaggggg gccgagccta tggaaaaacg ccagcaacgc    7457
ggccttttta cggttcctgg ccttttgctg gccttttgct cacatgttct ttcctgcgtt    7517
atcccctgat tctgtggata accgtattac cgcctttgag tgagctgata ccgctcgccg    7577
cagccgaacg accgagcgca gcgagtcagt gagcgaggaa gcggaagagc gcctgatgcg    7637
gtatttctc cttacgcatc tgtgcggtat ttcacaccgc atatatggtg cactctcagt     7697
acaatctgct ctgatgccgc atagttaagc cagtatacac tccgctatcg ctacgtgact    7757
gcaaggagat ggcgcccaac agtcccccgg ccacggggcc tgccaccata cccacgccga    7817
aacaagcgct catgagcccg aagtggcgag cccgatcttc cccatcggtg atgtcggcga    7877
tataggcgcc agcaaccgca cctgtggcgc cggtgatgcc ggccacgatg cgtccggcgt    7937
agaggatcga gatc                                                     7951
```

<210> SEQ ID NO 68
<211> LENGTH: 445
<212> TYPE: PRT
<213> ORGANISM: Artificial Sequence
<220> FEATURE:
<223> OTHER INFORMATION: Synthetic

<400> SEQUENCE: 68

Met Lys Thr Lys Ile Met Thr Gly Phe Leu Ile Thr Ser Ile Val Thr
1               5                   10                  15

Gly Ala Thr Ile Pro Ile Asn Thr Leu Ala Thr Pro Ile Val Gln Ala
            20                  25                  30

Glu Thr Gln Gln Glu Asn Met Asp Ile Ser Ser Leu Arg Lys Leu
        35                  40                  45

Gly Ala His Ser Lys Leu Val Gln Thr Tyr Ile Asp Gln Ser Leu Met
    50                  55                  60

Ser Pro Asn Val Gln Leu Glu Glu Val Pro Ala Leu Asn Thr Asn Gln
65                  70                  75                  80

Phe Leu Ile Lys Gln Asp Met Lys Glu Trp Ser Ser Glu Leu Tyr Pro
                85                  90                  95

Gln Leu Ile Leu Leu Asn Ser Lys Ser Lys Gly Phe Val Thr Lys Phe
            100                 105                 110

Asn Ser Tyr Tyr Pro Thr Leu Lys Leu Phe Val Asp Asn Lys Glu Asp
        115                 120                 125

Arg Glu Gly Phe Ser Asp Arg Leu Glu Val Leu Gln Glu Met Ala Met
130                 135                 140

Thr Asn Gln Glu Asn Ala Gln Arg Gln Ile Asn Glu Leu Thr Asp Leu
145                 150                 155                 160

Lys Leu Gln Leu Asp Lys Lys Leu Lys Asp Phe Asp Thr Asp Val Ala
                165                 170                 175

Thr Ala Gln Gly Ile Leu Ser Thr Asp Gly Thr Gly Lys Ile Asp Gln
            180                 185                 190

Leu Lys Asn Glu Ile Leu Asn Thr Lys Lys Ala Ile Gln Asn Asp Leu
        195                 200                 205

Gln Gln Ile Ala Leu Ile Pro Gly Ala Leu Asn Glu Gln Gly Phe Ala
    210                 215                 220

Ile Phe Lys Glu Val Tyr Ser Leu Ser Lys Glu Ile Ile Glu Pro Ala
225                 230                 235                 240

Ala Gln Ala Gly Val Ala Ala Tyr Asn Lys Gly Lys Glu Ile Asn Asn
                245                 250                 255

Ser Ile Leu Glu Ala Glu Lys Lys Ala Ala Gln Glu Ala Thr Glu Gln
            260                 265                 270

Gly Lys Thr Ala Leu Glu Ile Glu Ser Ala Lys Lys Ala Ala Arg Glu
        275                 280                 285

Ala Ile Glu Lys Ser Lys Gln Gly Glu Ile Ala Ala Ala Ala Ala
    290                 295                 300

Lys Thr Gln Glu Tyr Asp Leu Met Lys Ala Ile Asp Thr Glu Lys Ile
305                 310                 315                 320

Lys Lys Thr Phe Gly Val Phe Ala Glu Val Asn Lys Leu Thr Ala Glu
                325                 330                 335

Gln Arg Ala Tyr Leu Asp Asp Leu Glu Lys Gln Asn Gln Lys Ile Tyr
            340                 345                 350

Asp Leu Thr Thr Lys Leu Ser Ile Ala Asp Leu Gln Lys Ser Met Leu
        355                 360                 365

Leu Leu Thr Gln Asn Asp Leu His Thr Phe Ala Asn Gln Val Asp Val
    370                 375                 380

Glu Leu Asp Leu Leu Lys Arg Tyr Lys Glu Asp Leu Asn Leu Ile Lys
385                 390                 395                 400

```
            Asn Ser Ile Thr Lys Leu Ser Thr Asn Val Asp Thr Asn Glu Gln
                            405                 410                 415

Ser Gln Lys Asp Thr Leu Arg Gln Leu Lys Asn Val Ile Ser Tyr Leu
                        420                 425                 430

Glu Glu Gln Val Tyr Lys Phe His His His His His His
                        435                 440                 445

<210> SEQ ID NO 69
<211> LENGTH: 7777
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (2)..(1165)

<400> SEQUENCE: 69 t atg ttg gag gaa aat gaa atg ata aaa aaa atc cct tac aaa tta ctc      49
  Met Leu Glu Glu Asn Glu Met Ile Lys Lys Ile Pro Tyr Lys Leu Leu
  1               5                   10                  15 gct gta tcg acg tta tta act att aca act gct aat gta gtt tca cca        97
Ala Val Ser Thr Leu Leu Thr Ile Thr Thr Ala Asn Val Val Ser Pro
            20                  25                  30 gta aca act ttt gca agt gaa att gaa caa acg aac aat gaa gat aca       145
Val Thr Thr Phe Ala Ser Glu Ile Glu Gln Thr Asn Asn Glu Asp Thr
        35                  40                  45 gca ctt tct gca aat gaa gtg aga atg aaa gag acc ttg caa aag gct       193
Ala Leu Ser Ala Asn Glu Val Arg Met Lys Glu Thr Leu Gln Lys Ala
    50                  55                  60 gga tta ttt gca aaa tct atg aat gcc tat tct tat atg tta att aag       241
Gly Leu Phe Ala Lys Ser Met Asn Ala Tyr Ser Tyr Met Leu Ile Lys
65                  70                  75                  80 aat cct gat gtg aat ttt gag gga att acc att aat ggg tat gta gat       289
Asn Pro Asp Val Asn Phe Glu Gly Ile Thr Ile Asn Gly Tyr Val Asp
                85                  90                  95 tta cct ggt aga atc gta caa gat caa aag aat gca agg gca cat gcc       337
Leu Pro Gly Arg Ile Val Gln Asp Gln Lys Asn Ala Arg Ala His Ala
            100                 105                 110 gtt act tgg gat acg aaa gta aaa aaa cag ctt tta gat aca ttg aat       385
Val Thr Trp Asp Thr Lys Val Lys Lys Gln Leu Leu Asp Thr Leu Asn
        115                 120                 125 ggt att gtt gaa tac gat aca aca ttt gat aat tat tat gaa aca atg       433
Gly Ile Val Glu Tyr Asp Thr Thr Phe Asp Asn Tyr Tyr Glu Thr Met
    130                 135                 140 ata gag gcg att aat aca gga gat gga gaa act tta aaa gaa ggg att       481
Ile Glu Ala Ile Asn Thr Gly Asp Gly Glu Thr Leu Lys Glu Gly Ile
145                 150                 155                 160 aca gat tta cga ggt gaa att caa caa aat caa aag tat gca caa caa       529
Thr Asp Leu Arg Gly Glu Ile Gln Gln Asn Gln Lys Tyr Ala Gln Gln
                165                 170                 175 cta ata gaa gaa tta act aaa tta aga gac tct att gga cac gat gtt       577
Leu Ile Glu Glu Leu Thr Lys Leu Arg Asp Ser Ile Gly His Asp Val
            180                 185                 190 aga gca ttt gga agt aat aaa gag ctc ttg cag tca att tta aaa aat       625
Arg Ala Phe Gly Ser Asn Lys Glu Leu Leu Gln Ser Ile Leu Lys Asn
        195                 200                 205 caa ggt gca gat gtt gat gcc gat caa aag cgt cta gaa gaa gta tta       673
Gln Gly Ala Asp Val Asp Ala Asp Gln Lys Arg Leu Glu Glu Val Leu
    210                 215                 220
```

```
gga tca gta aac tat tat aaa caa tta gaa tct gat ggg ttt aat gta    721
Gly Ser Val Asn Tyr Tyr Lys Gln Leu Glu Ser Asp Gly Phe Asn Val
225                 230                 235                 240 atg aag ggc gct att ttg ggt cta cca ata att ggc ggt atc ata gtg    769
Met Lys Gly Ala Ile Leu Gly Leu Pro Ile Ile Gly Gly Ile Ile Val
            245                 250                 255 gga gta gca agg gat aat tta ggt aag tta gag cct tta tta gca gaa    817
Gly Val Ala Arg Asp Asn Leu Gly Lys Leu Glu Pro Leu Leu Ala Glu
        260                 265                 270 tta cgt cag acc gtg gat tat aaa gta acc tta aat cgt gta gtt gga    865
Leu Arg Gln Thr Val Asp Tyr Lys Val Thr Leu Asn Arg Val Val Gly
    275                 280                 285 gtt gct tac agt aat att aat gaa atg cac aag gcg ctt gat gat gct    913
Val Ala Tyr Ser Asn Ile Asn Glu Met His Lys Ala Leu Asp Asp Ala
290                 295                 300 att aac gct ctt act tat atg tcc acg cag tgg cat gat tta gat tct    961
Ile Asn Ala Leu Thr Tyr Met Ser Thr Gln Trp His Asp Leu Asp Ser
305                 310                 315                 320 caa tat tcg ggc gtt cta ggg cat att gag aat gca gct caa aaa gcc   1009
Gln Tyr Ser Gly Val Leu Gly His Ile Glu Asn Ala Ala Gln Lys Ala
            325                 330                 335 gat caa aat aaa ttt aaa ttc tta aaa cct aat tta aat gca gcg aaa   1057
Asp Gln Asn Lys Phe Lys Phe Leu Lys Pro Asn Leu Asn Ala Ala Lys
        340                 345                 350 gac agt tgg aaa aca tta cga aca gat gct gtt aca tta aaa gaa gga   1105
Asp Ser Trp Lys Thr Leu Arg Thr Asp Ala Val Thr Leu Lys Glu Gly
    355                 360                 365 ata aag gaa tta aaa gtg gaa act gtt act cca caa aaa cat cat cat   1153
Ile Lys Glu Leu Lys Val Glu Thr Val Thr Pro Gln Lys His His His
370                 375                 380 cac cat cac taa taaggatccc gggggtaag aattcggctg ctaacaaagc        1205
His His His
385 ccgaaaggaa gctgagttgg ctgctgccac cgctgagcaa taactagcat aaccccttgg 1265 ggcctctaaa cgggtcttga ggggtttttt gctgaaagga ggaactatat ccggatcgga 1325 gatcaattct ggcgtaatag cgaagaggcc cgcaccgatc gcccttccca acagttgcgt 1385 agcctgaatg gcgaatggga cgcgccctgt agcggcgcat aagcgcggc gggtgtggtg 1445 gttacgcgca gcgtgaccgc tacacttgcc agcgccctag cgcccgctcc tttcgctttc 1505 ttcccttcct ttctcgccac gttcgccggc tttccccgtc aagctctaaa tcggggctc 1565 cctttagggt tccgatttag tgctttacgg cacctcgacc ccaaaaaact tgattagggt 1625 gatggttcac gtagtgggcc atcgccctga tagacggttt ttcgcccttt gacgttggag 1685 tccacgttct ttaatagtgg actcttgttc caaactggaa caacactcaa ccctatctcg 1745 gtctattctt ttgatttata agggattttg ccgatttcgg cctattggtt aaaaaatgag 1805 ctgatttaac aaaaatttaa cgcgaatttt aacaaaatat aacgtttac aatttcaggt 1865 ggcactttc ggggaaatgt gcgcggaacc cctatttgtt tatttttcta atacattca 1925 aatatgtatc cgctcatgag acaataaccc tgataaatgc ttcaataata ttgaaaaagg 1985 aagagtatga gtattcaaca tttccgtgtc gcccttattc cctttttgc ggcattttgc 2045 cttcctgttt ttgctcaccc agaaacgctg gtgaaagtaa aagatgctga agatcagttg 2105 ggtgcacgag tgggttacat cgaactggat ctcaacagcg gtaagatcct gagagttt 2165 cgccccgaag aacgttttcc aatgatgagc acttttaaag ttctgctatg tggcgcggta 2225 ttatcccgta ttgacgccgg gcaagagcaa ctcggtcgcc gcatacacta ttctcagaat 2285
```

```
gacttggttg agtactcacc agtcacagaa aagcatctta cggatggcat gacagtaaga    2345
gaattatgca gtgctgccat aagcatgagt gataacactg cggccaactt acttctgaca    2405
acgatcggag gaccgaagga gctaaccgct ttttttcaca acatggggga tcatgtaact    2465
cgccttgatc gttgggaacc ggagctgaat gaagccatac caaacgacga gcgtgacacc    2525
acgatgcctg tagcaatggc aacaacgttg cgcaaactat taactggcga actacttact    2585
ctagcttccc ggcaacaatt aatagactgg atggaggcgg ataaagttgc aggaccactt    2645
ctgcgctcgg cccttccggc tggctggttt attgctgata atctggagc cggtgagcgt    2705 gggtctcgcg gtatcattgc agcactgggg ccagatggta agccctcccg tatcgtagtt    2765
atctacacga cgggcagtca ggcaactatg gatgaacgaa atagacagat cgctgagata    2825
ggtgcctcac tgattaagca ttggtaactg tcagaccaag tttactcata tatactttag    2885
attgatttaa aacttcattt ttaatttaaa aggatctagg tgaagatcct ttttgataat    2945
ctcatgacca aaatccctta acgtgagttt tcgttccact gagcgtcaga ccccgtagaa    3005
aagatcaaag gatcttcttg agatcctttt tttctgcgcg taatctgctg cttgcaaaca    3065
aaaaaaccac cgctaccagc ggtggtttgt ttgccggatc aagagctacc aactcttttt    3125
ccgaaggtaa ctggcttcag cagagcgcag ataccaaata ctgtccttct agtgtagccg    3185
tagttaggcc accacttcaa gaactctgta gcaccgccta catacctcgc tctgctaatc    3245
ctgttaccag tggctgctgc cagtggcgat aagtcgtgtc ttaccgggtt ggactcaaga    3305
cgatagttac cggataaggc gcagcggtcg ggctgaacgg ggggttcgtg cacacagccc    3365
agcttggagc gaacgaccta caccgaactg agatacctac agcgtgagca ttgagaaagc    3425
gccacgcttc ccgaagggag aaaggcggac aggtatccgg taagcggcag gtcggaaca    3485 ggagagcgca cgagggagct ccaggggggg aacgcctggt atctttatag tcctgtcggg    3545
tttcgccacc tctgacttga gcgtcgattt ttgtgatgct cgtcaggggg gcggagccta    3605
tggaaaaacg ccagcaacgc ggccttttta cggttcctgg ccttttgctg gccttttgct    3665
cacatgttct ttcctgcgtt atcccctgat tctgtggata accgtattac cgcctttgag    3725
tgagctgata ccgctcgccg cagccgaacg accgagcgca gcgagtcagt gagcgaggaa    3785
gcggaagagc gcctgatgcg gtattttctc cttacgcatc tgtgcggtat ttcacaccgc    3845
atatatggtg cactctcagt acaatctgct ctgatgccgc atagttaagc cagtatacac    3905
tccgctatcg ctacgtgact gcaaggagat ggcgcccaac agtccccgg ccacggggcc    3965 tgccaccata cccacgccga acaagcgct catgagcccg aagtggcgag cccgatcttc    4025
cccatcggtg atgtcggcga tataggcgcc agcaaccgca cctgtggcgc cggtgatgcc    4085
ggccacgatg cgtccggcgt agaggatcga gatccaggaa acaaaaacg attttttgag    4145 gaaagttata aattattttc cgaacgatat ggcaagcaaa atattgctta tgcaacagtt    4205
cataatgatg agcaaacccc tcacatgcat ttaggtgttg tgcctatgcg tgatggaaaa    4265
ctgcaaggaa aaaatgtgtt taatcgtcaa gaactgttat ggctacaaga taaattcccc    4325
gagcacatga aaaacaggg ttttgagttg aagcgtggtg aacgtggctc tgaccgtaaa    4385
catattgaga cagctaaatt taaaaaacaa actttggaaa aagagattga ttttctagaa    4445
aaaaatttag cagttaaaaa agatgaatgg actgcttata gcgataaagt taaatcagat    4505
ttagaagtac cagcgaaacg acacatgaaa agtgttgaag tgccaacggg tgaaaagtcc    4565
atgtttggtt tgggaaaaga aataatgaaa acagaaaaga aaccaaccaa aaatgttgtt    4625
```

```
atatcggagc gtgattataa aaacttagtg actgctgcga gagataacga taggttaaaa    4685
cagcatgtta gaaatctcat gagtactgat atggcgagag aatataaaaa attaagtaaa    4745
gaacatgggc aagttaaaga aaaatatagt ggtcttgtag agcgatttaa tgaaaatgta    4805
aatgattata atgagttgct tgaagaaaac aagtctttaa agtctaaaat aagcgattta    4865
aagcgtgatg tgagtttaat ctatgaaagc actaaggaat tccttaagga acgtacagac    4925
ggcttaaaag cctttaaaaa cgttttaag gggtttgtag acaaggtaaa ggataaaaca     4985
gcacaattcc aagaaaaaca cgatttagaa cctaaaaaga acgaatttga actaactcat    5045
aaccgagagg taaaaaaga acgaagtcga gatcagggaa tgagtttata aaataaaaaa    5105
agcacctgaa aaggtgtctt ttttgatgg ttttgaactt gttctttctt atcttgatac     5165
atatagaaat aacgtcattt ttattttagt tgctgaaagg tgcgttgaag tgttggtatg    5225
tatgtgtttt aaagtattga aaaccettaa aattggttgc acagaaaaac cccatctgtt    5285
aaagttataa gtgactaaac aaataactaa atagatgggg gtttctttta atattatgtg    5345
tcctaatagt agcatttatt cagatgaaaa atcaagggtt ttagtggaca agacaaaaag    5405
tggaaaagtg agaccatgga gagaaaagaa aatcgctaat gttgattact ttgaacttct    5465
gcatattctt gaatttaaaa aggctgaaag agtaaaagat tgtgctgaaa tattagagta    5525
taaacaaaat cgtgaaacag gcgaaagaaa gttgtatcga gtgtggtttt gtaaatccag    5585
gctttgtcca atgtgcaact ggaggagagc aatgaaacat ggcattcagt cacaaaaggt    5645
tgttgctgaa gttattaaac aaaagccaac agttcgttgg ttgtttctca cattaacagt    5705
taaaaatgtt tatgatggcg aagaattaaa taagagtttg tcagatatgg ctcaaggatt    5765
tcgccgaatg atgcaatata aaaaaattaa taaaaatctt gttggtttta tgcgtgcaac    5825
ggaagtgaca ataaataata aagataattc ttataatcag cacatgcatg tattggtatg    5885
tgtggaacca acttatttta agaatacaga aaactacgtg aatcaaaaac aatggattca    5945
attttggaaa aaggcaatga aattagacta tgatccaaat gtaaaagttc aaatgattcg    6005
accgaaaaat aaatataaat cggatataca atcggcaatt gacgaaactg caaatatcc     6065 tgtaaaggat acggatttta tgaccgatga tgaagaaaag aatttgaaac gtttgtctga    6125
tttggaggaa ggtttacacc gtaaaaggtt aatctcctat ggtggtttgt taaaagaaat    6185
acataaaaaa ttaaacctty atgacacaga agaaggcgat tgattcata cagatgatga      6245 cgaaaaagcc gatgaagatg gatttctat tattgcaatg tggaattggg aacggaaaaa     6305 ttatttatt aaagagtagt tcaacaaacg ggccagtttg ttgaagatta gatgctataa     6365
ttgttattaa aaggattgaa ggatgcttag gaagacgagt tattaatagc tgaataagaa    6425
cggtgctctc caaatattct tatttagaaa agcaaatcta aaattatctg aaagggaat    6485 gagaatagtg aatggaccaa taataatgac tagagaagaa agaatgaaga ttgttcatga    6545
aattaaggaa cgaatattgg ataaaatatg ggatgatgtt aaggctattg gtgtttatgg    6605
ctctcttggt cgtcagactg atgggcccta ttcggatatt gagatgatgt gtgtcatgtc    6665
aacagaggaa gcagagttca gccatgaatg gacaaccggt gagtggaagg tggaagtgaa    6725
ttttgatagc gaagagattc tactagatta tgcatctcag gtggaatcag attggccgct    6785
tacacatggt caatttttct ctattttgcc gatttatgat tcaggtggat acttagagaa    6845
agtgtatcaa actgctaaat cggtagaagc ccaaacgttc cacgatgcga tttgtgccct    6905
tatcgtagaa gagctgtttg aatatgcagg caaatgcgt aatattcgtg tgcaaggacc     6965
gacaacattt ctaccatcct tgactgtaca ggtagcaatg gcaggtgcca tgttgattgg    7025
```

-continued

```
tctgcatcat cgcatctgtt atacgacgag cgcttcggtc ttaactgaag cagttaagca      7085
atcagatctt ccttcaggtt atgaccatct gtgccagttc gtaatgtctg gtcaactttc      7145
cgactctgag aaacttctgg aatcgctaga gaatttctgg aatgggattc aggagtggac      7205
agaacgacac ggatatatag tggatgtgtc aaaacgcata ccattttgaa cgatgacctc      7265
taataattgt taatcatgtt ggttacgtat ttattaactt ctcctagtat tagtaattat      7325
catggctgtc atggcgcatt aacgaataaa agggtgtgct taaatcgggc cattttgcgt      7385
aataagaaaa aggattaatt atgagcgaat tgaattaata ataaggtaat agatttacat      7445
tagaaaatga aagggatttt tatgcgtgag aatgttacag tctatcccgg cattgccagt      7505
cggggatatt aaaaagagta taggtttttta ttgcgataaa ctaggtttca ctttggttca      7565
ccatgaagat ggattcgcag ttctaatgtg taatgaggtt cggattcatc ctattaaaca      7625
tataaattct ttttatgtt atatatttat aaaagttctg tttaaaaagc caaaaataaa       7685
taattatctc ttttatttta tattatattg aaactaaagt ttattaatttt caatataata    7745 taaatttaat tttatacaaa aaggagaacg ca                                    7777
```

<210> SEQ ID NO 70
<211> LENGTH: 387
<212> TYPE: PRT
<213> ORGANISM: Artificial Sequence
<220> FEATURE:
<223> OTHER INFORMATION: Synthetic

<400> SEQUENCE: 70

```
Met Leu Glu Glu Asn Glu Met Ile Lys Lys Ile Pro Tyr Lys Leu Leu
1               5                   10                  15

Ala Val Ser Thr Leu Leu Thr Ile Thr Thr Ala Asn Val Val Ser Pro
            20                  25                  30

Val Thr Thr Phe Ala Ser Glu Ile Glu Gln Thr Asn Asn Glu Asp Thr
        35                  40                  45

Ala Leu Ser Ala Asn Glu Val Arg Met Lys Glu Thr Leu Gln Lys Ala
    50                  55                  60

Gly Leu Phe Ala Lys Ser Met Asn Ala Tyr Ser Tyr Met Leu Ile Lys
65                  70                  75                  80

Asn Pro Asp Val Asn Phe Glu Gly Ile Thr Ile Asn Gly Tyr Val Asp
                85                  90                  95

Leu Pro Gly Arg Ile Val Gln Asp Gln Lys Asn Ala Arg Ala His Ala
            100                 105                 110

Val Thr Trp Asp Thr Lys Val Lys Lys Gln Leu Leu Asp Thr Leu Asn
        115                 120                 125

Gly Ile Val Glu Tyr Asp Thr Thr Phe Asp Asn Tyr Tyr Glu Thr Met
    130                 135                 140

Ile Glu Ala Ile Asn Thr Gly Asp Gly Glu Thr Leu Lys Glu Gly Ile
145                 150                 155                 160

Thr Asp Leu Arg Gly Glu Ile Gln Gln Asn Gln Lys Tyr Ala Gln Gln
                165                 170                 175

Leu Ile Glu Glu Leu Thr Lys Leu Arg Asp Ser Ile Gly His Asp Val
            180                 185                 190

Arg Ala Phe Gly Ser Asn Lys Glu Leu Leu Gln Ser Ile Leu Lys Asn
        195                 200                 205

Gln Gly Ala Asp Val Asp Ala Asp Gln Lys Arg Leu Glu Glu Val Leu
    210                 215                 220
```

Gly Ser Val Asn Tyr Tyr Lys Gln Leu Glu Ser Asp Gly Phe Asn Val
225                 230                 235                 240

Met Lys Gly Ala Ile Leu Gly Leu Pro Ile Ile Gly Gly Ile Ile Val
            245                 250                 255

Gly Val Ala Arg Asp Asn Leu Gly Lys Leu Glu Pro Leu Leu Ala Glu
        260                 265                 270

Leu Arg Gln Thr Val Asp Tyr Lys Val Thr Leu Asn Arg Val Val Gly
    275                 280                 285

Val Ala Tyr Ser Asn Ile Asn Glu Met His Lys Ala Leu Asp Asp Ala
290                 295                 300

Ile Asn Ala Leu Thr Tyr Met Ser Thr Gln Trp His Asp Leu Asp Ser
305                 310                 315                 320

Gln Tyr Ser Gly Val Leu Gly His Ile Glu Asn Ala Ala Gln Lys Ala
            325                 330                 335

Asp Gln Asn Lys Phe Lys Phe Leu Lys Pro Asn Leu Asn Ala Ala Lys
        340                 345                 350

Asp Ser Trp Lys Thr Leu Arg Thr Asp Ala Val Thr Leu Lys Glu Gly
    355                 360                 365

Ile Lys Glu Leu Lys Val Glu Thr Val Thr Pro Gln Lys His His His
    370                 375                 380

His His His
385

<210> SEQ ID NO 71
<211> LENGTH: 386
<212> TYPE: PRT
<213> ORGANISM: Bacillus anthracis

<400> SEQUENCE: 71

Met Gly Lys Thr Ser Lys Tyr Val Thr Ala Ala Ala Leu Cys Ser Thr
1               5                   10                  15

Ile Val Met Gly Gly Leu His Ala Ser Ser Val Ser Tyr Ala Ala Thr
            20                  25                  30

Asn Pro Thr Val Ala Thr Leu Gln Ser Asp Ala Lys Leu Leu Asn Asp
        35                  40                  45

Phe Lys Lys Glu Leu Lys Lys Gln Ile Asp Asn Arg Glu Glu Asn Ile
    50                  55                  60

Thr Ile Thr Tyr Lys Thr Lys Asp Arg Asn Ala Arg Asn Ile Met Asp
65                  70                  75                  80

Glu Leu Tyr Gly Glu Phe Asn Lys Ile Val Asp Ala Asp Glu Tyr Val
                85                  90                  95

Lys Tyr Asn Ile Ala Ser Thr Arg Tyr Ser Ile Lys Gly Leu Pro Gly
            100                 105                 110

Asn Tyr Thr Phe Thr Leu Gln Val Lys Tyr Arg Glu Ser Lys Glu Gln
        115                 120                 125

Thr Gln Tyr Val Lys Ser Gln Ala Lys Ala Ile Gly Ser Ile Val
    130                 135                 140

Lys Pro Gly Met Asp Glu His Glu Lys Val Lys Ala Ile His Asp Tyr
145                 150                 155                 160

Val Val Lys His Val Ser Tyr Asp Thr Ser Tyr Gln Ala Tyr Thr Ala
                165                 170                 175

Tyr Glu Ala Leu Ala Asn Arg Ser Ala Val Cys Gln Gly Tyr Thr Leu
            180                 185                 190

Leu Thr Tyr Glu Leu Leu Lys Glu Ala Gly Ile Gln Asn Arg Ile Val
        195                 200                 205

Thr Gly Thr Gly Asn Gly Gln Ala His Ser Trp Asn Leu Val Asn Ile
            210                 215                 220

Glu Asn Lys Trp Tyr His Leu Asp Thr Thr Phe Asp Pro Val Pro
225                 230                 235                 240

Asp Lys Ala Gly Arg Val Thr Tyr Ser Tyr Phe Asn Met Ser Asp Glu
                245                 250                 255

Gln Leu Ser Lys Asp His Asp Trp Asp Arg Ser Lys Tyr Pro Ala Ala
            260                 265                 270

Thr Thr Ser Tyr Phe Asn Glu Leu Thr Asn Lys Ile Lys Ala Gly Ser
            275                 280                 285

Ser Lys Thr Ala Thr Tyr Glu Gln Met Leu Lys Glu Thr Asn Leu Lys
            290                 295                 300

Tyr Leu Ser Ala Gln Tyr Gly Ala Asp Asn Tyr Ser Glu Phe Lys Glu
305                 310                 315                 320

Lys Leu Gln Gln Gln Phe Ala Ser Lys Pro Glu Lys Val Glu Val Arg
                325                 330                 335

Tyr Lys Gln Ser Met Asp Gly Thr Met Gln Asp Ile Lys Lys Val Leu
            340                 345                 350

Asn Glu Ile Asn Trp Pro Lys Gly Ala Lys Arg Val Ser Tyr Gln Val
            355                 360                 365

Ala Pro Tyr Ser Ala Met Ala Asp Tyr Ser Leu Ala Thr Ile Thr Phe
            370                 375                 380

Thr Tyr
385

<210> SEQ ID NO 72
<211> LENGTH: 82
<212> TYPE: PRT
<213> ORGANISM: Artificial Sequence
<220> FEATURE:
<223> OTHER INFORMATION: Synthetic

<400> SEQUENCE: 72

Met Gly Lys Thr Ser Lys Tyr Val Thr Ala Ala Ala Leu Cys Ser Thr
1               5                   10                  15

Thr Ser Ser Arg Ala Ala Ala Thr Ala Val Glu Leu Glu Val Pro Ile
            20                  25                  30

Pro Lys Phe Leu Phe Ser Arg Lys Tyr Arg Asn Phe Gln Leu Leu Glu
            35                  40                  45

Asn Glu Ile Asn Trp Pro Lys Gly Ala Lys Arg Val Ser Tyr Gln Val
50                  55                  60

Ala Pro Tyr Ser Ala Met Ala Asp Tyr Ser Leu Ala Thr Ile Thr Phe
65                  70                  75                  80

Thr Tyr

<210> SEQ ID NO 73
<211> LENGTH: 213
<212> TYPE: DNA
<213> ORGANISM: Artificial Sequence
<220> FEATURE:
<223> OTHER INFORMATION: Synthetic

<400> SEQUENCE: 73
tgttcaacta ctagttctag agcggccgcc accgcggtgg agctcgaagt tcctattccg      60
aagttcctat tctctagaaa gtataggaac ttccagctgc tcgagaatga aataaactgg     120
ccaaaaggtg caaagcgtgt atcttatcaa gtagcaccat atagtgctat ggcagattat     180
tcattagcga caattacatt tacgtattaa tcg 213

<210> SEQ ID NO 74
<211> LENGTH: 70
<212> TYPE: PRT
<213> ORGANISM: Artificial Sequence
<220> FEATURE:
<223> OTHER INFORMATION: Synthetic

<400> SEQUENCE: 74

```
Cys Ser Thr Thr Ser Ser Arg Ala Ala Ala Thr Ala Val Glu Leu Glu
1               5                   10                  15

Val Pro Ile Pro Lys Phe Leu Phe Ser Arg Lys Tyr Arg Asn Phe Gln
            20                  25                  30

Leu Leu Glu Asn Glu Ile Asn Trp Pro Lys Gly Ala Lys Arg Val Ser
        35                  40                  45

Tyr Gln Val Ala Pro Tyr Ser Ala Met Ala Asp Tyr Ser Leu Ala Thr
    50                  55                  60

Ile Thr Phe Thr Tyr Ser
65                  70
```

<210> SEQ ID NO 75
<211> LENGTH: 917
<212> TYPE: PRT
<213> ORGANISM: Bacillus anthracis

<400> SEQUENCE: 75

```
Met Lys Lys Thr Thr Ser Ile Leu Leu Ser Met Ala Leu Val Phe Ser
1               5                   10                  15

Ser Phe Gly Ala Leu Ser Ala His Ala Glu Ser Leu Gln Lys Glu Lys
            20                  25                  30

Gln Phe Ser Pro Gln Leu Lys Thr Thr Ile Glu Gln Trp Gly Glu Ser
        35                  40                  45

Lys Ile Ala Gln His Val Glu Thr Lys Thr Thr Lys Glu Ile Ser Val
    50                  55                  60

Ile Val Glu Leu Gln His Ala Pro Leu Ala Ala Gln Ser Asn Ile Gln
65                  70                  75                  80

His Ala Pro Asp Leu Gln Asn Ser His Ala Gln Ser Tyr His Thr Glu
            85                  90                  95

Leu Lys Lys Ala Gln Glu Glu Thr Thr Lys Lys Ile Lys Glu Lys Ala
            100                 105                 110

Pro Gly Ala Lys Ile Lys Glu Val Tyr Asn Thr Leu Phe Ser Gly Phe
        115                 120                 125

Ser Ile Ser Val Pro Gly Asp Gln Ile Thr Ala Leu Ala Ser Leu Pro
    130                 135                 140

Glu Val Lys Thr Val Tyr Pro Asn Leu Thr Tyr Lys Leu His Glu Thr
145                 150                 155                 160

Thr Lys Ser Ala Thr Ser Glu Glu Ala Pro Asn Ile Gly Gly Pro Thr
            165                 170                 175

Ile Gly Ala Pro Glu Ala Trp Asn Leu Lys Asp Pro Ser Gly Lys Ser
        180                 185                 190

Leu Asp Gly Lys Gly Met Lys Val Ala Ile Ile Asp Ser Gly Val Asp
    195                 200                 205

Tyr Thr His Pro Asp Leu Lys Ala Asn Tyr Ile Gly Gly Tyr Asp Thr
    210                 215                 220

Val Asp Glu Asp Ala Asp Pro Met Asp Gly Asn Val His Gly Thr His
```

```
                225                 230                 235                 240
        Val Ala Gly Ile Ile Ala Gly Asn Gly Lys Ile Lys Gly Val Ala Pro
                        245                 250                 255
        Asn Ala Ser Ile Leu Ala Tyr Arg Val Met Asn Asp Gly Gly Thr Gly
                        260                 265                 270
        Thr Thr Asp Asp Ile Ile Gln Gly Ile Glu Arg Ala Ile Gln Asp Gly
                        275                 280                 285
        Ala Asp Val Leu Asn Leu Ser Leu Gly Gln Asp Leu Asn Val Pro Asp
                        290                 295                 300
        Gln Pro Val Thr Leu Thr Leu Glu Arg Ala Ala Lys Leu Gly Ile Thr
        305                 310                 315                 320
        Ala Val Val Ser Asn Gly Asn Asp Gly Pro Lys Pro Trp Ser Val Asp
                        325                 330                 335
        Ala Pro Gly Asn Ala Ser Ser Val Ile Ser Val Gly Ala Ser Thr Val
                        340                 345                 350
        Ser Ile Pro Phe Pro Thr Phe Gln Val Ala Gly Ser Ser Lys Thr Tyr
                        355                 360                 365
        Gln Gly Leu Ser Leu Ser Lys Ser Asp Phe Pro Ile Gly Asn Asp Ser
                        370                 375                 380
        Pro Leu Val Tyr Val Gly Tyr Gly Asn Pro Ser Asp Tyr Ala Lys Gln
        385                 390                 395                 400
        Asp Val Lys Gly Lys Phe Ala Leu Val Leu Gln Gly Thr Ser Ser Thr
                        405                 410                 415
        Leu Val Lys Ala Glu Gln Ala Lys Gln Ala Gly Ala Ile Gly Val Leu
                        420                 425                 430
        Phe Ile Ser Thr Glu Lys Glu Met Asn Ser Met Pro Glu Tyr Phe Thr
                        435                 440                 445
        Arg Glu Asn Leu Ala Leu Pro Val Met Gln Leu Ser Asn Val Asn Gly
                        450                 455                 460
        Glu Glu Leu Lys Asn Leu Ile Thr Lys Arg Lys Lys Asn Ile Lys Ile
        465                 470                 475                 480
        Gly Gln Pro Val Pro Thr Glu Leu Ile Gly Asn Phe Ser Ser Arg Gly
                        485                 490                 495
        Pro Ser Gln Gly Ser Trp Leu Ile Lys Pro Asp Ile Val Ala Pro Gly
                        500                 505                 510
        Val Gln Ile Thr Ser Thr Val Pro Arg Gly Gly Tyr Glu Ser His Asn
                        515                 520                 525
        Gly Thr Ser Met Ala Ala Pro Gln Val Ala Gly Ala Val Ala Leu Leu
                        530                 535                 540
        Arg Gln Met His Pro Asp Trp Thr Thr Gln Gln Leu Lys Ala Ser Leu
        545                 550                 555                 560
        Ala Asn Thr Ala Lys Thr Leu Lys Asp Val Asn Glu Asn Thr Tyr Pro
                        565                 570                 575
        Ile Met Thr Gln Gly Ser Gly Leu Ile Asn Ile Pro Lys Ala Ala Gln
                        580                 585                 590
        Thr Asp Val Leu Val Lys Pro Asn Asn Val Ser Phe Gly Leu Ile Lys
                        595                 600                 605
        Pro Asn Ser Gly Lys Val Lys Leu Thr Gln Asn Ile Thr Leu Gln Asn
                        610                 615                 620
        Leu Ser Ser Lys Lys Lys Ser Phe Ser Thr Arg Val Glu Leu Leu Asp
        625                 630                 635                 640
        Thr Asn Thr Lys Thr Lys Val Lys Thr Ser Val Pro Ser Ser Ile Ser
                        645                 650                 655
```

```
Ile Gln Pro Asn Ser Ser Thr Glu Lys Pro Phe Thr Ile Thr Val Asp
            660                 665                 670

Ser Ser Leu Pro Gln Gly Val Tyr Thr Gly Asn Val Tyr Val Lys Glu
        675                 680                 685

Gln Gly Ala Lys Glu Thr Arg Ile Pro Phe Thr Phe Ser Ile Asp
    690                 695                 700

Pro Lys Asp Tyr Lys Arg Ile Asp Gly Leu Glu Ile Ile Asn Ser Thr
705                 710                 715                 720

Phe Ser Pro Asn Gly Asp Gln Ile Leu Asp Asp Asn Leu Ile Asn Tyr
                725                 730                 735

Tyr Leu Val Ala Pro Val Asp Asp Val Thr Leu His Ala Asn Leu Val
            740                 745                 750

Thr Lys Glu Arg Val Thr Tyr Gln Gly Ile Ile His Gln Ala Lys Asn
        755                 760                 765

Glu Thr Ala Gly Tyr Lys Pro Phe Lys Trp Asp Gly Thr Lys Ala Asp
    770                 775                 780

Gly Thr Pro Leu Ala Asp Gly Leu Tyr Gln Ile Glu Ala Val Ala Ser
785                 790                 795                 800

Asn Ser Gly Gly Glu Thr Lys Gln Thr Ala Ala Val Phe Leu Asp Arg
                805                 810                 815

Thr Ala Pro Lys Leu Thr Tyr Glu Ile Asp Gln Glu Asn Leu Val Ile
            820                 825                 830

Thr Gly Lys Val Asp Asp Ile Leu Leu Asp Trp Met Thr Glu Ser Gly
        835                 840                 845

Trp Val Ala Pro Gly Ile Pro Val Arg Leu Gln Tyr Glu Ile Asn Gly
    850                 855                 860

Asn Gly Val Trp Glu Ser Ala Phe Leu Asn Pro Trp Glu Lys Asn Tyr
865                 870                 875                 880

Gly Ile Tyr Leu Asp Arg Thr Gln Leu Gln Glu Gly Lys Asn Thr Ile
                885                 890                 895

His Ile Val Ala Thr Asp Ala Ala Gly Asn Thr Ser Asn Leu Asn Val
            900                 905                 910

Asp Leu Asp Val Lys
            915

<210> SEQ ID NO 76
<211> LENGTH: 14
<212> TYPE: PRT
<213> ORGANISM: Artificial Sequence
<220> FEATURE:
<223> OTHER INFORMATION: Synthetic

<400> SEQUENCE: 76

Met Lys Lys Thr Thr Ser Ile Leu Leu Ser Met Ala Leu Asp
1               5                   10

<210> SEQ ID NO 77
<211> LENGTH: 105
<212> TYPE: DNA
<213> ORGANISM: Artificial Sequence
<220> FEATURE:
<223> OTHER INFORMATION: Synthetic
<220> FEATURE:
<221> NAME/KEY: exon
<222> LOCATION: (1)..(105)

<400> SEQUENCE: 77 atg gca ctc gac tag ttc tag agc ggc cgc cac cgc ggt ggt gga gct      48
```

```
Met Ala Leu Asp     Phe      Ser Gly Arg His Arg Gly Gly Gly Ala
1              5                    10 cga agt tat tcc gaa gtt cct att ctc tag aaa gta tag gaa ctt cca      96
Arg Ser Tyr Ser Glu Val Pro Ile Leu     Lys Val     Glu Leu Pro
15              20                          25 gct gct cga                                                          105
Ala Ala Arg
     30

<210> SEQ ID NO 78
<211> LENGTH: 4
<212> TYPE: PRT
<213> ORGANISM: Artificial Sequence
<220> FEATURE:
<223> OTHER INFORMATION: Synthetic

<400> SEQUENCE: 78

Met Ala Leu Asp
1

<210> SEQ ID NO 79
<211> LENGTH: 30
<212> TYPE: DNA
<213> ORGANISM: Artificial Sequence
<220> FEATURE:
<223> OTHER INFORMATION: Synthetic

<400> SEQUENCE: 79
actgctcgag tgggctgaca catttaaaag                                      30

<210> SEQ ID NO 80
<211> LENGTH: 30
<212> TYPE: DNA
<213> ORGANISM: Artificial Sequence
<220> FEATURE:
<223> OTHER INFORMATION: Synthetic

<400> SEQUENCE: 80
actgactagt agttgaacaa agtgcggcag                                      30

<210> SEQ ID NO 81
<211> LENGTH: 35
<212> TYPE: DNA
<213> ORGANISM: Artificial Sequence
<220> FEATURE:
<223> OTHER INFORMATION: Synthetic

<400> SEQUENCE: 81
actgctcgag aatgaaataa actggccaaa aggtg                                35

<210> SEQ ID NO 82
<211> LENGTH: 30
<212> TYPE: DNA
<213> ORGANISM: Artificial Sequence
<220> FEATURE:
<223> OTHER INFORMATION: Synthetic

<400> SEQUENCE: 82
actgactagt cgggaaaaac ttcaaatcca                                      30

<210> SEQ ID NO 83
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 83
ttgccagagc ttttcattga                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
cgctaatgaa taatctgcca                                              20

<210> SEQ ID NO 85
<211> LENGTH: 30
<212> TYPE: DNA
<213> ORGANISM: Artificial Sequence
<220> FEATURE:
<223> OTHER INFORMATION: Synthetic

<400> SEQUENCE: 85
actgctcgag aagctgtcgg tactgctaaa                                   30

<210> SEQ ID NO 86
<211> LENGTH: 35
<212> TYPE: DNA
<213> ORGANISM: Artificial Sequence
<220> FEATURE:
<223> OTHER INFORMATION: Synthetic

<400> SEQUENCE: 86
actgactagt cgagtgccat acttaaaagt ataga                             35

<210> SEQ ID NO 87
<211> LENGTH: 36
<212> TYPE: DNA
<213> ORGANISM: Artificial Sequence
<220> FEATURE:
<223> OTHER INFORMATION: Synthetic

<400> SEQUENCE: 87
actgctcgag atccttggga gaaaaattac ggcatt                            36

<210> SEQ ID NO 88
<211> LENGTH: 35
<212> TYPE: DNA
<213> ORGANISM: Artificial Sequence
<220> FEATURE:
<223> OTHER INFORMATION: Synthetic

<400> SEQUENCE: 88
actgactagt cgccaaacat tcattcattt cttct                             35

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
tgagtgaaac ggcgtaactt                                              20

<210> SEQ ID NO 90
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 90
tattccttca aagccgatat                                                    20

<210> SEQ ID NO 91
<211> LENGTH: 538
<212> TYPE: PRT
<213> ORGANISM: Artificial Sequence
<220> FEATURE:
<223> OTHER INFORMATION: Synthetic

<400> SEQUENCE: 91
```

Ala Gly Gly His Gly Asp Val Gly Met His Val Lys Glu Lys Glu Lys
1               5                   10                  15

Asn Lys Asp Glu Asn Lys Arg Lys Asp Glu Arg Asn Lys Thr Gln
            20                  25                  30

Glu Glu His Leu Lys Glu Ile Met Lys His Ile Val Lys Ile Glu Val
        35                  40                  45

Lys Gly Glu Glu Ala Val Lys Lys Glu Ala Ala Glu Lys Leu Leu Glu
    50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser Thr
                245                 250                 255

Arg Phe Thr Gly Glu Ser Leu Gln Val Glu Ala Lys Glu Lys Thr Gly
            260                 265                 270

Gln Val Lys His Lys Asn Gln Ala Thr His Lys Glu Phe Ser Gln Leu
        275                 280                 285

Glu Lys Lys Phe Asp Ala Arg Leu Gly Val Tyr Ala Ile Asp Thr Gly
    290                 295                 300

Thr Asn Gln Thr Ile Ser Tyr Arg Pro Asn Glu Arg Phe Ala Phe Ala
305                 310                 315                 320

```
Ser Thr Tyr Lys Ala Leu Ala Ala Gly Val Leu Leu Gln Gln Asn Ser
            325                 330                 335

Ile Asp Ser Leu Asn Glu Val Ile Thr Tyr Thr Lys Glu Asp Leu Val
            340                 345                 350

Asp Tyr Ser Pro Val Thr Glu Lys His Val Asp Thr Gly Met Lys Leu
            355                 360                 365

Gly Glu Ile Ala Glu Ala Val Arg Ser Ser Asp Asn Thr Ala Gly
            370                 375                 380

Asn Ile Leu Phe Asn Lys Ile Gly Pro Lys Gly Tyr Glu Lys Ala
385                 390                 395                 400

Leu Arg His Met Gly Asp Arg Ile Thr Met Ser Asn Arg Phe Glu Thr
            405                 410                 415

Glu Leu Asn Glu Ala Ile Pro Gly Asp Ile Arg Asp Thr Ser Thr Ala
            420                 425                 430

Lys Ala Ile Ala Thr Asn Leu Lys Ala Phe Thr Val Gly Asn Ala Leu
            435                 440                 445

Pro Ala Glu Lys Arg Lys Ile Leu Thr Glu Trp Met Lys Gly Asn Ala
            450                 455                 460

Thr Gly Asp Lys Leu Ile Arg Ala Gly Ile Pro Thr Asp Trp Val Val
465                 470                 475                 480

Gly Asp Lys Ser Gly Ala Gly Ser Tyr Gly Thr Arg Asn Asp Ile Ala
            485                 490                 495

Val Val Trp Pro Pro Asn Arg Ala Pro Ile Ile Ala Ile Leu Ser
            500                 505                 510

Ser Lys Asp Glu Lys Glu Ala Ile Tyr Asp Asn Gln Leu Ile Ala Glu
            515                 520                 525

Ala Thr Lys Val Ile Val Lys Ala Leu Arg
            530                 535

<210> SEQ ID NO 92
<211> LENGTH: 733
<212> TYPE: PRT
<213> ORGANISM: Artificial Sequence
<220> FEATURE:
<223> OTHER INFORMATION: Synthetic

<400> SEQUENCE: 92

Glu Val Lys Gln Glu Asn Arg Leu Leu Asn Glu Ser Glu Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
            35                  40                  45

Glu Leu Glu Asn Ile Pro Ser Glu Asn Gln Tyr Phe Gln Ser Ala Ile
            50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
            85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
            130                 135                 140
```

-continued

```
Val Ile Ser Ser Asp Asn Leu Gln Leu Pro Glu Leu Lys Gln Lys Ser
145                 150                 155                 160

Ser Asn Ser Ser Asn Lys Glu Ser Thr Ser Ala Gly Pro Thr Val Pro
            165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
            210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
            245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
            275                 280                 285

Ile Ser Lys Asn Thr Ser Thr Ser Arg Thr His Thr Ser Glu Val His
            290                 295                 300

Gly Asn Ala Asp Val His Ala Ser Asp Ile Gly Gly Ser Val Ser Ala
305                 310                 315                 320

Gly Phe Ser Asn Ser Asn Ser Ser Thr Val Ala Ile Asp His Ser Leu
            325                 330                 335

Ser Leu Ala Gly Glu Arg Thr Trp Ala Glu Thr Met Gly Leu Asn Thr
            340                 345                 350

Ala Asp Thr Ala Arg Leu Asn Ala Asn Ile Arg Tyr Val Asn Thr Gly
            355                 360                 365

Thr Ala Pro Ile Tyr Asn Val Leu Pro Thr Thr Ser Leu Val Leu Gly
            370                 375                 380

Lys Asn Gln Thr Leu Ala Thr Ile Lys Ala Lys Glu Asn Gln Leu Ser
385                 390                 395                 400

Gln Ile Leu Ala Pro Asn Asn Tyr Tyr Pro Ser Lys Asn Leu Ala Pro
            405                 410                 415

Ile Ala Leu Asn Ala Gln Asp Asp Phe Ser Ser Thr Pro Ile Thr Met
            420                 425                 430

Asn Tyr Asn Gln Phe Leu Glu Leu Glu Lys Thr Lys Gln Leu Arg Leu
            435                 440                 445

Asp Thr Asp Gln Val Tyr Gly Asn Ile Ala Thr Tyr Asn Phe Glu Asn
            450                 455                 460

Gly Arg Val Arg Val Asp Thr Gly Ser Asn Trp Ser Glu Val Leu Pro
465                 470                 475                 480

Gln Ile Gln Glu Thr Thr Ala Arg Ile Ile Phe Asn Gly Lys Asp Leu
            485                 490                 495

Asn Leu Val Glu Arg Arg Ile Ala Ala Val Asn Pro Ser Asp Pro Leu
            500                 505                 510

Glu Thr Thr Lys Pro Asp Met Thr Leu Lys Glu Ala Leu Lys Ile Ala
            515                 520                 525

Phe Gly Phe Asn Glu Pro Asn Gly Asn Leu Gln Tyr Gln Gly Lys Asp
            530                 535                 540

Ile Thr Glu Phe Asp Phe Asn Phe Asp Gln Gln Thr Ser Gln Asn Ile
545                 550                 555                 560
```

```
Lys Asn Gln Leu Ala Glu Leu Asn Ala Thr Asn Ile Tyr Thr Val Leu
                565                 570                 575

Asp Lys Ile Lys Leu Asn Ala Lys Met Asn Ile Leu Ile Arg Asp Lys
            580                 585                 590

Arg Phe His Tyr Asp Arg Asn Asn Ile Ala Val Gly Ala Asp Glu Ser
        595                 600                 605

Val Val Lys Glu Ala His Arg Glu Val Ile Asn Ser Ser Thr Glu Gly
    610                 615                 620

Leu Leu Leu Asn Ile Asp Lys Asp Ile Arg Lys Ile Leu Ser Gly Tyr
625                 630                 635                 640

Ile Val Glu Ile Glu Asp Thr Glu Gly Leu Lys Glu Val Ile Asn Asp
                645                 650                 655

Arg Tyr Asp Met Leu Asn Ile Ser Ser Leu Arg Gln Asp Gly Lys Thr
            660                 665                 670

Phe Ile Asp Phe Lys Lys Tyr Asn Asp Lys Leu Pro Leu Tyr Ile Ser
        675                 680                 685

Asn Pro Asn Tyr Lys Val Asn Val Tyr Ala Val Thr Lys Glu Asn Thr
    690                 695                 700

Ile Ile Asn Pro Ser Glu Asn Gly Asp Thr Ser Thr Asn Gly Ile Lys
705                 710                 715                 720

Lys Ile Leu Ile Phe Ser Lys Lys Gly Tyr Glu Ile Gly
                725                 730
```

```
<210> SEQ ID NO 93
<211> LENGTH: 767
<212> TYPE: PRT
<213> ORGANISM: Artificial Sequence
<220> FEATURE:
<223> OTHER INFORMATION: Synthetic

<400> SEQUENCE: 93

His Asn Glu His Tyr Thr Glu Ser Asp Ile Lys Arg Asn His Lys Thr
1               5                   10                  15

Glu Lys Asn Lys Thr Glu Lys Glu Lys Phe Lys Asp Ser Ile Asn Asn
            20                  25                  30

Leu Val Lys Thr Glu Phe Thr Asn Glu Thr Leu Asp Lys Ile Gln Gln
        35                  40                  45

Thr Gln Asp Leu Leu Lys Lys Ile Pro Lys Asp Val Leu Glu Ile Tyr
    50                  55                  60

Ser Glu Leu Gly Gly Glu Ile Tyr Phe Thr Ile Asp Leu Val Glu
65                  70                  75                  80

His Lys Glu Leu Gln Asp Leu Ser Glu Glu Lys Asn Ser Met Asn
                85                  90                  95

Ser Arg Gly Glu Lys Val Pro Phe Ala Ser Arg Phe Val Phe Glu Lys
            100                 105                 110

Lys Arg Glu Thr Pro Lys Leu Ile Ile Asn Ile Lys Asp Tyr Ala Ile
        115                 120                 125

Asn Ser Glu Gln Ser Lys Glu Val Tyr Tyr Glu Ile Gly Lys Gly Ile
    130                 135                 140

Ser Leu Asp Ile Ile Ser Lys Asp Lys Ser Leu Asp Pro Glu Phe Leu
145                 150                 155                 160

Asn Leu Ile Lys Ser Leu Ser Asp Asp Ser Asp Ser Ser Asp Leu Leu
                165                 170                 175

Phe Ser Gln Lys Phe Lys Glu Lys Leu Glu Leu Asn Asn Lys Ser Ile
            180                 185                 190
```

```
Asp Ile Asn Phe Ile Lys Glu Asn Leu Thr Glu Phe Gln His Ala Phe
            195                 200                 205

Ser Leu Ala Phe Ser Tyr Tyr Phe Ala Pro Asp His Arg Thr Val Leu
210                 215                 220

Glu Leu Tyr Ala Pro Asp Met Phe Glu Tyr Met Asn Lys Leu Glu Lys
225                 230                 235                 240

Gly Gly Phe Glu Lys Ile Ser Glu Ser Leu Lys Lys Glu Gly Val Glu
            245                 250                 255

Lys Asp Arg Ile Asp Val Leu Lys Gly Glu Lys Ala Leu Lys Ala Ser
            260                 265                 270

Gly Leu Val Pro Glu His Ala Asp Ala Phe Lys Lys Ile Ala Arg Glu
            275                 280                 285

Leu Asn Thr Tyr Ile Leu Phe Arg Pro Val Asn Lys Leu Ala Thr Asn
290                 295                 300

Leu Ile Lys Ser Gly Val Ala Thr Lys Gly Leu Asn Val His Gly Lys
305                 310                 315                 320

Ser Ser Asp Trp Gly Pro Val Ala Gly Tyr Ile Pro Phe Asp Gln Asp
            325                 330                 335

Leu Ser Lys Lys His Gly Gln Gln Leu Ala Val Glu Lys Gly Asn Leu
            340                 345                 350

Glu Asn Lys Lys Ser Ile Thr Glu His Glu Gly Glu Ile Gly Lys Ile
            355                 360                 365

Pro Leu Lys Leu Asp His Leu Arg Ile Glu Glu Leu Lys Glu Asn Gly
            370                 375                 380

Ile Ile Leu Lys Gly Lys Lys Glu Ile Asp Asn Gly Lys Lys Tyr Tyr
385                 390                 395                 400

Leu Leu Glu Ser Asn Asn Gln Val Tyr Glu Phe Arg Ile Ser Asp Glu
                405                 410                 415

Asn Asn Glu Val Gln Tyr Lys Thr Lys Glu Gly Lys Ile Thr Val Leu
            420                 425                 430

Gly Glu Lys Phe Asn Trp Arg Asn Ile Glu Val Met Ala Lys Asn Val
            435                 440                 445

Glu Gly Val Leu Lys Pro Leu Thr Ala Asp Tyr Asp Leu Phe Ala Leu
450                 455                 460

Ala Pro Ser Leu Thr Glu Ile Lys Lys Gln Ile Pro Gln Lys Glu Trp
465                 470                 475                 480

Asp Lys Val Val Asn Thr Pro Asn Ser Leu Glu Lys Gln Lys Gly Val
                485                 490                 495

Thr Asn Leu Leu Ile Lys Tyr Gly Ile Glu Arg Lys Pro Asp Ser Thr
            500                 505                 510

Lys Gly Thr Leu Ser Asn Trp Gln Lys Gln Met Leu Asp Arg Leu Asn
            515                 520                 525

Glu Ala Val Lys Tyr Thr Gly Tyr Thr Gly Gly Asp Val Val Asn His
530                 535                 540

Gly Thr Glu Gln Asp Asn Glu Glu Phe Pro Gly Lys Asp Asn Glu Ile
545                 550                 555                 560

Phe Ile Ile Asn Pro Glu Gly Glu Phe Ile Leu Thr Lys Asn Trp Glu
                565                 570                 575

Met Thr Gly Arg Phe Ile Glu Lys Asn Ile Thr Gly Lys Asp Tyr Leu
            580                 585                 590

Tyr Tyr Phe Asn Arg Ser Tyr Asn Lys Ile Ala Pro Gly Asn Lys Ala
            595                 600                 605

Tyr Ile Glu Trp Thr Asp Pro Ile Thr Lys Ala Lys Ile Asn Thr Ile
```

```
                610                 615                 620
Pro Thr Ser Ala Glu Phe Ile Lys Asn Leu Ser Ser Ile Arg Arg Ser
625                 630                 635                 640

Ser Asn Val Gly Val Tyr Lys Asp Ser Gly Asp Lys Asp Glu Phe Ala
                645                 650                 655

Lys Lys Glu Ser Val Lys Lys Ile Ala Gly Tyr Leu Ser Asp Tyr Tyr
                660                 665                 670

Asn Ser Ala Asn His Ile Phe Ser Gln Glu Lys Arg Lys Ile Ser
                675                 680                 685

Ile Phe Arg Gly Ile Gln Ala Tyr Asn Glu Ile Glu Asn Val Leu Lys
690                 695                 700

Ser Lys Gln Ile Ala Pro Glu Tyr Lys Asn Tyr Phe Gln Tyr Leu Lys
705                 710                 715                 720

Glu Arg Ile Thr Asn Gln Val Gln Leu Leu Thr His Gln Lys Ser
                725                 730                 735

Asn Ile Glu Phe Lys Leu Leu Tyr Lys Gln Leu Asn Phe Thr Glu Asn
                740                 745                 750

Glu Thr Asp Asn Phe Glu Val Phe Gln Lys Ile Ile Asp Glu Lys
                755                 760                 765
```

<210> SEQ ID NO 94
<211> LENGTH: 767
<212> TYPE: PRT
<213> ORGANISM: Artificial Sequence
<220> FEATURE:
<223> OTHER INFORMATION: Synthetic

<400> SEQUENCE: 94

```
Cys Asn Glu His Tyr Thr Glu Ser Asp Ile Lys Arg Asn His Lys Thr
1               5                   10                  15

Glu Lys Asn Lys Thr Glu Lys Glu Lys Phe Lys Asp Ser Ile Asn Asn
                20                  25                  30

Leu Val Lys Thr Glu Phe Thr Asn Glu Thr Leu Asp Lys Ile Gln Gln
                35                  40                  45

Thr Gln Asp Leu Leu Lys Lys Ile Pro Lys Asp Val Leu Glu Ile Tyr
    50                  55                  60

Ser Glu Leu Gly Gly Glu Ile Tyr Phe Thr Asp Ile Asp Leu Val Glu
65                  70                  75                  80

His Lys Glu Leu Gln Asp Leu Ser Glu Glu Lys Asn Ser Met Asn
                85                  90                  95

Ser Arg Gly Glu Lys Val Pro Phe Ala Ser Arg Phe Val Phe Glu Lys
                100                 105                 110

Lys Arg Glu Thr Pro Lys Leu Ile Ile Asn Ile Lys Asp Tyr Ala Ile
            115                 120                 125

Asn Ser Glu Gln Ser Lys Glu Val Tyr Tyr Glu Ile Gly Lys Gly Ile
        130                 135                 140

Ser Leu Asp Ile Ile Ser Lys Asp Lys Ser Leu Asp Pro Glu Phe Leu
145                 150                 155                 160

Asn Leu Ile Lys Ser Leu Ser Asp Asp Ser Asp Ser Ser Asp Leu Leu
                165                 170                 175

Phe Ser Gln Lys Phe Lys Glu Lys Leu Glu Leu Asn Asn Lys Ser Ile
                180                 185                 190

Asp Ile Asn Phe Ile Lys Glu Asn Leu Thr Glu Phe Gln His Ala Phe
            195                 200                 205

Ser Leu Ala Phe Ser Tyr Tyr Phe Ala Pro Asp His Arg Thr Val Leu
```

```
            210                 215                 220
Glu Leu Tyr Ala Pro Asp Met Phe Glu Tyr Met Asn Lys Leu Glu Lys
225                 230                 235                 240

Gly Gly Phe Glu Lys Ile Ser Glu Ser Leu Lys Lys Glu Gly Val Glu
                245                 250                 255

Lys Asp Arg Ile Asp Val Leu Lys Gly Glu Lys Ala Leu Lys Ala Ser
            260                 265                 270

Gly Leu Val Pro Glu His Ala Asp Ala Phe Lys Lys Ile Ala Arg Glu
        275                 280                 285

Leu Asn Thr Tyr Ile Leu Phe Arg Pro Val Asn Lys Leu Ala Thr Asn
290                 295                 300

Leu Ile Lys Ser Gly Val Ala Thr Lys Gly Leu Asn Val His Gly Lys
305                 310                 315                 320

Ser Ser Asp Trp Gly Pro Val Ala Gly Tyr Ile Pro Phe Asp Gln Asp
                325                 330                 335

Leu Ser Lys Lys His Gly Gln Gln Leu Ala Val Glu Lys Gly Asn Leu
            340                 345                 350

Glu Asn Lys Lys Ser Ile Thr Glu His Glu Gly Glu Ile Gly Lys Ile
        355                 360                 365

Pro Leu Lys Leu Asp His Leu Arg Ile Glu Glu Leu Lys Glu Asn Gly
370                 375                 380

Ile Ile Leu Lys Gly Lys Lys Gly Ile Asp Asn Gly Lys Lys Tyr Tyr
385                 390                 395                 400

Leu Leu Glu Ser Asn Asn Gln Val Tyr Glu Phe Arg Ile Ser Asp Glu
                405                 410                 415

Asn Asn Glu Val Gln Tyr Lys Thr Lys Glu Gly Lys Ile Thr Val Leu
            420                 425                 430

Gly Glu Lys Phe Asn Trp Arg Asn Ile Glu Val Met Ala Lys Asn Val
        435                 440                 445

Glu Gly Val Leu Lys Pro Leu Thr Ala Asp Tyr Asp Leu Phe Ala Leu
450                 455                 460

Ala Pro Ser Leu Thr Glu Ile Lys Lys Gln Ile Pro Gln Lys Glu Trp
465                 470                 475                 480

Asp Lys Val Val Asn Thr Pro Asn Ser Leu Glu Lys Gln Lys Gly Val
                485                 490                 495

Thr Asn Leu Leu Ile Lys Tyr Gly Ile Glu Arg Lys Pro Asp Ser Thr
            500                 505                 510

Lys Gly Thr Leu Ser Asn Trp Gln Lys Gln Met Leu Asp Arg Leu Asn
        515                 520                 525

Glu Ala Val Lys Tyr Thr Gly Tyr Thr Gly Gly Asp Val Val Asn His
530                 535                 540

Gly Thr Glu Gln Asp Asn Glu Glu Phe Pro Glu Lys Asp Asn Glu Ile
545                 550                 555                 560

Phe Ile Ile Asn Pro Glu Gly Glu Phe Ile Leu Thr Lys Asn Trp Glu
                565                 570                 575

Met Thr Gly Arg Phe Ile Glu Lys Asn Ile Thr Gly Lys Asp Tyr Leu
            580                 585                 590

Tyr Tyr Phe Asn Arg Ser Tyr Asn Lys Ile Ala Pro Gly Asn Lys Ala
        595                 600                 605

Tyr Ile Glu Trp Thr Asp Pro Ile Thr Lys Ala Lys Ile Asn Thr Ile
610                 615                 620

Pro Thr Ser Ala Glu Phe Ile Lys Asn Leu Ser Ser Ile Arg Arg Ser
625                 630                 635                 640
```

```
Ser Asn Val Gly Val Tyr Lys Asp Ser Gly Asp Lys Asp Glu Phe Ala
                645                 650                 655

Lys Lys Glu Ser Val Lys Lys Ile Ala Gly Tyr Leu Ser Asp Tyr Tyr
            660                 665                 670

Asn Ser Ala Asn His Ile Phe Ser Gln Glu Lys Arg Lys Ile Ser
            675                 680                 685

Ile Phe Arg Gly Ile Gln Ala Tyr Asn Glu Ile Glu Asn Val Leu Lys
        690                 695                 700

Ser Lys Gln Ile Ala Pro Glu Tyr Lys Asn Tyr Phe Gln Tyr Leu Lys
705                 710                 715                 720

Glu Arg Ile Thr Asn Gln Val Gln Leu Leu Leu Thr His Gln Lys Ser
                725                 730                 735

Asn Ile Glu Phe Lys Leu Leu Tyr Lys Gln Leu Asn Phe Thr Glu Asn
            740                 745                 750

Glu Thr Asp Asn Phe Glu Val Phe Gln Lys Ile Ile Asp Glu Lys
            755                 760                 765

<210> SEQ ID NO 95
<211> LENGTH: 766
<212> TYPE: PRT
<213> ORGANISM: Artificial Sequence
<220> FEATURE:
<223> OTHER INFORMATION: Synthetic

<400> SEQUENCE: 95

Asn Glu His Tyr Thr Glu Ser Asp Ile Lys Arg Asn His Lys Thr Glu
1               5                   10                  15

Lys Asn Lys Thr Glu Lys Glu Lys Phe Lys Asp Ser Ile Asn Asn Leu
                20                  25                  30

Val Lys Thr Glu Phe Thr Asn Glu Thr Leu Asp Lys Ile Gln Gln Thr
            35                  40                  45

Gln Asp Leu Leu Lys Lys Ile Pro Lys Asp Val Leu Glu Ile Tyr Ser
    50                  55                  60

Glu Leu Gly Gly Glu Ile Tyr Phe Thr Asp Ile Asp Leu Val Glu His
65                  70                  75                  80

Lys Glu Leu Gln Asp Leu Ser Glu Glu Lys Asn Ser Met Asn Ser
                85                  90                  95

Arg Gly Glu Lys Val Pro Phe Ala Ser Arg Phe Val Phe Glu Lys Lys
            100                 105                 110

Arg Glu Thr Pro Lys Leu Ile Ile Asn Ile Lys Asp Tyr Ala Ile Asn
        115                 120                 125

Ser Glu Gln Ser Lys Glu Val Tyr Tyr Glu Ile Gly Lys Gly Ile Ser
    130                 135                 140

Leu Asp Ile Ile Ser Lys Asp Lys Ser Leu Asp Pro Glu Phe Leu Asn
145                 150                 155                 160

Leu Ile Lys Ser Leu Ser Asp Asp Ser Asp Ser Ser Asp Leu Leu Phe
                165                 170                 175

Ser Gln Lys Phe Lys Glu Lys Leu Glu Leu Asn Asn Lys Ser Ile Asp
            180                 185                 190

Ile Asn Phe Ile Lys Glu Asn Leu Thr Glu Phe Gln His Ala Phe Ser
        195                 200                 205

Leu Ala Phe Ser Tyr Tyr Phe Ala Pro Asp His Arg Thr Val Leu Glu
    210                 215                 220

Leu Tyr Ala Pro Asp Met Phe Glu Tyr Met Asn Lys Leu Glu Lys Gly
225                 230                 235                 240
```

```
Gly Phe Glu Lys Ile Ser Glu Ser Leu Lys Lys Glu Gly Val Glu Lys
                245                 250                 255

Asp Arg Ile Asp Val Leu Lys Gly Glu Lys Ala Leu Lys Ala Ser Gly
            260                 265                 270

Leu Val Pro Glu His Ala Asp Ala Phe Lys Lys Ile Ala Arg Glu Leu
        275                 280                 285

Asn Thr Tyr Ile Leu Phe Arg Pro Val Asn Lys Leu Ala Thr Asn Leu
    290                 295                 300

Ile Lys Ser Gly Val Ala Thr Lys Gly Leu Asn Val His Gly Lys Ser
305                 310                 315                 320

Ser Asp Trp Gly Pro Val Ala Gly Tyr Ile Pro Phe Ser Gln Asp Leu
                325                 330                 335

Ser Lys Lys His Gly Gln Gln Leu Ala Val Glu Lys Gly Asn Leu Glu
            340                 345                 350

Asn Lys Lys Ser Ile Thr Glu His Glu Gly Glu Ile Gly Lys Ile Pro
        355                 360                 365

Leu Lys Leu Asp His Leu Arg Ile Glu Glu Leu Lys Glu Asn Gly Ile
    370                 375                 380

Ile Leu Lys Gly Lys Lys Glu Ile Asp Asn Gly Lys Lys Tyr Tyr Leu
385                 390                 395                 400

Leu Glu Ser Asn Asn Gln Val Tyr Glu Phe Arg Ile Ser Asp Glu Asn
                405                 410                 415

Asn Glu Val Gln Tyr Lys Thr Lys Glu Gly Lys Ile Thr Val Leu Gly
            420                 425                 430

Glu Lys Phe Asn Trp Arg Asn Ile Glu Val Met Ala Lys Asn Val Glu
        435                 440                 445

Gly Val Leu Lys Pro Leu Thr Ala Asp Tyr Asp Leu Phe Ala Leu Ala
    450                 455                 460

Pro Ser Leu Thr Glu Ile Lys Lys Gln Ile Pro Gln Lys Glu Trp Asp
465                 470                 475                 480

Lys Val Val Asn Thr Pro Asn Ser Leu Glu Lys Gln Lys Gly Val Thr
                485                 490                 495

Asn Leu Leu Ile Lys Tyr Gly Ile Glu Arg Lys Pro Asp Ser Thr Lys
            500                 505                 510

Gly Thr Leu Ser Asn Trp Gln Lys Gln Met Leu Asp Arg Leu Asn Glu
        515                 520                 525

Ala Val Lys Tyr Thr Gly Tyr Thr Gly Gly Asp Val Val Asn His Gly
    530                 535                 540

Thr Glu Gln Asp Asn Glu Phe Pro Glu Lys Asp Asn Glu Ile Phe
545                 550                 555                 560

Ile Ile Asn Pro Glu Gly Glu Phe Ile Leu Thr Lys Asn Trp Glu Met
                565                 570                 575

Thr Gly Arg Phe Ile Glu Lys Asn Ile Thr Gly Lys Asp Tyr Leu Tyr
            580                 585                 590

Tyr Phe Asn Arg Ser Tyr Asn Lys Ile Ala Pro Gly Asn Lys Ala Tyr
        595                 600                 605

Ile Glu Trp Thr Asp Pro Ile Thr Lys Ala Lys Ile Asn Thr Ile Pro
    610                 615                 620

Thr Ser Ala Glu Phe Ile Lys Asn Leu Ser Ser Ile Arg Arg Ser Ser
625                 630                 635                 640

Asn Val Gly Val Tyr Lys Asp Ser Gly Asp Lys Asp Glu Phe Ala Lys
                645                 650                 655
```

-continued

```
Lys Glu Ser Val Lys Lys Ile Ala Gly Tyr Leu Ser Asp Tyr Tyr Asn
            660             665             670

Ser Ala Asn His Ile Phe Ser Gln Glu Lys Lys Arg Lys Ile Ser Ile
        675             680             685

Phe Arg Gly Ile Gln Ala Tyr Asn Glu Ile Glu Asn Val Leu Lys Ser
    690             695             700

Lys Gln Ile Ala Pro Glu Tyr Lys Asn Tyr Phe Gln Tyr Leu Lys Glu
705             710             715             720

Arg Ile Thr Asn Gln Val Gln Leu Leu Thr His Gln Lys Ser Asn
            725             730             735

Ile Glu Phe Lys Leu Leu Tyr Lys Gln Leu Asn Phe Thr Glu Asn Glu
        740             745             750

Thr Asp Asn Phe Glu Val Phe Gln Lys Ile Ile Asp Glu Lys
        755             760             765
```

PROTEASE-DEFICIENT *BACILLUS ANTHRACIS*

CROSS REFERENCE TO RELATED APPLICATIONS

This application is a national stage application under 35 U.S.C. 371 and claims the benefit of PCT Application No. PCT/US2012/049321 having an international filing date of Aug. 2, 2012, which designated the United States, which PCT application claimed the benefit of U.S. Provisional Application No. 61/514,384 filed Aug. 2, 2011, and U.S. Provisional Application No. 61/521,617 filed Aug. 9, 2011, the disclosure of each of which are incorporated herein by reference.

REFERENCE TO SEQUENCE LISTING

This application contains a Sequence Listing submitted as an electronic text file named "6137NIAID-24-PCT_Sequence_Listing_ST25.txt", having a size in bytes of 195 KB, and created on Aug. 2, 2012. The information contained in this electronic file is hereby incorporated by reference in its entirety pursuant to 37 CFR §1.52(e)(5).

FIELD

The invention relates to a protease-deficient *Bacillus anthracis* and its use as a production microorganism to produce stable (i.e., intact) proteins, including recombinant secreted proteins.

BACKGROUND

Species of *Bacillus*, such as *Bacillus anthracis*, *Bacillus cereus*, and *Bacillus subtilis*, are attractive microorganisms for recombinant protein production in view of their fast growth rate, high yield, and ability to secrete produced products directly into the medium. *Bacillus anthracis* is also attractive in view of its ability to produce anthrax toxin and ability to fold proteins correctly. However, the attractiveness of *Bacillus* is reduced in view of the large quantities of extracellular proteases that the microorganisms secrete into the medium, leading to protein degradation, and the fact that they form spores.

The Gram-positive bacterial pathogen *Bacillus anthracis* (also referred to herein as *B. anthracis*) secretes high levels of the three proteins that are collectively termed anthrax toxin: protective antigen (PA), edema factor (EF), and lethal factor (LF), when grown under conditions thought to mimic those in an infected animal host. PA is a receptor-binding component which acts to deliver LF and EF to the cytosol of eukaryotic cells; EF is a calmodulin-dependent adenylate cyclase, and LF is a zinc metalloprotease that cleaves most members of the mitogen-activated protein kinase kinase family; see, for example, Leppla S H et al., 2000, in Anthrax toxin, bacterial protein toxins, 445-472, Aktories K et al., (Eds.), Springer, Berlin; Moayeri M et al., 2011, Anthrax toxins, *Bacillus anthracis* and Anthrax, 121-156, Bergman (Ed.), John Wiley & Sons, Inc., Hoboken, N.J.; Moayeri M et al., 2009, Mol. Aspects. Med. 30, 439-455; Young J A et al., 2007, Annu Rev. Biochem. 76, 243-265. PA, EF, and LF are encoded on virulence plasmid pXO1 by pag, cya, and lef, respectively. Virulence plasmid pXO2 encodes proteins required for capsule formation and depolymerization. *B. anthracis* that lack one or both virulence plasmids are typically attenuated in most animal hosts. Single PA, EF, and LF components are non-toxic; a combination of one PA and at least two EFs, at least two LFs, or mixtures of EF and LF are required for toxicity.

Because anthrax pathogenesis is highly dependent on the actions of the anthrax toxin proteins, vaccine and therapeutic development efforts have focused on countering toxin action, typically by generating antibodies to PA. The anthrax vaccine currently licensed in the USA, and developed almost 50 years ago (see, e.g., Puziss M et al., 1963, J. Bacteriol. 85, 230-236), consists of a partially purified culture supernatant of a protease-deficient *B. anthracis* strain (V770-NP1-R). PA is the most abundant protein and the key immunogen in this vaccine. Efforts to produce a recombinant PA vaccine from *B. anthracis* by scale-up of an established process (see, e.g., Farchaus J W et al., 1998, Appl. Environ. Microbiol. 64, 982-991) appear to have been hampered by instability of the final product.

While the toxin components can be purified as recombinant proteins from *B. anthracis* culture supernatants (see, e.g., Farchaus J W et al., ibid.; Varughese M et al., 1999, Infect. Immun. 67, 1860-1865; Singh Y et al., 1991, J. Biol. Chem. 266, 15493-15497; Park S et al., 2000, Protein Expr. Purif. 18, 293-302), the integrity and yields are limited by the *B. anthracis* proteolytic enzymes that are co-secreted.

Two extracellular proteases are reported to be abundant in the *B. anthracis* secretome: NprB (GBAA_0599), neutral protease B, a thermolysin-like enzyme highly homologous to bacillolysins from other *Bacillus* species; and InhA1 (GBAA_1295), immune inhibitor A1, a homolog of the immune inhibitors A from other members of the *Bacillus cereus* group (see, e.g., Antelmann H et al., 2005, Proteomics 5, 3684-3695; Chitlaru T et al., 2006, J. Bacteriol 188, 3551-3571; Chung M C et al., 2006, J. Biol. Chem. 281, 31408-31418. These two proteases contain zinc-binding motifs typical for the zincin tribe of metallopeptidases (His-Glu-Xxx-Xxx-His (SEQ ID NO:31)) and belong, respectively, to the M4 and M6 families of metalloproteases according to the MEROPS database, Wellcome Trust Sanger Institute (see e.g., website of Wellcome Trust Sanger Institute).

A third metalloprotease, camelysin (GBAA_1290), belonging to the M73 family is found in the secretome of several *B. anthracis* strains. This protease is similar to the camelysin of *B. cereus*, a novel surface metalloprotease; see, e.g., Grass G et al, 2004, Infect. Immun. 219-228.

*B. anthracis* also contains a gene encoding InhA2 metalloprotease (GBAA_0672, M6 family), although it is not known whether this protease is expressed and secreted. This gene is an ortholog of the InhA1 described above (68% amino acid identity). Similarly, the genome of *B. anthracis* also contains genes encoding TasA (GBAA_1288, M73 superfamily), which is an ortholog of camelysin (60% amino acid identity), and MmpZ (GBAA_3159, ZnMc superfamily), which is a putative extracellular zinc-dependent matrix metalloprotease, a member of the metzincin clan of metallopeptidases. This clan is characterized by an extended zinc-binding motif (His-Glu-Xxx-Xxx-His-Xxx-Xxx-Gly/Asn-Xxx-Xxx-His/Asp (SEQ ID NO:32)) (see, e.g., Gomis-Ruth, F X, 2009, J. Biol. Chem. 284, 15353-15357).

*Bacillus subtilis* strains having more than one protease inactivated have been produced and analyzed. For example, Wu X C et al., 1991, J. Bacteriol. 173, 4952-4958 produced a *B. subtilis* strain deficient in six extracellular proteases (WB600), namely neutral protease A, subtilisin, extracellular protease, metalloprotease, bacillopeptidase F, and neutral protease B. WB600 showed only 0.32% of the extracellular protease activity of wild-type *B. subtilis* strains. Kurashima K et al., 2002, J. Bacteriol. 184, 76-81, expressed apparently intact *Clostridium cellulovorans* EngB cellulase in a *B. subtilis* strain deficient in eight proteases (WB800). WB800 was derived from WB600 through inactivation of VpR protease and cell wall protease WprA. WB700 was derived from WB600 through inactivation of VpR (see, e.g., Wu et al, 2002, Appl. Environ. Microbiol. 68, 3261-3269).

There have been reports of inactivation of certain individual *B. anthracis* proteases: Inactivation of *B. anthracis* NprB led to reduced proteolysis of casein (see, e.g., Pomerantsev A P et al., 2006, Infect. Immun. 74, 682-693. Inactivation of InhA1 indicated that coagulation of human blood by *B. anthracis* required InhA1 for proteolytic activation of prothrombin and factor X (see, e.g., Kastrup C J et al., 2008, Nat. Chem. Biol. 4, 742-750. However, production of anthrax toxin proteins in both of these strains led to protein degradation over time, albeit at a later time than production in *B. anthracis* A35.

There remains a need for a *B. anthracis* that can produce large amounts of stable (i.e., intact) proteins, such as anthrax toxin proteins PA, EF, and LF.

SUMMARY

The invention relates to a *B. anthracis* in which more than one secreted protease is inactivated by genetic modification. Such a protease-deficient *B. anthracis* has an improved ability to produce recombinant secreted proteins compared to other bacteria, particularly other *Bacillus*. Improvements include production of intact (i.e., mature full-length) proteins, often at high yield.

The disclosure provides a *B. anthracis* that comprises a genetic modification that inactivates a protease of the M4 family of metalloproteases and a genetic modification that inactivates a protease of the M6 family of metalloproteases. One embodiment is a *B. anthracis* that comprises a genetic modification that inactivates a protease of the M4 family of metalloproteases and a genetic modification that inactivates a protease of the M6 family of metalloproteases. One embodiment is a *B. anthracis* that comprises a genetic modification that inactivates a protease of the M4 family of metalloproteases, a genetic modification that inactivates a protease of the M6 family of metalloproteases, and a genetic modification that inactivates a protease of the M73 family of metalloproteases. One embodiment is a *B. anthracis* that comprises a genetic modification that inactivates a protease of the M4 family of metalloproteases, a genetic modification that inactivates a protease of the M6 family of metalloproteases, a genetic modification that inactivates a protease of the M73 family of metalloproteases, and a genetic modification that inactivates a *B. anthracis* protease of the ZnMc superfamily of zinc-dependent metalloproteases. An example of a M4 protease is NprB. Examples of M6 proteases include InhA1 and InhA2. Examples of M73 proteases are camelysin and TasA. An example of a ZnMc protease is MmpZ.

One embodiment is a *B. anthracis* comprising a genetic modification that inactivates NprB protease and a genetic modification that inactivates InhA1 protease. One embodiment is a *B. anthracis* comprising a genetic modification that inactivates NprB protease, a genetic modification that inactivates camelysin protease, and a genetic modification that inactivates InhA1 protease. One embodiment is a *B. anthracis* comprising a genetic modification that inactivates NprB protease, a genetic modification that inactivates TasA protease, a genetic modification that inactivates camelysin protease, and a genetic modification that inactivates InhA1 protease. One embodiment is a *B. anthracis* comprising a genetic modification that inactivates NprB protease, a genetic modification that inactivates InhA2 protease, a genetic modification that inactivates TasA protease, a genetic modification that inactivates camelysin protease, and a genetic modification that inactivates InhA1 protease. One embodiment is a *B. anthracis* comprising a genetic modification that inactivates NprB protease, a genetic modification that inactivates InhA2 protease, a genetic modification that inactivates TasA protease, a genetic modification that inactivates camelysin protease, and a genetic modification that inactivates InhA1 protease. One embodiment is a *B. anthracis* comprising a genetic modification that inactivates NprB protease, a genetic modification that inactivates InhA2 protease, a genetic modification that inactivates TasA protease, a genetic modification that inactivates camelysin protease, a genetic modification that inactivates InhA1 protease, and a genetic modification that inactivates MmpZ protease.

The disclosure provides that any of these protease-deficient *B. anthracis* can also comprise a genetic modification selected from the group consisting of a genetic modification that inactivates BA1995 protease, a genetic modification that inactivates VpR protease, a genetic modification that inactivates BA5414 protease, and combinations thereof.

The disclosure also provides that any of these protease-deficient *B. anthracis* can lack SinR and SinI regulatory proteins. The disclosure also provides that any of these protease-deficient *B. anthracis* can be sporulation deficient. The disclosure also provides that any of these protease-deficient *B. anthracis* can lack one or more virulence plasmids. Genetic modification of any of these protease-deficient *B. anthracis* can be selected from the group consisting of deletion, insertion, inversion, substitution, derivatization, and combinations thereof, wherein such genetic modification affects one or more nucleotides in a gene encoding the protein. In one embodiment, genetic modification comprises deletion of one or more nucleotides in a gene encoding a protein, insertion of one or more nucleotides in a gene encoding a protein, or a combination thereof.

The disclosure provides a *B. anthracis* comprising: a genetic modification that inactivates NprB protease, wherein the inactivated NprB protease is encoded by a genetically modified nprB gene at locus GBAA_0599 of *B. anthracis*; a genetic modification that inactivates InhA2 protease, wherein the inactivated InhA2 protease is encoded by a genetically modified inhA2 gene at locus GBAA_0672 of *B. anthracis*; a genetic modification that inactivates TasA protease, wherein the inactivated TasA protease is encoded by a genetically modified tasA gene at locus GBAA_1288 of the *B. anthracis*; a genetic modification that inactivates camelysin, wherein the inactivated camelysin is encoded by a genetically modified calY gene at locus GBAA_1290 of the *B. anthracis*; a genetic modification that inactivates InhA1 protease, wherein the inactivated InhA1 protease is encoded by a genetically modified inhA1 gene at locus GBAA_1295 of the *B. anthracis*; a genetic modification that inactivates MmpZ protease, wherein the inactivated MmpZ protease is encoded by a genetically modified mmpZ gene at locus GBAA_3159 of the *B. anthracis*; and a genetic modification that inactivates Spo0A protein, wherein the inactivated Spo0A protein is encoded by a genetically modified spo0A gene at locus GBAA_4394 of the *B. anthracis*, wherein the *B. anthracis* lacks virulence plasmids pXO1 and pXO2. One embodiment is a *B. anthracis* having the identifying characteristics of BH460, deposited under ATCC Accession No. PTA-12024. One embodiment is *B. anthracis* BH460, deposited under ATCC Accession No. PTA-12024.

The disclosure provides that any of these protease-deficient *B. anthracis* can also comprise a genetic modification that inactivates a protease selected from the group consisting of a protease of the transglutaminase-like superfamily, a protease of peptidase family S8, and a combination thereof. One embodiment is a *B. anthracis* that comprises a genetic modification that inactivates a protease of the M4 family of metalloproteases, a genetic modification that inactivates a protease of the M6 family of metalloproteases, a genetic modification that inactivates a protease of the M73 family of metalloproteases, a genetic modification that inactivates a *B. anthracis* protease of the ZnMc superfamily of zinc-dependent metalloproteases, a genetic modification that inactivates a *B. anthracis* protease of the transglutaminase-like superfamily, and a genetic modification that inactivates a *B. anthracis* protease of peptidase family S8. One example of a transglutaminase-like superfamily protease is CysP1 protease. One example of a peptidase family S8 protease is VpR protease. In one embodiment, the protease of the transglutaminase-like superfamily is CysP1 protease. In one embodiment, the protease of peptidase family S8 is VpR protease. In one embodiment, the protease of the transglutaminase-like superfamily is CysP1 protease, and the protease of peptidase family S8 is VpR protease. As used herein, CysP1 protease is also referred to as BA1995 protease.

The disclosure provides a *B. anthracis* comprising a genetic modification that inactivates NprB protease, a genetic modification that inactivates InhA2 protease, a genetic modification that inactivates TasA protease, a genetic modification that inactivates camelysin protease, a genetic modification that inactivates InhA1 protease, a genetic modification that inactivates MmpZ protease, a genetic modification that inactivates CysP1 protease, and a genetic modification that inactivates VpR protease. In one embodiment, the inactivated NprB protease is encoded by a genetically modified nprB gene at locus GBAA_0599 of *B. anthracis*; the inactivated InhA2 protease is encoded by a genetically modified inhA2 gene at locus GBAA_0672 of *B. anthracis*; the inactivated TasA protease is encoded by a genetically modified tasA gene at locus GBAA_1288 of the *B. anthracis*; the inactivated camelysin is encoded by a genetically modified calY gene at locus GBAA_1290 of the *B. anthracis*; the inactivated InhA1 protease is encoded by a genetically modified inhA1 gene at locus GBAA_1295 of the *B. anthracis*; the inactivated MmpZ protease is encoded by a genetically modified mmpZ gene at locus GBAA_3159 of the *B. anthracis*; the inactivated CysP1 protease is encoded by a genetically modified cysP1 gene at locus GBAA_1995 of the *B. anthracis*; and the inactivated VpR protease is encoded by a genetically modified vpR gene at locus GBAA_4584 of the *B. anthracis*.

The disclosure provides that any of the protease-deficient *B. anthracis* can also comprise a genetic modification selected from the group consisting of a genetic modification that inactivates NprC protease, a genetic modification that inactivates SprA protease, a genetic modification that inactivates HtrA protease, a genetic modification that inactivates HsIV protease, and combinations thereof. As used herein, SprA protease is also referred to as BA5414 protease.

The disclosure provides a *B. anthracis* comprising a genetic modification that inactivates NprB protease, a genetic modification that inactivates InhA2 protease, a genetic modification that inactivates TasA protease, a genetic modification that inactivates camelysin protease, a genetic modification that inactivates InhA1 protease, a genetic modification that inactivates MmpZ protease, a genetic modification that inactivates CysP1 protease, a genetic modification that inactivates VpR protease, and a genetic modification selected from the group consisting of a genetic modification that inactivates NprC protease, a genetic modification that inactivates SprA protease, a genetic modification that inactivates HtrA protease, a genetic modification that inactivates HsIV protease, and combinations thereof.

The disclosure also provides that any of these protease-deficient *B. anthracis* can lack SinR and SinI regulatory proteins. The disclosure also provides that any of these protease-deficient *B. anthracis* can be sporulation deficient. The disclosure also provides that any of these protease-deficient *B. anthracis* can lack one or more virulence plasmids. Genetic modification of any of these protease-deficient *B. anthracis* can be selected from the group consisting of deletion, insertion, inversion, substitution, derivatization, and combinations thereof, wherein such genetic modification affects one or more nucleotides in a gene encoding the protein.

The disclosure provides a *B. anthracis* comprising: a genetic modification that inactivates NprB protease, wherein the inactivated NprB protease is encoded by a genetically modified nprB gene at locus GBAA_0599 of *B. anthracis*; a genetic modification that inactivates InhA2 protease, wherein the inactivated InhA2 protease is encoded by a genetically modified inhA2 gene at locus GBAA_0672 of *B. anthracis*; a genetic modification that inactivates TasA protease, wherein the inactivated TasA protease is encoded by a genetically modified tasA gene at locus GBAA_1288 of the *B. anthracis*; a genetic modification that inactivates camelysin, wherein the inactivated camelysin is encoded by a genetically modified calY gene at locus GBAA_1290 of the *B. anthracis*; a genetic modification that inactivates InhA1 protease, wherein the inactivated InhA1 protease is encoded by a genetically modified inhA1 gene at locus GBAA_1295 of the *B. anthracis*; a genetic modification that inactivates MmpZ protease, wherein the inactivated MmpZ protease is encoded by a genetically modified mmpZ gene at locus GBAA_3159 of the *B. anthracis*; a genetic modification that inactivates CysP1 protease, wherein the inactivated CysP1 protease is encoded by a genetically modified cysP1 gene at locus GBAA_1995 of the *B. anthracis*; a genetic modification that inactivates VpR protease, wherein the inactivated VpR protease is encoded by a genetically modified vpR gene at locus GBAA_4584 of the *B. anthracis*; and a genetic modification that inactivates Spo0A protein, wherein the inactivated Spo0A protein is encoded by a genetically modified spo0A gene at locus GBAA_4394 of the *B. anthracis*, wherein the *B. anthracis* lacks virulence plasmids pXO1 and pXO2. One embodiment is a *B. anthracis* having the identifying characteristics of BH480, deposited under ATCC Accession No. PTA-13162. One embodiment is *B. anthracis* BH480, deposited under ATCC Accession No. PTA-13162.

The disclosure provides a method to produce a *B. anthracis* comprising genetically modifying a *B. anthracis* to inactivate a protease of the M4 family of metalloproteases and to inactivate a protease of the M6 family of metalloproteases. The disclosure provides a method to produce a *B. anthracis* comprising genetically modifying a *B. anthracis* to inactivate a protease of the M4 family of metalloproteases, to inactivate a protease of the M6 family of metalloproteases, and to inactivate a protease of the M73 family of metalloproteases. The disclosure provides a method to produce a *B. anthracis* comprising genetically modifying a *B. anthracis* to inactivate a protease of the M4 family of metalloproteases, to inactivate a protease of the M6 family of metalloproteases, to inactivate a protease of the M73 family of metalloproteases, and to inactivate a protease of the ZnMc superfamily of zinc-dependent metalloproteases. The disclosure provides a method to produce a *B. anthracis* comprising genetically modifying a *B. anthracis* to inactivate a protease of the M4 family of metalloproteases, to inactivate a protease of the M6 family of metalloproteases, to inactivate a protease of the M73 family of metalloproteases, to inactivate a protease of the ZnMc superfamily of zinc-dependent metalloproteases, to inactivate a protease of the transglutaminase-like superfamily, and to inactivate a protease of peptidase family S8.

The disclosure provides a method to produce any *B. anthracis* of the embodiments. Such a method comprises culturing the *B. anthracis* in a medium; and recovering the *B. anthracis*.

The disclosure provides a modified *B. anthracis* transformed with a recombinant molecule encoding a product, wherein: the *B. anthracis* comprises a genetic modification that inactivates a protease of the M4 family of metalloproteases and a genetic modification that inactivates a protease of the M6 family of metalloproteases; and the recombinant molecule comprises a nucleic acid molecule encoding the product operatively linked to an expression vector. The disclosure provides a modified *B. anthracis* transformed with a recombinant molecule encoding a product, wherein: the *B. anthracis* comprises a genetic modification that inactivates a protease of the M4 family of metalloproteases, a genetic modification that inactivates a protease of the M6 family of metalloproteases, and a genetic modification that inactivates a protease of the M73 family of metalloproteases; and the recombinant molecule comprises a nucleic acid molecule encoding the product operatively linked to an expression vector. The disclosure provides a modified *B. anthracis* transformed with a recombinant molecule encoding a product, wherein: the *B. anthracis* comprises a genetic modification that inactivates a protease of the M4 family of metalloproteases, a genetic modification that inactivates a protease of the M6 family of metalloproteases, a genetic modification that inactivates a protease of the M73 family of metalloproteases, and a genetic modification that inactivates a protease of the ZnMc superfamily of zinc-dependent metalloproteases; and the recombinant molecule comprises a nucleic acid molecule encoding the product operatively linked to an expression vector. The disclosure provides a modified *B. anthracis* transformed with a recombinant molecule encoding a product, wherein: the *B. anthracis* comprises a genetic modification that inactivates a protease of the M4 family of metalloproteases, a genetic modification that inactivates a protease of the M6 family of metalloproteases, a genetic modification that inactivates a protease of the M73 family of metalloproteases, a genetic modification that inactivates a protease of the ZnMc superfamily of zinc-dependent metalloproteases, a genetic modification that inactivates a *B. anthracis* protease of the transglutaminase-like superfamily, and a genetic modification that inactivates a *B. anthracis* protease of peptidase family S8; and the recombinant molecule comprises a nucleic acid molecule encoding the product operatively linked to an expression vector. One embodiment of a product is a product selected from the group consisting of a protein, an amino acid, a nucleic acid molecule, a compound produced via a recombinant biosynthetic pathway, a small molecule, a drug, a vitamin, a drug conjugate, and a peptide nucleic acid conjugate. In one embodiment, such a product is a toxin. Examples of toxins include an anthrax toxin, a cholera toxin, a diphtheria toxin, a hemolysin, and a ricin. Additional examples of toxins include a *Pseudomonas* toxin, a *Haemophilus ducreyi* toxin, an *Escherichia coli* toxin, and a ribosome-inactivating protein (RIP) toxin.

The disclosure provides a recombinant molecule that comprises a nucleic acid molecule encoding the product operatively linked to an expression vector. Examples of recombinant molecules include a recombinant molecule comprising a nucleic acid sequence selected from the group consisting of a recombinant molecule comprising nucleic acid sequence SEQ ID NO:62, a recombinant molecule comprising nucleic acid sequence SEQ ID NO:65, a recombinant molecule comprising nucleic acid sequence SEQ ID NO:67, and a recombinant molecule comprising nucleic acid sequence SEQ ID NO:69.

One embodiment is a recombinant molecule comprising a pSJ115 plasmid that encodes a protein comprising amino acid sequence SEQ ID NO:91. One embodiment is a recombinant molecule comprising a pYS5 plasmid that encodes a protein comprising amino acid sequence SEQ ID NO:92. One embodiment is a recombinant molecule selected from the group consisting of recombinant molecule pSJ136EF-His, recombinant molecule pSJ136EF-Cys, and recombinant molecule pSJ136EF-NEHY. The disclosure also provides a protein comprising an amino acid sequence selected from the group consisting of amino acid sequence SEQ ID NO:93, amino acid sequence SEQ ID NO:94, and amino acid sequence SEQ ID NO:95.

The disclosure provides a method to produce a product comprising: culturing a modified *B. anthracis* of the embodiments in a medium to produce the product; and recovering the product.

BRIEF DESCRIPTION OF THE FIGURES

FIG. 1 provides sequences of truncated and inactivated *B. anthracis* proteases. FIG. 1A provides sequences of truncated and inactivated *B. anthracis* NprB and InhA1 proteases. FIG. 1B provides sequences of truncated and inactivated *B. anthracis* InhA2, TasA, camelysin, and MmpZ proteases, as well as sequences used to produce the deletion of a *B. anthracis* genome spanning a portion of tasA through a portion of inhA1, as described in the Examples. Protease genes were inactivated using a procedure that results in the insertion of the 34-bp pair loxP sequence (underlined in the nucleotide sequences) flanked by several endonuclease restriction sites (positions not indicated). The large region between the TasA and InhA1 genes was replaced by a loxP sequence using the same procedure. For each protease, the amino acid and nucleotide sequences shown in bold in the upper section identify the final three amino acids retained from the original protease. The amino acid sequences following this trimer are nonsense and/or out of frame translations encoded by the restriction sites and loxP sequences; translation terminates at the codons indicated by asterisks. The lower section of each of InhA2, TasA, camelysin, and MmpZ protease shows the entire amino acid sequence (including signal sequence) for each respective protease. The frame shift that occurs following the three amino acids shown in each upper section causes only the underlined portion of the respective original amino acid sequence to be translated. The zinc-binding active site sequences for NprB and InhA1 are shown in bold in FIG. 1A. Identical zinc-binding active site sequences are shown in bold in the InhA2 and MmpZ amino acid sequences in FIG. 1B. For the large TasA-InhA1 deletion, truncation of the TasA protein occurs at the same site as for the single TasA deletion. The deleted DNA sequence extends through the corresponding sequence encoding the first 402 amino acids of InhA1 (not indicated). The remaining DNA begins with the sequence that would encode the last 393 amino acids of InhA1, which begins with the sequence IMSGGSWAGKIAGTTPTSFS (SEQ ID NO:33) (dashed underlining). FIG. 1C provides sequences of truncated and inactivated B. anthracis CysP1 and VpR proteases. These protease genes were inactivated using a procedure that results in replacement of at least a portion of the genes with a 48-bp FRT-site (underlined in the nucleotide sequences) using Flp recombinase.

FIG. 2 provides growth curves of certain B. anthracis strains and production analyses of edema factor (EF), anthrolysin O (ALO), protective antigen (PA), lethal factor (LF), and camelysin by these strains. Growth curves in LB medium are shown for ten B. anthracis strains over 24 h. Western blot analyses of EF, ALO, PA, LF, and camelysin at various time points are shown for each strain. The most slowly migrating band in each set of blots appears to correspond to the respective intact, or nearly intact, protein.

DETAILED DESCRIPTION

Figure 3:
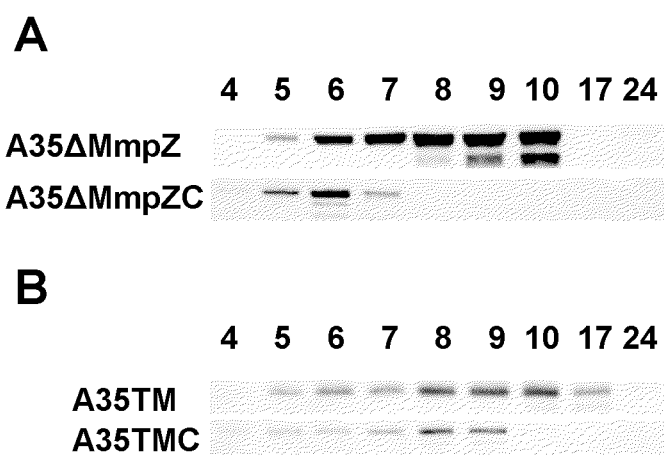
FIG. 3 provides production analyses of LF and ALO by certain genetically modified strains, some of which had a deficient protease function complemented by a plasmid encoding active protease. Western blot analyses are shown of (A) LF production by A35ΔMmpZ compared to A35ΔMmpZC and (B) ALO production by A35TM compared to A35TMC. (C at the end of the strain name indicates a complemented strain.) Numbers on the top of each lane indicate time in hours at which samples were taken.

The present disclosure describes the novel finding that genetic modifications of Bacillus anthracis (B. anthracis) that inactivate more than one secreted protease provide a protease-deficient B. anthracis with an improved ability to produce recombinant secreted proteins compared to other bacteria, e.g., other B. anthracis strains, including those with a single inactivated secreted protease. Improvements include production of intact (i.e., mature full-length) proteins, often at high yield. For example, one embodiment is B. anthracis BH460. BH460 has genetic modifications that inactivate six proteases, is sporulation-deficient, and is free of the virulence plasmids. This strain provides an improved host for production of recombinant proteins. As an example, EF produced from BH460 is highly active, whereas previous B. anthracis host strains produced truncated EF proteins having low potency. The ability to produce an intact EF allows EF to be a component of a recombinant anthrax vaccine. As another example, one embodiment is B. anthracis BH480. BH480 has genetic modifications that inactivate eight proteases, is sporulation-deficient, and is free of the virulence plasmids. This strain also provides an improved host for production of recombinant proteins as shown herein.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a genetic modification refers to one or more genetic modifications. As such, the terms "a", "an", "one or more" and "at least one" can be used interchangeably. Similarly the terms "comprising", "including" and "having" can be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

The disclosure provides a *B. anthracis* comprising genetic modifications that inactivate more than one protease. In one embodiment, such inactivated proteases are inactivated secreted proteases. As used herein the phrase "a *B. anthracis* comprising a genetic modification that inactivates a protease" refers to a *B. anthracis* strain (also referred to as a *B. anthracis* organism or a *B. anthracis* microorganism) in which at least one of its proteases has been inactivated by at least one genetic modification. It is to be noted that the terms inactivated, inactive, defective, and deficient can be used interchangeably.

As used herein, a protease (also referred to as a proteinase or a peptidase) is any enzyme that conducts proteolysis, i.e., an enzyme that initiates protein catabolism by hydrolyzing the peptide bonds that link amino acids together in a chain to form a protein. A protein is any compound that has two or more amino acids linked together by a peptide bond between the carboxyl and amino groups of adjacent amino acids; as such, the term protein includes polypeptides and peptides. A secreted protease is a protease that is secreted from the cell (e.g., *B. anthracis*) that produces it. An inactivated protease is a protease that no longer functions to hydrolyze peptide bonds. An inactivated protease can have amino acids that have been deleted (e.g., to form a truncated protein), inserted, inverted, substituted, derivatized (e.g., by glycosylation, phosphorylation, acetylation, myristylation, prenylation, palmitation, amidation and/or addition of glycosylphosphatidyl inositol), or subjected to any other change known to those skilled in the art in order to deactivate the protease. An inactivated protease can be produced by effecting deletion, insertion, inversion, substitution, derivatization, and/or or any other change of amino acids at the amino acid level in order to deactivate the protease. Alternatively, inactivation can occur at the nucleic acid level by genetic modification (also referred to herein as mutation). Genetic modification includes deletion, insertion, inversion, substitution, derivatization, and/or any other change known to those skilled in the art of one or more nucleotides in a gene encoding the protease such that the genetically modified nucleic acid does not encode an active protease. In some embodiments, no protease is produced at all. In some embodiments, the encoded protease is truncated. In one embodiment, genetic modification comprises deletion of one or more nucleotides in a gene encoding a protease. In one embodiment, such a deletion comprises Cre-loxP gene knockout, a technique further described in the Examples herein. One embodiment is a conditionally inactivated protease, which can be produced, for example, using inducible antisense or anti-parallel loxP sites bracketing the structural gene encoding such a protease so that the Cre recombinase flips the gene between active and inactive forms. In one embodiment, a protease gene is inactivated via a *Saccharomyces cerevisiae* Flp-FRT recombinase system.

One embodiment is a *B. anthracis* comprising genetic modification that inactivates at least two secreted proteases. One embodiment is a *B. anthracis* comprising genetic modification that inactivates at least three *B. anthracis* secreted proteases. One embodiment is a *B. anthracis* comprising genetic modification that inactivates at least four *B. anthracis* secreted proteases. One embodiment is a *B. anthracis* comprising genetic modification that inactivates at least five *B. anthracis* secreted proteases. One embodiment is a *B. anthracis* comprising genetic modification that inactivates at least six *B. anthracis* secreted proteases. One embodiment is a *B. anthracis* comprising genetic modification that inactivates at least seven *B. anthracis* secreted proteases. One embodiment is a *B. anthracis* comprising genetic modification that inactivates at least eight *B. anthracis* secreted proteases. One embodiment is a *B. anthracis* comprising genetic modification that inactivates at least nine *B. anthracis* secreted proteases. One embodiment is a *B. anthracis* comprising genetic modification that inactivates at least ten *B. anthracis* secreted proteases. One embodiment is a *B. anthracis* comprising genetic modification that inactivates at least eleven *B. anthracis* secreted proteases. One embodiment is a *B. anthracis* comprising genetic modification that inactivates at least twelve *B. anthracis* secreted proteases The disclosure provides a *B. anthracis* comprising a genetic modification that inactivates a protease of the M4 family of metalloproteases and a genetic modification that inactivates a protease of the M6 family of metalloproteases. The M4 and M6 families of metalloproteases are as defined in the MEROPS database, Wellcome Trust Sanger Institute, ibid. One embodiment is a *B. anthracis* comprising an inactivated protease of the M4 family and an inactivated protease of the M6 family. One embodiment is a *B. anthracis* comprising an inactivated protease of the M4 family and at least two inactivated proteases of the M6 family. One embodiment is a *B. anthracis* comprising an inactivated protease of the M4 family and two inactivated proteases of the M6 family.

A non-limiting example of a protease of the M4 family of metalloproteases is *B. anthracis* NprB protease, also referred to herein as NprB. In one embodiment a genetic modification that inactivates a protease of the M4 family of metalloproteases is a genetic modification that inactivates NprB. Non-limiting examples of a protease of the M6 family of metalloproteases are *B. anthracis* InhA1 protease and *B. anthracis* InhA2 protease (also referred to herein as InhA1 and InhA2, respectively). In one embodiment a genetic modification that inactivates a protease of the M6 family of metalloproteases is a genetic modification that inactivates a protease of the M6 family selected from the group consisting of InhA1, InhA2, and combinations thereof. As such, genetic modification can inactivate InhA1, genetic modification can inactivate InhA2, or genetic modification can inactivate both InhA1 and InhA2. One embodiment is a *B. anthracis* that has genetic modifications that inactivate NprB and InhA1. One embodiment is a *B. anthracis* that has genetic modifications that inactivate NprB and InhA2. One embodiment is a *B. anthracis* that has genetic modifications that inactivate NprB, InhA1, and InhA2.

The disclosure provides a *B. anthracis* comprising a genetic modification that inactivates a protease of the M4 family of metalloproteases, a genetic modification that inactivates a protease of the M6 family of metalloproteases, and a genetic modification that inactivates a protease of the M73 family of metalloproteases. The M73 family of metalloproteases is as defined in the MEROPS database, Wellcome Trust Sanger Institute, ibid. Surprisingly, a *B. anthracis* comprising such genetic modifications produced significantly more intact secreted protein than did strains having inactivated proteases of the M4 and/or M6 families of metalloproteases but an active protease of the M73 family. Such improved production is exemplified in the Examples.

One embodiment is a *B. anthracis* comprising an inactivated protease of the M4 family, an inactivated protease of the M6 family, and an inactivated protease of the M73 family. One embodiment is a *B. anthracis* comprising an inactivated protease of the M4 family, an inactivated protease of the M6 family, and at least two inactivated proteases of the M73 family. One embodiment is a *B. anthracis* comprising an inactivated protease of the M4 family, at least two inactivated proteases of the M6 family, and an inactivated protease of the M73 family. One embodiment is a *B. anthracis* comprising an inactivated protease of the M4 family, at least two inactivated proteases of the M6 family, and at least two inactivated proteases of the M73 family. One embodiment is a *B. anthracis* comprising an inactivated protease of the M4 family, an inactivated protease of the M6 family, and two inactivated proteases of the M73 family. One embodiment is a *B. anthracis* comprising an inactivated protease of the M4 family, two inactivated proteases of the M6 family, and an inactivated protease of the M73 family. One embodiment is a *B. anthracis* comprising an inactivated protease of the M4 family, two inactivated proteases of the M6 family, and two inactivated proteases of the M73 family.

Non-limiting examples of a protease of the M73 family of metalloproteases are *B. anthracis* camelysin protease and *B. anthracis* TasA protease (also referred to herein as camelysin and TasA, respectively.) In one embodiment a genetic modification that inactivates a protease of the M73 family of metalloproteases is a genetic modification that inactivates a protease of the M73 family selected from the group consisting of camelysin, TasA, and combinations thereof. As such, genetic modification can inactivate camelysin, genetic modification can inactivate TasA, or genetic modification can inactivate both camelysin and TasA. One embodiment is a *B. anthracis* that has genetic modifications that inactivate NprB, InhA1, and camelysin. One embodiment is a *B. anthracis* that has genetic modifications that inactivate NprB, InhA2, and camelysin. One embodiment is a *B. anthracis* that has genetic modifications that inactivate NprB, InhA1, InhA2, and camelysin. One embodiment is a *B. anthracis* that has genetic modifications that inactivate NprB, InhA1, and TasA. One embodiment is a *B. anthracis* that has genetic modifications that inactivate NprB, InhA2, and TasA. One embodiment is a *B. anthracis* that has genetic modifications that inactivate NprB, InhA1, InhA2, and TasA. One embodiment is a *B. anthracis* that has genetic modifications that inactivate NprB, InhA1, camelysin, and TasA. One embodiment is a *B. anthracis* that has genetic modifications that inactivate NprB, InhA2, camelysin, and TasA. One embodiment is a *B. anthracis* that has genetic modifications that inactivate NprB, InhA1, InhA2, camelysin, and TasA.

The disclosure provides a *B. anthracis* comprising a genetic modification that inactivates a protease of the M4 family of metalloproteases, a genetic modification that inactivates a protease of the M6 family of metalloproteases, a genetic modification that inactivates a protease of the M73 family of metalloproteases, and a genetic modification that inactivates a protease of the ZnMc superfamily of zinc-dependent metalloproteases. The ZnMc superfamily of zinc-dependent metalloproteases is as defined in the MEROPS database, Wellcome Trust Sanger Institute, ibid. One embodiment is a *B. anthracis* comprising an inactivated protease of the M4 family, an inactivated protease of the M6 family, an inactivated protease of the M73 family, and an inactivated protease of the ZnMc superfamily. One embodiment is a *B. anthracis* comprising an inactivated protease of the M4 family, an inactivated protease of the M6 family, at least two inactivated proteases of the M73 family, and an inactivated protease of the ZnMc superfamily. One embodiment is a *B. anthracis* comprising an inactivated protease of the M4 family, at least two inactivated proteases of the M6 family, an inactivated protease of the M73 family, and an inactivated protease of the ZnMc superfamily. One embodiment is a *B. anthracis* comprising an inactivated protease of the M4 family, at least two inactivated proteases of the M6 family, at least two inactivated proteases of the M73 family, and an inactivated protease of the ZnMc superfamily. One embodiment is a *B. anthracis* comprising an inactivated protease of the M4 family, an inactivated protease of the M6 family, two inactivated proteases of the M73 family, and an inactivated protease of the ZnMc superfamily. One embodiment is a *B. anthracis* comprising an inactivated protease of the M4 family, two inactivated proteases of the M6 family, an inactivated protease of the M73 family, and an inactivated protease of the ZnMc superfamily. One embodiment is a *B. anthracis* comprising an inactivated protease of the M4 family, two inactivated proteases of the M6 family, two inactivated proteases of the M73 family, and an inactivated protease of the ZnMc superfamily.

A non-limiting example of a protease of the ZnMc superfamily of metalloproteases is *B. anthracis* MmpZ protease, also referred to herein as MmpZ. In one embodiment a genetic modification that inactivates a protease of the ZnMc superfamily of metalloproteases is a genetic modification that inactivates MmpZ. One embodiment is a *B. anthracis* that has genetic modifications that inactivate NprB, InhA1, camelysin, and MmpZ. One embodiment is a *B. anthracis* that has genetic modifications that inactivate NprB, InhA2, camelysin, and MmpZ. One embodiment is a *B. anthracis* that has genetic modifications that inactivate NprB, InhA1, InhA2, camelysin, and MmpZ. One embodiment is a *B. anthracis* that has genetic modifications that inactivate NprB, InhA1, TasA, and MmpZ. One embodiment is a *B. anthracis* that has genetic modifications that inactivate NprB, InhA2, TasA, and MmpZ. One embodiment is a *B. anthracis* that has genetic modifications that inactivate NprB, InhA1, InhA2, TasA, and MmpZ. One embodiment is a *B. anthracis* that has genetic modifications that inactivate NprB, InhA1, camelysin, TasA, and MmpZ. One embodiment is a *B. anthracis* that has genetic modifications that inactivate NprB, InhA2, camelysin, TasA, and MmpZ. One embodiment is a *B. anthracis* that has genetic modifications that inactivate NprB, InhA1, InhA2, camelysin, TasA, and MmpZ.

The disclosure provides a *B. anthracis* comprising a genetic modification that inactivates at least two proteases, wherein the proteases are selected from the group consisting of a protease of the M4 family of metalloproteases, a protease of the M6 family of metalloproteases, a protease of the M73 family of proteases, and a protease of the ZnMc superfamily of zinc-dependent metalloproteases. The disclosure encompasses any combination of two or more such inactivated proteases. One or more genetic modifications can lead to the inactivation of such two or more proteases. For example, a deletion spanning at least a portion of two genes that encode such proteases can effect at least two inactivated proteases. One embodiment is a *B. anthracis* comprising a genetic modification that inactivates at least two proteases, wherein the proteases are selected from the group consisting of NprB, InhA2, TasA, camelysin, InhA1, and MmpZ.

The disclosure provides a *B. anthracis* that comprises a genetic modification that inactivates NprB protease, a genetic modification that inactivates InhA2 protease, a genetic modification that inactivates TasA protease, a genetic modification that inactivates camelysin protease, a genetic modification that inactivates InhA1 protease, and a genetic modification that inactivates MmpZ protease. It is to be appreciated that a genetic modification that inactivates one protease can be the same genetic modification that inactivates one or more additional proteases. For example, a genetic modification that deletes a region of the *B. anthracis* genome that spans from at least a portion of the tasA gene through at least a portion of the inhA1 gene is an example of a genetic modification that inactivates a TasA protease, a genetic modification that inactivates a camelysin protease, and a genetic modification that inactivates an InhA1 protease. In one embodiment, such a deletion spans from the codon that encodes amino acid residue 63 of SEQ ID NO:9 through the codon that encodes amino acid 402 of SEQ ID NO:17. SEQ ID NO:9 and SEQ ID NO:17 encode wild-type TasA and InhA1, respectively. Such a deletion also deletes the genes encoding regulatory proteins SinR and SinI.

One embodiment is a *B. anthracis* that comprises a genetic modification that inactivates NprB protease and a genetic modification that inactivates InhA1 protease. One embodiment of a *B. anthracis* that comprises genetic modifications that inactivate NprB protease and InhA1 proteases is a *B. anthracis* in which: (a) the inactivated NprB protease is encoded by a genetically modified nprB gene at locus GBAA_0599 of *B. anthracis*; and (b) the inactivated InhA1 protease is encoded by a genetically modified inhA1 gene at locus GBAA_1295 of the *B. anthracis*. Each of these gene loci corresponds to an equivalently named locus of *B. anthracis* "Ames ancestor" strain chromosome (GenBank Accession No. NC 003997), as described in the Examples.

One embodiment is *B. anthracis* that comprises a genetic modification that inactivates NprB protease, a genetic modification that inactivates camelysin protease, and a genetic modification that inactivates InhA1 protease. One embodiment of a *B. anthracis* that comprises genetic modifications that inactivate NprB protease, camelysin, and InhA1 proteases is a *B. anthracis* in which: (a) the inactivated NprB protease is encoded by a genetically modified nprB gene at locus GBAA_0599 of *B. anthracis*; (b) the inactivated camelysin is encoded by a genetically modified calY gene at locus GBAA_1290 of the *B. anthracis*; and (c) the inactivated InhA1 protease is encoded by a genetically modified inhA1 gene at locus GBAA_1295 of the *B. anthracis*. Each of these gene loci corresponds to an equivalently named locus of *B. anthracis* "Ames ancestor" strain chromosome (GenBank Accession No. NC 003997), as described in the Examples.

One embodiment is a *B. anthracis* that comprises a genetic modification that inactivates NprB protease, a genetic modification that inactivates TasA protease, a genetic modification that inactivates camelysin protease, and a genetic modification that inactivates InhA1 protease. One embodiment of a *B. anthracis* that comprises genetic modifications that inactivate NprB protease, TasA, camelysin, and InhA1 proteases is a *B. anthracis* in which: (a) the inactivated NprB protease is encoded by a genetically modified nprB gene at locus GBAA_0599 of *B. anthracis*; (b) the inactivated TasA protease is encoded by a genetically modified tasA gene at locus GBAA_1288 of the *B. anthracis*; (c) the inactivated camelysin is encoded by a genetically modified calY gene at locus GBAA_1290 of the *B. anthracis*; and (d) the inactivated InhA1 protease is encoded by a genetically modified inhA1 gene at locus GBAA_1295 of the *B. anthracis*. Each of these gene loci corresponds to an equivalently named locus of *B. anthracis* "Ames ancestor" strain chromosome (GenBank Accession No. NC 003997), as described in the Examples.

One embodiment is a *B. anthracis* that comprises a genetic modification that inactivates NprB protease, a genetic modification that inactivates InhA2 protease, a genetic modification that inactivates TasA protease, a genetic modification that inactivates camelysin protease, and a genetic modification that inactivates InhA1 protease. One embodiment of a *B. anthracis* that comprises genetic modifications that inactivate NprB protease, InhA2, TasA, camelysin, and InhA1 proteases is a *B. anthracis* in which: (a) the inactivated NprB protease is encoded by a genetically modified nprB gene at locus GBAA_0599 of *B. anthracis*; (b) the inactivated InhA2 protease is encoded by a genetically modified inhA2 gene at locus GBAA_0672 of *B. anthracis*; (c) the inactivated TasA protease is encoded by a genetically modified tasA gene at locus GBAA_1288 of the *B. anthracis*; (d) the inactivated camelysin is encoded by a genetically modified calY gene at locus GBAA_1290 of the *B. anthracis*; and (e) the inactivated InhA1 protease is encoded by the genetically modified inhA1 gene at locus GBAA_1295 of the *B. anthracis*. Each of these gene loci corresponds to an equivalently named locus of *B. anthracis* "Ames ancestor" strain chromosome (GenBank Accession No. NC 003997), as described in the Examples.

One embodiment is a *B. anthracis* that comprises a genetic modification that inactivates NprB protease, a genetic modification that inactivates InhA2 protease, a genetic modification that inactivates TasA protease, a genetic modification that inactivates camelysin protease, a genetic modification that inactivates InhA1 protease, and a genetic modification that inactivates MmpZ protease.

One embodiment of a *B. anthracis* that comprises genetic modifications that inactivate NprB, InhA2, TasA, camelysin, InhA1 and MmpZ proteases is a *B. anthracis* in which: (a) the inactivated NprB protease is encoded by a genetically modified nprB gene at locus GBAA_0599 of *B. anthracis*; (b) the inactivated InhA2 protease is encoded by a genetically modified inhA2 gene at locus GBAA_0672 of *B. anthracis*; (c) the inactivated TasA protease is encoded by a genetically modified tasA gene at locus GBAA_1288 of the *B. anthracis*; (d) the inactivated camelysin is encoded by a genetically modified calY gene at locus GBAA_1290 of the *B. anthracis*; (e) the inactivated InhA1 protease is encoded by a genetically modified inhA1 gene at locus GBAA_1295 of the *B. anthracis*; and (f) the inactivated MmpZ protease is encoded by a genetically modified mmpZ gene at locus GBAA_3159 of the *B. anthracis*. Each of these gene loci corresponds to an equivalently named locus of *B. anthracis* "Ames ancestor" strain chromosome (GenBank Accession No. NC 003997), as described in the Examples.

One embodiment of a *B. anthracis* that comprises genetic modifications that inactivate NprB, InhA2, TasA, camelysin, InhA1 and MmpZ proteases is a *B. anthracis* in which: (a) the inactivated NprB protease is encoded by a nprB gene that encodes an inactivated NprB comprising amino acid sequence SEQ ID NO:2; (b) the inactivated InhA2 protease is encoded by an inhA2 gene that encodes an inactivated InhA2 comprising amino acid sequence SEQ ID NO:6; (c) the inactivated TasA protease is encoded by a tasA gene that encodes an inactivated TasA comprising amino acid sequence SEQ ID NO:10; (d) the inactivated camelysin protease is encoded by a calY gene that encodes an inactivated camelysin comprising amino acid sequence SEQ ID NO:14; (e) the inactivated InhA1 protease is encoded by an inhA1 gene that encodes an inactivated InhA1 comprising amino acid sequence SEQ ID NO:18; and (f) the inactivated MmpZ protease is encoded by a mmpZ gene that encodes an inactivated MmpZ comprising amino acid sequence SEQ ID NO:22. In one embodiment, the amino acid sequence of the encoded inactivated NprB protease is SEQ ID NO:2. In one embodiment, the amino acid sequence of the encoded inactivated InhA2 protease is SEQ ID NO:6. In one embodiment, the amino acid sequence of the encoded inactivated TasA protease is SEQ ID NO:10. In one embodiment, the amino acid sequence of the encoded inactivated camelysin protease is SEQ ID NO:14. In one embodiment, the amino acid sequence of the encoded inactivated InhA1 protease is SEQ ID NO:18. In one embodiment, the amino acid sequence of the encoded inactivated MmpZ protease is SEQ ID NO:22.

One embodiment of a *B. anthracis* that comprises genetic modifications that inactivate NprB, InhA2, TasA, camelysin, InhA1 and MmpZ proteases is a *B. anthracis* in which: (a) the genetic modification that inactivates NprB protease is a nprB gene that encodes an inactivated NprB comprising amino acid sequence SEQ ID NO:2; (b) the genetic modification that inactivates InhA2 protease is an inhA2 gene that encodes an inactivated InhA2 comprising amino acid sequence SEQ ID NO:6; (c) the genetic modification that inactivates TasA protease, camelysin protease, and InhA1 protease is a deletion that spans from the codon that encodes amino acid residue 63 of SEQ ID NO:9 through the codon that encodes amino acid 402 of SEQ ID NO:17 (such a deletion also deletes genes encoding SinR and SinI); and (d) the genetic modification that inactivates MmpZ protease is a mmpZ gene that encodes an inactivated MmpZ comprising amino acid sequence SEQ ID NO:22.

One embodiment of a *B. anthracis* that comprises genetic modifications that inactivate NprB, InhA2, TasA, camelysin, InhA1, and MmpZ proteases is a *B. anthracis* in which: (a) the genetic modification that inactivates NprB protease is a nprB gene that encodes an inactivated NprB consisting of amino acid sequence SEQ ID NO:2; (b) the genetic modification that inactivates InhA2 protease is an inhA2 gene that encodes an inactivated InhA2 consisting of amino acid sequence SEQ ID NO:6; (c) the genetic modification that inactivates TasA protease, camelysin protease, and InhA1 protease is a deletion that spans from the codon that encodes amino acid residue 63 of SEQ ID NO:9 through the codon that encodes amino acid 402 of SEQ ID NO:17 (such a deletion also deletes genes encoding SinR and SinI); (d) the genetic modification that inactivates MmpZ protease is a mmpZ gene that encodes an inactivated MmpZ consisting of amino acid sequence SEQ ID NO:22.

In some embodiments, *B. anthracis* of the disclosure can also include genetic modifications that inactivate regulatory protein SinR, regulatory protein SinI, or both SinR and SinI. SinR and SinI are encoded by genes located at GBAA_1292 and GBAA_1293, respectively, of the *B. anthracis* genome.

The disclosure provides a *B. anthracis* comprising a genetic modification that inactivates a protease of the M4 family of metalloproteases, a genetic modification that inactivates a protease of the M6 family of metalloproteases, a genetic modification that inactivates a protease of the M73 family of metalloproteases, a genetic modification that inactivates a protease of the ZnMc superfamily of metalloproteases and a genetic modification selected from the group consisting of a genetic modification that inactivates BA1995 protease, a genetic modification that inactivates VpR protease, a genetic modification that inactivates BA5414 protease, and combinations thereof. BA1995, VpR and BA5414 proteases have been identified as secreted proteases present in the supernatant of *B. anthracis* in which NprB, InhA2, TasA, camelysin, InhA1, and MmpZ proteases have been inactivated. BA1995 is encoded by a gene located at locus GBAA_1995 of *B. anthracis* (see, e.g., Sastalla I et al., 2010, Microbiology 156, 2982-2993). VpR, or BA4584, is a minor extracellular protease that is encoded by the vpR gene located at locus GBAA_4584 of *B. anthracis*. BA 5414, is a serine protease that is encoded by a gene located at locus GBAA_5414 of *B. anthracis*.

The disclosure provides a *B. anthracis* that comprises a genetic modification that inactivates NprB protease, a genetic modification that inactivates InhA2 protease, a genetic modification that inactivates TasA protease, a genetic modification that inactivates camelysin protease, a genetic modification that inactivates InhA1 protease, a genetic modification that inactivates MmpZ protease, and a genetic modification selected from the group consisting of a genetic modification that inactivates BA1995 protease, a genetic modification that inactivates VpR protease, a genetic modification that inactivates BA5414 protease, and combinations thereof.

Additional secreted proteases, the inactivation of which would further improve protein production by *B. anthracis* of the embodiments, can be identified using techniques known to those skilled in the art. For example, a protease-deficient *B. anthracis* of the embodiments can be cultured in a medium, and the resulting medium, or supernatant produced from the medium, can be tested for protease activity against desired proteins being produced by such *B. anthracis*. Protease(s) responsible for such activity can be isolated, sequenced, and the sequence(s) compared to the genomic map of *B. anthracis* in order to identify the gene(s) that encode it (them). Such gene(s) can then be inactivated using techniques described herein.

The disclosure provides that any of the *B. anthracis* of the embodiments can be sporulation-deficient. That is, any of the *B. anthracis* described herein can also comprise a genetic modification that prevents sporulation, such as a genetic modification that inactivates the Spo0A protein. The Spo0A protein, a key regulator of sporulation in *Bacillus* (see, e.g., Molle V et al., 2003, Molec. Microbiol. 50, 1683-1701), is encoded by the spo0A gene, located at locus GBAA_4394 of *B. anthracis*. *B. anthracis* that are unable to sporulate are advantageous as production organisms.

The disclosure also provides that any of the *B. anthracis* of the embodiments can be deficient in one or more virulence plasmids. One embodiment is a *B. anthracis* of the embodiments that is pXβ1−, i.e., the *B. anthracis* lacks virulence plasmid pXO1. One embodiment is a *B. anthracis* of the embodiments that is pXO1−, pXO2−; i.e., the *B. anthracis* lacks virulence plasmids pXO1 and pXO2. One embodiment is a *B. anthracis* of the embodiments that is pXO1−, pXO2+.

The disclosure provides a *B. anthracis* comprising: a genetic modification that inactivates NprB protease, wherein the inactivated NprB protease is encoded by a genetically modified nprB gene at locus GBAA_0599 of *B. anthracis*; a genetic modification that inactivates InhA2 protease, wherein the inactivated InhA2 protease is encoded by a genetically modified inhA2 gene at locus GBAA_0672 of *B. anthracis*; a genetic modification that inactivates TasA protease, wherein the inactivated TasA protease is encoded by a genetically modified tasA gene at locus GBAA_1288 of the *B. anthracis*; a genetic modification that inactivates camelysin, wherein the inactivated camelysin is encoded by a genetically modified calY gene at locus GBAA_1290 of the *B. anthracis*; a genetic modification that inactivates InhA1 protease, wherein the inactivated InhA1 protease is encoded by a genetically modified inhA1 gene at locus GBAA_1295 of the *B. anthracis*; a genetic modification that inactivates MmpZ protease, wherein the inactivated MmpZ protease is encoded by a genetically modified mmpZ gene at locus GBAA_3159 of the *B. anthracis*; and a genetic modification that inactivates Spo0A protein, wherein the inactivated Spo0A protein is encoded by a genetically modified spo0A gene at locus GBAA_4394 of the *B. anthracis*, wherein the *B. anthracis* lacks virulence plasmids pXO1 and pXO2.

The disclosure provides a *Bacillus anthracis* having the identifying characteristics of BH460, deposited under ATCC Accession No. PTA-12024. A deposit of *Bacillus anthracis* BH460 has been made on Aug. 9, 2011 at the American Type Culture Collection (ATCC), 10801 University Boulevard, Manassas, Va. 20110-2209, USA, under ATCC accession number PTA-12024. The ATCC deposit was made pursuant to the terms of the Budapest Treaty on the International Recognition of the Deposit of Microorganisms for Purposes of Patent Procedure. Identifying characteristics of BH460 include (a) inactivated NprB, InhA2, TasA, camelysin, InhA1, and MmpZ proteases, (b) sporulation-deficiency, and (c) lack of virulence plasmids pXO1 and pXO2. One embodiment of the disclosure is *Bacillus anthracis* BH460.

The disclosure provides that any of these protease-deficient *B. anthracis* can also comprise a genetic modification that inactivates a protease selected from the group consisting of a protease of the transglutaminase-like superfamily, a protease of peptidase family S8, and a combination thereof. One embodiment is a *B. anthracis* that comprises a genetic modification that inactivates a protease of the M4 family of metalloproteases, a genetic modification that inactivates a protease of the M6 family of metalloproteases, a genetic modification that inactivates a protease of the M73 family of metalloproteases, a genetic modification that inactivates a *B. anthracis* protease of the ZnMc superfamily of zinc-dependent metalloproteases, and a genetic modification that inactivates a *B. anthracis* protease of the transglutaminase-like superfamily. One embodiment is a *B. anthracis* that comprises a genetic modification that inactivates a protease of the M4 family of metalloproteases, a genetic modification that inactivates a protease of the M6 family of metalloproteases, a genetic modification that inactivates a protease of the M73 family of metalloproteases, a genetic modification that inactivates a *B. anthracis* protease of the ZnMc superfamily of zinc-dependent metalloproteases, and a genetic modification that inactivates a *B. anthracis* protease of peptidase family S8. One embodiment is a *B. anthracis* that comprises a genetic modification that inactivates a protease of the M4 family of metalloproteases, a genetic modification that inactivates a protease of the M6 family of metalloproteases, a genetic modification that inactivates a protease of the M73 family of metalloproteases, a genetic modification that inactivates a *B. anthracis* protease of the ZnMc superfamily of zinc-dependent metalloproteases, a genetic modification that inactivates a *B. anthracis* protease of the transglutaminase-like superfamily, and a genetic modification that inactivates a *B. anthracis* protease of peptidase family S8. One embodiment is a *B. anthracis* comprising an inactivated protease of the M4 family, an inactivated protease of the M6 family, an inactivated protease of the M73 family, an inactivated protease of the ZnMc superfamily, and an inactivated protease of the transglutaminase-like superfamily. One embodiment is a *B. anthracis* comprising an inactivated protease of the M4 family, an inactivated protease of the M6 family, an inactivated protease of the M73 family, an inactivated protease of the ZnMc superfamily, and an inactivated protease of peptidase family S8. One embodiment is a *B. anthracis* comprising an inactivated protease of the M4 family, an inactivated protease of the M6 family, an inactivated protease of the M73 family, an inactivated protease of the ZnMc superfamily, an inactivated protease of the transglutaminase-like superfamily, and an inactivated protease of peptidase family S8.

A non-limiting example of a protease of the transglutaminase-like superfamily is *B. anthracis* CysP1 protease, also referred to herein as CysP1. In one embodiment, a genetic modification that inactivates a protease of the transglutaminase-like superfamily is a genetic modification that inactivates CysP1. A non-limiting example of a protease of peptidase family S8 is *B. anthracis* VpR protease (also referred to herein as VpR). In one embodiment, a genetic modification that inactivates a protease of peptidase family S8 is a genetic modification that inactivates VpR. As such, genetic modification can inactivate CysP1, genetic modification can inactivate VpR, or genetic modification can inactivate both CysP1 and VpR. One embodiment is a *B. anthracis* that has genetic modifications that inactivate NprB, InhA2, TasA, camelysin, InhA1, MmpZ, and CysP1.

One embodiment is a *B. anthracis* that has genetic modifications that inactivate NprB, InhA2, TasA, camelysin, InhA1, MmpZ, and VpR. One embodiment is a *B. anthracis* that has genetic modifications that inactivate NprB, InhA2, TasA, camelysin, InhA1, MmpZ, CysP1, and VpR.

The disclosure provides a *B. anthracis* that comprises a genetic modification that inactivates NprB protease, a genetic modification that inactivates InhA2 protease, a genetic modification that inactivates TasA protease, a genetic modification that inactivates camelysin protease, a genetic modification that inactivates InhA1 protease, a genetic modification that inactivates MmpZ protease, a genetic modification that inactivates CysP1 protease, and a genetic modification that inactivates VpR protease. It is to be appreciated that a genetic modification that inactivates one protease can be the same genetic modification that inactivates one or more additional proteases. For example, as disclosed above, a genetic modification that deletes a region of the *B. anthracis* genome that spans from at least a portion of the tasA gene through at least a portion of the inhA1 gene is an example of a genetic modification that inactivates a TasA protease, a genetic modification that inactivates a camelysin protease, and a genetic modification that inactivates an InhA1 protease. In one embodiment, such a deletion spans from the codon that encodes amino acid residue 63 of SEQ ID NO:9 through the codon that encodes amino acid 402 of SEQ ID NO:17. SEQ ID NO:9 and SEQ ID NO:17 encode wild-type TasA and InhA1, respectively. Such a deletion also deletes the genes encoding regulatory proteins SinR and SinI.

One embodiment is a *B. anthracis* that comprises a genetic modification that inactivates NprB protease, a genetic modification that inactivates InhA2 protease, a genetic modification that inactivates TasA protease, a genetic modification that inactivates camelysin protease, a genetic modification that inactivates InhA1 protease, a genetic modification that inactivates MmpZ protease, a genetic modification that inactivates CysP1 protease, and a genetic modification that inactivates VpR protease.

One embodiment of a *B. anthracis* that comprises genetic modifications that inactivate NprB, InhA2, TasA, camelysin, InhA1, MmpZ, CysP1, and VpR proteases is a *B. anthracis* in which: (a) the inactivated NprB protease is encoded by a genetically modified nprB gene at locus GBAA_0599 of *B. anthracis*; (b) the inactivated InhA2 protease is encoded by a genetically modified inhA2 gene at locus GBAA_0672 of *B. anthracis*; (c) the inactivated TasA protease is encoded by a genetically modified tasA gene at locus GBAA_1288 of the *B. anthracis*; (d) the inactivated camelysin is encoded by a genetically modified calY gene at locus GBAA_1290 of the *B. anthracis*; (e) the inactivated InhA1 protease is encoded by a genetically modified inhA1 gene at locus GBAA_1295 of the *B. anthracis*; (f) the inactivated MmpZ protease is encoded by a genetically modified mmpZ gene at locus GBAA_3159 of the *B. anthracis*; (g) the inactivated CysP1 protease is encoded by a genetically modified cysP1 gene at locus GBAA_1995 of the *B. anthracis*; and (h) the inactivated VpR protease is encoded by a genetically modified vpR gene at locus GBAA_34584 of the *B. anthracis*. Each of these gene loci corresponds to an equivalently named locus of *B. anthracis* "Ames ancestor" strain chromosome (GenBank Accession No. NC 003997), as described in the Examples.

One embodiment of a *B. anthracis* that comprises genetic modifications that inactivate NprB, InhA2, TasA, camelysin, InhA1, MmpZ, CysP1, and VpR proteases is a *B. anthracis* in which: (a) the inactivated NprB protease is encoded by a nprB gene that encodes an inactivated NprB comprising amino acid sequence SEQ ID NO:2; (b) the inactivated InhA2 protease is encoded by an inhA2 gene that encodes an inactivated InhA2 comprising amino acid sequence SEQ ID NO:6; (c) the inactivated TasA protease is encoded by a tasA gene that encodes an inactivated TasA comprising amino acid sequence SEQ ID NO:10; (d) the inactivated camelysin protease is encoded by a calY gene that encodes an inactivated camelysin comprising amino acid sequence SEQ ID NO:14; (e) the inactivated InhA1 protease is encoded by an inhA1 gene that encodes an inactivated InhA1 comprising amino acid sequence SEQ ID NO:18; (f) the inactivated MmpZ protease is encoded by a mmpZ gene that encodes an inactivated MmpZ comprising amino acid sequence SEQ ID NO:22; (g) the inactivated CysP1 protease is encoded by a cysP1 gene that encodes an inactivated CysP1 comprising amino acid sequence SEQ ID NO:72; and (h) the inactivated VpR protease is encoded by a vpR gene that encodes an inactivated VpR comprising amino acid sequence SEQ ID NO:76. In one embodiment, the amino acid sequence of the encoded inactivated NprB protease is SEQ ID NO:2. In one embodiment, the amino acid sequence of the encoded inactivated InhA2 protease is SEQ ID NO:6. In one embodiment, the amino acid sequence of the encoded inactivated TasA protease is SEQ ID NO:10. In one embodiment, the amino acid sequence of the encoded inactivated camelysin protease is SEQ ID NO:14. In one embodiment, the amino acid sequence of the encoded inactivated InhA1 protease is SEQ ID NO:18. In one embodiment, the amino acid sequence of the encoded inactivated MmpZ protease is SEQ ID NO:22. In one embodiment, the amino acid sequence of the encoded inactivated CysP1 protease is SEQ ID NO:72. In one embodiment, the amino acid sequence of the encoded inactivated VpR protease is SEQ ID NO:76.

One embodiment of a *B. anthracis* that comprises genetic modifications that inactivate NprB, InhA2, TasA, camelysin, InhA1, MmpZ, CysP1, and VpR proteases is a *B. anthracis* in which: (a) the genetic modification that inactivates NprB protease is a nprB gene that encodes an inactivated NprB comprising amino acid sequence SEQ ID NO:2; (b) the genetic modification that inactivates InhA2 protease is an inhA2 gene that encodes an inactivated InhA2 comprising amino acid sequence SEQ ID NO:6; (c) the genetic modification that inactivates TasA protease, camelysin protease, and InhA1 protease is a deletion that spans from the codon that encodes amino acid residue 63 of SEQ ID NO:9 through the codon that encodes amino acid 402 of SEQ ID NO:17 (such a deletion also deletes genes encoding SinR and SinI); (d) the genetic modification that inactivates MmpZ protease is a mmpZ gene that encodes an inactivated MmpZ comprising amino acid sequence SEQ ID NO:22; (e) the inactivated CysP1 protease is encoded by a cysP1 gene that encodes an inactivated CysP1 comprising amino acid sequence SEQ ID NO:72; and (f) the inactivated VpR protease is encoded by a vpR gene that encodes an inactivated VpR comprising amino acid sequence SEQ ID NO:76.

One embodiment of a *B. anthracis* that comprises genetic modifications that inactivate NprB, InhA2, TasA, camelysin, InhA1, MmpZ, CysP1, and VpR proteases is a *B. anthracis* in which: (a) the genetic modification that inactivates NprB protease is a nprB gene that encodes an inactivated NprB consisting of amino acid sequence SEQ ID NO:2; (b) the genetic modification that inactivates InhA2 protease is an inhA2 gene that encodes an inactivated InhA2 consisting of amino acid sequence SEQ ID NO:6; (c) the genetic modification that inactivates TasA protease, camelysin protease, and InhA1 protease is a deletion that spans from the codon that encodes amino acid residue 63 of SEQ ID NO:9 through the codon that encodes amino acid 402 of SEQ ID NO:17 (such a deletion also deletes genes encoding SinR and SinI); (d) the genetic modification that inactivates MmpZ protease is a mmpZ gene that encodes an inactivated MmpZ consisting of amino acid sequence SEQ ID NO:22; (e) the inactivated CysP1 protease is encoded by a cysP1 gene that encodes an inactivated CysP1 consisting of amino acid sequence SEQ ID NO:72; and (f) the inactivated VpR protease is encoded by a vpR gene that encodes an inactivated VpR consisting of amino acid sequence SEQ ID NO:76.

In some embodiments, a *B. anthracis* of the disclosure also includes a genetic modification selected from the group consisting of a genetic modification that inactivates NprC protease, a genetic modification that inactivates SprA protease, a genetic modification that inactivates HtrA protease, a genetic modification that inactivates HslV protease, and combinations thereof. *B. anthracis* NprC is a neutral metalloprotease encoded by nprC, located at gene locus GBAA_2183 of *B. anthracis* "Ames ancestor" strain chromosome (GenBank Accession No. NC 003997). *B. anthracis* SprA is a serine protease encoded by sprA, located at gene locus GBAA_5414 of *B. anthracis* "Ames ancestor" strain chromosome. *B. anthracis* HtrA is a serine protease encoded by htrA, located at gene locus GBAA_3660 of *B. anthracis* "Ames ancestor" strain chromosome. HslV protease is ATP-dependent protease HslV that has been found in BH480 secrotome and is encoded at gene locus GBAA_3968 of *B. anthracis* "Ames ancestor" strain chromosome. Protease HslV and the ATPase/chaperone HslU are part of an ATP-dependent proteolytic system that is the prokaryotic homolog of the proteasome. HslV is a dimer of hexamers (a dodecamer) that forms a central proteolytic chamber with active sites on the interior walls of the cavity. HslV shares significant sequence and structural similarity with the proteasomal beta-subunit and both are members of the Ntn-family of hydrolases. HslV has a nucleophilic threonine residue at its N-terminus that is exposed after processing of the propeptide and is directly involved in active site catalysis.

The disclosure provides a *B. anthracis* comprising a genetic modification that inactivates a protease of the M4 family of metalloproteases, a genetic modification that inactivates a protease of the M6 family of metalloproteases, a genetic modification that inactivates a protease of the M73 family of metalloproteases, a genetic modification that inactivates a protease of the ZnMc superfamily of metalloproteases, a genetic modification that inactivates a protease of the transglutaminase-like superfamily, a genetic modification that inactivates a protease of peptidase family S8, and a genetic modification selected from the group consisting of a genetic modification that inactivates NprC protease, a genetic modification that inactivates SprA protease, a genetic modification that inactivates HtrA protease, a genetic modification that inactivates HslV protease, and combinations thereof.

The disclosure provides a *B. anthracis* comprising genetic modification that inactivates NprB, InhA2, TasA, camelysin, InhA1, MmpZ, CysP1, and VpR proteases that also includes a genetic modification selected from the group consisting of a genetic modification that inactivates NprC protease, a genetic modification that inactivates SprA protease, a genetic modification that inactivates HtrA protease, a genetic modification that inactivates HslV protease, and combinations thereof. One embodiment is a *B. anthracis* comprising a genetic modification that inactivates NprB protease, a genetic modification that inactivates InhA2 protease, a genetic modification that inactivates TasA protease, a genetic modification that inactivates camelysin protease, a genetic modification that inactivates InhA1 protease, a genetic modification that inactivates MmpZ protease, a genetic modification that inactivates CysP1 protease, a genetic modification that inactivates VpR protease, and a genetic modification selected from the group consisting of a genetic modification that inactivates NprC protease, a genetic modification that inactivates SprA protease, a genetic modification that inactivates HtrA protease, a genetic modification that inactivates HslV protease, and combinations thereof.

In some embodiments, *B. anthracis* of the disclosure that comprise genetic modifications that inactivate NprB, InhA2, TasA, camelysin, InhA1, MmpZ, CysP1, and VpR proteases also include genetic modifications that inactivate regulatory protein SinR, regulatory protein SinI, or both SinR and SinI. SinR and SinI are encoded by genes located at GBAA_1292 and GBAA_1293, respectively, of the *B. anthracis* genome.

Additional secreted proteases, the inactivation of which would further improve protein production by *B. anthracis* of the embodiments, can be identified using techniques known to those skilled in the art and as described herein.

In some embodiments, *B. anthracis* of the disclosure that comprise genetic modifications that inactivate NprB, InhA2, TasA, camelysin, InhA1, MmpZ, CysP1, and VpR proteases are sporulation-deficient. That is, any of the *B. anthracis* described herein can also comprise a genetic modification that prevents sporulation, such as a genetic modification that inactivates the Spo0A protein. The Spo0A protein, a key regulator of sporulation in *Bacillus* (see, e.g., Molle V et al., 2003, Molec. Microbiol. 50, 1683-1701), is encoded by the spo0A gene, located at locus GBAA_4394 of *B. anthracis*. *B. anthracis* that are unable to sporulate are advantageous as production organisms.

In some embodiments, *B. anthracis* of the disclosure that comprise genetic modifications that inactivate NprB, InhA2, TasA, camelysin, InhA1, MmpZ, CysP1, and VpR proteases are deficient in one or more virulence plasmids. One embodiment is a *B. anthracis* of the embodiments that is pXO1−, i.e., the *B. anthracis* lacks virulence plasmid pXO1. One embodiment is a *B. anthracis* of the embodiments that is pXO1−, pXO2−; i.e., the *B. anthracis* lacks virulence plasmids pXO1 and pXO2. One embodiment is a *B. anthracis* of the embodiments that is pXO1−, pXO2+.

The disclosure provides a *B. anthracis* comprising: a genetic modification that inactivates NprB protease, wherein the inactivated NprB protease is encoded by a genetically modified nprB gene at locus GBAA_0599 of *B. anthracis*; a genetic modification that inactivates InhA2 protease, wherein the inactivated InhA2 protease is encoded by a genetically modified inhA2 gene at locus GBAA_0672 of *B. anthracis*; a genetic modification that inactivates TasA protease, wherein the inactivated TasA protease is encoded by a genetically modified tasA gene at locus GBAA_1288 of the *B. anthracis*; a genetic modification that inactivates camelysin, wherein the inactivated camelysin is encoded by a genetically modified calY gene at locus GBAA_1290 of the *B. anthracis*; a genetic modification that inactivates InhA1 protease, wherein the inactivated InhA1 protease is encoded by a genetically modified inhA1 gene at locus GBAA_1295 of the *B. anthracis*; a genetic modification that inactivates MmpZ protease, wherein the inactivated MmpZ protease is encoded by a genetically modified mmpZ gene at locus GBAA_3159 of the *B. anthracis*; a genetic modification that inactivates CysP1 protease, wherein the inactivated CysP1 protease is encoded by a genetically modified cysP1 gene at locus GBAA_1995 of the *B. anthracis*; a genetic modification that inactivates VpR protease, wherein the inactivated VpR protease is encoded by a genetically modified vpR gene at locus GBAA_34584 of the *B. anthracis*, and a genetic modification that inactivates Spo0A protein, wherein the inactivated Spo0A protein is encoded by a genetically modified spo0A gene at locus GBAA_4394 of the *B. anthracis*, wherein the *B. anthracis* lacks virulence plasmids pXO1 and pXO2.

The disclosure provides a *Bacillus anthracis* having the identifying characteristics of *B. anthracis* BH480, deposited under ATCC Accession No. PTA-13162. A deposit of *Bacillus anthracis* BH480 has been made on Jul. 31, 2012 at the American Type Culture Collection (ATCC), 10801 University Boulevard, Manassas, Va. 20110-2209, USA, under ATCC accession number PTA-13162. The ATCC deposit was made pursuant to the terms of the Budapest Treaty on the International Recognition of the Deposit of Microorganisms for Purposes of Patent Procedure. Identifying characteristics of BH480 include (a) inactivated NprB, InhA2, TasA, camelysin, InhA1, MmpZ, CysP1, and VpR proteases, (b) sporulation-deficiency, and (c) lack of virulence plasmids pXO1 and pXO2. One embodiment of the disclosure is *Bacillus anthracis* BH480.

*B. anthracis* lacking more than one secreted protease can be produced using the methods disclosed herein. The disclosure provides a method to produce a *B. anthracis* of the embodiments comprising: effecting a genetic modification to inactivate a protease of the M4 family of metalloproteases; and effecting a genetic modification to inactivate a protease of the M6 family of metalloproteases. The disclosure also provides a method to produce a *B. anthracis* of the embodiments comprising: effecting a genetic modification to inactivate a protease of the M4 family of metalloproteases; effecting a genetic modification to inactivate a protease of the M6 family of metalloproteases; and effecting a genetic modification to inactivate a protease of the M73 family of metalloproteases. The disclosure also provides a method to produce a *B. anthracis* of the embodiments comprising: effecting a genetic modification to inactivate a protease of the M4 family of metalloproteases; effecting a genetic modification to inactivate a protease of the M6 family of metalloproteases; effecting a genetic modification to inactivate a protease of the M73 family of metalloproteases; and effecting a genetic modification to inactivate a protease of the ZnMc superfamily of zinc-dependent metalloproteases. The disclosure also provides a method to produce a *B. anthracis* of the embodiments comprising: effecting a genetic modification to inactivate a protease of the M4 family of metalloproteases; effecting a genetic modification to inactivate a protease of the M6 family of metalloproteases; effecting a genetic modification to inactivate a protease of the M73 family of metalloproteases; effecting a genetic modification to inactivate a protease of the ZnMc superfamily of zinc-dependent metalloproteases; effecting a genetic modification to inactivate a protease of the transglutaminase-like superfamily; and effecting a genetic modification to inactivate a protease of peptidase family S8. One embodiment is a method to produce a *B. anthracis* of the embodiments comprising genetically modifying a *B. anthracis* to inactivate a protease of the M4 family of metalloproteases and to inactivate a protease of the M6 family of metalloproteases. One embodiment is a method to produce a *B. anthracis* of the embodiments comprising genetically modifying a *B. anthracis* to inactivate a protease of the M4 family of metalloproteases, to inactivate a protease of the M6 family of metalloproteases, and to inactivate a protease of the M73 family of metalloproteases. One embodiment is a method to produce a *B. anthracis* of the embodiments comprising genetically modifying a *B. anthracis* to inactivate a protease of the M4 family of metalloproteases, to inactivate a protease of the M6 family of metalloproteases, to inactivate a protease of the M73 family of metalloproteases, and to inactivate a protease of the ZnMc superfamily of zinc-dependent metalloproteases. One embodiment is a method to produce a *B. anthracis* of the embodiments comprising genetically modifying a *B. anthracis* to inactivate a protease of the M4 family of metalloproteases, to inactivate a protease of the M6 family of metalloproteases, to inactivate a protease of the M73 family of metalloproteases, to inactivate a protease of the ZnMc superfamily of zinc-dependent metalloproteases, to inactivate a protease of the transglutaminase-like superfamily, and to inactivate a protease of peptidase family S8. Genetic modifications taught herein as well as those known to those skilled in the art can be used to inactivate proteases specified herein. Sporulation-deficient *B. anthracis* can be produced using techniques as taught herein or other techniques known to those skilled in the art. Those skilled in the art can also produce *B. anthracis* free of one or both virulence plasmids.

The disclosure provides a method to produce *B. anthracis* of the embodiments comprising: culturing the *B. anthracis* in a medium; and recovering the *B. anthracis*. Any suitable medium and culture conditions known to those skilled in the art can be used to produce such *B. anthracis*. Non-limiting examples of media include LB and FA, the compositions of which are specified in the Examples. Methods to recover the bacteria are also known to those skilled in the art.

The disclosure also provides a method to produce an endogenous *B. anthracis* protein, such as an endogenous secreted protein. Such a method comprises culturing a *B. anthracis* of the embodiments in a medium; and recovering the protein. In one embodiment, the protein is an endogenous secreted protein of *B. anthracis*. Culturing methods, recovery methods, and media to use are known to those skilled in the art.

The disclosure provides a modified *Bacillus anthracis* (*B. anthracis*) transformed with a recombinant molecule encoding a product, wherein the *B. anthracis* comprises any of the genetically modified *B. anthracis* disclosed herein (i.e., any *B. anthracis* of the embodiments), and the recombinant molecule comprises a nucleic acid molecule encoding the product operatively linked to an expression vector. One embodiment is a modified *B. anthracis* transformed with a recombinant molecule encoding a product, wherein: the *B. anthracis* comprises a genetic modification that inactivates a protease of the M4 family of metalloproteases and a genetic modification that inactivates a protease of the M6 family of metalloproteases; and the recombinant molecule comprises a nucleic acid molecule encoding the product operatively linked to an expression vector. One embodiment is a modified *B. anthracis* transformed with a recombinant molecule encoding a product, wherein: the *B. anthracis* comprises a genetic modification that inactivates a protease of the M4 family of metalloproteases, a genetic modification that inactivates a protease of the M6 family of metalloproteases, and a genetic modification that inactivates a protease of the M73 family of metalloproteases; and the recombinant molecule comprises a nucleic acid molecule encoding the product operatively linked to an expression vector. One embodiment is a modified *B. anthracis* transformed with a recombinant molecule encoding a product, wherein: the *B. anthracis* comprises a genetic modification that inactivates a protease of the M4 family of metalloproteases, a genetic modification that inactivates a protease of the M6 family of metalloproteases, a genetic modification that inactivates a protease of the M73 family of metalloproteases, and a genetic modification that inactivates a protease of the ZnMc superfamily of zinc-dependent metalloproteases; and the recombinant molecule comprises a nucleic acid molecule encoding the product operatively linked to an expression vector. One embodiment is a modified *B. anthracis* transformed with a recombinant molecule encoding a product, wherein: the *B. anthracis* comprises a genetic modification that inactivates a protease of the M4 family of metalloproteases, a genetic modification that inactivates a protease of the M6 family of metalloproteases, a genetic modification that inactivates a protease of the M73 family of metalloproteases, a genetic modification that inactivates a protease of the ZnMc superfamily of zinc-dependent metalloproteases, a genetic modification that inactivates a protease of the transglutaminase-like superfamily, and a genetic modification that inactivates a protease of peptidase family S8; and the recombinant molecule comprises a nucleic acid molecule encoding the product operatively linked to an expression vector.

As used herein, a recombinant molecule comprises an expression vector operatively linked to a nucleic acid molecule encoding a desired product. A modified *B. anthracis* can comprise one or more recombinant molecules. A recombinant molecule can comprise one or more nucleic acid molecules encoding one or more desired products. As used herein, the phrase operatively linked means that the nucleic acid molecule encoding a desired product is joined to the vector in such a way that the product is produced. An expression vector is any vector that can transform *B. anthracis* (i.e., deliver a nucleic acid molecule encoding a product into *B. anthracis*) and that comprises expression control sequences that can effect expression in *B. anthracis* of the nucleic acid molecule encoding a desired product. Non-limiting examples of expression vectors are plasmid expression vectors, viral expression vectors, and other vectors known to those skilled in the art. Such a vector can be DNA, RNA, or a derivative of DNA or RNA. Examples of expression control sequences include, but are not limited to, a promoter, an enhancer, a repressor, a ribosome binding site, an RNA splice site, a polyadenylation site, a transcriptional terminator sequence, and a microRNA binding site. Examples of promoters include, but are not limited to, a promoter that controls expression of the pag gene that encodes *B. anthracis* protective antigen (PA), referred to herein as a pag promoter or PA promoter, and other promoters that function in *B. anthracis*. In one embodiment, the promoter is a pag promoter. A recombinant molecule can also comprise replication control sequences that can effect vector replication, such as an origin of replication. Selection of replication and expression control sequences to include can be accomplished by one skilled in the art. One embodiment is a recombinant molecule that is heterologous to *B. anthracis*; i.e., at least a portion of the recombinant molecule is not a natural *B. anthracis* plasmid. One embodiment is a recombinant molecule comprising a *B. anthracis* plasmid that is attenuated, for example, a virulence plasmid from which at least one component that would lead to virulence has been removed.

One embodiment is recombinant molecule pSJ136EFOS. One embodiment is a recombinant molecule comprising nucleic acid sequence SEQ ID NO:62.

One embodiment is a recombinant molecule selected from the group consisting of a recombinant molecule comprising nucleic acid sequence SEQ ID NO:65, a recombinant molecule comprising nucleic acid sequence SEQ ID NO:67, and a recombinant molecule comprising nucleic acid sequence SEQ ID NO:69. One embodiment is a recombinant molecule selected from the group consisting of pSW4-HBL L1 His, pSW4-HBL L2 His, and pSW4-HBL B His. One embodiment is recombinant molecule pSW4-HBL L1 His. One embodiment is recombinant molecule pSW4-HBL L2 His. One embodiment is recombinant molecule pSW4-HBL B His.

One embodiment is a recombinant molecule comprising a pSJ115 plasmid that encodes a protein comprising amino acid sequence SEQ ID NO:91. One embodiment is a recombinant molecule comprising a pYS5 plasmid that encodes a protein comprising amino acid sequence SEQ ID NO:92. One embodiment is a recombinant molecule selected from the group consisting of recombinant molecule pSJ136EF-His, recombinant molecule pSJ136EF-Cys, and recombinant molecule pSJ136EF-NEHY. One embodiment is recombinant molecule pSJ136EF-His. One embodiment is recombinant molecule pSJ136EF-Cys. One embodiment is recombinant molecule pSJ136EF-NEHY.

The disclosure also provides a protein comprising an amino acid sequence selected from the group consisting of amino acid sequence SEQ ID NO:93, amino acid sequence SEQ ID NO:94, and amino acid sequence SEQ ID NO:95. One embodiment is a protein comprising amino acid sequence SEQ ID NO:93. One embodiment is a protein comprising amino acid sequence SEQ ID NO:94. One embodiment is a protein comprising amino acid sequence SEQ ID NO:95.

Methods to transform *B. anthracis* of the embodiments and to select and produce expression vectors and recombinant molecules with which to transform *B. anthracis* are described in the Examples, and can also be found, for example, in Sambrook J et al., 2001, *Molecular Cloning: a Laboratory Manual*, 3$^{rd}$ edition, Cold Spring Harbor Laboratory Press, and Ausubel F et al., 1994, *Current Protocols in Molecular Biology*, John Wiley & Sons.

A nucleic acid molecule encoding a desired product of the embodiments can encode a product that *B. anthracis* produces naturally (e.g., an anthrax toxin protein) or a product heterologous to *B. anthracis* (e.g., a toxin from a different organism). A heterologous product can be a combination of an endogenous and non-endogenous product (e.g., a tumor-targeting anthrax toxin). Examples of products include, but are not limited to, a protein, an amino acid, a nucleic acid molecule, a compound produced via a recombinant biosynthetic pathway, a small molecule, a drug, a vitamin, a drug conjugate, and a peptide nucleic acid conjugate.

One embodiment is a product comprising a toxin. Examples of toxins include, but are not limited to, an anthrax toxin, a cholera toxin, a diphtheria toxin, a hemolysin, and a ricin. Additional examples include, but are not limited to a *Pseudomonas* toxin, a *Haemophilus ducreyi* toxin, an *Escherichia coli* toxin, and a ribosome-inactivating protein (RIP) toxin. One embodiment is a product selected from the group consisting of an anthrax edema factor (EF), an anthrax lethal factor (LF), an anthrax protective antigen (PA), and combinations thereof. One embodiment is a product comprising an anthrax edema factor. One embodiment is a product comprising intact anthrax edema factor. One embodiment is a product comprising an anthrax lethal factor. One embodiment is a product comprising intact anthrax lethal factor. One embodiment is a product comprising an anthrax protective antigen. One embodiment is a product comprising intact anthrax protective antigen. One embodiment is a product comprising an anthrolysin. One embodiment is a product comprising intact anthrolysin. One embodiment is a product comprising a hemolysin. One embodiment is a product comprising a *Bacillus cereus* hemolysin HBL. One embodiment is a product selected from the group consisting of a *B. cereus* hemolysin HBL L1, a *B. cereus* hemolysin HBL L2, a *B. cereus* hemolysin HBL B, and combinations thereof. One embodiment is a product comprising a diphtheria toxin. One embodiment is a product comprising a cholera toxin. One embodiment is a product comprising a ricin. One embodiment is a product comprising a *Pseudomonas* toxin. One embodiment is a product comprising a *Haemophilus ducreyi* toxin. One embodiment is a product comprising an *Escherichia coli* toxin. One embodiment is a product comprising a ribosome-inactivating protein (RIP) toxin.

One embodiment is a product comprising a toxin fusion protein. One embodiment is a product comprising a toxin conjugated to a tumor target. Examples of tumor targets are known to those skilled in the art. Examples of conjugates include, but are not limited to, an anthrax toxin conjugated to a tumor target, a cholera toxin conjugated to a tumor target, a diphtheria toxin conjugated to a tumor target, a hemolysin conjugated to a tumor target, and a ricin conjugated to a tumor target. One embodiment is an anthrax toxin conjugated to a tumor target. One embodiment is a product comprising a fusion protein comprising a PA binding moiety located in the amino terminal region of EF or LF (e.g., the amino terminal about 250 to about 260 amino acids of the mature protein) joined to a protein of interest that can be delivered to a cell via the protective antigen (PA) cellular translocation mechanism known to those skilled in the art.

A nucleic acid molecule of the embodiments can encode a natural product or any variant thereof that retains the activity of the natural product. Nucleic acid molecules of the embodiments can be produced using a number of methods known to those skilled in the art; see, for example, Sambrook J et al., ibid. and Ausubel F et al., ibid. For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecules of the embodiments can be selected from a mixture of modified nucleic acids by screening for the function of the protein encoded by the nucleic acid (e.g., EF expressed from a nucleic acid molecule that encodes an EF protein can be tested for its activity in a potency assay, such as that described in the Examples).

Products of the embodiments can be produced by culturing modified *B. anthracis* transformed with a recombinant molecule encoding a product of the embodiments. The disclosure provides a method to produce a product comprising: culturing a modified *B. anthracis* transformed with a recombinant molecule encoding a product of the embodiments; and recovering the product. Methods to effect such production, including culturing such modified *B. anthracis* and recovering such products are described in the Examples and are known to those skilled in the art, see for example Sambrook J et al., ibid, and Ausubel, F et al., ibid.

The disclosure provides antibodies against products produced by *B. anthracis* of the embodiments. Examples of antibodies include polyclonal antibodies, monoclonal antibodies, and functional equivalents such as antibody fragments and genetically-engineered antibodies (including, but not limited to, single chain antibodies and chimeric antibodies that can bind to more than one epitope) that retain antibody binding activity. One embodiment is an antibody against an anthrax edema factor produced by a modified *B. anthracis* of the embodiments.

The disclosure provides methods to use products of the embodiments. The disclosure provides that antibodies produced against products produced by modified *B. anthracis* of the embodiments can be used to detect such products or, as appropriate, organisms or toxins corresponding to such products. One embodiment is a method to determine if a sample comprises anthrax toxin, the method comprising: contacting a sample with an antibody against an anthrax edema factor produced by a modified *B. anthracis* of the embodiments; and determining whether the antibody forms a complex, wherein detection of a complex indicates that the sample comprises anthrax. One embodiment is a method to determine if a sample comprises anthrax toxin, the method comprising: contacting a sample with an antibody against intact anthrax edema factor produced by a *B. anthracis* of the embodiments; and determining whether the antibody forms a complex, wherein detection of a complex indicates that the sample comprises anthrax. Methods to accomplish such detection are known to those skilled in the art.

The disclosure provides that products produced by modified *B. anthracis* of the embodiments can be used for their intended purpose. For example, products of agents that cause disease can be used to protect (e.g., prevent or treat) an animal from such disease. One embodiment is a method to protect an animal from anthrax, the method comprising administering an anthrax edema factor produced by a modified *B. anthracis* of the embodiments to the animal. One embodiment is a method to protect an animal from anthrax, the method comprising administering intact anthrax edema factor produced by a modified *B. anthracis* of the embodiments to the animal. Such an anthrax edema factor can be administered alone or in combination with one or more other agents, such as with an anthrax lethal factor and/or protective antigen. One embodiment is a method to protect an animal from anthrax, the method comprising administering an antibody against intact anthrax edema factor produced by a modified *B. anthracis* of the embodiments to the animal. Such an anti-anthrax edema factor can be administered alone or in combination with one or more other agents, such as with an antibody against an anthrax lethal factor and/or protective antigen. Methods to accomplish such administration are known to those skilled in the art.

The following is a listing of the SEQ ID NOs disclosed in the application. It is to be appreciated that since nucleic acid sequencing technology is not entirely error-free, the nucleic acid sequences and amino acid sequences presented herein represent, respectively, apparent nucleic acid sequences of nucleic acid molecules of the embodiments and apparent amino acid sequences of proteins of the embodiments.

| SEQ ID NO: | Species | Description |
|---|---|---|
| 1 | B. anthracis | Wild-type NprB protease (full-length encoded protein (i.e., includes signal sequence)); note that the mature NprB protease begins at amino acid 28 of SEQ ID NO: 1 |
| 2 | Synthetic | Inactivated NprB protease (full-length encoded protein) |
| 3 | Synthetic | Portion of nprB nucleic acid comprising loxP insert |
| 4 | Synthetic | Translation of SEQ ID NO: 3 |
| 5 | B. anthracis | Wild-type InhA2 protease (full-length encoded protein); note that the mature InhA2 protease begins at amino acid 33 of SEQ ID NO: 5 |
| 6 | Synthetic | Inactivated InhA2 protease (full-length encoded protein) |
| 7 | Synthetic | Portion of inhA2 nucleic acid comprising loxP insert |
| 8 | Synthetic | Translation of SEQ ID NO: 7 |
| 9 | B. anthracis | Wild-type TasA protease (full-length encoded protein); note that the mature TasA protease begins at amino acid 30 of SEQ ID NO: 9 |
| 10 | Synthetic | Inactivated TasA protease (full-length encoded protein) |
| 11 | Synthetic | Portion of tasA nucleic acid comprising loxP insert |
| 12 | Synthetic | Translation of SEQ ID NO: 11 |
| 13 | B. anthracis | Wild-type camelysin protease (full-length encoded protein); note that the mature camelysin protease begins at amino acid 30 of SEQ ID NO: 13 |
| 14 | Synthetic | Inactivated camelysin protease (full-length encoded protein) |
| 15 | Synthetic | Portion of calY nucleic acid comprising loxP insert |
| 16 | Synthetic | Translation of SEQ ID NO: 15 |
| 17 | B. anthracis | Wild-type InhA1 protein (full-length encoded protein); note that the mature InhA1 protease begins at amino acid 32 of SEQ ID NO: 17 |
| 18 | Synthetic | Inactivated InhA1 protease (full-length encoded protein) |
| 19 | Synthetic | Portion of inhA1 nucleic acid comprising loxP insert |
| 20 | Synthetic | Translation of SEQ ID NO: 19 |
| 21 | B. anthracis | Wild-type MmpZ protein (full-length encoded protein); note that the mature MmpZ protease begins at amino acid 27 of SEQ ID NO: 21 |
| 22 | Synthetic | Inactivated MmpZ protease (full-length encoded protein) |
| 23 | Synthetic | Portion of mmpZ nucleic acid comprising loxP insert |
| 24 | Synthetic | Translation of SEQ ID NO: 23 |
| 25 | Synthetic | Inactive TasA-InhA1 translation product |
| 26 | Synthetic | Portion of tasA-inhA1 nucleic acid comprising loxP insert |
| 27 | Synthetic | Translation of SEQ ID NO: 26 |
| 28 | B. anthracis | Wild-type BA1995 protein (full-length encoded protein) |
| 29 | B. anthracis | Wild-type VpR protein (full-length encoded protein) |
| 30 | B. anthracis | Wild-type BA5414 protein (full-length encoded protein) |
| 31 | Synthetic | Zinc-binding motif for zincin tribe of metalloproteases: His-Glu-Xxx-Xxx-His |
| 32 | Synthetic | Extended zinc-binding motif of metzincin metalloproteases: His-Glu-Xxx-Xxx-His-Xxx-Xxx-Gly/Asn-Xxx-Xxx-His/Asp |

-continued

| SEQ ID NO: | Species | Description |
|---|---|---|
| 33 | B. anthracis | IMSGGSWAGKIAGTTPTSFS |
| 34 | Synthetic | Primer 0672LL: GCTCGAGCGGATGTACATCTGTAATGAGT |
| 35 | Synthetic | Primer 0672LR: GGATATCTTGAACGATGTGACCAAATG |
| 36 | Synthetic | Primer 0672RL: GCCCGGGCCTGTCGAAGCTTGGTCATT |
| 37 | Synthetic | Primer 0672RR: GCCGCGGTTTGCATACCTGTGTTACCG |
| 38 | Synthetic | Primer 0672seqF: GGTCAAGAAGCTGGTGGAGGTA |
| 39 | Synthetic | Primer 0672seqR: TCTGTTCCTGCAATTTTCCC |
| 40 | Synthetic | Primer 1288LL: GCTCGAGTAATTTGGAAGGTGATTAGC |
| 41 | Synthetic | Primer 1288LR: GCCCGGGTTCACATCTTCTACATTGTAAT |
| 42 | Synthetic | Primer 1288RL: GACTAGTAACAATCGTAAAAGAAACAGCG |
| 43 | Synthetic | Primer 1288RR: GGAGCTCTATCGATCGCCTGTAAATTC |
| 44 | Synthetic | Primer 1288seqF: GGGGATATGGACATGACTTT |
| 45 | Synthetic | Primer 1288seqR: CAGTAAGTGTGTCACCCTTC |
| 46 | Synthetic | Primer 1290L: GAGAAGATAGCTGCTGAGAG |
| 47 | Synthetic | Primer 1290R: TAGAGGGAGTTTAATGGGGA |
| 48 | Synthetic | Primer 1290seqF: GAAATTGCGCAAAAAGAT |
| 49 | Synthetic | Primer 1290seqR: AGAGCCATTCCAGAACGC |
| 50 | Synthetic | Primer 3159LL: GCTCGAGGGTAATAACTTTCAATTAATAC |
| 51 | Synthetic | Primer 3159LR: GGATATCGAAAAAACAAACACAGTACC |
| 52 | Synthetic | Primer 3159RL: GCCCGGGGGTTGGCAAGCTGCCGATTC |
| 53 | Synthetic | Primer 3159RR: GCCGCGGCGAATGGTTCAATTGCTCCG |
| 54 | Synthetic | Primer 3159seqF: GGTACTGTGTTTGTTTTTTC |
| 55 | Synthetic | Primer 3159seqR: GAATCGGCAGCTTGCCAACC |
| 56 | Synthetic | Primer 3159CF: CCTCGAGTTTCATTTTTGAAGTCTTCTTC |
| 57 | Synthetic | Primer 3159CR: CACTAGTCAGCGAAACGATGATTGATTTT |
| 58 | Synthetic | Primer deltaF: TCCGATTAGGAAGTTGACAA |
| 59 | Synthetic | Primer deltaR: CAGTTACCACCAATTGTTTT |
| 60 | Synthetic | Primer deltaCF: CCTCGAGTTTTCTTATTGCATTTCTAATGTG |
| 61 | Synthetic | Primer deltaCR: CCCGCGGTTAGCGATATAAGCGAACAG |
| 62 | Synthetic | pSJ136EFOS |
| 63 | Synthetic | Translation of EF from SEQ ID NO: 62 |
| 64 | Synthetic | Translation of Mature EF from SEQ ID NO: 62 |
| 65 | Synthetic | pSW4-HBL L1 His |
| 66 | Synthetic | Translation of HBL L1 from SEQ ID NO: 65 |
| 67 | Synthetic | pSW4-HBL L2 His |
| 68 | Synthetic | Translation of HBL L2 from SEQ ID NO: 67 |
| 69 | Synthetic | pSW4-HBL B His |
| 70 | Synthetic | Translation of HBL B His from SEQ ID NO: 69 |

-continued

| SEQ ID NO: | Species | Description |
|---|---|---|
| 71 | B. anthracis | Wild-type CysP1 protein (full-length encoded protein); note that the mature CysP1 protease begins at amino acid 31 of SEQ ID NO: 71 |
| 72 | Synthetic | Inactivated CysP1 protease (full-length encoded protein) |
| 73 | Synthetic | Portion of cysP1 nucleic acid comprising FRT insert |
| 74 | Synthetic | Translation of SEQ ID NO: 73 |
| 75 | B. anthracis | Wild-type VpR protein (full-length encoded protein); note that the mature VpR protease begins at amino acid 26 of SEQ ID NO: 75 |
| 76 | Synthetic | Inactivated VpR protease (full-length encoded protein) |
| 77 | Synthetic | Portion of vpR nucleic acid comprising FRT insert |
| 78 | Synthetic | Translation of SEQ ID NO: 77 |
| 79 | Synthetic | Primer 1995LL: ACTGCTCGAGTGGGCTGACACATTTAAAAG |
| 80 | Synthetic | Primer 1995LR: ACTGACTAGTAGTTGAACAAAGTGCGGCAG |
| 81 | Synthetic | Primer 1995RL: ACTGCTCGAGAATGAAATAAACTGGCCAAAAGGTG |
| 82 | Synthetic | Primer 1995RR: ACTGACTAGTCGGGAAAAACTTCAAATCCA |
| 83 | Synthetic | Primer 1995 seqF: TTGCCAGAGCTTTTCATTGA |
| 84 | Synthetic | Primer 1995 seqR: CGCTAATGAATAATCTGCCA |
| 85 | Synthetic | Primer 4584LL: ACTGCTCGAGAAGCTGTCGGTACTGCTAAA |
| 86 | Synthetic | Primer 4584LR: ACTGACTAGTCGAGTGCCATACTTAAAAGTATAGA |
| 87 | Synthetic | Primer 4584RL: ACTGCTCGAGATCCTTGGGAGAAAAATTACGGCATT |
| 88 | Synthetic | Primer 4584RR: ACTGACTAGTCGCCAAACATTCATTCATTTCTTCT |
| 89 | Synthetic | Primer 4584 seqF: TGAGTGAAACGGCGTAACTT |
| 90 | Synthetic | Primer 4584 seqR: TATTCCTTCAAAGCCGATAT |
| 91 | Synthetic | LFn-B1aY protein |
| 92 | Synthetic | PA SNKE dFF E308D protein |
| 93 | Synthetic | EF-His protein |
| 94 | Synthetic | EF-Cys protein |
| 95 | Synthetic | EF-NEHY protein |

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Celsius. Standard abbreviations are used.

Example 1

Materials and Methods

Materials

Proteases and genes encoding such proteases that were used and/or analyzed herein are listed in Table 1.

TABLE 1

B. anthracis Ames ancestor strain genes and proteins inactivated and/or analyzed herein.

| Protein | Gene | Function/Name | Locus Tag |
|---|---|---|---|
| NprB | nprB | Metallopeptidase | GBAA_0599 |
| InhA2 | inhA2 | Metallopeptidase | GBAA_0672 |
| TasA | tasA | Metallopeptidase | GBAA_1288 |

TABLE 1-continued

*B. anthracis* Ames ancestor strain genes and proteins inactivated and/or analyzed herein.

| Protein | Gene | Function/Name | Locus Tag |
|---|---|---|---|
| Camelysin | calY | Metallopeptidase | GBAA_1290 |
| SinR | sinR | regulatory protein | GBAA_1292 |
| SinI | sinI | regulatory protein | GBAA_1293 |
| InhA1 | inhA1 | Metallopeptidase | GBAA_1295 |
| MmpZ | mmpZ | Metallopeptidase | GBAA_3159 |
| CysP1 | cysP1 | putative cysteine protease | GBAA_1995 |
| VpR | vpR | minor extracellular protease | GBAA_4584 |
| SprA | sprA | serine protease | GBAA_5414 |
| NprC | nprC | neutral metalloprotease | GBAA_2183 |
| HtrA | htrA | serine protease | GBAA_3660 |
| HsIV | hsIV | Prokaryotic homolog of proteasome HsIV | GBAA_3968 |
| ALO | alo | thiol-activated cytolysin (anthrolysin) | GBAA_3355 |
| Spo0A | spo0A | sporulation regulator | GBAA_4394 |
| EF | cya | edema factor | GBAA_pXO1_0142 |
| PA | pag | protective antigen | GBAA_pXO1_0164 |
| LF | lef | lethal factor | GBAA_pXO1_0172 |

Oligonucleotide primers produced and/or used herein are listed in Table 2.

TABLE 2

Primers produced and/or used herein.

| Primer | Sequence *a* (5'-3') (location) | Relevant property | Site |
|---|---|---|---|
| 0672LL | GCTCGAGCGGATGTACATCTGTAATGAGT (SEQ ID NO: 34) | Primer pair to amplify left fragment of inhA2gene to clone it into pDC | XhoI |
| 0672LR | GGATATCTTGAACGATGTGACCAAATG (SEQ ID NO: 35) | | EcoRV |
| 0672RL | GCCCGGGCCTGTCGAAGCTTGGTCATT (SEQ ID NO: 36) | Primer pair to amplify right fragment of inhA2 gene to clone it into pDC | SmaI |
| 0672RR | GCCGCGGTTTGCATACCTGTGTTACCG (SEQ ID NO: 37) | | SacII |
| 0672seqF | GGTCAAGAAGCTGGTGGAGGTA (SEQ ID NO: 38) | Primer pair to verify inhA2gene disruption | |
| 0672seqR | TCTGTTCCTGCAATTTTCCC (SEQ ID NO: 39) | | |
| 1288LL | GCTCGAGTAATTTGGAAGGTGATTAGC (SEQ ID NO: 40) | Primer pair to amplify left fragment of tasA gene to clone it into pSC | XhoI |
| 1288LR | GCCCGGGTTCACATCTTCTACATTGTAAT (SEQ ID NO: 41) | | SmaI |
| 1288RL | GACTAGTAACAATCGTAAAAGAAACAGCG (SEQ ID NO: 42) | Primer pair to amplify right fragment of tasA gene to clone it into pSC | SpeI |
| 1288RR | GGAGCTCTATCGATCGCCTGTAAATTC (SEQ ID NO: 43) | | SacI |
| 1288seqF | GGGGATATGGACATGACTTT (SEQ ID NO: 44) | Primer pair to verify tasA gene disruption | |
| 1288seqR | CAGTAAGTGTGTCACCCTTC (SEQ ID NO: 45) | | |
| 1290L | GAGAAGATAGCTGCTGAGAG (SEQ ID NO: 46) | Primer pair to amplify calY gene to clone it into pDC | |
| 1290R | TAGAGGGAGTTTAATGGGGA (SEQ ID NO: 47) | | |
| 1290seqF | GAAATTGCGCAAAAAGAT (SEQ ID NO: 48) | Primer pair to verify calY gene disruption | |
| 1290seqR | AGAGCCATTCCAGAACGC (SEQ ID NO: 49) | | |
| 3159LL | GCTCGAGGGGTAATAACTTTCAATTAATAC (SEQ ID NO: 50) | Primer pair to amplify left fragment of mmpZ gene to clone it into pSC | XhoI |
| 3159LR | GGATATCGAAAAAACAAACACAGTACC (SEQ ID NO: 51) | | EcoRV |
| 3159RL | GCCCGGGGGTTGGCAAGCTGCCGATTC (SEQ ID NO: 52) | Primer pair to amplify right fragment of mmpZ gene to clone it into pSC | SmaI |
| 3159RR | GCCGCGGCGAATGGTTCAATTGCTCCG (SEQ ID NO: 53) | | SacII |
| 3159seqF | GGTACTGTGTTTGTTTTTTC (SEQ ID NO: 54) | Primer pair to verify mmpZ gene disruption | |
| 3159seqR | GAATCGGCAGCTTGCCAACC (SEQ ID NO: 55) | | |
| 3159CF | CCTCGAGTTTCATTTTTGAAGTCTTCTTC (SEQ ID NO: 56) | Primer pair to complement mmpZ gene disruption | XhoI |
| 3159CR | CACTAGTCAGCGAAACGATGATTGATTTT (SEQ ID NO: 57) | | SpeI |

TABLE 2-continued

Primers produced and/or used herein.

| Primer | Sequence $^a$ (5'-3')(location) | Relevant property | Site |
|---|---|---|---|
| 1995LL | ACTG<u>CTCGAG</u>TGGGCTGACACATTTAAAAG (SEQ ID NO: 79) | Primer pair to amplify left fragment of cysP1 gene to clone it into pSCF | XhoI |
| 1995LR | ACTG<u>ACTAGT</u>AGTTGAACAAAGTGCGGCAG (SEQ ID NO: 80) | | SpeI |
| 1995RL | ACTG<u>CTCGAG</u>AATGAAATAAACTGGCCAAA (SEQ ID NO: 81) | Primer pair to amplify right fragment of cysP1 gene to clone it into pSCF | XhoI |
| 1995RR | ACTG<u>ACTAGT</u>CGGGAAAAACTTCAAATCCA (SEQ ID NO: 82) | | SpeI |
| 1995 seqF | TTGCCAGAGCTTTTCATTGA (SEQ ID NO: 83) | Primer pair to verify cysP1 gene disruption | |
| 1995 seqR | CGCTAATGAATAATCTGCCA (SEQ ID NO: 84) | | |
| 4584LL | ACTG<u>CTCGAG</u>AAGCTGTCGGTACTGCTAAA (SEQ ID NO: 85) | Primer pair to amplify left fragment of vpR gene to clone it into pSCF | XhoI |
| 4584LR | ACTG<u>ACTAGT</u>CGAGTGCCATACTTAAAAGT ATAGA (SEQ ID NO: 86) | | SpeI |
| 4584RL | ACTG<u>CTCGAG</u>ATCCTTGGGAGAAAAATTAC GGCATT (SEQ ID NO: 87) | Primer pair to amplify right fragment of vpR gene to clone it into pSCF | XhoI |
| 4584RR | ACTG<u>ACTAGT</u>CGCCAAACATTCATTCATTTC TTCT (SEQ ID NO: 88) | | SpeI |
| 4584 seqF | TGAGTGAAACGGCGTAACTT (SEQ ID NO: 89) | Primer pair to verify vpR gene disruption | |
| 4584 seqR | TATTCCTTCAAAGCCGATAT (SEQ ID NO: 90) | | |
| deltaF | TCCGATTAGGAAGTTGACAA (SEQ ID NO: 58) | Primer pair to verify deletion of tasA-inhA1 region | |
| deltaR | CAGTTACCACCAATTGTTTT (SEQ ID NO: 59) | | |
| deltaCF | <u>CCTCGAG</u>TTTTCTTATTGCATTTCTAATGTG TTCG (SEQ ID NO: 60) | Primer pair to complement tasA-inhA1 region deletion | XhoI |
| deltaCR | <u>CCCGCGG</u>TTAGCGATATAAGCGAACAG (SEQ ID NO: 61) | | SacII |

$^a$ Restriction site is underlined

Plasmids produced, used, and/or analyzed herein are listed in Table 3.

TABLE 3

Plasmids produced and/or used herein.

| Plasmid | Relevant characteristic(s) |
|---|---|
| pHY304 | Contains Em$^R$ gene and strongly temperature-sensitive replicon for both E. coli and gram-positive bacteria; Em$^R$ in both E. coli and B. anthracis |
| pDC | Ω-sp cassette flanked by two similarly oriented loxP sites and two external multiple restriction sites (single XhoI, SalI, and EcoRV upstream of first loxP and single PstI, XmaI and SacII downstream of second loxP) inserted into pHY304 |
| pSC | Plasmid used for single crossovers in B. anthracis. Ap$^R$ in E. coli; Em$^R$ both in E. coli and B. anthracis |
| pSCF | Plasmid used for single crossovers in B. anthracis. Ap$^R$ in E. coli; Em$^R$ both in E. coli and B. anthracis. Two FRT sites flank multiple restriction sites area. |
| pInhA2I | pDC with loxP-Ω-sp-loxP flanked 3' and 5' by inhA2 gene sequences |
| pTasALI | pSC containing tasA fragment amplified with primer pair 1288LL/1288LR |
| pTasARI | pSC containing tasA fragment amplified with primer pair 1288RL/1288RR |
| pCamI | pHY304 with loxP-Ω-sp-loxP flanked 3' and 5' by calY gene sequences |
| pMmpZLI | pSC containing mmpZ fragment amplified with primer pair 3159LL/3159LR |
| pMmpZRI | pSC containing mmpZ fragment amplified with primer pair 3159RL/3159RR |
| pCysP1LI | pSCF containing cysP1 fragment amplified with primer pair 1995LL/1993LR |
| pCysP1RI | pSCF containing cysP1 fragment amplified with primer pair 1995RL/1995RR |
| pVpRLI | pSCF containing vpR fragment amplified with primer pair 4584LL/4584LR |
| pVpRRI | pSCF containing vpR fragment amplified with primer pair 4584RL/4584RR |
| pCrePA | Contains cre gene and strongly temperature-sensitive replicon for both E. coli and gram-positive bacteria; Em$^R$ in both E. coli and B. anthracis |
| pCrePAS | Contains cre gene and strongly temperature-sensitive replicon for both E. coli and gram-positive bacteria; Sp$^R$ in both E. coli and B. anthracis |
| pFPAS | Contains flp gene and strongly temperature-sensitive replicon for both E. coli and gram-positive bacteria; Sp$^R$ in both E. coli and B. anthracis |
| pMmpZC | pSC with 3159F/3159R PCR fragment containing entire mmpZ gene |

TABLE 3-continued

Plasmids produced and/or used herein.

| Plasmid | Relevant characteristic(s) |
| --- | --- |
| pΔTasA-InhA1C | pSC with deltaCF/deltaCR fragment containing entire tasA-inhA1 DNA region |
| pSΩL304 | pDC with loxP-Ω-sp-loxP flanked 3' and 5' by spo0A sequences |
| pSJ136EFOS | Contains B. anthracis cya gene instead of the lef gene in pSJ115 (Park S et al., 2000, Protein Expr. Purif. 18, 293-302. |
| pSW4-HBL L1 His | Encodes B. cereus HBL L1 His |
| pSW4-HBL L2 His | Encodes B. cereus HBL L2 His |
| pSW4-HBL B His | Encodes B. cereus HBL B His |

Bacterial strains produced, used, and/or analyzed herein are listed in Table 4.

TABLE 4

Bacterial strains produced and/or used herein.

| Strain | Relevant characteristic(s) |
| --- | --- |
| A33 | B. anthracis Ames 33 strain (pXO1⁻ pXO2⁻) |
| A35 | B. anthracis Ames 35 strain (pXO1⁺ pXO2⁻) |
| A35ΔSpo0A | Spo0A knockout containing one loxP site, previous name of this strain is SΩL35 |
| A35ΔNprB | nprB knockout containing one loxP site |
| A35ΔInhA2 | inhA2 knockout containing one loxP site |
| A35ΔTasA | tasA knockout containing one loxP site |
| A35ΔCam | calY knockout containing one loxP site |
| A35ΔInhA1 | inhA1 knockout containing one loxP site |
| A35ΔMmpZ | mmpZ knockout containing one loxP site |
| A35ΔmmpZC | A35ΔMmpZ complemented in situ by insertion of native mmpZ gene |
| A35DM | Ames 35 double mutant with nprB and inhA1 knockouts; each gene contains one loxP site |
| A35TM | Ames 35 tetra-protease mutant; has nprB knockout containing one loxP site and deleted DNA region including tasA, calY, sinI, sinR, and inhA1 genes |
| A35TMC | A35TM with tasA-inhA1 deletion restored in situ by insertion of native DNA region including tasA, calY, sinI, sinR, and inhA1 genes |
| A35PM | Ames 35 penta-protease mutant; 35TM with inhA2 knockout containing one loxP site; total of 3 loxP sites in chromosome |
| A35HM | Ames 35 hexa-protease mutant: A35PM with mmpZ knockout containing one loxP site; total of 4 loxP sites in chromosome |
| A35HMS | A35HM with spo0A knockout containing one loxP site; total of 5 loxP sites in chromosome |
| BH460 | A35HMS cured of pXO1 |
| BH480 | BH460 with both cysP1 and vpR knockout containing FRT site in each knockout gene; total of 5 loxP and two FRT sites in chromosome |
| BH450 | A33; nprB and spo0A knockouts, residual loxP sites in both nprB and spo0A genes; strain was previously named MSLL33 |

Bacterial Growth Conditions and Phenotypic Characterization

E. coli strains were grown in Luria-Bertani (LB) broth and used as hosts for cloning. LB agar was used for selection of transformants (Sambrook J et al., 2001, Molecular Cloning: A Laboratory Manual, Third Edition, Cold Spring Harbor Laboratory Press, Cold. Spring Harbor, N.Y.). B. anthracis strains were also grown in LB or FA medium (Singh Y et al., 1989, J. Biol. Chem. 264, 19103-19107). FA medium contains, per liter, 33 g of tryptone, 20 g of yeast extract, 7.4 g of NaCl, 8 g of Na$_2$HPO$_4$, and 4 g of KH$_2$PO$_4$, pH 7.5. Antibiotics (Sigma-Aldrich, St. Louis, Mo.) were added to the medium when appropriate to give the following final concentrations: ampicillin (Ap), 100 μg/ml (only for E. coli); erythromycin (Em), 400 μg/ml for E. coli and 10 μg/ml for B. anthracis; spectinomycin (Sp), 150 μg/ml for both E. coli and B. anthracis; kanamycin (Km), 20 μg/ml (only for B. anthracis). SOC medium (Quality Biologicals, Inc., Gaithersburg, Md.) was used for outgrowth of transformation mixtures prior to plating on selective medium. B. anthracis spores were prepared from strains capable of sporulating as previously described (Thorne C, 1993, in Bacillus subtilis and other gram-positive bacteria: biochemistry, physiology, and molecular genetics, 113-124, Sonenshein A B et al., (Eds.), American Society for Microbiology, Washington, D.C.) after growth on NBY minimal agar (nutrient broth, 8 g/liter; yeast extract, 3 g/liter; MnSO$_4$.H$_2$O, 25 mg/liter; agar, 15 g/liter) at 30° C. 5 days. Spores and vegetative cells were visualized with a Nikon Eclipse E600W light microscope (Nikon Instrument Inc., New York).

DNA Isolation and Manipulation

Preparation of plasmid DNA from E. coli, transformation of E. coli, and recombinant DNA techniques were carried out by standard procedures (Sambrook J et al., ibid.). E. coli SCS110 competent cells were purchased from Stratagene (La Jolla, Calif.), and E. coli TOP10 competent cells were purchased from Invitrogen (Carlsbad, Calif.). Recombinant plasmid construction was carried out in E. coli TOP10. Plasmid DNA from B. anthracis was isolated according to the protocol for the purification of plasmid DNA from B. subtilis (Qiagen, Valencia, Calif.). Chromosomal DNA from B. anthracis was isolated with the Wizard genomic purification kit (Promega, Madison, Wis.). B. anthracis was electroporated with unmethylated plasmid DNA isolated from E. coli SCS110 (dam⁻ dcm⁻). Electroporation-competent B. anthracis cells were prepared and transformed as previously described (Pomerantsev A P et al., 2009, J. Bacteriol. 191, 5134-5136). Restriction enzymes. T4 ligase, and Antarctic phosphatase were purchased from New England Biolabs (Ipswich, Mass.). Taq polymerase, Platinum PCR SuperMix High Fidelity kit and the TOPO TA cloning kit were from Invitrogen. The pGEM-T Easy Vector system was from Promega. Ready-To-Go PCR Beads were from GE Healthcare Biosciences Corp. (Piscataway, N.J.). For routine PCR analysis, a single colony was suspended in 200 μl of TE buffer (pH 8.0), heated to 95° C. for 45 s, and then cooled to room temperature (Sambrook J et al., ibid.). Cellular debris was removed by centrifugation at 15,000×g for 10 min. Two microliters of the lysate contained sufficient template to support PCR. The GeneRuler DNA Ladder Mix from MBI Fermentas (Glen Burnie, Md.) was used to assess DNA fragment length. All constructs were verified by DNA sequencing and/or restriction enzyme digestion.

Construction of Vectors for Protease Gene Inactivation

B. anthracis Ames 35 (pXO1+pXO2−) (A35) was used for genetic manipulations. The GenBank database (GenBank Accession No. for the Ames strain is NC_003997) was analyzed for the identification of target genes and for the corresponding primer design. The Cre/Lox genetic modification method was adapted to introduce precise genetic knockouts into B. anthracis genes encoding putative proteases. The general schemes for producing B. anthracis mutants using Cre-loxP system were described previously (Pomerantsev A P et al., 2006, ibid.; Pomerantsev A P et al., 2009, ibid.). The system employs vectors designated generically as pDC, for double-crossover plasmid or pSC, for single-crossover plasmid. These plasmids are derived from the highly temperature-sensitive plasmid pHY304 (Pritzlaff et al., 2001, Mol. Microbiol. 39, 236-247), which has permissive and restrictive temperatures of 30° C. and 37° C., respectively. The pDC plasmid (Pomerantsev A P et al., 2006, ibid.) was used to inactivate the spo0A (GBAA_4394), nprB (GBAA_0599) (Pomerantsev A P et al., 2006, ibid.), inhA1 (GBAA_1295) (Kastrup C J et al., ibid.), inhA2 (GBAA_0672), and calY (GBAA_1290) genes. The pSC plasmid (Pomerantsev A P et al., 2009, ibid.) was used to inactivate the tasA (GBAA_1288) and mmpZ (GBAA_3159) genes. Both plasmids were used in the production of a genomic deletion of the region from tasA (GBAA_1288) to inhA1 (GBAA_1295).

The nprB gene was inactivated as described in Pomerantsev et al., 2006, ibid. The inhA1 gene was inactivated as described in Kastrup C J et al., ibid. To inactivate the inhA2 gene, left and right fragments were amplified with primer pairs 0672LL/0672LR and 0672RL/0672RR, respectively, (Table 2) and inserted into pDC to produce the pInhA2I plasmid (I at the end of the proteases gene number means inactivation). To inactivate the tasA gene, left and right fragments were amplified with primer pairs 1288LL/1288LR and 1288RL/1288RR, respectively, and inserted into pSC to produce the pTasALI and pTasARi plasmids. To inactivate the camelysin gene calY, a DNA fragment overlapping the protease gene was amplified with primer pair 1290L/1290R and inserted into the EcoRI-site of pHY304. The internal BglII-fragment of the calY gene was replaced with a loxP-Ω-sp-loxP cassette flanked by two BglII sites (Pomerantsev A P et al., 2006, ibid.) to create the pCamI plasmid for the gene inactivation. To inactivate the mmpZ gene, left and right fragments were amplified with primer pairs 3159LL/3159LR and 3159RL/3159RR, respectively, and inserted into pSC to produce pMmpZLI and pMmpZRI plasmids. To delete the tasA-inhA1 gene cluster, the double protease mutant A35DM strain (having a LoxP site in the inhA1 gene) was transformed with pTasALI, and the plasmid was integrated into the genome as described previously (Pomerantsev A P et al., 2009, ibid.). Subsequent transformation of the recombinant strain with the pCrePAS plasmid (Pomerantsev A P et al., 2009, ibid.) eliminated the complete tasA-inhA1 gene cluster and produced the tetra-protease mutant strain A35TM.

The Crc recombinase-expressing plasmids pCrePAS (Pomerantsev A P et al., 2009, ibid.) and pCrePA (Pomerantsev A P et al., 2006, ibid.) both have permissive and restrictive temperatures of 30° C. and 37° C., respectively, and differ only in the selectable marker. The pCrePA was used for elimination of DNA regions containing a spectinomycin resistance cassette located between two similarly oriented loxP sites (Pomerantsev A P et al., 2006, ibid.), while pCrePAS was used in a similar way when the recipient strain did not contain a spectinomycin marker. In that case, the region to be deleted generally contained an erythromycin resistance gene along with backbone plasmid pSC (Pomerantsev A P et al., 2009, ibid.). In both cases, a single loxP site replaced the DNA region targeted for deletion.

To complement the mutation in the mmpZ gene (A35ΔMmpZ strain) and to restore the deleted taksA-inhA1 region in the A35TM strain, the 3159CF/3159CR PCR fragment (amplified using primer pair 3159CF/3159CR) and the deltaCF/deltaCR PCR fragment (amplified using primer pair delta CF/delta CR) were inserted into the pSC plasmid. The resulting pMmpZC and pΔTasA-InhA1C plasmids containing, respectively, the intact mmpZ gene and the whole tasA-inhA1 region (C at the end of the proteases gene means complementation), were used for complementation. Each plasmid was inserted separately into the corresponding mutant by a single crossover event. During the crossover, both the mmpZ gene and whole tasA-inhA1 region were inserted into the genomes of the corresponding mutants. Subsequent elimination of the plasmid sequences by Cre recombinase left an intact functional copy of the originally mutated gene along with an inactive duplicate copy of a fragment of the gene.

Preparation of Protease-Deficient B. anthracis

B. anthracis strains A33 (Pomerantsev A P et al., 2003, Infect Immun 71, 6591-6606), A35, A35ΔSpo0A, A35ΔNprB, BH450 (the latter four all described in Pomerantsev A P et al., 2006, ibid.), and A35ΔInhA1 (Kastrup C J et al., ibid.) and their relevant characteristics are listed in Table 4. Also listed in Table 4 are protease-deficient B. anthracis strains produced as described herein. B. anthracis that was genetically modified to inactivate NprB, InhA2, TasA, camelysin. InhA1, or MmpZ, respectively, was constructed in the A35 strain by the replacement of the respective coding sequences with the loxP element as described herein.

The double NprB, InhA1 mutant (A35DM), a B. anthracis comprising a genetic modification to inactivate NprB and a genetic modification to inactivate InhA1, was created starting from the A35ΔNprB strain. The tetra-protease mutant, A35TM (a B. anthracis comprising a genetic modification to inactivate NprB, a genetic modification to inactivate TasA, a genetic modification to inactivate camelysin, and a genetic modification to inactivate InhA1) was created by deletion of the tasA-inhA1 gene region in the A35DM strain. The A35TM was then used for inactivation of the inhA2 and mmpZ genes with plasmids pInhA21 and pMmpZLI/pMmpZR1. The resulting penta- and hexa-protease mutants were designated A35PM (a B. anthracis comprising a genetic modification to inactivate NprB, a genetic modification to inactivate TasA, a genetic modification to inactivate camelysin, a genetic modification to inactivate InhA1, and a genetic modification to inactivate InhA2) and A35HM (a B. anthracis comprising a genetic modification to inactivate NprB, a genetic modification to inactivate TasA, a genetic modification to inactivate camelysin, a genetic modification to inactivate InhA1, a genetic modification to inactivate InhA2, and a genetic modification to inactivate MmpZ), respectively.

The mutant strains were checked at each step to ensure they had retained the ability to sporulate (Sastalla et al., 2010, Appl. Environ. Microbiol. 76, 6318-6321). To intentionally produce a sporulation-deficient hexa-protease mutant of A35HM, A35HMS was produced by inactivating the spo0A (GBAA_4394) gene in A35HM using the plasmid pSLΩL304 (Pomerantsev et al., 2006). The final protease-deficient spo0A-negative mutant lacking pXO1 was obtained by repeated passage of the A35HMS mutant at elevated temperatures to cure pXO1 as described previously (Pomerantsev et al., 2003, ibid.). The final strain was designated B. anthracis BH460 (Table 4).

PCR and Sequence Analysis of Chromosomal Modifications

PCR fragments containing loxP sites within mutated (i.e., inactivated) genes were amplified and sequenced using primers listed in Table 2 (0672seqF/0672seqR, 1288seqF/1288seqR, 1290seqF/1290seqR, 3159seqF/3159seqR). All primers for PCR and sequencing were synthesized by Operon Biotechnologies, Inc. (Huntsville, Ala.) or the FDA core facility (Bethesda, Md.). Sequences were determined from both sides of the PCR fragments (Macrogen, Rockville, Md.). For verification of the genomic deletion in the tasA-inhA1 gene area, the region encompassing the start of tasA gene and the end of inhA1 gene was amplified in the mutant strains by PCR using the primer pair deltaF/deltaR.

The location of the loxP site inside the PCR fragments was determined by sequencing the fragments.

Western Blot Analysis

The A35 strain and genetically modified *B. anthracis* mutants were grown at 37° C. in LB in air to analyze *B. anthracis* toxin production by Western blot. Overnight cultures were diluted into fresh LB to give $A_{600}$=0.002, and growth was measured at 1, 2, 3, 4, 5, 6, 7, 8, 9, 10, 17 and 24 h. Supernatant samples (6 ml) from each time point were filtered (0.22 μm Millex syringe-driven filter units. Millipore, Cork, Ireland) and concentrated 10-fold using Amicon Ultra-4 membranes (Millipore). Samples of 5 μl were mixed with 5 μl of 2× Tris-glycine SDS sample loading buffer (126 mM Tris-HCl, pH 6.8, 4% SDS, 20% glycerol, 0.005% bromophenol blue) (Invitrogen), heated (96° C., 10 min) and separated on 4-12% Bis-Tris NuPAGE gels) using NuPAGE MOPS SDS running buffer (Invitrogen). Precision Plus Protein Standard (All Blue, Bio-Rad, Hercules, Calif.) was used as a molecular weight marker. Proteins were transferred to MagnaCharge 0.45 μm nylon membranes (Osmonics Inc., Minnetonka, Minn.) using transfer buffer (25 mM Tris, 190 mM glycine, and 20% methanol), blocked in PBS+3% skim milk (Difco, Lawrence, K S) for 1 h at room temperature, followed by three 10 min washes in PBST (PBS+0.05% Tween20). Membranes were then incubated with primary antibody diluted in PBS+1% skim milk overnight at 4° C. Mouse monoclonal antibody PA-05-A-G1 Lot#071100-02, 5.9 mg/ml (Naval Medical Research Center, Biological Defense Research Directorate), for detection of PA, and mouse monoclonal antibody LF-03-A-G1 Lot#150900-01, 7.4 mg/ml (NMRC, BDRD), for detection of LF, were both used at 1:2000. Rabbit antisera for development of blots included anti-EF serum #5900 (used at 1:8000; produced in inventors' laboratory), anti-camelysin serum (used at 1:2000; Molecular Biology Institute of Barcelona, Spain), and anti-recombinant ALO serum (used at 1:2000; R. Rest, Drexel University College of Medicine. Philadelphia, Pa.). Appropriate HRP-conjugated secondary IgGs (KPL, Gaithersburg, Md.) were used at 1:10000 followed by development with TMB (3,3',5,5'-tetramethylbenzidine) (KPL).

Isolation and Purification of EF Protein

EF (*B. anthracis* edema factor) protein with an N-terminal six-histidine tag was expressed from plasmid pProEx-H6-EF (provided by Wei-Jen Tang) in *E. coli* BL21(DE3) (Promega) as previously described (Soelaiman S et al., 2003, J. Biol. Chem., 278, 25990-25997). pProEx-H6-EF comprises a nucleic acid molecule encoding EF with an N-terminal six-histidine tag operatively linked to pPROEX HTa (Addgene, Cambridge, Mass.).

Figure 6:
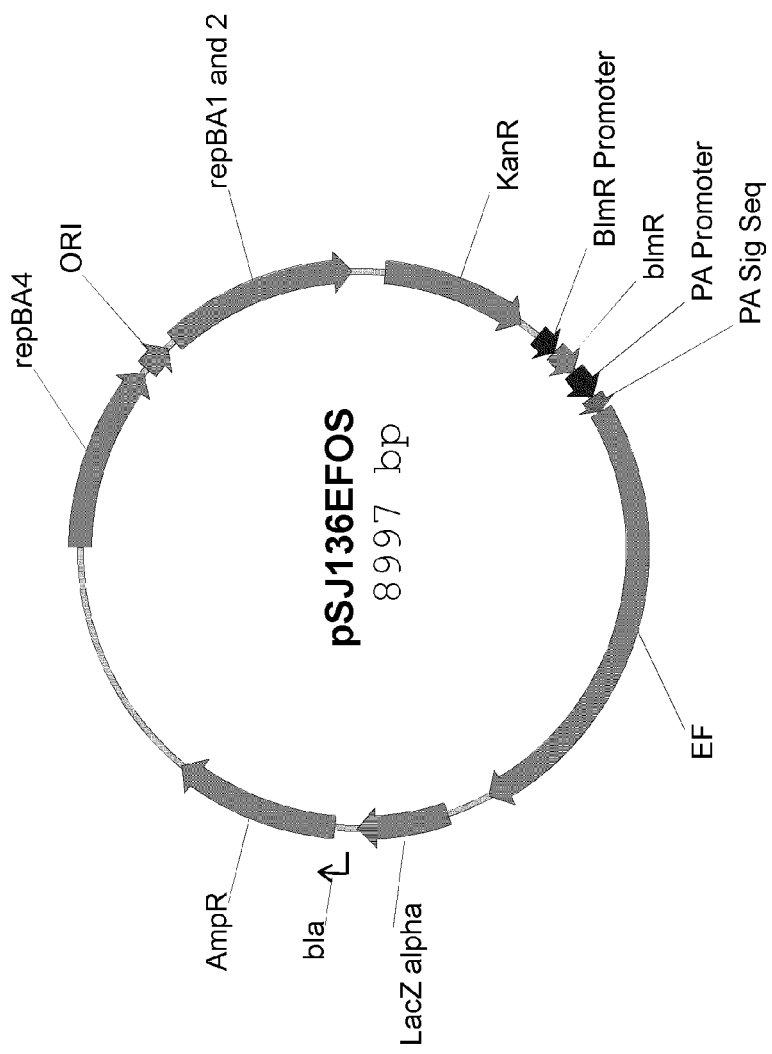
FIG. 6 provides a schematic map of recombinant molecule pSJ136EFOS (SEQ ID NO:62), which comprises a nucleic acid molecule encoding mature EF with a PA signal sequence (SEQ ID NO:63) operatively linked to a pag promoter. The pag promoter spans approximately nucleotides 3496-3658 of SEQ ID NO:62. The PA signal sequence is encoded by nucleotides beginning at nucleotide 3659 of SEQ ID NO:62. The EF mature protein (SEQ ID NO:64) is encoded by nucleotides beginning at nucleotide 3746 of SEQ ID NO:62. The E. coli ORI (not shown) spans approximately nucleotides 6286-6755 of SEQ ID NO:62.

EF was expressed in *B. anthracis* host strains from plasmid pSJ136EFOS (SEQ ID NO:62 and FIG. 6, which contains the EF structural gene in plasmid pYS5 under the control of (i.e., operatively linked to) the PA (*B. anthracis* protective antigen) promoter and signal sequence (Singh Y et al., 1989, J. Biol. Chem. 264, 19103-19107). Host strains BH450 and BH460 containing pSJ136EFOS were grown in FA medium containing 15 μg/ml of kanamycin at 37° C. for 14 h, essentially following procedures previously used for production of LF (Park S et al., 2000, Protein Expr. Purif. 18, 293-302). The cultures were cooled, supplemented with 2 μg/ml of AEBSF [4-(2-Aminoethyl)-benzenesulfonylfluoride.HCl] (US Biological, Swampscott, Mass.) and centrifuged at 4550×g for 30 min. All subsequent steps were performed at 4° C.

The supernatants were filter sterilized and supplemented with 5 mM EDTA. Solid ammonium sulfate was added to the supernatants to obtain 40% saturation. Phenyl-Sepharose Fast Flow (low substitution, GE Healthcare Biosciences Corp.) was added and supernatants gently mixed in the cold for 1.5 h. The resins were collected on porous plastic funnels (BelArt Plastics, Pequannock, N.J.) and washed with buffer containing 1.5 M ammonium sulfate, 10 mM Tris-HCl, and 1 mM EDTA (pH 8.0). The EF proteins were eluted with 0.3 M ammonium sulfate, 10 mM Tris-HCl, and 1 mM EDTA (pH 8.0), precipitated by adding an additional 30 g ammonium sulfate per 100 ml eluate, and centrifuged at 18,370×g for 20 min. The proteins were dissolved and dialyzed against 5 mM HEPES, 0.5 mM EDTA (pH 7.5). The dialyzed samples were applied to a Q-Sepharose Fast Flow column (GE Healthcare Biosciences Corp.) and eluted with a 0-0.5 M NaCl gradient in 20 mM Tris-HCl, 0.5 mM EDTA (pH 8.0). The EF-containing fractions identified by SDS-Phast-Gel analysis were purified on a column of ceramic hydroxyapatite (Bio-Rad Laboratories, Hercules, Calif.) with a gradient of 0.02-1.0 M potassium phosphate containing 0.1 M NaCl (pH 7.0). The fractions containing EF were dialyzed overnight against 5 mM HEPES and 0.5 mM EDTA, pH 7.5, concentrated as necessary, frozen, and stored at −80° C. The molecular mass of purified EF was estimated by liquid chromatogram-electrospray mass spectrometry using an HP/Agilent 1100 MSD instrument (Hewlett Packard, Palo Alto, Calif.) at the NIDDK core facility, Bethesda, Md.).

Analysis of EF Activity In Vitro and In Vivo

EF activity was measured by analysis of cyclic AMP (cAMP) production in the RAW264.7 macrophage cell line (ATCC TIB-71). Cells were grown in Dulbecco's Modified Eagle Medium (DMEM) with 10% fetal bovine serum, 2 mM Glutamax, 2 mM HEPES and 50 μg/ml gentamicin (all from Invitrogen) at 37° C. in 5% $CO_2$. Cells were seeded in 96-well plates 24 h prior to assays. EF preparations were serially diluted in a constant PA (*B. anthracis* protective antigen) concentration (250 ng/ml) prior to addition to cells and incubation for 1 h at 37° C. Total cAMP levels were assessed using the BioTRAK cAMP enzyme immunoassay kit (GE Healthcare Biosciences Corp.) according to the manufacturer's protocol. For analysis of EF potency, groups of five 8-week old female Balb/cJ mice (Jackson Laboratories, Bar Harbor, Me.) were injected via tail vein with EF preparations combined with an equal dose of PA. Toxin was prepared in sterile PBS. Mice were monitored for survival for 168 h. All experiments involving animals were performed under protocols approved by the Animal Care and Use Committee of the National Institute of Allergy and Infectious Diseases, National Institutes of Health.

Example 2

Genetic Modification of *B. anthracis* Protease Genes

This Example demonstrates that a genetic modification of *B. anthracis* in which loxP is inserted into genes encoding *B. anthracis* proteases results in truncation of corresponding proteins.

A number of protease genes on the *B. anthracis* chromosome as well as the spo0A gene were targeted for inactivation in this study. They are identified here with the gene numbers assigned by The Institute for Genomic Research, now the J Craig Ventner Institute (Rockville, Md.), for the "Ames ancestor" strain chromosome (GenBank Accession No. NC 007530, gene designation GBAA_gene number) (Ravel J et al, 2009, J. Bacteriol. 191, 445-446). The gene numbers are coincident with the previous "Ames" strain chromosome (GenBank Accession No. NC 003997, gene designation BA_gene number) (Read T D et al., 2003, Nature 423, 81-86). All genes and proteins inactivated or analyzed in this study are listed in Table 1 together with corresponding locus tags.

The inactivation of the nprB and inhA1 genes has been previously described (Pomerantsev A P et al., 2006, ibid., Kastrup CJ, ibid.). The inhA2, tasA, calY, and mmpZ genes were inactivated as described herein. The B. anthracis InhA2 protein is 96% identical in sequence to the InhA2 protease of Bacillus thuringiensis, which is an essential virulence factor in that insect pathogen (Fedhila S et al., 2003, J. Bacteriol. 185, 2820-2825). The tasA gene (GBAA_1288) located downstream of the putative signal protease gene sipW (GBAA_1287) is only 5 genes upstream of the InhA1 gene (GBAA_1295). The intervening genes include the calY protease gene, and the two regulatory genes sinI and sinR (Table 4). The SinI and SinR proteins play important roles in B. subtilis biofilm formation, acting through protease-dependent processes (Chai Y, 2010, Mol. Microbiol. 78, 218-229), while in B. anthracis these proteins regulate secreted proteases (Pflughoeft K J et al., 2010, J. Bacteriol. 193, 631-639). It is interesting that the genes corresponding to calY and inhA1 are not found in the sinI, sinR region of the B. subtilis genome. Only the gene for the TasA protease, tasA, is located downstream of sipW and upstream of sinR and sinI (Pflughoeft et al., ibid.). Both TasA and camelysin are similar to the B. subtilis TasA protease (36% and 34% sequence identities, respectively). The final gene selected for inactivation, mmpZ, is reported to form an operon with the downstream gene (GBAA_3160) (Passalacqua K D et al., 2009, J. Bacteriol. 191, 3203-3211). The latter gene encodes a hypothetical secreted protein that is overproduced in B. anthracis (Antelmann H et al., ibid.). The absence of the MmpZ protease in the B. anthracis secretome indicates that this protease could be a target for proteolytic degradation by other proteases during the stationary phase of growth Antelmann H et al., ibid.).

The protease genes were inactivated as described in Example 1, followed by sequencing to locate the loxP insertions and infer the corresponding amino acid changes in the mutated proteins. These are shown in FIG. 1. Typically, the 34-bp loxP sequence will generate a frameshift and early downstream occurrence of a stop codon in an alternative reading frame either within the loxP sequence or soon thereafter. Thus, all four inactivated protease genes encoded greatly shortened proteins.

Example 3

Comparison of Protein Degradation by Genetically Modified B. anthracis and A35 Strain This Example compares protein degradation by several genetically modified B. anthracis, including some B. anthracis of the embodiments, and the Ames 35 strain.

Figure 2:
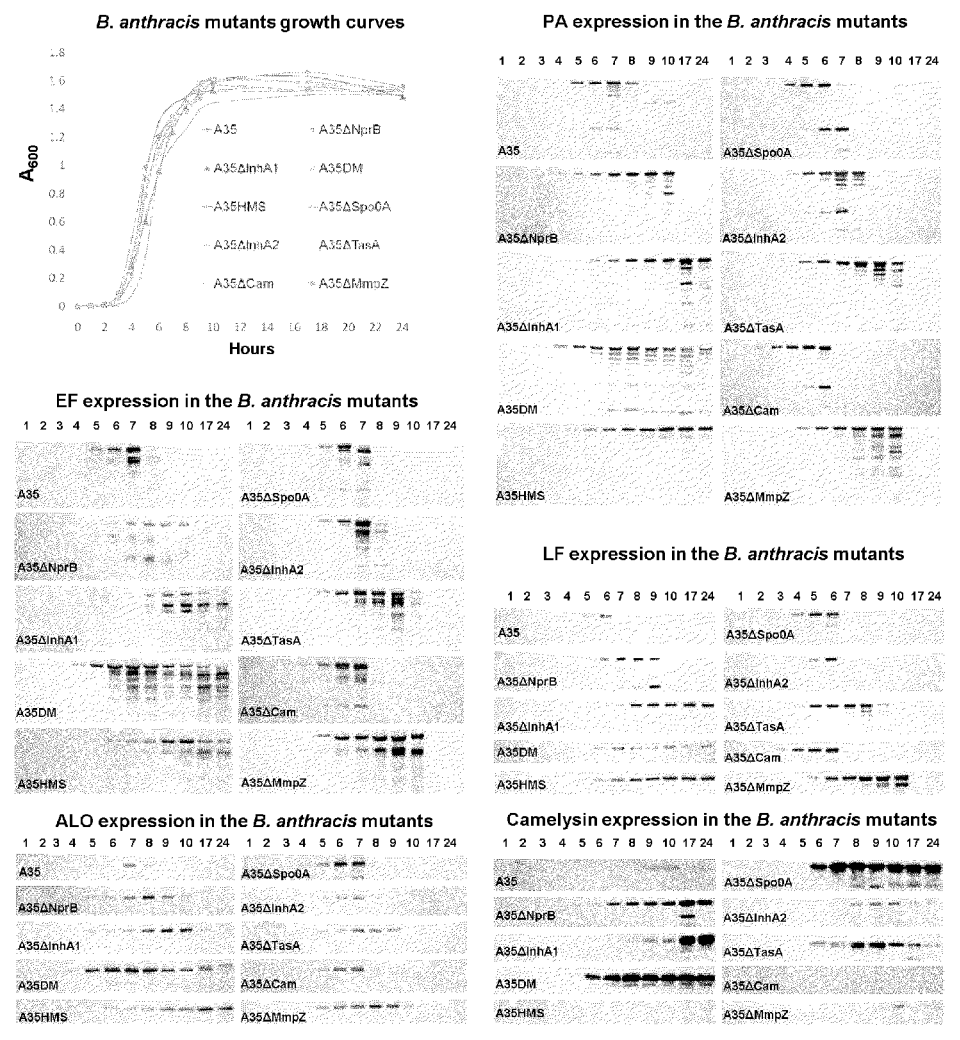

The levels of the three B. anthracis toxin components, ALO, and camelysin produced by the B. anthracis mutants were compared to those of the parental A35 strain by Western blot (FIG. 2). The ten strains were grown in LB at 37° C. over a 24-h period. All strains grew similarly except the six-protease mutant BH460, which appeared to have a slight lag before reaching exponential growth phase.

Expression of PA by Ames 35 was detectable starting at 5 h of growth. However, intact PA (83 kDa) disappeared by the 9th hour of growth due to proteolytic degradation. Inactivation of the InhA2 protease did not influence production of PA while inactivation of SpoOA or camelysin actually reduced the half-life of PA by 1-2 h. Inactivation of NprB, TasA, or MmpZ resulted in increased PA stability up to 10 h. However, PA produced by all these strains was completely degraded after 17 h. The most stable production of PA among the single knockout mutants was found in the InhA1 strain. PA was present even at 24 h of growth with this strain, although some degradation occurred. Surprisingly, the A35DM double mutant did not demonstrate enhanced PA production. PA degradation generally began at 6-7 h of growth and continued through 24 h. Strikingly, the A35HMS strain with six inactivated proteases produced PA with minimal to no degradation during the full 24 h of growth. Similar analyses were performed to follow production of the other B. anthracis toxin components, EF and LF. Intact EF (89 kDa) was found to be more vulnerable to degradation than PA, while LF (90 kDa) was quite stable when produced from most mutant strains. The levels of intact EF and LF, and the timing of their production, paralleled what was seen for PA for each mutant strain.

The enhanced breakdown of PA and EF found in the A35DM strain may be explained by increased production of camelysin in A35DM compared with A35 or the two corresponding single protease knockouts. Although both the NprB and InhA1 knockout strains had increased levels of camelysin, the double mutation produced what seems to be a greater than additive effect. The camelysin levels produced by the A35DM strain were similar to those by the SpoOA mutant strain, A35ΔSpoOA. Both strains produced camelysin (19 kDa) that remained stable over the 24-h period. These observations on post-translational regulation of camelysin production by several proteases support and expand recently published data demonstrating that the concentration of InhA1 in culture supernatants is inversely proportional to the concentration of camelysin (Pflughoeft et al., ibid.). Another interesting finding of these studies was that the global transcriptional regulator SpoOA inhibited camelysin production. Pflughoeft et al. ibid., recently demonstrated that B. anthracis sinR (which was deleted in those mutants containing the tasA-ihhA1 deletion) also negatively regulates transcription of camelysin and InhA1, both of which have been suggested to be associated with virulence (Chung M C et al., ibid., Liu Y T et al., 2008, Protein Expr. Purif. 57, 72-80).

Knocking out TasA also increased production of camelysin but to a lesser extent than elimination of NprB and InhA1. The InhA2 knockout did not result in any change in camelysin degradation or production when compared to A35, while MmpZ elimination was actually detrimental to camelysin production. These studies indicate that inactivation of six proteases in B. anthracis leads to increased production of intact toxin proteins in culture supernatants relative to A35, single, or double protease mutants.

Very low levels of ALO were produced from the A35 strain compared to all the protease knockouts, with the exception of the InhA2 mutant. The ALO produced by the A35 strain completely disappeared after 9 hours of growth. Every protease knockout strain showed increased levels of production or greater stability of ALO (53-kDa band). It is interesting that ALO breakdown started in A35DM (less in A35ΔInhA1) only after 17 h of growth. A similar effect was not seen in the A35HMS strain, which allowed accumulation of intact ALO throughout the 24 h of growth. The ALO gene is under control of a PlcR-dependent promoter, so that the truncation of the PlcR protein in B. anthracis is expected to greatly limit ALO synthesis, along with all the other PlcR-dependent proteins (Sastalla, 2010, Microbiology 156, 2892-2993). The fact that ALO can be observed in several of the protease-deficient mutants implies that previous reports of low ALO production may be attributed, at least in part, to its degradation rather than to low expression. Camelysin overexpression did not influence ALO production, indicating that this toxin is not a target for camelysin. Taken together, the results demonstrate the involvement of multiple proteases in controlling the accumulation of extracellular proteins in B. anthracis.

Example 4

Complementation of Genetic Modifications to Inactivate a B. anthracis Protease

This Example demonstrates that complementation of genetic modifications to inactivate a B. anthracis protease restores proteolytic activity.

To verify that the changes observed above were due to the intended gene knockouts rather than to unrecognized second-site mutations, studies to assess complementation of several mutants were conducted. To complement the mmpZ mutation, the A35ΔMmpZ strain was transformed with pMmpZC. This plasmid undergoes a single crossover to insert the full length, wild-type mmpZ gene next to the mutated one. The pSC vector was eliminated by Cre-recombinase treatment as described previously (Pomerantsev A P et al., 2009, ibid.). The presence of the intact mmpZ gene in A35MmpZC was confirmed by PCR and sequencing. Western blot analysis of LF production from A35ΔMmpZC (FIG. 3A) over 24 h indicated that proteolytic activity was restored to levels similar to that of A35 (FIG. 2). To restore the large tasA-inhA1 deletion in the genome of the A35TM strain, the strain was transformed with the plasmid pΔTasA-InhA1C (containing the entire tasA-inhA1 region) and complementation was assessed in a manner similar to that described above. Analysis of ALO production from the complemented strain verified restoration of proteolytic activity (FIG. 3B). Complementation of the A35ΔInhA2 strain, and restoration of the InhA2 protease in the same manner, however, did not result in any difference in secreted proteins (data not shown).

All the studies described above were done in derivatives of Ames 35, where the toxin proteins are encoded on the large virulence plasmid pXO1. Production of the toxin proteins and secreted proteases in these strains is highly dependent on the growth medium. In particular, the production of the three toxin proteins and certain proteases is greatly enhanced by the addition of bicarbonate (Chitlaru T et al., ibid., Passalacqua K D et al., ibid., Bartkus J M, 1989, Infect. Immun. 57, 2295-2300. Thus, it is likely that growth in certain media could produce higher concentrations of both proteases and substrates (e.g., PA. LF, EF, etc.), and this could lead to even greater degradation than observed here.

Bacillus host strains are widely used in biotechnological processes, and avirulent B. anthracis strains have been used for a number of years to produce PA and LF (see, for example, Varughese M et al., ibid., Park S et al., ibid., Gupta P K et al., 2008, PLoS. ONE 3, e3130. However, these strains have not been useful as generic hosts for recombinant protein production due to the secreted proteases demonstrated by the work presented above. The successful elimination of many of the most abundant proteases described herein suggested that the resulting strains could have value as protein expression hosts. To create an optimal host, the A351-HMS strain was further modified by curing it of plasmid pXO1. The resulting strain, designated BH460, is non-toxigenic, and can be considered innocuous since it lacks the major virulence factors of B. anthracis. The permanent deletion of the spo0A gene assures that the strain dies rapidly at the end of exponential growth, eliminating concerns regarding laboratory contamination.

Example 5

Production of Intact EF Protein by B. anthracis BH460

This Example demonstrates production of intact EF by a modified B. anthracis of the embodiments, namely B. anthracis BH460 transformed with recombinant molecule pSJ136EFOS.

Figure 4:
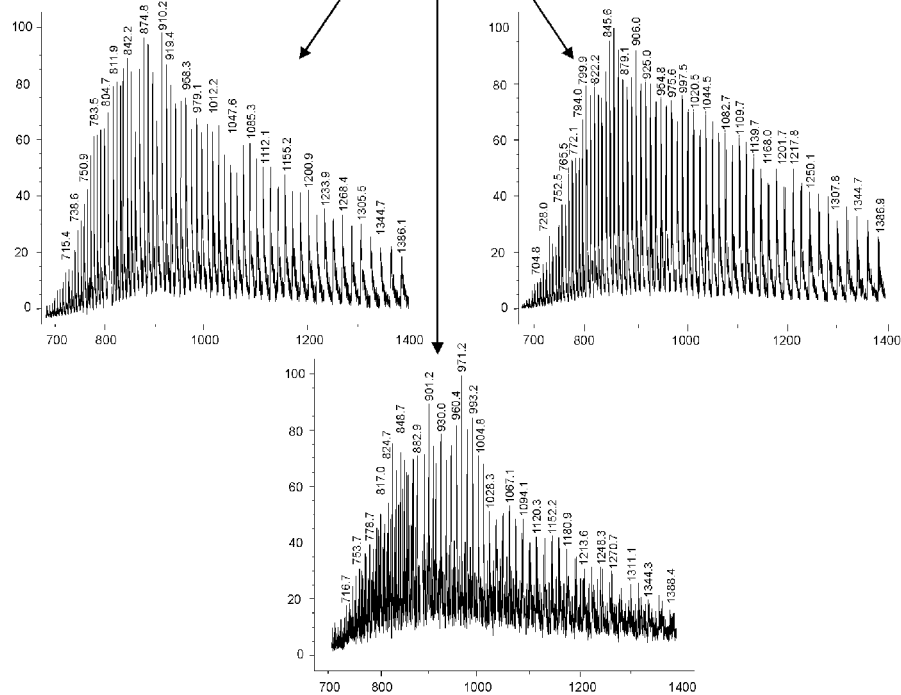
FIG. 4 provides a comparison of EF proteins purified from E. coli BL21(DE3), B. anthracis BH450 (with a genetic modification in nprB and in spo0A), and B. anthracis BH460. A) SDS-PAGE analysis of the EF proteins. M—molecular mass markers (Page Ruler Unstained Protein Ladder, Fermentas). B) Electron Spray Ionization—Mass Spectra (ESI-MS) of the EF samples shown in A). The Y-axis represents relative abundance and the X-axis represents mass/charge ratio (m/z). C) Comparison of the experimental molecular masses of the EF samples extrapolated from ESI-MS data to the molecular masses calculated from the amino acid sequences. Relative abundances of the resulting components from the ESI-MS data are shown in parentheses. The final line shows differences between experimental and calculated masses.

Production of EF from B. anthracis hosts has previously been difficult because this protein is more susceptible to proteolytic degradation than are PA and LF. The plasmid pSJ136EFOS (the nucleic acid sequence of which is SEQ ID NO:62) encodes the mature EF protein with its native N-terminus (thus, the "OS" for original sequence) fused to the PA signal sequence and under the control of the pag promoter. This plasmid is otherwise similar to the plasmids pYS5 and pSJ115 that are routinely used by the inventors to produce PA and LF, respectively; see, e.g., Park S et al., ibid. Protein purified from the transformant BH460 (pSJ136EFOS) was compared to a preparation made in a similar way from the single protease mutant host BH450, and to a His6-tagged EF protein purified from E. coli (Soelaiman S et al., ibid.), the latter being the type of material used in previous toxicity analyses reported in Firoved A M et al., 2005, Am. J. Pathol. 167, 1306-1320. SDS-PAGE profiles of the recombinant EF proteins are shown in FIG. 4A. The EF produced from BH460 appeared to be slightly less degraded than that isolated from BH450. This finding was confirmed by mass-spectrometry analyses (FIG. 4B). The molecular mass of the recombinant protein isolated from BH460 (88,820 Da) compared well with the theoretical molecular weight for EF (88,822 Da), differing by 2 Da, which is within the instrumental error. A second species was found that had a lower mass (88,687 Da) consistent with loss of the N-terminal methionine. These two protein species were present in about equal amounts (47% for the larger, 53% for the smaller). Mass spectra of the EF produced from BH450 showed degradation as indicated by losses of 1495.7 and 2455.7 Da, resulting in proteins of 87,326 and 86,366 Da, found with similar abundances of 54% and 46%, respectively (FIG. 4C). Apparent protease cleavage sites in mature EF produced by BH450 were mapped to amino acid residues Arg-12 and Lys-20. EF purified from E. coli was monomorphic, with a mass of 89,995 Da, differing by only 6 Da from the theoretical molecular weight (89,989 Da, FIG. 4C). These results clearly demonstrate production of intact EF from BH460 compared to the truncated proteins made by BH450.

Example 6

Activity of EF Produced by Genetically Modified Protease-Deficient B. anthracis

This Example demonstrates the EF produced by a modified B. anthracis of the embodiments, namely B. anthracis BH460 transformed with recombinant molecule pSJ136EFOS, is active in a potency assay.

As noted above, recombinant EF has previously been difficult to produce from B. anthracis host strains transduced with plasmids such as pSJ136. Furthermore, the EF that was obtained either from *B. anthracis* Sterne strain culture supernatant (Leppla S H, 1991, Methods Enzymol. 195, 153-168) or *E. coli* (Soelaiman S et al., ibid.) consistently had higher potency in inducing cAMP production in cultured cells or lethality to mice than EF produced from *B. anthracis* (data not shown). In fact, no previous recombinant EF preparations from *B. anthracis* have been lethal to mice even when injected in doses as high as 100 µg (combined with equimolar PA) (data not shown). The ES-MS analyses shown in FIG. 4 suggest that the low potency of previous *B. anthracis*-derived EF preparations could be due to degradation. Consistent with prior results, the BH450-derived EF displayed an extremely low level of specific activity and was not lethal for mice (FIG. 5A and FIG. 5B). However, the recombinant EF purified from the BH460 culture supernatant had a specific activity exceeding that of highly active *E. coli* BL21(DE3)-derived EF (FIG. 5A). Similarly, when injected with equal doses of PA, recombinant EF prepared from BH460 was lethal to animals at the 25 µg dose, whereas this dose of *E. coli*-derived EF had minimal effect (FIG. 5B). EF purified from BH450 was not lethal at 50 µg (FIG. 5B) and even at doses up to 100 µg (data not shown). Thus, the BH460 strain, which produces 5-7 mg of EF per liter of culture, allows for the first time the purification of substantial amounts of highly active EF from *B. anthracis*. Because other proteins purified in the same way from *B. anthracis* have consistently been free of endotoxin, use of these EF preparations also eliminates concerns regarding endotoxin-mediated cAMP co-signaling associated with *E. coli*-derived preparations. The BH460 strain has also proven very useful for expression of a variety of other proteins, typically yielding in excess of 10 mg of final pure protein per liter of culture, an Example of which is provided in Example 7.

Example 7

Production of Intact *B. cereus* Hemolysin HBL Toxins by *B. anthracis* BH460

This Example demonstrates that modified a *B. anthracis* of the embodiments, namely *B. anthracis* BH460 transformed with recombinant molecule pSW4-HBL L1 His, pSW4-HBL L2 His, or pSW4-HBL B His, produces large quantities of intact HBL L1, HBL L2, or HBL B, respectively.

*B. cereus* can cause infections in immune-compromised patients, such as sepsis, meningitis, pneumonia, and wound infections. There are also reports on impetigo-like lesions in non-compromised patients. HBL toxins have been shown to contribute to *B. cereus* caused diarrheal food poisoning, and their presence is used as an indicator for *B. cereus* food contaminations.

*B. cereus* 569 has two HBL operons. The first operon is located on the chromosome, and the second on a plasmid. The chromosomal operon appears to comprise three genes that encode the following proteins: L2 (1320 bp, 439 amino acids, 49.3 kDa with signal sequence); L1 (1221 bp, 406 amino acids, 43.8 kDa with signal sequence); and B (1146 bp, 381 amino acids, 42.5 kDa with signal sequence). These proteins do not share high homology on the protein level: L1 vs. L2 has 24% identity; L1 vs B has 26% identity; and L2 vs B also has 26% identity. All of these HBL proteins have been shown to be secreted via the Sec pathway and contain a Gram-positive signal sequence (Fagerlund A et al., 2010, BMC Microbiol 10, 304).

Single HBL toxin components are non-toxic; all three components (i.e., L1, L2, and B) are needed to effect cell lysis. The exact mechanism by which the toxin components function in concert is still not well understood.

HBL has been shown to affect a variety of cell types and tissues such as retinal tissue (Beecher D J et al., 1995, Infect. Immun. 63, 4423-4428), rabbit skin, ileum, CHO cells (Beecher D J et al., 1997, J. Biol. Chem. 272, 233-239), and red blood cells from guinea pig, swine, bovine, sheep, rabbit, goat, and human (activity in descending order). Studies performed by Beecher et al., 1997, ibid. showed that the B (binding) moiety can prime erythrocytes to lyse when followed by incubation with L1 and L2 components. Cells can also be primed with either L component, indicating that all three components can bind to erythrocyte membranes. In addition, toxin action can be inhibited by addition of antibodies specific to the binding component, as well as by addition of excess L1 component, indicating that L1 binds either L2 or the binding component (Beecher et al., 1997, ibid.).

Figure 7:
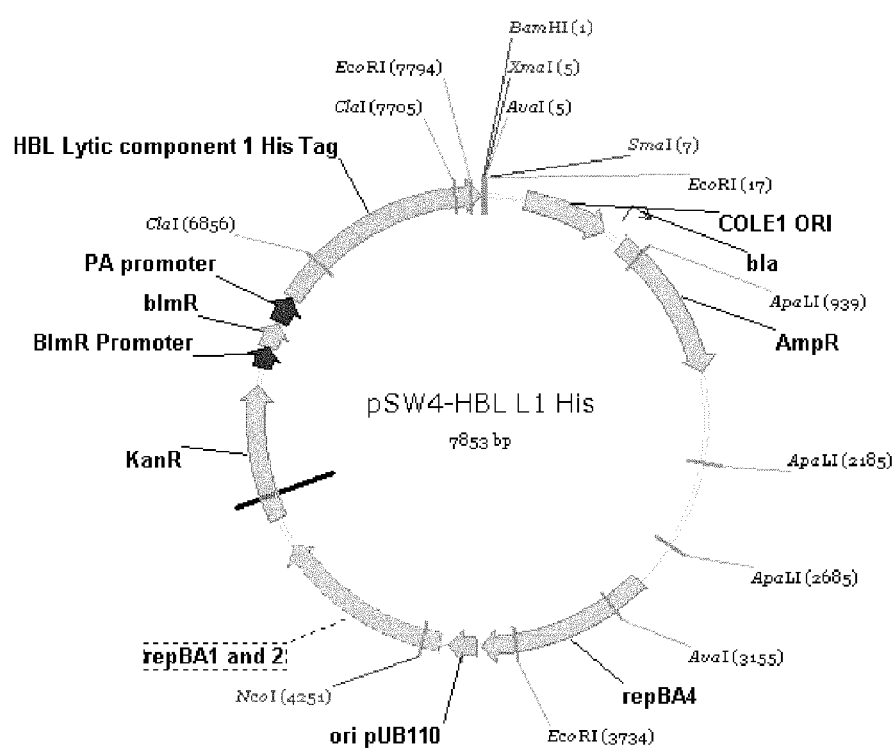
FIG. 7 provides a schematic map of recombinant molecule pSW4-HBL L1 His (SEQ ID NO:65), which comprises a nucleic acid molecule encoding HBL L1 His operatively linked to a pag promoter. The HBL L1 His protein (SEQ ID NO:66) is encoded by nucleotides beginning at nucleotide 6611 of SEQ ID NO:65.

Recombinant molecule pSW4-HBL L1 His (depicted in FIG. 7) was produced by operatively linking a nucleic acid molecule encoding HBL L1 (including its natural signal sequence) and a C-terminal 6×His tag to expression vector pSW4, such that expression of HBL L1 His was under the control of the *B. anthracis* pag promoter. *B. anthracis* BH460 was transformed with recombinant molecule pSW4-HBL L1 His, and the modified *B. anthracis*, when grown in 2 liters FA broth overnight (~16 h), produced 28 mg of pure HBL L1 His protein.

Figure 8:
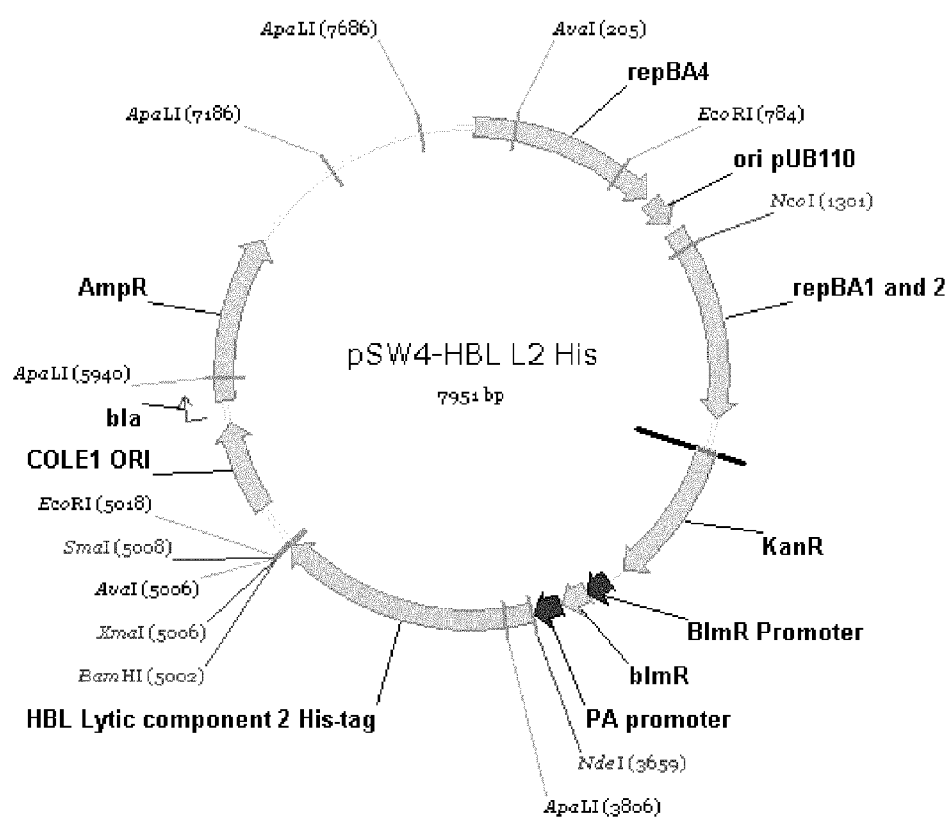
FIG. 8 provides a schematic map of recombinant molecule pSW4-HBL L2 His (SEQ ID NO:67), which comprises a nucleic acid molecule encoding HBL L2 His operatively linked to a pag promoter. The HBL L2 His protein (SEQ ID NO:68) is encoded by nucleotides beginning at nucleotide 3660 of SEQ ID NO:67.

Recombinant molecule pSW4-HBL L2 His (depicted in FIG. 8) was produced by operatively linking a nucleic acid molecule encoding HBL L2 (including its natural signal sequence) and a C-terminal 6×His tag to expression vector pSW4, such that expression of HBL L2 His was under the control of the *B. anthracis* pag promoter. *B. anthracis* BH460 was transformed with recombinant molecule pSW4-HBL L2 His, and the modified *B. anthracis*, when grown in 2 liters FA broth overnight (~16 h), produced 151 mg of pure HBL L2 His protein.

Figure 9:
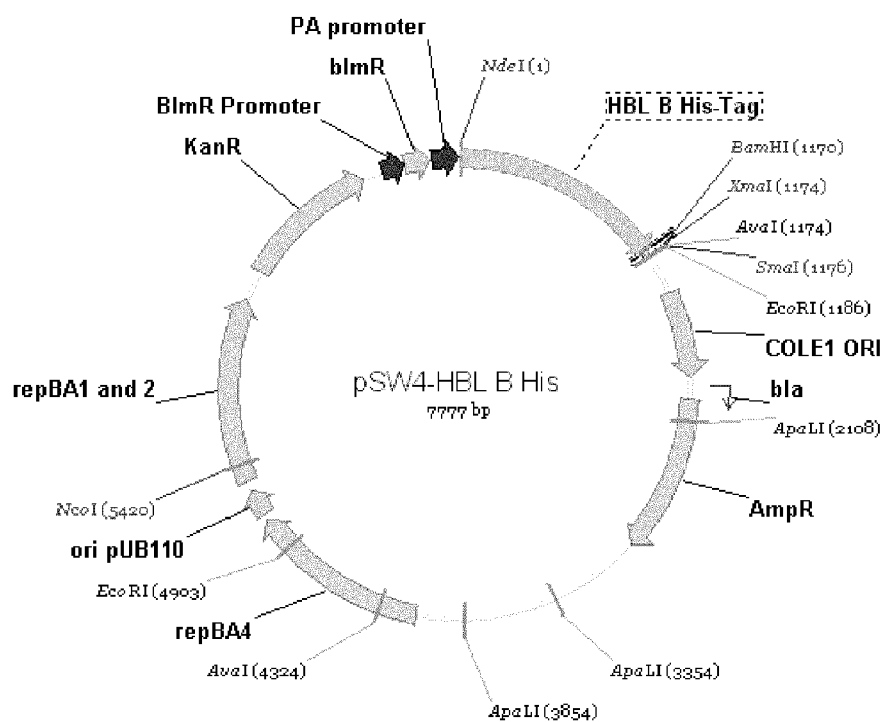
FIG. 9 provides a schematic map of recombinant molecule pSW4-HBL B His (SEQ ID NO:69), which comprises a nucleic acid molecule encoding HBL B His operatively linked to a pag promoter. The HBL B His protein (SEQ ID NO:70) is encoded by nucleotides beginning at nucleotide 2 of SEQ ID NO:69.

Recombinant molecule pSW4-HBL B His (depicted in FIG. 9) was produced by operatively linking a nucleic acid molecule encoding HBL B (including its natural signal sequence) and a C-terminal 6×His tag to expression vector pSW4, such that expression of HBL B H is was under the control of the *B. anthracis* pag promoter. *B. anthracis* BH460 was transformed with recombinant molecule pSW4-HBL B His, and the modified *B. anthracis*, when grown in 2 liters of FA broth overnight (−16 h), produced 75 mg of pure HBL B His protein.

Purification of the respective proteins was accomplished by the following steps: adsorbed protein to phenyl-Sepharose at 2 M ammonium sulfate; eluted protein from phenyl-Sepharose with 0.3 M ammonium sulfate; precipitated protein, resuspended, and dialyzed against 5 mM HEPES, 0.5 mM EDTA, pH 7.5 prior to loading onto a Q-Sepharose column (GE Healthcare); eluted protein from Q-Sepharose using a NaCl gradient (buffer A was 20 mM Tris-HCl, 0.5 mM EDTA, pH 8.0; buffer B was 20 mM Tris-HCl, 0.5 mM EDTA, pH 8.0, plus 0.5 M NaCl); combined protein-containing fractions and dialyzed against 5 mM HEPES, 0.5 mM EDTA, pH 7.5 prior to loading onto a hydroxyapatite (BioRad ceramic type) column; eluted protein from hydroxyapatite using a phosphate gradient (buffer A was 0.02 mM potassium phosphate, pH 7.0, 0.10 M NaCl; buffer B was 1 M potassium phosphate, pH 7.0, 0.10 M NaCl);

collected protein peak; and dialyzed pure protein prior to concentration on an ultrafiltration unit.

Example 8

Genetic Modification of *B. anthracis* Protease Genes

This Example demonstrates that genetic modification of a gene encoding a protease protein in *B. anthracis* using a Flp-FRT recombinase system results in truncation of the corresponding protein and production of a *B. anthracis* strain that no longer expresses such active protease.

Culture supernatants of strain BH460 were analyzed by mass spec to determine which proteases continued to be produced that might degrade valuable endogenous proteins (e.g., anthrax toxin proteins that are vaccine candidates) or heterologous proteins. Two additional proteases were identified (GBAA_1995 cysteine protease CysP1 and GBAA_4584 minor extracellular protease VpR). At least a portion of genes encoding these proteases were genetically deleted from *B. anthracis* BH460, leading to *B. anthracis* BH480, which lacks eight active proteases, due to genetic modification of the following genes leading to inactivation of the respectively encoded proteins: nprB, inhA2, tasA, calY, inhA1, mmpZ, cysP1, and vpR. Mutations engineered into *B. anthracis* cysP1 and vpR are indicated in FIG. 1C.

Specifically, a *Saccharomyces cerevisiae* Flp-FRT recombinase system (Park, Y N, et al., 2011, Yeast 28, 673-681) was adapted to use for *B. anthracis* cysP1 and vpR gene deletions by introducing *S. cerevisiae* Flp recombinase and *S. cerevisiae* FRT sites into the genome of *B. anthracis*; both FRT sites and Flp-recombinase genes were inserted into vectors suitable for replication, expression, and recombination in *B. anthracis*. The system was used in a manner similar to the Cre-loxP recombinase system described previously (Pomerantsev A P et al., 2009, ibid.) and herein. The Flp-FRT method allowed the replacement of both cysP1 and vpR genes with a 48-bp FRT-site using Flp recombinase. Both FRT-site and flp-genes were cloned into plasmids pSCF and pFPAS, respectively, which are described in Table 3. Additional plasmids used in the genetic modifications of the cysP1 and vpR genes included plasmid pCysP1L1, pCysP1RI, pVpRLI, and pVpRR1, which are described in Table 3. Primer pair 1995 seqF and 1995 seqR was used to verify cysP1 gene disruption; and primer pair 4584 seqF and 4584 seqR was used to verify vpR gene disruption. Table 5 provides mass spec (MS) analysis that confirms the absence of both CysP1 and VpR proteases in the secretome of the *B. anthracis* BH480 strain.

TABLE 5

MS-peptide hits for CysP1 and VpR proteases in supernatants of *B. anthracis* BH460 and *B. anthracis* BH480.

| Protease | BH460 | BH480 |
| --- | --- | --- |
| GBAA_1995_CysP1 | 69 | 0 |
| GBAA_4584_VpR | 36 | 0 |

Table 10 demonstrates the absence of both CysP1 and VpR proteases in the supernatant of *B. anthracis* BH480 in comparison to that of *B. anthracis* BH460.

Supernatants of BH480 have been examined as described above, and several additional proteases have been identified: (GBAA_2183 neutral metalloprotease NprC, GBAA_5414 serine protease SprA, GBAA_3660 serine protease HtrA and GBAA_3968 prokaryotic homolog of proteasome HslV).

Example 9

Production of Intact EF, LF, and uPA Proteins by *B. anthracis* BH480

This Example demonstrates production of EF proteins by modified *B. anthracis* of the embodiments, namely *B. anthracis* BH480 transformed with recombinant molecules encoding a variety of EF proteins. Also demonstrated is production of intact LF and uPA proteins.

*B. anthracis* BH480 was transformed with recombinant molecule pSJ136EFOS in a manner similar to transformation of *B. anthracis* BH460 with recombinant molecule pSJ136EFOS as described herein. *B. anthracis* BH480 was also transformed with recombinant molecule pSJ136EF-His, recombinant pSJ136EF-Cys, or recombinant molecule pSJ136EF-NEHY, which are identical to pSJ136EFOS except that they encode mature EF proteins having small modifications in the N-terminal sequence as indicated in Table 6.

TABLE 6

Recombinant molecules and proteins encoded by such recombinant molecules

| Recombinant molecule | Encoded EF protein | N-terminus of EF protein |
| --- | --- | --- |
| pSJ136EFOS | EFOS (SEQ ID NO: 64) | MNEHY . . . |
| pSJ136EF-His | EF-His (SEQ ID NO: 93) | HNEHY . . . |
| pSJ136EF-Cys | EF-Cys (SEQ ID NO: 94) | CNEHY . . . |
| pSJ136EF-NEHY | EF-NEHY (SEQ ID NO: 95) | NEHY . . . |

Figure 10:
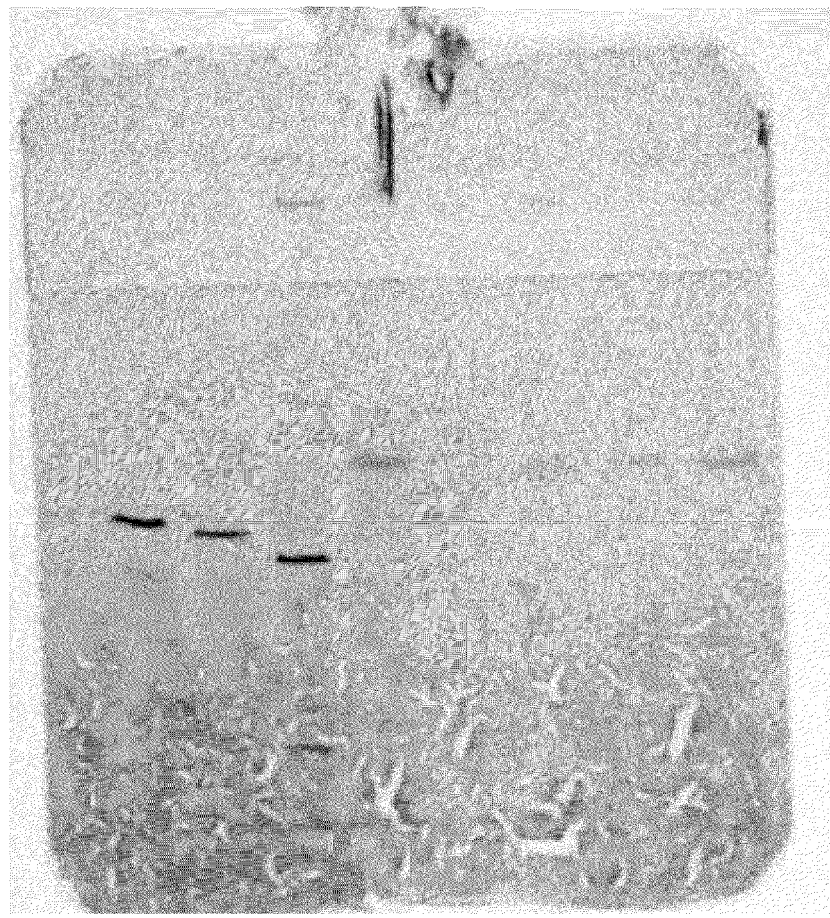
FIG. 10 provides native Phast gel (native 8-25% acrylamide gradient) analysis of production of EF proteins EFOS (lane 4), EF-His (lane 6), EF-Cys (lane 7), and EF-NEHY (lane 8) by B. anthracis BH480 transformed with recombinant molecule pSJ136EFOS, B. anthracis BH480 transformed with recombinant molecule pSJ136EF-His, B. anthracis BH480 transformed with recombinant molecule pSJ136EF-Cys, or B. anthracis BH480 transformed with recombinant molecule pSJ136EF-NEHY, respectively. Lanes 1 and 2 show production of PA-U2f and PA-U7f by modified B. anthracis BH480. Lane 3 shows production of mature lethal factor (LF-OS) by B. anthracis BH480 transformed with pSJ115-LF-OS. Lane 5 shows production of Hfq1-FLAG by B. anthracis BH480 transformed with pSJ136 Hfq1-FLAG.

*B. anthracis* strains transformed with pSJ136EFOS, pSJ136EF-His, pSJ136EF-Cys, or pSJ136EF-NEHY were inoculated into 10 ml FA media that included 10 micrograms per ml (μg/ml) kanamycin. Protein production for each sample was demonstrated by native Phast gel (native 8-25% acrylamide gradient) analysis, the proteins being stained by Coomassie blue. Results are shown in FIG. 10. The results indicate production of intact EF proteins by *B. anthracis* BH480 transformed with pSJ136EFOS, pSJ136EF-His, pSJ136EF-Cys, or pSJ136EF-NEHY, as shown in lanes 4, 6, 7, and 8 of FIG. 10, respectively.

FIG. 10 also shows production of intact urokinase plasminogen activator (uPA) variants PA-U2f (lane 1) and PA-U7f (lane 2) by *B. anthracis* BH480 transformed with pYS5 plasmids encoding PA-U2f and PA-U7f, respectively, and cultured as described herein; PA-U2, PA-U7, and recombinant molecules comprising nucleic acid molecules encoding such proteins are described in International Publication No. WO 01/21656, published 29 Mar. 2001; PA-U2f and PA-U7f lack a C-terminal serine present in PA-U2 and PA-U7.

FIG. 10, lane 3 shows production of intact mature lethal factor (LF-OS) by *B. anthracis* BH480 transformed with pSJ115-LF-OS and cultured as described herein. Lane 5 shows that *B. anthracis* BH480 transformed with pSJ136 Hfq1-FLAG and cultured as described herein did not produce detectable amounts of protein. Hfq1-FLAG is a small RNA chaperone Hfq1 with a C-terminal FLAG tag.

Example 10

Production of Intact Recombinant Proteins by B. anthracis BH480

This Example demonstrates production of recombinant proteins by modified B. anthracis of the embodiments.

Figure 11:
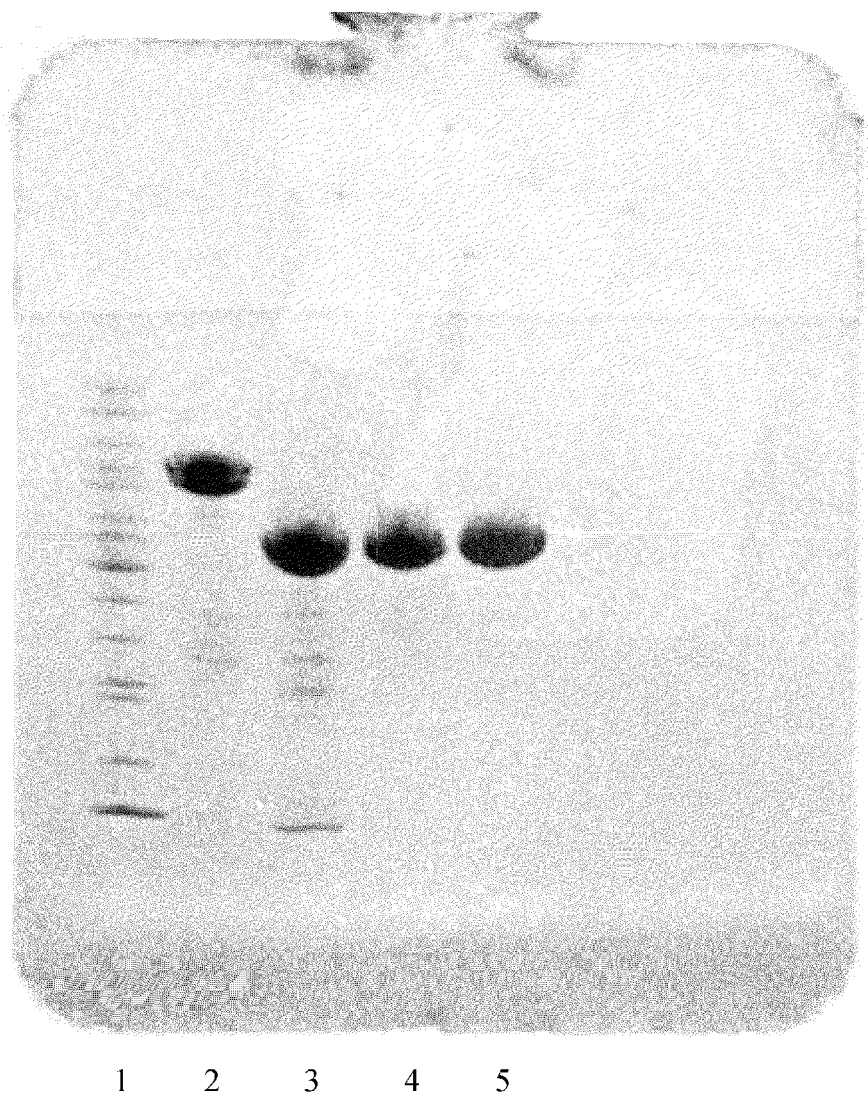
FIG. 11 provides SDS Phast gel analysis of production of LFnBlaY (SEQ ID NO:91) and PA-SNKE-deltaFF-E308D (SEQ ID NO:92) proteins by B. anthracis BH480 transformed with recombinant molecules encoding either LFnBlaY or PA-SNKE-deltaFF-E308D, respectively. Lane 1: SDS molecular weight marker mix. Lane 2: PA-SNKE-deltaFF-E308D produced by B. anthracis BH480 transformed with a pYS5 plasmid encoding PA-SNKE-deltaFF-E308D; Lane 3: LF-BLA, recombinantly produced in E. coli; Lanes 4 and 5: LFnBlaY produced by B. anthracis BH480 transformed with a pSJ115 plasmid encoding LFnBlaY.

Intact fusion protein LFnBlaY was produced as follows: B. anthracis BH480 was transformed with a recombinant molecule comprising a pSJ115 plasmid encoding LFnBlaY. LFnBlaY is a fusion protein of B. anthracis lethal factor LFn to B. cereus beta-lactamase (BlaY) that has an amino acid sequence represented by SEQ ID NO:91. A similar fusion protein, LF-BLA, produced in E. coli, is described in Hobson J P et al., 2006, Nature Methods 3, 259-261. The modified B. anthracis was cultured and LFnBlaY purified as described herein. A 2-liter preparation yielded 184 mg of intact LFnBlaY, the purity of which is demonstrated in FIG. 11, lanes 4 and 5, and compared to the purity of LF-BLA from E. coli (lane 3).

Figure 5:
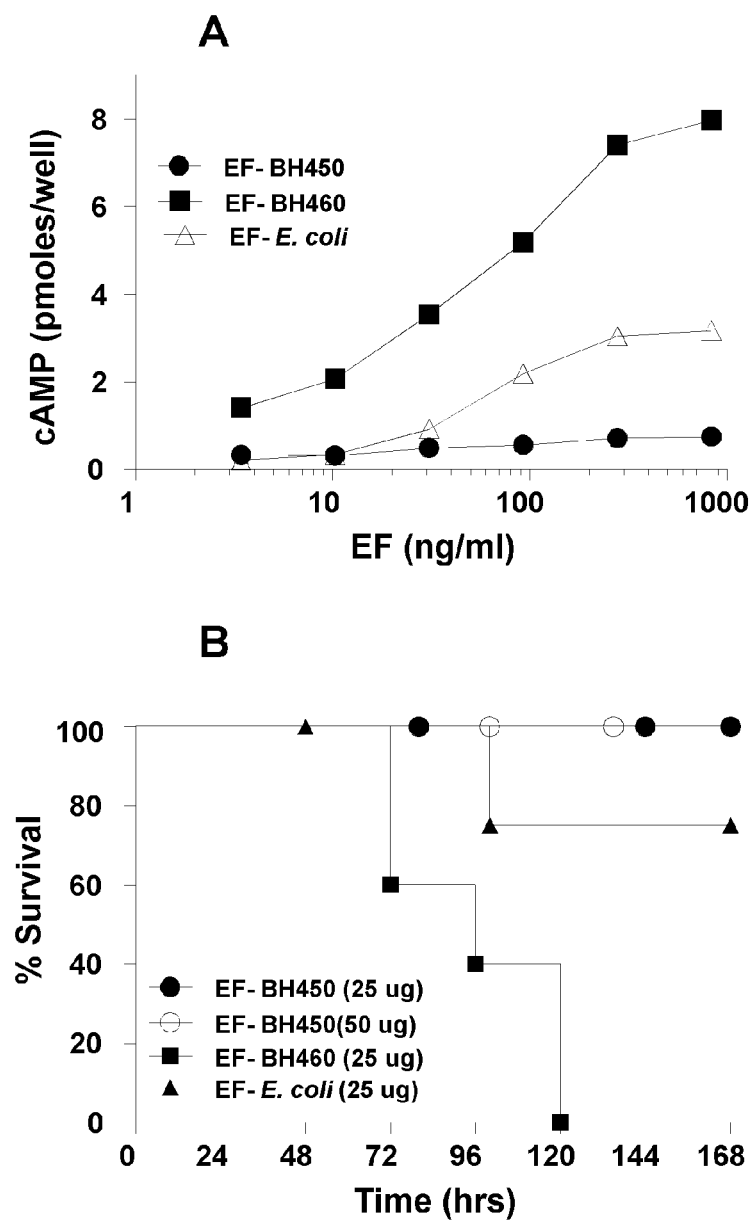
FIG. 5 provides EF activity analyses. A) cAMP production by different EF preparations was measured following treatment of RAW264.7 cells for 1 h with a range of EF concentrations and a set PA concentration (250 ng/ml). B) Potency of EF prepared from BH460 was compared to EF prepared from BH450 or from E. coli BL21(DE3) in Balb/cJ mice challenged with either 25 μg EF+25 μg PA (for EF made from BH450, BH460, or E. coli, respectively) or 50 μg EF+50 μg PA (for EF made from BH450 only).

Intact protective antigen (PA) variant PA-SNKE-deltaFF-E308D was produced as follows: B. anthracis BH480 was transformed with a recombinant molecule comprising a pYS5 plasmid encoding PA-SNKE-deltaFF-E308D. PA-SNKE-deltaFF-E308D is described in Ramirez D M et al., 2002, J Industrial Microbiology & Biotechnology 28, 232-238. The PA variant's amino acid sequence is represented by amino acid sequence SEQ ID NO:92. The modified B. anthracis was cultured and PA-SNKE-deltaFF-E308D purified using techniques similar to those described in US 2004/0076638 A1, published Apr. 22, 2004. A 2-liter preparation yielded 122 mg of intact PA-SNKE-deltaFF-E308D, the purity of which is shown in FIG. 5, lane 2.

This Example along with other examples herein demonstrate the abilities of B. anthracis BH460 and B. anthracis BH480 to make a variety of intact recombinant proteins.

Example 11

Summary and Conclusions

These Examples describe the adaptation of an improved Cre-loxP system for sequentially deleting additional protease-encoding genes of B. anthracis. They also describe a role of each protease in degradation of B. anthracis toxin components and another potential virulence factor, anthrolysin O (ALO) (Shannon J G et al., 2003, Infect. Immun. 71, 3183-318).

Bacillus anthracis produces a number of extracellular proteases that impact the integrity and yield of other proteins in the B. anthracis secretome. This study shows that anthrolysin O (ALO) and the three anthrax toxin proteins, protective antigen (PA), lethal factor (LF), and edema factor (EF), produced from the B. anthracis Ames 35 strain (pXO1$^+$, pXO2$^-$), are completely degraded at the onset of stationary phase due to the action of proteases. An improved Cre-loxP gene knockout system was used to sequentially delete the genes encoding six proteases (NprB, InhA2, TasA, camelysin, InhA1, and MmpZ). The role of each protease in degradation of the B. anthracis toxin components and ALO was demonstrated. Levels of the anthrax toxin components and ALO in the supernatant of the sporulation defective, pXO1$^+$ A35HMS mutant strain deleted for the six proteases were significantly increased and remained stable over 24 h. A pXO1-free variant of this six-protease mutant strain, designated BH460, provides an improved host strain for the preparation of recombinant proteins. As an example, BH460 was used to produce recombinant EF, which previously has been difficult to obtain from B. anthracis. The EF protein produced from BH460 had the highest in vivo potency of any EF previously purified from B. anthracis or E. coli hosts. BH460 is recommended as an effective host strain for recombinant protein production, typically yielding greater than 10 mg pure protein per liter of culture.

These Examples also describe the successful adaptation of a modified Saccharomyces cerevisiae Flp-FRT recombinase system for deleting additional protease-encoding genes of B. anthracis. This system was used to inactivate CysP1 and VpR proteases in BH460, thereby creating B. anthracis BH480. BH480 is also recommended as an effective host strain for recombinant protein production, typically yielding greater than 10 mg pure intact protein per liter of culture. In some embodiments, the yield is greater than 50 mg pure intact protein per liter of culture. In some embodiments, the yield is greater than 90 mg pure intact protein per liter of culture.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

---

What is claimed is:

1. A *Bacillus anthracis* (*B. anthracis*) transformed with a recombinant molecule encoding a product, wherein:
   (a) the *B. anthracis* comprises genetic modifications that inactivates proteases
   NprB encoded by a genetically modified nprB gene at locus GBAA_0599 of *B. anthracis*,
   InhA2 encoded by a genetically modified inhA2 gene at locus GBAA_0672 of *B. anthracis*,
   TasA encoded by a genetically modified tasA4 gene at locus GBAA_1288 of *B. anthracis*,
   Camelysin encoded by a genetically modified calY gene at locus GBAA_1290 of *B. anthracis*,
   InhA1 encoded by a genetically modified inhA1 gene at locus GBAA_1295 of *B. anthracis* and
   MmpZ encoded by a genetically modified mmpZ gene at locus GBAA_3159 of *B. anthracis*,
   and the *B. anthracis* is selected from the group consisting of a *B. anthracis* that is sporulation-deficient, a *B. anthracis* that lacks virulence plasmid pXO1, virulence plasmid pXO2, or virulence plasmids pXO1 and pXO2, and a *B. anthracis* that is sporulation-deficient and lacks virulence plasmid pXO1, virulence plasmid pXO2, or virulence plasmids pXO1 and pXO2; and
   (b) the recombinant molecule comprises a nucleic acid molecule encoding the product operatively linked to an expression vector, wherein the product comprises an intact protein.

2. The *B. anthracis* of claim 1, wherein the product is a toxin.

3. The *B. anthracis* of claim 2, wherein the toxin is selected from the group consisting of an anthrax toxin, a cholera toxin, a diphtheria toxin, a hemolysin, a ricin, a *Pseudomonas* toxin, a *Haemophilus ducreyi* toxin, an *Escherichia coli* toxin, and a ribosome-inactivating protein (RIP) toxin.

4. The *B. anthracis* of claim 1, wherein the intact protein is selected from the group consisting of an anthrax edema factor (EF), an anthrax lethal factor (LF), an anthrax protective antigen (PA), anthrolysin (ALO), a *Bacillus cereus* hemolysin, and combinations thereof.

5. A method to produce a product comprising:
   (a) culturing the *B. anthracis* of claim 1 in a medium to produce the product; and
   (b) recovering the product.

6. The *B. anthracis* of claim 1, wherein the *B. anthracis* is derived from strain Ames 35 (pXO1⁺pXO2⁻).

7. The *B. anthracis* of claim 1, wherein the *B. anthracis* is sporulation-deficient and lacks virulence plasmids pXO1 and pXO2.

8. The *B. anthracis* of claim 1, wherein the *B. anthracis* is BH460.

* * * * *